(12) United States Patent
Kambe et al.

(10) Patent No.: US 9,029,574 B2
(45) Date of Patent: *May 12, 2015

(54) BICYCLIC COMPOUND AND USE THEREOF FOR MEDICAL PURPOSES

(75) Inventors: Tohru Kambe, Osaka (JP); Isamu Sugimoto, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/982,001

(22) PCT Filed: Jan. 26, 2012

(86) PCT No.: PCT/JP2012/051721
§ 371 (c)(1),
(2), (4) Date: Aug. 21, 2013

(87) PCT Pub. No.: WO2012/102357
PCT Pub. Date: Aug. 2, 2012

(65) Prior Publication Data
US 2013/0324577 A1     Dec. 5, 2013

(30) Foreign Application Priority Data

Jan. 27, 2011  (JP) ................. 2011-014736

(51) Int. Cl.
| | |
|---|---|
| C07D 313/00 | (2006.01) |
| C07D 313/06 | (2006.01) |
| C07D 313/08 | (2006.01) |
| C07D 407/04 | (2006.01) |
| C07D 417/04 | (2006.01) |
| C07D 405/06 | (2006.01) |
| C07D 407/06 | (2006.01) |
| C07D 407/12 | (2006.01) |
| C07D 407/14 | (2006.01) |
| C07F 7/18 | (2006.01) |

(52) U.S. Cl.
CPC ............ *C07D 313/06* (2013.01); *C07D 313/08* (2013.01); *C07D 407/04* (2013.01); *C07D 417/04* (2013.01); *C07D 405/06* (2013.01); *C07D 407/06* (2013.01); *C07D 407/12* (2013.01); *C07D 407/14* (2013.01); *C07F 7/1856* (2013.01)

(58) Field of Classification Search
CPC .................................................... C07D 313/08
USPC ........................................................ 549/355
See application file for complete search history.

(56) References Cited

U.S. PATENT DOCUMENTS

| | | | |
|---|---|---|---|
| 4,230,721 A | 10/1980 | Gandolfi et al. | |
| 4,367,237 A | 1/1983 | Wakatsuka et al. | |
| 4,490,537 A | 12/1984 | Johnson | |
| 6,583,174 B1 | 6/2003 | Ueno et al. | |
| 2006/0035949 A1 | 2/2006 | Donde et al. | |

FOREIGN PATENT DOCUMENTS

| | | |
|---|---|---|
| JP | 50-37780 A | 4/1975 |
| JP | 53-84959 A | 7/1978 |
| JP | 53-132573 A | 11/1978 |
| JP | 55-73678 A | 6/1980 |
| JP | 64-68367 A | 3/1989 |
| WO | 01/27099 A2 | 4/2001 |
| WO | 2007/149829 A2 | 12/2007 |
| WO | 2011/013651 A1 | 2/2011 |
| WO | 2012/102355 A1 | 8/2012 |

OTHER PUBLICATIONS

International Search Report (PCT/ISA/210), dated Mar. 13, 2012, issued by the International Searching Authority in counterpart International Patent Application No. PCT/JP2012/051721.
International Search Report (PCT/ISA/210), dated Mar. 13, 2012, issued by the International Searching Authority in related International Patent Application No. PCT/JP2012/051718.
International Search Report (PCT/ISA/210), dated Sep. 14, 2010, issued by the International Searching Authority in related International Patent Application No. PCT/JP2010/062587.
Extended European Search Report, dated Dec. 3, 2012, issued by the European Patent Office in related European Patent Application No. 10804397.7.

*Primary Examiner* — Andrew D Kosar
*Assistant Examiner* — Raymond Covington
(74) *Attorney, Agent, or Firm* — Sughrue Mion, PLLC

(57) ABSTRACT

Provided is a compound which has strong and sustaining intraocular pressure lowering action and, further, has no fear of side effect on eyes.
Since a compound represented by the formula (I):

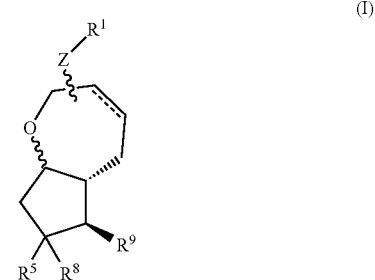

(I)

wherein definition of each group is as described in the specification, or a salt thereof, a solvate thereof, or a prodrug thereof has strong and sustaining intraocular pressure lowering action and, further, has no side effect on eyes such as ocular stimulating property (hyperemia, corneal clouding etc.), aqueous humor protein rise etc., it has high safety, and can be an excellent agent for preventing and/or treating glaucoma etc.

8 Claims, 1 Drawing Sheet

BICYCLIC COMPOUND AND USE THEREOF FOR MEDICAL PURPOSES

TECHNICAL FIELD

The present invention relates to a compound represented by the formula (I):

[Chemical formula 1]

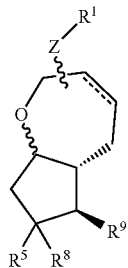

(I)

(wherein all symbols represent the same meanings as those described below), a salt thereof, or a solvate thereof, or a prodrug thereof (hereinafter, abbreviated as compound of the present invention in some cases).

BACKGROUND ART

Glaucoma is an ocular disease having the characteristic of a visual functional disorder which causes a transient or permanent visual field defect and decreased vision. This is derived from that since an aqueous humor is accumulated by a circulatory disorder of an aqueous humor, and an intraocular pressure is continuously increased, an optic nerve is compressed. Decrease in an intraocular pressure is effective for treatment of glaucoma and, in order to decrease an intraocular pressure, for example, drug treatment (eye drops, internal remedy, infusion treatment), laser treatment, or operation treatment is performed.

Previously, among prostaglandins (PGs) which are physiologically active substances, as those that decrease an intraocular pressure, PGFs and PGIs are known. Development of a drug for treating glaucoma or ocular hypertension has been progressed with using derivatives of them, and there are some drugs which are actually sold (e.g. latanoprost etc.). However, the existing glaucoma treating drug alone is insufficient in intraocular pressure lowering action and sustainability of drug efficacy and, in at site of glaucoma treatment, since administration at a frequent time or a high concentration, or therapy of joint use of drugs having different mechanisms of action has been performed for seeking stronger intraocular pressure lowering action, manifestation of side effects is feared. For this reason, drugs having stronger and sustaining intraocular pressure lowering action, and high safety are desired.

Meanwhile, as the prior art of the compound of the present invention, the following PG derivatives are exemplified.

As a PG derivative having a bicyclic skeleton, for example, a compound of the formula (a):

[Chemical formula 2]

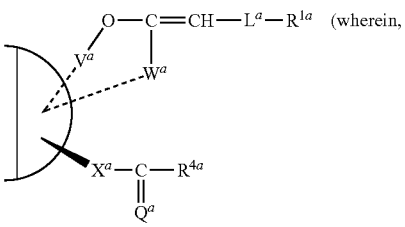

(a)

(wherein,

[Chemical formula 3]

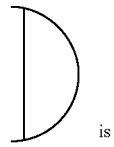

is

[Chemical formula 4]

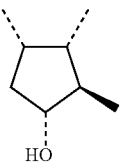

etc., $L^a$ is $-(CH_2)_{da}-C(R^{2a})_2-$ (wherein da is 0 to 5, and $R^2$ as are hydrogen, methyl or fluoro, and are the same or different) etc., $Q^a$ is an oxygen atom etc., $R^{1a}$ is $COOR^{3a}$ (wherein $R^{3a}$ is hydrogen, alkyl of 1 to 12 carbon atoms etc.) etc., $R^{4a}$ is

[Chemical formula 5]

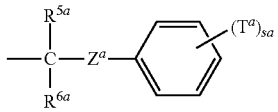

(wherein $R^{5a}$ and $R^{6a}$ are hydrogen, alkyl of 1 to 4 carbon atoms or fluoro, and are the same or different, $Z^a$ is an oxygen atom etc., $T^a$ is alkyl of 1 to 4 carbon atoms, fluoro, chloro etc., and sa is 0 to 3) etc., $V^a$ is a valence bond or $-CH_2$, $W^a$ is $-(CH_2)_h$, h is 1 or 2, and $X^a$ is trans-$CH=CH-$ etc. (a part of definitions of groups was extracted) is known (see Patent Literature 1).

In addition, a compound represented by the formula (b):

[Chemical formula 6]

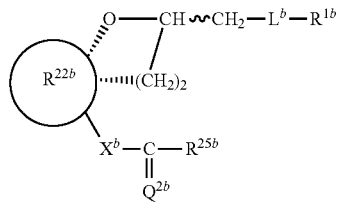

(b)

(wherein $L^b$ represents $-(CH_2)_{db}-$ (wherein db represents 1 to 5) etc., $Q^{2b}$ represents O etc., $R^{1b}$ represents $-COOR^{19b}$ (wherein $R^{19b}$ represents a C1-12 alkyl group or a hydrogen atom etc.) etc., a ring $R^{22b}$ represents

[Chemical formula 7]

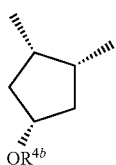

(wherein $R^{4b}$ represents a hydrogen atom etc.) etc., $R^{25b}$ represents

[Chemical formula 8]

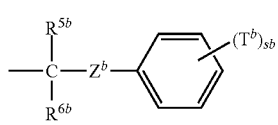

(wherein $R^{5b}$ and $R^{6b}$ represent a hydrogen atom etc., $Z^b$ represents —O— etc., $T^b$ represents a C1-4 alkyl group, fluorine, chlorine, trifluoromethyl or —$OR^{7b}$— (wherein $R^{7b}$ represents C1-4 alkyl), sb represents 0, 1, 2 or 3, and $X^b$ represents

[Chemical formula 9]

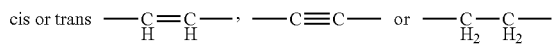

(a part of definitions of groups was extracted)) (see Patent Literature 2) is known.

Further, a process for producing a compound represented by the formula (c):

[Chemical formula 10]

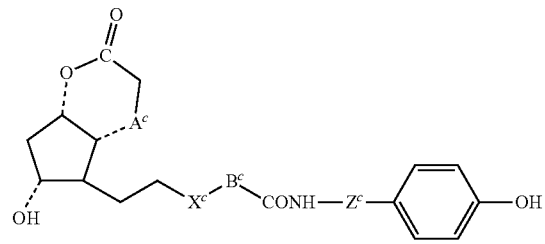

(wherein $A^c$ represents a C1-2 alkylene group, $B^c$ represents a C2-6 alkylene group, $X^c$ represents C(O) etc., and $Z^c$ represents a C1-4 alkylene group etc. (a part of definitions of groups was extracted)) is known (see Patent Literature 3).

Meanwhile, it has been reported that agonistic activity on an IP receptor among PG receptors causes hyperemia and rise in an aqueous humor protein, and inducement of stimulation on eyes has been feared (see Non-Patent Literatures 1 and 2). For this reason, since the compound described in Patent Literature 2 which is a PGI2 derivative has agonistic activity on an IP receptor, there is a probability that property of stimulating eyes etc. are induced.

Further, it has been also known that agonistic activity on an EP1 receptor among PGE subtype receptors causes itching of eyes (see Non-Patent Literature 3).

Although the compound of the present invention is a compound which has low agonistic activity on an IP receptor and an EP1 receptor, and has selective agonistic activity on an FP receptor, there is neither the description nor the suggestion regarding such a characteristic (selectivity) in any prior arts.

PRIOR ART LITERATURES

Patent Literatures

Patent Literature 1: JP-A-52-95644
Patent Literature 2: U.S. Pat. No. 4,490,548
Patent Literature 3: JP-A-50-37780 NON-PATENT LITERATURES
Non-Patent Literature 1: Investigative Ophthalmology & Visual Science, Vol. 28, p. 470-476, 1987
Non-Patent Literature 2: Investigative Ophthalmology & Visual Science, Vol. 23, p. 383-392, 1982
Non-Patent Literature 3: The Journal of Pharmacology and Experimental Therapeutics, Vol. 279, No. 1, p. 137-142, 1996

SUMMARY OF THE INVENTION

Problems to be Solved by the Invention

A compound which has strong and sustaining intraocular pressure lowering action and, further, has no fear of side effects on eyes is desired.

Means to Solve the Problems

In order to solve the aforementioned problems, the inventors of the present invention intensively studied to find out a compound which has improved selectivity on a PG receptor subtype, namely, a compound which has low agonistic activity on an IP receptor and an EP1 receptor, and has selective agonistic activity on an FP receptor and, as a result, accomplished the present invention.

That is, the present invention relates to:
1. a compound represented by the formula (I):

[Chemical formula 11]

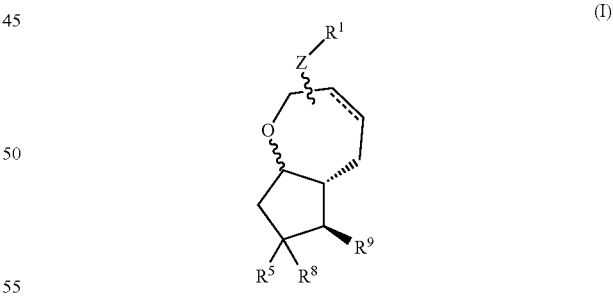

(wherein Z represents (1) —$(CH_2)_m$—, (2) —$(CH_2)_n$—CH=CH—, (3) —$(CH_2)_p$-A-$CH_2$— or (4) ring 1; A represents an oxygen atom or a sulfur atom; $R^1$ represents (1) COOH, (2) $COOR^2$, (3) $CH_2OH$ or (4) $CONR^3R^4$; $R^2$ represents a C1-6 alkyl group which may be substituted with a hydroxyl group, $ONO_2$ or a C1-4 alkoxy group; $R^3$ and $R^4$ each independently represent a hydrogen atom, or a C1-4 alkyl group which may be substituted with $ONO_2$; $R^5$ represents a halogen atom, a hydroxyl group or a C1-4 alkoxy group; $R^8$ represents a hydrogen atom or a halogen atom; $R^9$ represents

[Chemical formula 12]

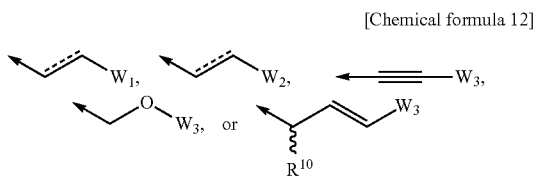

(wherein the arrow represents a bonding site), $W_1$ represents a C1-6 alkyl group which may be substituted with 1 to 5 substituents selected from the group consisting of (1) a hydroxyl group, (2) an oxo group, (3) a halogen atom, (4) a C1-4 alkyl group, (5) a C1-4 alkoxy group, (6) ring 2, (7) —O-ring 2 and (8) —S-ring 2; $W_2$ represents a C2-6 alkenyl group or a C2 to 4 alkyl group wherein any one carbon atom is replaced by an oxygen atom, which is which may be substituted with 1 to 5 substituents selected from the group consisting of (1) a hydroxyl group, (2) an oxo group, (3) a halogen atom, (4) a C1-4 alkyl group, (5) a C1-4 alkoxy group, (6) ring 2, (7) —O-ring 2 and (8) —S-ring 2; $W_3$ represents a C1-6 alkyl group, a C2-6 alkenyl group or a C2-4 alkyl group wherein any one carbon atom is replaced by an oxygen atom, which is which may be substituted with 1 to 5 substituents selected from the group consisting of (1) a hydroxyl group, (2) an oxo group, (3) a halogen atom, (4) a C1-4 alkyl group, (5) a C1-4 alkoxy group, (6) ring 2, (7) —O-ring 2 and (8) —S-ring 2; $R^{10}$ represents a hydrogen atom or a halogen atom, ring 1 and ring 2 each independently represent a C3-10 carbocyclic ring or a 3- to 10-membered heterocyclic ring which may be substituted with 1 to 5 substituents selected from the group consisting of (1) a halogen atom, (2) $CF_3$, (3) $OCF_3$, (4) a C1-4 alkoxy group, (5) a C1-4 alkyl group, (6) a hydroxyl group and (7) a nitrile group; m represents an integer of 1 to 6; n represents an integer of 1 to 4; p represents an integer of 1 to 4,

[Chemical formula 13]

----- represents a single bond or a double bond,

[Chemical formula 14]

⋯⋯ⁿ represents α configuration,

[Chemical formula 15]

◂ represents β configuration, and

[Chemical formula 16]

∿ represents α configuration, β configuration or an arbitrary mixture thereof), or a salt thereof, a solvate thereof, or a prodrug thereof;
2. the compound according to 1, wherein $R^8$ is a halogen atom, and $R^9$ is

[Chemical formula 17]

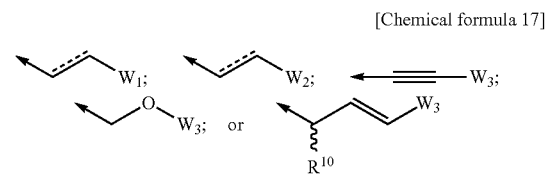

(wherein all symbols represent the same meanings as those described in 1); or $R^8$ is a hydrogen atom, and $R^9$ is

[Chemical formula 18]

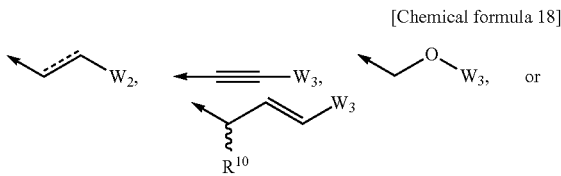

(wherein all symbols represent the same meanings as those described in 1), or a salt thereof, a solvate thereof, or a prodrug thereof;
3. the compound according to 2, which is represented by the formula (I-1);

[Chemical formula 19]

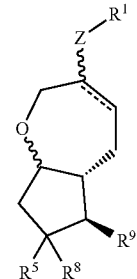

(wherein all symbols represent the same meanings as those described in 2), or a salt thereof, a solvate thereof, or a prodrug thereof;
4. the compound according to 1, which is a compound selected from the group consisting of
(1) 4-{(3S,5aR,6R,7R,8aS)-7-hydroxy-6-[(1E,3S)-3-hydroxy-4-phenoxy-1-buten-1-yl]octahydro-2H-cyclopenta[b]oxepin-3-yl}butanoic acid,
(2) 4-{(3S,5aR,6R,7R,8aS)-7-hydroxy-6-[(1E,3R)-3-hydroxy-5-phenyl-1-penten-1-yl]octahydro-2H-cyclopenta[b]oxepin-3-yl}butanoic acid,
(3) 4-{(3S,5aR,6R,7R,8aS)-6-[(1E,3R)-5-(3-fluorophenyl)-3-hydroxy-1-penten-1-yl]-7-hydroxyoctahydro-2H-cyclopenta[b]oxepin-3-yl}butanoic acid,
(4) 4-{(3S,5aR,6R,7R,8aS)-6-[(1E,3S)-5-(3-fluorophenyl)-3-hydroxy-1-penten-1-yl]-7-hydroxyoctahydro-2H-cyclopenta[b]oxepin-3-yl}butanoic acid,
(5) 4-{(3S,5aR,6R,7R,8aS)-6-[(1E,3R)-5-(4-fluorophenyl)-3-hydroxy-1-penten-1-yl]-7-hydroxyoctahydro-2H-cyclopenta[b]oxepin-3-yl}butanoic acid,
(6) 4-{(3S,5aR,6R,7R,8aS)-6-[(1E,3S)-5-(4-fluorophenyl)-3-hydroxy-1-penten-1-yl]-7-hydroxyoctahydro-2H-cyclopenta[b]oxepin-3-yl}butanoic acid,
(7) 4-{(3S,5aR,6R,7R,8aS)-6-[(1E,3R)-5-(2-fluorophenyl)-3-hydroxy-1-penten-1-yl]-7-hydroxyoctahydro-2H-cyclopenta[b]oxepin-3-yl}butanoic acid, (8) 4-{(3S,5aR,6R,7R,8aS)-6-[(1E,3S)-5-(2-fluorophenyl)-3-hydroxy-1-penten-1-yl]-7-hydroxyoctahydro-2H-cyclopenta[b]oxepin-3-yl}butanoic acid, (9) 4-{(3S,5aR,6R,7R,8aS)-6-[(1E,3R)-5-(3-chlorophenyl)-3-hydroxy-1-penten-1-yl]-7-hydroxyoctahydro-2H-cyclopenta[b]oxepin-3-yl}butanoic acid,

(10) 4-{(3S,5aR,6R,7R,8aS)-6-[(1E,3S)-5-(3-chlorophenyl)-3-hydroxy-1-penten-1-yl]-7-hydroxyoctahydro-2H-cyclopenta[b]oxepin-3-yl}butanoic acid,

(11) 4-[(3S,5aR,6R,7R,8aS)-7-hydroxy-6-{(1E,3R)-3-hydroxy-5-[3-(trifluoromethyl)phenyl]-1-penten-1-yl}octahydro-2H-cyclopenta[b]oxepin-3-yl]butanoic acid,

(12) 4-[(3S,5aR,6R,7R,8aS)-7-hydroxy-6-{(1E,3S)-3-hydroxy-5-[3-(trifluoromethyl)phenyl]-1-penten-1-yl}octahydro-2H-cyclopenta[b]oxepin-3-yl]butanoic acid,

(13) 4-[(3S,5aR,6R,7R,8aS)-7-hydroxy-6-{(1E,3S)-3-hydroxy-4-[3-(trifluoromethyl)phenoxy]-1-buten-1-yl}octahydro-2H-cyclopenta[b]oxepin-3-yl]butanoic acid,

(14) 4-{(3S,5aR,6R,7R,8aS)-6-[(1E,3S)-4-(2-fluorophenoxy)-3-hydroxy-1-buten-1-yl]-7-hydroxyoctahydro-2H-cyclopenta[b]oxepin-3-yl}butanoic acid,

(15) 4-{(3S,5aR,6R,7R,8aS)-6-[(1E,3S)-4-(3-fluorophenoxy)-3-hydroxy-1-buten-1-yl]-7-hydroxyoctahydro-2H-cyclopenta[b]oxepin-3-yl}butanoic acid,

(16) 4-{(3S,5aR,6R,7R,8aS)-6-[(1E,3S)-4-(4-fluorophenoxy)-3-hydroxy-1-buten-1-yl]-7-hydroxyoctahydro-2H-cyclopenta[b]oxepin-3-yl}butanoic acid,

(17) 4-{(3S,5aR,6R,7R,8aS)-6-[(1E,3S)-5-cyclohexyl-3-hydroxy-1-penten-1-yl]-7-hydroxyoctahydro-2H-cyclopenta[b]oxepin-3-yl}butanoic acid,

(18) 4-{(3S,5aR,6R,7R,8aS)-7-hydroxy-6-[(3S)-3-hydroxy-4-phenoxybutyl]octahydro-2H-cyclopenta[b]oxepin-3-yl}butanoic acid,

(19) 4-{(3S,5aR,6R,7R,8aS)-7-hydroxy-6-[(3S)-3-hydroxy-5-phenylpentyl]octahydro-2H-cyclopenta[b]oxepin-3-yl}butanoic acid,

(20) 4-{(3S,5aR,6R,7R,8aS)-6-[(3S)-5-(3-fluorophenyl)-3-hydroxypentyl]-7-hydroxyoctahydro-2H-cyclopenta[b]oxepin-3-yl}butanoic acid,

(21) 4-{(3S,5aR,6R,7R,8aS)-6-[(3R)-5-(3-fluorophenyl)-3-hydroxypentyl]-7-hydroxyoctahydro-2H-cyclopenta[b]oxepin-3-yl}butanoic acid,

(22) 4-{(3S,5aR,6R,7R,8aS)-6-[(3S)-5-(4-fluorophenyl)-3-hydroxypentyl]-7-hydroxyoctahydro-2H-cyclopenta[b]oxepin-3-yl}butanoic acid,

(23) 4-{(3S,5aR,6R,7R,8aS)-6-[(3R)-5-(4-fluorophenyl)-3-hydroxypentyl]-7-hydroxyoctahydro-2H-cyclopenta[b]oxepin-3-yl}butanoic acid,

(24) 4-{(3S,5aR,6R,7R,8aS)-6-[(3S)-5-(2-fluorophenyl)-3-hydroxypentyl]-7-hydroxyoctahydro-2H-cyclopenta[b]oxepin-3-yl}butanoic acid,

(25) 4-{(3S,5aR,6R,7R,8aS)-6-[(3R)-5-(2-fluorophenyl)-3-hydroxypentyl]-7-hydroxyoctahydro-2H-cyclopenta[b]oxepin-3-yl}butanoic acid,

(26) 4-{(3S,5aR,6R,7R,8aS)-6-[(3S)-5-(3-chlorophenyl)-3-hydroxypentyl]-7-hydroxyoctahydro-2H-cyclopenta[b]oxepin-3-yl}butanoic acid,

(27) 4-{(3S,5aR,6R,7R,8aS)-6-[(3R)-5-(3-chlorophenyl)-3-hydroxypentyl]-7-hydroxyoctahydro-2H-cyclopenta[b]oxepin-3-yl}butanoic acid,

(28) 4-[(3S,5aR,6R,7R,8aS)-7-hydroxy-6-{(3S)-3-hydroxy-5-[3-(trifluoromethyl)phenyl]pentyl}octahydro-2H-cyclopenta[b]oxepin-3-yl]butanoic acid,

(29) 4-[(3S,5aR,6R,7R,8aS)-7-hydroxy-6-{(3R)-3-hydroxy-5-[3-(trifluoromethyl)phenyl]pentyl}octahydro-2H-cyclopenta[b]oxepin-3-yl]butanoic acid,

(30) 4-[(3S,5aR,6R,7R,8aS)-7-hydroxy-6-{(3R)-3-hydroxy-4-[3-(trifluoromethyl)phenoxy]butyl}octahydro-2H-cyclopenta[b]oxepin-3-yl]butanoic acid,

(31) 4-{(3S,5aR,6R,7R,8aS)-6-[(1E)-3-fluoro-4-phenoxy-1-buten-1-yl]-7-hydroxyoctahydro-2H-cyclopenta[b]oxepin-3-yl}butanoic acid,

(32) 4-{(3S,5aR,6R,7R,8aS)-6-[(1E)-4-(3-chlorophenoxy)-1-buten-1-yl]-7-hydroxyoctahydro-2H-cyclopenta[b]oxepin-3-yl}butanoic acid,

(33) 4-{(3S,5aR,6R,7R,8aS)-6-[(1E)-4-(2-fluorophenoxy)-1-buten-1-yl]-7-hydroxyoctahydro-2H-cyclopenta[b]oxepin-3-yl}butanoic acid,

(34) 4-{(3S,5aR,6R,7R,8aS)-6-[(1E)-4-(3-fluorophenoxy)-1-buten-1-yl]-7-hydroxyoctahydro-2H-cyclopenta[b]oxepin-3-yl}butanoic acid,

(35) 4-{(3S,5aR,6R,7R,8aS)-6-[(1E)-4-(2,5-difluorophenoxy)-1-buten-1-yl]-7-hydroxyoctahydro-2H-cyclopenta[b]oxepin-3-yl}butanoic acid,

(36) 4-{(3S,5aR,6R,7R,8aS)-7-hydroxy-6-[(1E)-4-hydroxy-6-phenyl-1-hexen-1-yl]octahydro-2H-cyclopenta[b]oxepin-3-yl}butanoic acid,

(37) 4-[(3S,5aR,6R,7R,8aS)-7-hydroxy-6-(4-phenoxybutyl)octahydro-2H-cyclopenta[b]oxepin-3-yl]butanoic acid,

(38) 4-{(3S,5aR,6R,7R,8aS)-7-hydroxy-6-[(1E)-3-hydroxy-1-decen-1-yl]octahydro-2H-cyclopenta[b]oxepin-3-yl}butanoic acid,

(39) 4-{(3S,5aR,6R,7R,8aS)-7-hydroxy-6-[(1E)-3-hydroxy-5-(5-methyl-2-furyl)-1-penten-1-yl]octahydro-2H-cyclopenta[b]oxepin-3-yl}butanoic acid,

(40) 4-{(3S,5aR,6R,7R,8aS)-6-[(1E)-5-cyclopentyl-3-hydroxy-1-penten-1-yl]-7-hydroxyoctahydro-2H-cyclopenta[b]oxepin-3-yl}butanoic acid,

(41) 4-{(3S,5aR,6R,7R,8aS)-6-[(1E)-3-(1-benzofuran-2-yl)-3-hydroxy-1-propen-1-yl]-7-hydroxyoctahydro-2H-cyclopenta[b]oxepin-3-yl}butanoic acid,

(42) 4-{(3S,5aR,6R,7R,8aS)-7-hydroxy-6-[(1E)-3-hydroxy-5-(3-hydroxyphenyl)-1-penten-1-yl]octahydro-2H-cyclopenta[b]oxepin-3-yl}butanoic acid,

(43) 4-{(3S,5aR,6R,7R,8aS)-6-[(1E)-3,3-difluoro-5-phenyl-1-penten-1-yl]-7-hydroxyoctahydro-2H-cyclopenta[b]oxepin-3-yl}butanoic acid,

(44) 4-[(3S,5aR,6R,7R,8aS)-6-(3,3-difluoro-5-phenylpentyl)-7-hydroxyoctahydro-2H-cyclopenta[b]oxepin-3-yl]butanoic acid,

(45) 4-{(3S,5aR,6R,7R,8aS)-6-[(1E)-5-cyclopentyl-3,3-difluoro-1-penten-1-yl]-7-hydroxyoctahydro-2H-cyclopenta[b]oxepin-3-yl}butanoic acid,

(46) 4-{(3S,5aR,6R,7R,8aS)-6-[(1E)-5-cyclohexyl-3,3-difluoro-1-penten-1-yl]-7-hydroxyoctahydro-2H-cyclopenta[b]oxepin-3-yl}butanoic acid,

(47) 4-{(3S,5aR,6R,7R,8aS)-6-[(1E)-3,3-difluoro-1-octen-1-yl]-7-hydroxyoctahydro-2H-cyclopenta[b]oxepin-3-yl}butanoic acid, and isomers thereof or a salt thereof, a solvate thereof, or a prodrug thereof;

5. the compound according to 2, which is a compound selected from the group consisting of (1) 4-[(3S,5aR,6S,7R,8aS)-7-hydroxy-6-({[(2E)-3-phenyl-2-propen-1-yl]oxy}methyl)octahydro-2H-cyclopenta[b]oxepin-3-yl]butanoic acid, (2) 4-{(3S,5aR,6R,7R,8aS)-7-hydroxy-6-[2-(2-phenylethoxy)ethyl]octahydro-2H-cyclopenta[b]oxepin-3-yl}butanoic acid, (3) 4-[(3S,5aR,6S,7R,8aS)-7-hydroxy-6-(3-hydroxy-5-phenyl-1-pentyn-1-yl)octahydro-2H-cyclopenta[b]oxepin-3-yl]butanoic acid,
(4) 4-{(3S,5aR,6R,7R,8aS)-6-[(2E)-1-fluoro-4-phenoxy-2-buten-1-yl]-7-hydroxyoctahydro-2H-cyclopenta[b]oxepin-3-yl}butanoic acid,
(5) 4-{(3S,5aR,6R,7R,8aS)-7-hydroxy-6-[(1E)-3-hydroxy-8-methyl-1,7-nonadien-1-yl]octahydro-2H-cyclopenta[b]oxepin-3-yl}butanoic acid,
(6) 4-{(3S,5aR,6R,7R,8aS)-6-[(1E)-4-(benzyloxy)-3-hydroxy-1-buten-1-yl]-7-hydroxyoctahydro-2H-cyclopenta[b]oxepin-3-yl}butanoic acid,
(7) 4-{(3S,5aR,6R,7R,8aS)-7-hydroxy-6-[(1E)-3-hydroxy-1,7-octadien-1-yl]octahydro-2H-cyclopenta[b]oxepin-3-yl}butanoic acid,
(8) 4-{(3S,5aR,6R,7R,8aS)-7-hydroxy-6-[(1E,6Z)-3-hydroxy-1,6-nonadien-1-yl]octahydro-2H-cyclopenta[b]oxepin-3-yl}butanoic acid,
(9) 4-{(3S,5aR,6R,7R,8aS)-7-hydroxy-6-[(1E)-3-hydroxy-4,8-dimethyl-1,7-nonadien-1-yl]octahydro-2H-cyclopenta[b]oxepin-3-yl}butanoic acid,
(10) 4-{(3S,5aR,6R,8aS)-7,7-difluoro-6-[(1E)-3-hydroxy-1-octen-1-yl]octahydro-2H-cyclopenta[b]oxepin-3-yl}butanoic acid,
(11) 4-{(3S,5aR,6R,8aS)-7,7-difluoro-6-[(1E)-3-hydroxy-5-phenyl-1-penten-1-yl]octahydro-2H-cyclopenta[b]oxepin-3-yl}butanoic acid,
(12) 4-{(3S,5aR,6R,7R,8aS)-6-[(1E)-3,3-difluoro-8-methyl-1,7-nonadien-1-yl]-7-hydroxyoctahydro-2H-cyclopenta[b]oxepin-3-yl}butanoic acid, and isomers thereof, or a salt thereof, a solvate thereof, or a prodrug thereof;
6. a pharmaceutical composition comprising the compound, or a salt thereof, a solvate thereof, or a prodrug thereof described in 2;
7. the pharmaceutical composition according to 6, wherein the compound, or a salt thereof, a solvate thereof, or a prodrug thereof described in 2 is an FP agonist;
8. the pharmaceutical composition according to 6, which is an agent for preventing and/or treating an ocular disease;
9. the pharmaceutical composition according to 8, wherein the ocular disease is glaucoma, ocular hypertension, macular edema, macular degeneration, retina and optic nerve tensile force rise, myopia, hypermetropia, astigmatism, dry eye, retinal detachmente, cataract, intraocular pressure rise due to trauma or inflammation, intraocular pressure rise due to a drug, or intraocular pressure rise after operation;
10. a method of preventing and/or treating an ocular disease, comprising administering an effective amount of the compound, or a salt thereof, a solvate thereof, or a prodrug thereof described in 2 to a mammal;
11. the compound, or a salt thereof, a solvate thereof, or a prodrug thereof described in 2, for use in the prevention and/or treatment of an ocular disease; and
12. use of the compound, or a salt thereof, a solvate thereof, or a prodrug thereof described in 2, in the manufacture of a medicament for the prevention and/or treatment of an ocular disease; etc.

Effects of the Invention

The compound of the present invention has strong and sustained intraocular pressure lowering action, and is useful as a therapeutic agent for glaucoma having no side effect on eyes such as ocular stimulating property (hyperemia, cloudy cornea etc.), humor protein rise etc.

MODE FOR CARRYING OUT THE INVENTION

Figure 1:
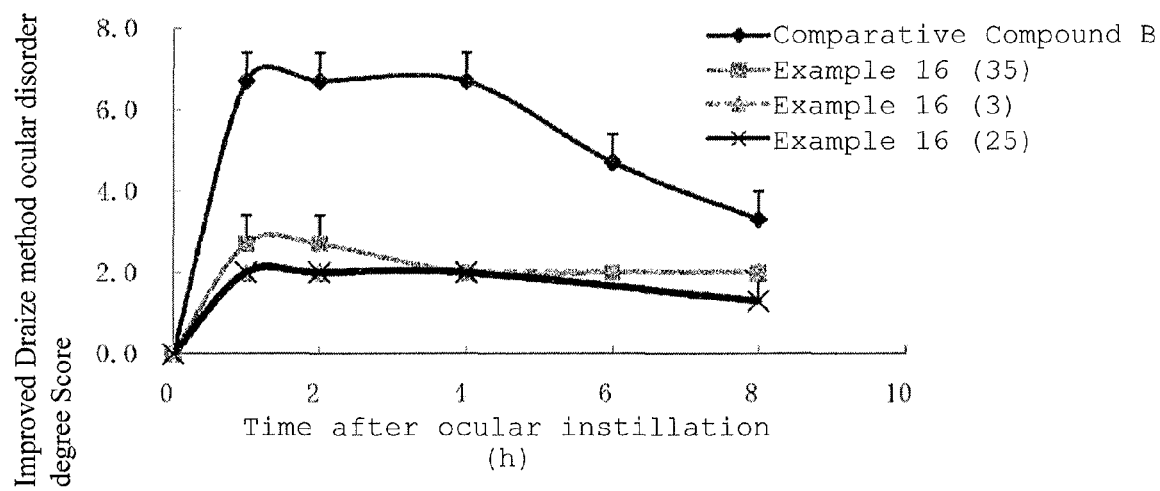
FIG. 1 A graph showing transition of ocular stimulating property based on the Draize score after ocular instillation of the compound of the present invention and a comparative compound.

The present invention will be explained in detail below.
In the present invention, the C1-6 alkyl group means a straight or branched C1-6 alkyl group such as methyl, ethyl, propyl, isopropyl, butyl, sec-butyl, tert-butyl, pentyl, isopentyl, tert-pentyl, neopentyl, hexyl etc.
In the present invention, the C1-4 alkyl group means a straight or branched C1-4 alkyl group such as methyl, ethyl, propyl, isopropyl, butyl, sec-butyl, tert-butyl etc.
In the present invention, the C2-4 alkyl group of the "C2-4 alkyl group wherein any one carbon atom is replaced by an oxygen atom" means ethyl, propyl, butyl groups etc.
In the present invention, the C2-4 alkyl group wherein any one carbon atom is replaced by an oxygen atom means —O—CH$_3$, —CH$_2$—OH, —O—C$_2$H$_5$, —CH$_2$—O—CH$_3$, —(CH$_2$)$_2$—OH, —O—(CH$_2$)$_2$—CH$_3$, —CH$_2$—O—C$_2$H$_5$, —(CH$_2$)$_2$—O—CH$_3$ or —(CH$_2$)$_3$—OH.
In the present invention, the C2-6 alkenyl group means a straight or branched C2-6 alkenyl group such as ethenyl, 1-propenyl, 2-propenyl, 1-methylvinyl, 1-butenyl, 2-butenyl, 3-butenyl, 1-methyl-1-propenyl, 1-methyl-2-propenyl, 2-methyl-2-propenyl, 1-ethyl-2-vinyl, 1-pentenyl, 2-pentenyl, 3-pentenyl, 4-pentenyl, 1,2-dimethyl-1-propenyl, 1,2-dimethyl-2-propenyl, 1-ethyl-1-propenyl, 1-ethyl-2-propenyl, 1-methyl-1-butenyl, 1-methyl-2-butenyl, 2-methyl-1-butenyl, 1-i-propylvinyl, 2,4-pentadienyl, 1-hexenyl, 2-hexenyl, 3-hexenyl, 4-hexenyl, 5-hexenyl, 2,4-hexadienyl, 1-methyl-1-pentenyl etc.
In the present invention, the C1-4 alkoxy group means a straight or branched C1-4 alkoxy group such as methoxy, ethoxy, propoxy, isopropoxy, butoxy, isobutyloxy, tert-butoxy etc.
In the present invention, the halogen atom means fluorine, chlorine, bromine, and iodine.
In the present invention, the C3-10 carbocyclic ring means a C3-10 monocyclic or bicyclic carbocyclic ring, a part or all of which may be saturated, and examples thereof include cyclopropane, cyclobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, perhydroindane, naphthalene, dihydronaphthalene, tetrahydronaphthalene, perhydronaphthalene etc.
In the present invention, the C3-7 carbocyclic ring means a C3-7 monocyclic carbocyclic ring, a part or all of which may be saturated, and examples thereof include cyclopropane, cyclobutane, cyclopentane, cyclohexane, cycloheptane, cyclopentene, cyclohexene, cycloheptene, cyclopentadiene, cyclohexadiene, cycloheptadiene, benzene etc.
In the present invention, the 3- to 10-membered heterocyclic ring means a 3- to 10-membered monocyclic or bicyclic heterocyclic ring, a part or all of which may be saturated, comprising 1 to 5 hetero atoms selected from an oxygen atom, a nitrogen atom and a sulfur atom, and examples thereof include pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isooxazole, thiazole, isothiazole, furazan, oxadiazole, oxazine, oxadiazine, oxazepine, oxadiazepine, thiadiazole, thiazine, thiadiazine, thiazepine, thiadiazepine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisooxazole, tetrahydroisooxazole (isooxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, pyrrolopyridine, benzoxazole, benzothiazole, benzimidazole, chromene, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, tetrahydropyrrolopyridine, dihydrocinnoline, tetrahydrocinnoline, perhydrocinnnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, and perhydrobenzimidazole.

In the present invention, the sulfur atom in A includes an oxidized sulfur atom, that is, —SO— or —$SO_2$— in addition to —S—.

In the present invention, as $R^1$, COOH or $COOR^2$ is preferable.

In the present invention, $R^2$ represents a C1-6 alkyl group, and the group may be substituted with a hydroxyl group, $ONO_2$ or a C1-4 alkoxy group. As $R^2$, methyl, ethyl, propyl, or isopropyl is preferable.

In the present invention, as $R^5$, a hydroxyl group, or a halogen atom is preferable.

In the present invention, as Z, —$(CH_2)_m$—, —$(CH_2)_n$—CH=CH—, —$(CH_2)_p$-A-$CH_2$— or ring 1 is preferable; —$(CH_2)_m$— or —$(CH_2)_p$-A-$CH_2$— is more preferable; and —$(CH_2)_m$— is further preferable. Herein, as A, an oxygen atom is preferable.

In the present invention, as $R^8$, a halogen atom is preferable.

In the present invention, as $R^9$,

[Chemical formula 20]

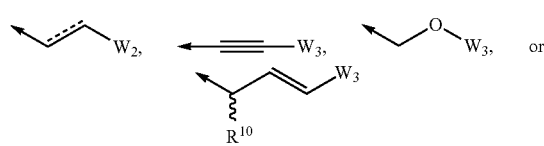

(wherein all symbols represent the same meanings as those described above) is preferable.

In the present invention, the combination of $R^8$ and $R^9$ is preferably a combination in which $R^8$ is a halogen atom and $R^9$ is

[Chemical formula 21]

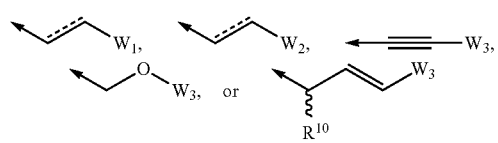

(wherein all symbols represent the same meanings as those described above), or $R^8$ is a hydrogen atom and $R^9$ is

[Chemical formula 22]

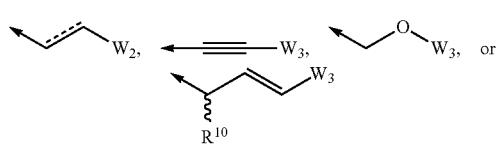

(wherein all symbols represent the same meanings as those described above).

In the present invention, as the "C1-6 alkyl group" represented by $W_1$, an ethyl group, or a propyl group is preferable. Herein, as a substituent of the "C1-6 alkyl group", a hydroxyl group, an oxo group, a halogen atom, a C1-4 alkyl group, a C1-4 alkoxy group, —O-ring 2 or ring 2 is preferable.

In the present invention, as the "C2-6 alkenyl group" represented by $W_2$, a straight chain C3-6 alkenyl group is preferable; a pentenyl group or a hexenyl group is more preferable; and a 4-pentenyl group or a 5-hexenyl group is further preferable. Herein, as a substituent of the "C2-6 alkenyl group", a hydroxyl group, an oxo group, a halogen atom, a C1-4 alkyl group, a C1-4 alkoxy group, —O-ring 2 or ring 2 is preferable; and a hydroxyl group, a halogen atom, a C1-4 alkyl group or ring 2 is more preferable.

In the present invention, as the "C2-4 alkyl group" of the "C2-4 alkyl group wherein any one carbon atom is replaced by an oxygen atom", which is represented by $W_2$, a propyl group or a butyl group is preferable.

In the present invention, as the "C2-4 alkyl group wherein any one carbon atom is replaced by an oxygen atom", which is represented by $W_2$, —O—$C_2H_5$ or —$(CH_2)_2$—O—$CH_3$ is preferable. Herein, as a substituent of the "C2-4 alkyl group wherein any one carbon atom is replaced by an oxygen atom", a hydroxyl group, an oxo group, a halogen atom, a C1-4 alkyl group, a C1-4 alkoxy group, —O-ring 2 or ring 2 is preferable, and a hydroxyl group or ring 2 is more preferable.

In the present invention, as the "C1-6 alkyl group" represented by $W_3$, a methyl group, an ethyl group or a propyl group is preferable. Herein, as a substituent of the "C1-6 alkyl group", a hydroxyl group, an oxo group, a halogen atom, a C1-4 alkyl group, a C1-4 alkoxy group, —O-ring 2 or ring 2 is preferable, and a hydroxyl group, —O-ring 2 or ring 2 is more preferable.

In the present invention, as the "C2-6 alkenyl group" represented by $W_3$, a straight chain C3-6 alkenyl group is preferable, a propenyl group is more preferable, and a 2-propenyl group is further preferable. Herein, as a substituent of the "C2-6 alkenyl group", a hydroxyl group, an oxo group, a halogen atom, a C1-4 alkyl group, a C1-4 alkoxy group, —O-ring 2 or ring 2 is preferable, and a hydroxyl group, a halogen atom, a C1-4 alkyl group or ring 2 is more preferable.

In the present invention, as the "C2-4 alkyl group" of the "C2-4 alkyl group wherein any one carbon atom is replaced by an oxygen atom", which is represented by $W_3$, a propyl group or a butyl group is preferable.

In the present invention, the "C2-4 alkyl group wherein any one carbon atom is replaced by an oxygen atom", which is represented by $W_3$, —O—$C_2H_5$ or —$(CH_2)_2$—O—$CH_3$ is preferable. Herein, as a substituent of the "C2-4 alkyl group wherein any one carbon atom is replaced by an oxygen atom", a hydroxyl group, an oxo group, a halogen atom, a C1-4 alkyl group, a C1-4 alkoxy group, —O-ring 2 or ring 2 is preferable, and a hydroxyl group or ring 2 is more preferable.

In the present invention, as the ring 1, benzene or a thiazole ring is preferable.

In the present invention, as the ring 2, a C3- to C7-membered carbocyclic ring is preferable, benzene or a cyclohexane ring is more preferable, and benzene is further preferable. Herein, as a substituent of the ring 2, a C1-4 alkyl group, a C1-4 alkoxy group, $CF_3$, $OCF_3$ or a halogen atom is preferable, and a C1-4 alkyl group, $CF_3$, $OCF_3$ or a halogen atom is more preferable.

In the present invention, as m, an integer of 2 to 4 is preferable, and 3 is more preferable.

In the present invention, as n, 1 is preferable.

In the present invention, the α chain means a side chain binding to a 7-membered ring, and the ω chain means a side chain binding to a 5-membered ring, in each formula.

In the present invention, among the compounds represented by the formula (I), a compound represented by the formula (I-1):

[Chemical formula 23]

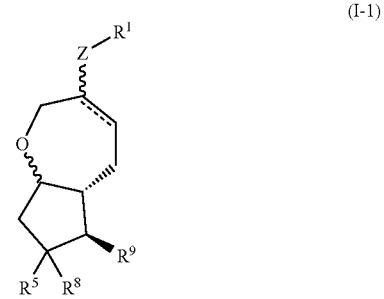

(I-1)

(wherein all symbols represent the same meanings as those described above) is preferable. Herein, it is preferable that the combination of $R^8$ and $R^9$ is a combination in which $R^8$ is a halogen atom and $R^9$ is

[Chemical formula 24]

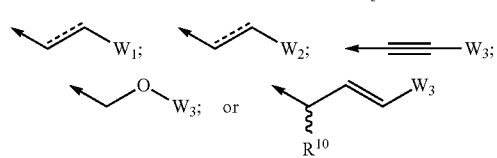

or $R^8$ is a hydrogen atom and $R^9$ is

[Chemical formula 25]

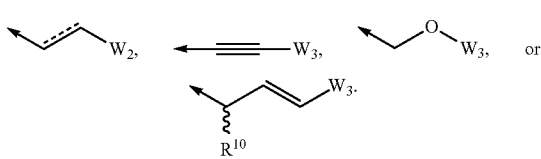

a compound represented by the formula (I-1-1):

[Chemical formula 26]

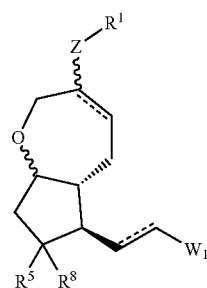

(I-1-1)

(wherein all symbols represent the same meanings as those described above), a compound represented by the formula (I-1-2):

[Chemical formula 27]

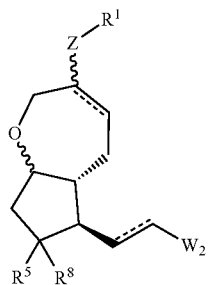
(I-1-2)

(wherein all symbols represent the same meanings as those described above), a compound represented by the formula (I-1-3):

[Chemical formula 28]

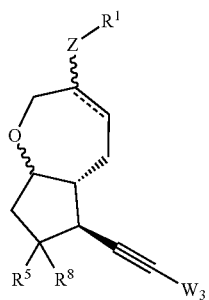
(I-1-3)

(wherein all symbols represent the same meanings as those described above), a compound represented by the formula (I-1-4):

[Chemical formula 29]

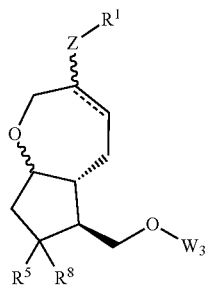
(I-1-4)

(wherein all symbols represent the same meanings as those described above), a compound represented by the formula (I-1-5):

[Chemical formula 30]

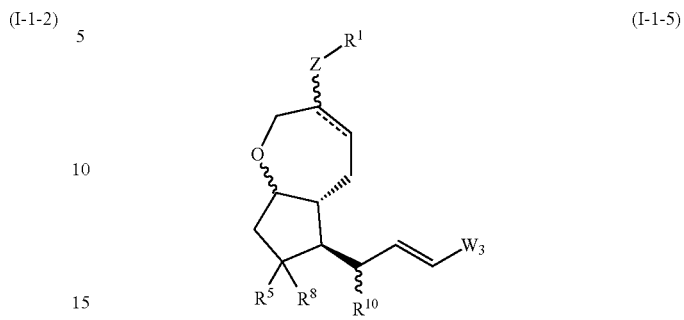
(I-1-5)

(wherein all symbols represent the same meanings as those described above), or a compound represented by the formula (I-2):

[Chemical formula 31]

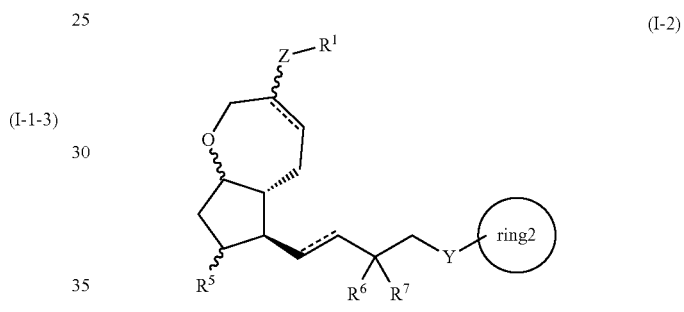
(I-2)

(wherein $R^6$ and $R^7$ each independently represent a hydrogen atom, a hydroxyl group, a halogen atom, a C1-4 alkyl group or a C1-4 alkoxy group and $R^6$ and $R^7$ may be taken together to form an oxo group; Y represents —$CH_2$—, —O— or —S—; and other symbols represent the same meanings as those described above) is also preferable.

Furthermore, a compound represented by the formula (I-1-6):

[Chemical formula 32]

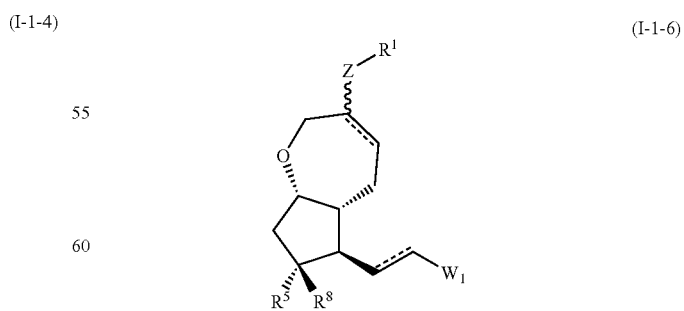
(I-1-6)

(wherein $R^8$ represents a halogen atom and other symbols represent the same meanings as those described above), a compound represented by the formula (I-1-7):

[Chemical formula 33]

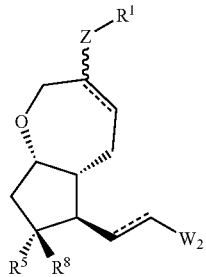
(I-1-7)

(wherein R⁸ represents a halogen atom, other symbols represent the same meanings as those described above), a compound represented by the formula (I-1-8):

[Chemical formula 34]

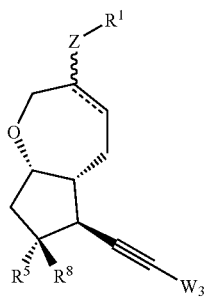
(I-1-8)

(wherein R⁸ represents a halogen atom and other symbols represent the same meanings as those described above), a compound represented by the formula (I-1-9):

[Chemical formula 35]

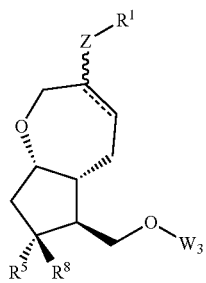
(I-1-9)

(wherein R⁸ represents a halogen atom and other symbols represent the same meanings as those described above), a compound represented by the formula (I-1-10)

[Chemical formula 36]

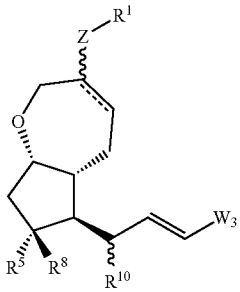
(I-1-10)

(wherein R⁸ represents a halogen atom and other symbols represent the same meanings as those described above), a compound represented by the formula (I-1-11):

[Chemical formula 37]

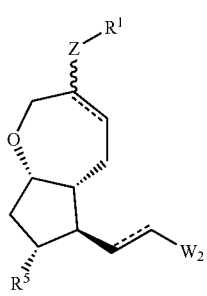
(I-1-11)

(wherein all symbols represent the same meanings as those described above), a compound represented by the formula (I-1-12):

[Chemical formula 38]

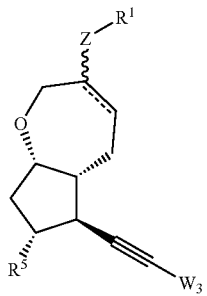
(I-1-12)

(wherein all symbols represent the same meanings as those described above), a compound represented by the formula (I-1-13):

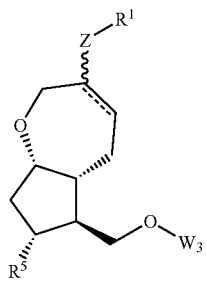

(I-1-13)

(wherein all symbols represent the same meanings as those described above), or a compound represented by the formula (I-1-14):

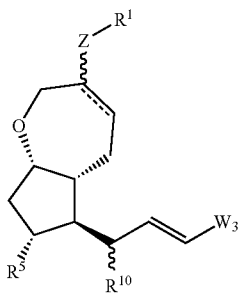

(I-1-14)

(wherein all symbols represent the same meanings as those described above) is further preferable. In the formulae (I-1-6) to (I-1-10), as $R^5$, a halogen atom is preferable. In the formulae (I-1-11) to (I-1-14), as $R^5$, a hydroxyl group or a halogen atom is preferable; and a halogen atom is further preferable.

In the present invention, examples of a preferable compound include (1) 4-{(3S,5aR,6R,7R,8aS)-7-hydroxy-6-[(1E,3S)-3-hydroxy-4-phenoxy-1-buten-1-yl]octahydro-2H-cyclopenta[b]oxepin-3-yl}butanoic acid, (2) 4-{(3S,5aR,6R,7R,8aS)-7-hydroxy-6-[(1E,3R)-3-hydroxy-5-phenyl-1-penten-1-yl]octahydro-2H-cyclopenta[b]oxepin-3-yl}butanoic acid, (3) 4-{(3S,5aR,6R,7R,8aS)-6-[(1E,3R)-5-(3-fluorophenyl)-3-hydroxy-1-penten-1-yl]-7-hydroxyoctahydro-2H-cyclopenta[b]oxepin-3-yl}butanoic acid, (4) 4-{(3S,5aR,6R,7R,8aS)-6-[(1E,3S)-5-(3-fluorophenyl)-3-hydroxy-1-penten-1-yl]-7-hydroxyoctahydro-2H-cyclopenta[b]oxepin-3-yl}butanoic acid, (5) 4-{(3S,5aR,6R,7R,8aS)-6-[(1E,3R)-5-(4-fluorophenyl)-3-hydroxy-1-penten-1-yl]-7-hydroxyoctahydro-2H-cyclopenta[b]oxepin-3-yl}butanoic acid, (6) 4-{(3S,5aR,6R,7R,8aS)-6-[(1E,3S)-5-(4-fluorophenyl)-3-hydroxy-1-penten-1-yl]-7-hydroxyoctahydro-2H-cyclopenta[b]oxepin-3-yl}butanoic acid, (7) 4-{(3S,5aR,6R,7R,8aS)-6-[(1E,3R)-5-(2-fluorophenyl)-3-hydroxy-1-penten-1-yl]-7-hydroxyoctahydro-2H-cyclopenta[b]oxepin-3-yl}butanoic acid, (8) 4-{(3S,5aR,6R,7R,8aS)-6-[(1E,3S)-5-(2-fluorophenyl)-3-hydroxy-1-penten-1-yl]-7-hydroxyoctahydro-2H-cyclopenta[b]oxepin-3-yl}butanoic acid, (9) 4-{(3S,5aR,6R,7R,8aS)-6-[(1E,3R)-5-(3-chlorophenyl)-3-hydroxy-1-penten-1-yl]-7-hydroxyoctahydro-2H-cyclopenta[b]oxepin-3-yl}butanoic acid,

(10) 4-{(3S,5aR,6R,7R,8aS)-6-[(1E,3S)-5-(3-chlorophenyl)-3-hydroxy-1-penten-1-yl]-7-hydroxyoctahydro-2H-cyclopenta[b]oxepin-3-yl}butanoic acid,

(11) 4-[(3S,5aR,6R,7R,8aS)-7-hydroxy-6-{(1E,3R)-3-hydroxy-5-[3-(trifluoromethyl)phenyl]-1-penten-1-yl}octahydro-2H-cyclopenta[b]oxepin-3-yl]butanoic acid,

(12) 4-[(3S,5aR,6R,7R,8aS)-7-hydroxy-6-{(1E,3S)-3-hydroxy-5-[3-(trifluoromethyl)phenyl]-1-penten-1-yl}octahydro-2H-cyclopenta[b]oxepin-3-yl]butanoic acid,

(13) 4-[(3S,5aR,6R,7R,8aS)-7-hydroxy-6-{(1E,3S)-3-hydroxy-4-[3-(trifluoromethyl)phenoxy]-1-buten-1-yl}octahydro-2H-cyclopenta[b]oxepin-3-yl]butanoic acid,

(14) 4-{(3S,5aR,6R,7R,8aS)-6-[(1E,3S)-4-(2-fluorophenoxy)-3-hydroxy-1-buten-1-yl]-7-hydroxyoctahydro-2H-cyclopenta[b]oxepin-3-yl}butanoic acid,

(15) 4-{(3S,5aR,6R,7R,8aS)-6-[(1E,3S)-4-(3-fluorophenoxy)-3-hydroxy-1-buten-1-yl]-7-hydroxyoctahydro-2H-cyclopenta[b]oxepin-3-yl}butanoic acid,

(16) 4-{(3S,5aR,6R,7R,8aS)-6-[(1E,3S)-4-(4-fluorophenoxy)-3-hydroxy-1-buten-1-yl]-7-hydroxyoctahydro-2H-cyclopenta[b]oxepin-3-yl}butanoic acid,

(17) 4-{(3S,5aR,6R,7R,8aS)-6-[(1E,3S)-5-cyclohexyl-3-hydroxy-1-penten-1-yl]-7-hydroxyoctahydro-2H-cyclopenta[b]oxepin-3-yl}butanoic acid,

(18) 4-{(3S,5aR,6R,7R,8aS)-7-hydroxy-6-[(3S)-3-hydroxy-4-phenoxybutyl]octahydro-2H-cyclopenta[b]oxepin-3-yl}butanoic acid,

(19) 4-{(3S,5aR,6R,7R,8aS)-7-hydroxy-6-[(3S)-3-hydroxy-5-phenylpentyl]octahydro-2H-cyclopenta[b]oxepin-3-yl}butanoic acid,

(20) 4-{(3S,5aR,6R,7R,8aS)-6-[(3S)-5-(3-fluorophenyl)-3-hydroxypentyl]-7-hydroxyoctahydro-2H-cyclopenta[b]oxepin-3-yl}butanoic acid,

(21) 4-{(3S,5aR,6R,7R,8aS)-6-[(3R)-5-(3-fluorophenyl)-3-hydroxypentyl]-7-hydroxyoctahydro-2H-cyclopenta[b]oxepin-3-yl}butanoic acid,

(22) 4-{(3S,5aR,6R,7R,8aS)-6-[(3S)-5-(4-fluorophenyl)-3-hydroxypentyl]-7-hydroxyoctahydro-2H-cyclopenta[b]oxepin-3-yl}butanoic acid,

(23) 4-{(3S,5aR,6R,7R,8aS)-6-[(3R)-5-(4-fluorophenyl)-3-hydroxypentyl]-7-hydroxyoctahydro-2H-cyclopenta[b]oxepin-3-yl}butanoic acid,

(24) 4-{(3S,5aR,6R,7R,8aS)-6-[(3S)-5-(2-fluorophenyl)-3-hydroxypentyl]-7-hydroxyoctahydro-2H-cyclopenta[b]oxepin-3-yl}butanoic acid,

(25) 4-{(3S,5aR,6R,7R,8aS)-6-[(3R)-5-(2-fluorophenyl)-3-hydroxypentyl]-7-hydroxyoctahydro-2H-cyclopenta[b]oxepin-3-yl}butanoic acid,

(26) 4-{(3S,5aR,6R,7R,8aS)-6-[(3S)-5-(3-chlorophenyl)-3-hydroxypentyl]-7-hydroxyoctahydro-2H-cyclopenta[b]oxepin-3-yl}butanoic acid,

(27) 4-{(3S,5aR,6R,7R,8aS)-6-[(3R)-5-(3-chlorophenyl)-3-hydroxypentyl]-7-hydroxyoctahydro-2H-cyclopenta[b]oxepin-3-yl}butanoic acid,

(28) 4-[(3S,5aR,6R,7R,8aS)-7-hydroxy-6-{(3S)-3-hydroxy-5-[3-(trifluoromethyl)phenyl]pentyl}octahydro-2H-cyclopenta[b]oxepin-3-yl]butanoic acid,

(29) 4-[(3S,5aR,6R,7R,8aS)-7-hydroxy-6-{(3R)-3-hydroxy-5-[3-(trifluoromethyl)phenyl]pentyl}octahydro-2H-cyclopenta[b]oxepin-3-yl]butanoic acid,

(30) 4-[(3S,5aR,6R,7R,8aS)-7-hydroxy-6-{(3R)-3-hydroxy-4-[3-(trifluoromethyl)phenoxy]butyl}octahydro-2H-cyclopenta[b]oxepin-3-yl]butanoic acid,

(31) 4-{(3S,5aR,6R,7R,8aS)-6-[(1E)-3-fluoro-4-phenoxy-1-buten-1-yl]-7-hydroxyoctahydro-2H-cyclopenta[b]oxepin-3-yl}butanoic acid,

(32) 4-{(3S,5aR,6R,7R,8aS)-6-[(1E)-4-(3-chlorophenoxy)-1-buten-1-yl]-7-hydroxyoctahydro-2H-cyclopenta[b]oxepin-3-yl}butanoic acid,

(33) 4-{(3S,5aR,6R,7R,8aS)-6-[(1E)-4-(2-fluorophenoxy)-1-buten-1-yl]-7-hydroxyoctahydro-2H-cyclopenta[b]oxepin-3-yl}butanoic acid,

(34) 4-{(3S,5aR,6R,7R,8aS)-6-[(1E)-4-(3-fluorophenoxy)-1-buten-1-yl]-7-hydroxyoctahydro-2H-cyclopenta[b]oxepin-3-yl}butanoic acid,

(35) 4-{(3S,5aR,6R,7R,8aS)-6-[(1E)-4-(2,5-difluorophenoxy)-1-buten-1-yl]-7-hydroxyoctahydro-2H-cyclopenta[b]oxepin-3-yl}butanoic acid,

(36) 4-{(3S,5aR,6R,7R,8aS)-7-hydroxy-6-[(1E)-4-hydroxy-6-phenyl-1-hexen-1-yl]octahydro-2H-cyclopenta[b]oxepin-3-yl}butanoic acid,

(37) 4-[(3S,5aR,6R,7R,8aS)-7-hydroxy-6-(4-phenoxybutyl)octahydro-2H-cyclopenta[b]oxepin-3-yl]butanoic acid,

(38) 4-{(3S,5aR,6R,7R,8aS)-7-hydroxy-6-[(1E)-3-hydroxy-1-decen-1-yl]octahydro-2H-cyclopenta[b]oxepin-3-yl}butanoic acid,

(39) 4-{(3S,5aR,6R,7R,8aS)-7-hydroxy-6-[(1E)-3-hydroxy-5-(5-methyl-2-furyl)-1-penten-1-yl]octahydro-2H-cyclopenta[b]oxepin-3-yl}butanoic acid,

(40) 4-{(3S,5aR,6R,7R,8aS)-6-[(1E)-5-cyclopentyl-3-hydroxy-1-penten-1-yl]-7-hydroxyoctahydro-2H-cyclopenta[b]oxepin-3-yl}butanoic acid,

(41) 4-{(3S,5aR,6R,7R,8aS)-6-[(1E)-3-(1-benzofuran-2-yl)-3-hydroxy-1-propen-1-yl]-7-hydroxyoctahydro-2H-cyclopenta[b]oxepin-3-yl}butanoic acid,

(42) 4-{(3S,5aR,6R,7R,8aS)-7-hydroxy-6-[(1E)-3-hydroxy-5-(3-hydroxyphenyl)-1-penten-1-yl]octahydro-2H-cyclopenta[b]oxepin-3-yl}butanoic acid,

(43) 4-{(3S,5aR,6R,7R,8aS)-6-[(1E)-3,3-difluoro-5-phenyl-1-penten-1-yl]-7-hydroxyoctahydro-2H-cyclopenta[b]oxepin-3-yl}butanoic acid,

(44) 4-[(3S,5aR,6R,7R,8aS)-6-(3,3-difluoro-5-phenylpentyl)-7-hydroxyoctahydro-2H-cyclopenta[b]oxepin-3-yl]butanoic acid,

(45) 4-{(3S,5aR,6R,7R,8aS)-6-[(1E)-5-cyclopentyl-3,3-difluoro-1-penten-1-yl]-7-hydroxyoctahydro-2H-cyclopenta[b]oxepin-3-yl}butanoic acid,

(46) 4-{(3S,5aR,6R,7R,8aS)-6-[(1E)-5-cyclohexyl-3,3-difluoro-1-penten-1-yl]-7-hydroxyoctahydro-2H-cyclopenta[b]oxepin-3-yl}butanoic acid,

(47) 4-{(3S,5aR,6R,7R,8aS)-6-[(1E)-3,3-difluoro-1-octen-1-yl]-7-hydroxyoctahydro-2H-cyclopenta[b]oxepin-3-yl}butanoic acid,

(48) 4-{(3S,5aR,6R,7R,8aS)-6-[(1E,3R)-3-fluoro-4-phenoxy-1-buten-1-yl]-7-hydroxyoctahydro-2H-cyclopenta[b]oxepin-3-yl}butanoic acid,

(49) 4-{(3S,5aR,6R,7R,8aS)-6-[(1E,3S)-3-fluoro-4-phenoxy-1-buten-1-yl]-7-hydroxyoctahydro-2H-cyclopenta[b]oxepin-3-yl}butanoic acid,

(50) 4-{(3S,5aR,6R,7R,8aS)-7-hydroxy-6-[(1E,4R)-4-hydroxy-6-phenyl-1-hexen-1-yl]octahydro-2H-cyclopenta[b]oxepin-3-yl}butanoic acid,

(51) 4-{(3S,5aR,6R,7R,8aS)-7-hydroxy-6-[(1E,4S)-4-hydroxy-6-phenyl-1-hexen-1-yl]octahydro-2H-cyclopenta[b]oxepin-3-yl}butanoic acid,

(52) 4-{(3S,5aR,6R,7R,8aS)-7-hydroxy-6-[(1E,3R)-3-hydroxy-1-decen-1-yl]octahydro-2H-cyclopenta[b]oxepin-3-yl}butanoic acid,

(53) 4-{(3S,5aR,6R,7R,8aS)-7-hydroxy-6-[(1E,3S)-3-hydroxy-1-decen-1-yl]octahydro-2H-cyclopenta[b]oxepin-3-yl}butanoic acid,

(54) 4-{(3S,5aR,6R,7R,8aS)-7-hydroxy-6-[(1E,3R)-3-hydroxy-5-(5-methyl-2-furyl)-1-penten-1-yl]octahydro-2H-cyclopenta[b]oxepin-3-yl}butanoic acid,

(55) 4-{(3S,5aR,6R,7R,8aS)-7-hydroxy-6-[(1E,3S)-3-hydroxy-5-(5-methyl-2-furyl)-1-penten-1-yl]octahydro-2H-cyclopenta[b]oxepin-3-yl}butanoic acid,

(56) 4-{(3S,5aR,6R,7R,8aS)-6-[(1E,3R)-5-cyclopentyl-3-hydroxy-1-penten-1-yl]-7-hydroxyoctahydro-2H-cyclopenta[b]oxepin-3-yl}butanoic acid,

(57) 4-{(3S,5aR,6R,7R,8aS)-6-[(1E,3S)-5-cyclopentyl-3-hydroxy-1-penten-1-yl]-7-hydroxyoctahydro-2H-cyclopenta[b]oxepin-3-yl}butanoic acid,

(58) 4-{(3S,5aR,6R,7R,8aS)-6-[(1E,3R)-3-(1-benzofuran-2-yl)-3-hydroxy-1-propen-1-yl]-7-hydroxyoctahydro-2H-cyclopenta[b]oxepin-3-yl}butanoic acid,

(59) 4-{(3S,5aR,6R,7R,8aS)-6-[(1E,3S)-3-(1-benzofuran-2-yl)-3-hydroxy-1-propen-1-yl]-7-hydroxyoctahydro-2H-cyclopenta[b]oxepin-3-yl}butanoic acid,

(60) 4-{(3S,5aR,6R,7R,8aS)-7-hydroxy-6-[(1E,3R)-3-hydroxy-5-(3-hydroxyphenyl)-1-penten-1-yl]octahydro-2H-cyclopenta[b]oxepin-3-yl}butanoic acid, or

(61) 4-{(3S,5aR,6R,7R,8aS)-7-hydroxy-6-[(1E,3S)-3-hydroxy-5-(3-hydroxyphenyl)-1-penten-1-yl]octahydro-2H-cyclopenta[b]oxepin-3-yl}butanoic acid, or a salt thereof, a solvate thereof, or a prodrug thereof.

In the present invention, as the compound, (1) 4-[(3S,5aR,6S,7R,8aS)-7-hydroxy-6-({[(2E)-3-phenyl-2-propen-1-yl]oxy}methyl)octahydro-2H-cyclopenta[b]oxepin-3-yl]butanoic acid, (2) 4-{(3S,5aR,6R,7R,8aS)-7-hydroxy-6-[2-(2-phenylethoxy)ethyl]octahydro-2H-cyclopenta[b]oxepin-3-yl}butanoic acid, (3) 4-[(3S,5aR,6S,7R,8aS)-7-hydroxy-6-(3-hydroxy-5-phenyl-1-pentyn-1-yl)octahydro-2H-cyclopenta[b]oxepin-3-yl]butanoic acid, (4) 4-{(3S,5aR,6R,7R,8aS)-6-[(2E)-1-fluoro-4-phenoxy-2-buten-1-yl]-7-hydroxyoctahydro-2H-cyclopenta[b]oxepin-3-yl}butanoic acid, (5) 4-{(3S,5aR,6R,7R,8aS)-7-hydroxy-6-[(1E)-3-hydroxy-8-methyl-1,7-nonadien-1-yl]octahydro-2H-cyclopenta[b]oxepin-3-yl}butanoic acid, (6) 4-{(3S,5aR,6R,7R,8aS)-6-[(1E)-4-(benzyloxy)-3-hydroxy-1-buten-1-yl]-7-hydroxyoctahydro-2H-cyclopenta[b]oxepin-3-yl}butanoic acid, (7) 4-{(3S,5aR,6R,7R,8aS)-7-hydroxy-6-[(1E)-3-hydroxy-1,7-octadien-1-yl]octahydro-2H-cyclopenta[b]oxepin-3-yl}butanoic acid, (8) 4-{(3S,5aR,6R,7R,8aS)-7-hydroxy-6-[(1E,6Z)-3-hydroxy-1,6-nonadien-1-yl]octahydro-2H-cyclopenta[b]oxepin-3-yl}butanoic acid, (9) 4-{(3S,5aR,6R,7R,8aS)-7-hydroxy-6-[(1E)-3-hydroxy-4,8-dimethyl-1,7-nonadien-1-yl]octahydro-2H-cyclopenta[b]oxepin-3-yl}butanoic acid,

(10) 4-{(3S,5aR,6R,8aS)-7,7-difluoro-6-[(1E)-3-hydroxy-1-octen-1-yl]octahydro-2H-cyclopenta[b]oxepin-3-yl}butanoic acid,

(11) 4-{(3S,5aR,6R,8aS)-7,7-difluoro-6-[(1E)-3-hydroxy-5-phenyl-1-penten-1-yl]octahydro-2H-cyclopenta[b]oxepin-3-yl}butanoic acid,

(12) 4-{(3S,5aR,6R,7R,8aS)-6-[(1E)-3,3-difluoro-8-methyl-1,7-nonadien-1-yl]-7-hydroxyoctahydro-2H-cyclopenta[b]oxepin-3-yl}butanoic acid,
(13) 4-[(3S,5aR,6S,7R,8aS)-7-hydroxy-6-((3R)-3-hydroxy-5-phenyl-1-pentyn-1-yl)octahydro-2H-cyclopenta[b]oxepin-3-yl]butanoic acid,
(14) 4-[(3S,5aR,6S,7R,8aS)-7-hydroxy-6-((3S)-3-hydroxy-5-phenyl-1-pentyn-1-yl)octahydro-2H-cyclopenta[b]oxepin-3-yl]butanoic acid,
(15) 4-{(3S,5aR,6R,7R,8aS)-6-[(1R,2E)-1-fluoro-4-phenoxy-2-buten-1-yl]-7-hydroxyoctahydro-2H-cyclopenta[b]oxepin-3-yl}butanoic acid,
(16) 4-{(3S,5aR,6R,7R,8aS)-6-[(1S,2E)-1-fluoro-4-phenoxy-2-buten-1-yl]-7-hydroxyoctahydro-2H-cyclopenta[b]oxepin-3-yl}butanoic acid,
(17) 4-{(3S,5aR,6R,7R,8aS)-7-hydroxy-6-[(1E,3R)-3-hydroxy-8-methyl-1,7-nonadien-1-yl]octahydro-2H-cyclopenta[b]oxepin-3-yl}butanoic acid,
(18) 4-{(3S,5aR,6R,7R,8aS)-7-hydroxy-6-[(1E,3S)-3-hydroxy-8-methyl-1,7-nonadien-1-yl]octahydro-2H-cyclopenta[b]oxepin-3-yl}butanoic acid,
(19) 4-{(3S,5aR,6R,7R,8aS)-6-[(1E,3R)-4-(benzyloxy)-3-hydroxy-1-buten-1-yl]-7-hydroxyoctahydro-2H-cyclopenta[b]oxepin-3-yl}butanoic acid,
(20) 4-{(3S,5aR,6R,7R,8aS)-6-[(1E,3S)-4-(benzyloxy)-3-hydroxy-1-buten-1-yl]-7-hydroxyoctahydro-2H-cyclopenta[b]oxepin-3-yl}butanoic acid,
(21) 4-{(3S,5aR,6R,7R,8aS)-7-hydroxy-6-[(1E,3R)-3-hydroxy-1,7-octadien-1-yl]octahydro-2H-cyclopenta[b]oxepin-3-yl}butanoic acid,
(22) 4-{(3S,5aR,6R,7R,8aS)-7-hydroxy-6-[(1E,3S)-3-hydroxy-1,7-octadien-1-yl]octahydro-2H-cyclopenta[b]oxepin-3-yl}butanoic acid,
(23) 4-{(3S,5aR,6R,7R,8aS)-7-hydroxy-6-[(1E,3R,6Z)-3-hydroxy-1,6-nonadien-1-yl]octahydro-2H-cyclopenta[b]oxepin-3-yl}butanoic acid,
(24) 4-{(3S,5aR,6R,7R,8aS)-7-hydroxy-6-[(1E,3S,6Z)-3-hydroxy-1,6-nonadien-1-yl]octahydro-2H-cyclopenta[b]oxepin-3-yl}butanoic acid,
(25) 4-{(3S,5aR,6R,7R,8aS)-7-hydroxy-6-[(1E,3R,4R)-3-hydroxy-4,8-dimethyl-1,7-nonadien-1-yl]octahydro-2H-cyclopenta[b]oxepin-3-yl}butanoic acid,
(26) 4-{(3S,5aR,6R,7R,8aS)-7-hydroxy-6-[(1E,3R,4S)-3-hydroxy-4,8-dimethyl-1,7-nonadien-1-yl]octahydro-2H-cyclopenta[b]oxepin-3-yl}butanoic acid,
(27) 4-{(3S,5aR,6R,7R,8aS)-7-hydroxy-6-[(1E,3S,4R)-3-hydroxy-4,8-dimethyl-1,7-nonadien-1-yl]octahydro-2H-cyclopenta[b]oxepin-3-yl}butanoic acid,
(28) 4-{(3S,5aR,6R,7R,8aS)-7-hydroxy-6-[(1E,3S,4S)-3-hydroxy-4,8-dimethyl-1,7-nonadien-1-yl]octahydro-2H-cyclopenta[b]oxepin-3-yl}butanoic acid,
(29) 4-{(3S,5aR,6R,8aS)-7,7-difluoro-6-[(1E,3R)-3-hydroxy-1-octen-1-yl]octahydro-2H-cyclopenta[b]oxepin-3-yl}butanoic acid,
(30) 4-{(3S,5aR,6R,8aS)-7,7-difluoro-6-[(1E,3S)-3-hydroxy-1-octen-1-yl]octahydro-2H-cyclopenta[b]oxepin-3-yl}butanoic acid,
(31) 4-{(3S,5aR,6R,8aS)-7,7-difluoro-6-[(1E,3R)-3-hydroxy-5-phenyl-1-penten-1-yl]octahydro-2H-cyclopenta[b]oxepin-3-yl}butanoic acid, or
(32) 4-{(3S,5aR,6R,8aS)-7,7-difluoro-6-[(1E,3S)-3-hydroxy-5-phenyl-1-penten-1-yl]octahydro-2H-cyclopenta[b]oxepin-3-yl}butanoic acid, or a salt thereof, a solvate thereof, or a prodrug thereof.

[Isomer]

In the present invention, an isomer includes all isomers unless otherwise is indicated. For example, the alkyl group includes a straight chain alkyl group and a branched chain alkyl group. Further, all of an isomer at a double bond, a ring, or a condensed ring (E isomer, Z isomer, cis isomer, trans isomer), an isomer due to the presence of an asymmetric carbon etc. (R, S isomer, α, β configuration, enantiomer, diastereomer), an optically active body having optical rotation (D, L, d, l isomer), a polar body derived from chromatographic separation (high polar compound, low polar compound), an equilibrated compound, a rotation isomer, a mixture of them at an arbitrary ratio, and a racemic mixture are included in the present invention. In addition, in the present invention, the isomer includes all isomers derived from tautomers.

In addition, the optically active compound in the present invention may include not only 100% pure compounds, but also other optical isomers or diastereomers which are less than 50% pure. As the optically active compound and a diastereomer thereof in the present invention, for example, in the case of Example 108 (13): 4-[(3S,5aR,6R,7R,8aS)-7-hydroxy-6-{(3R)-3-hydroxy-4-[3-(trifluoromethyl)phenoxy]butyl}octahydro-2H-cyclopenta[b]oxepin-3-yl]butanoic acid, for example, a relationship between 4-[(3S,5aR,6R,7R,8aS)-7-hydroxy-6-{(3R)-3-hydroxy-4-[3-(trifluoromethyl)phenoxy]butyl}octahydro-2H-cyclopenta[b]oxepin-3-yl]butanoic acid and 4-[(3R,5aR,6R,7R,8aS)-7-hydroxy-6-{(3R)-3-hydroxy-4-[3-(trifluoromethyl)phenoxy]butyl}octahydro-2H-cyclopenta[b]oxepin-3-yl]butanoic acid, between 4-[(3S,5aR,6R,7R,8aS)-7-hydroxy-6-{(3R)-3-hydroxy-4-[3-(trifluoromethyl)phenoxy]butyl}octahydro-2H-cyclopenta[b]oxepin-3-yl]butanoic acid and 4-[(3S,5aR,6R,7S,8aS)-7-hydroxy-6-{(3R)-3-hydroxy-4-[3-(trifluoromethyl)phenoxy]butyl}octahydro-2H-cyclopenta[b]oxepin-3-yl]butanoic acid, between 4-[(3S,5aR,6R,7R,8aS)-7-hydroxy-6-{(3R)-3-hydroxy-4-[3-(trifluoromethyl)phenoxy]butyl}octahydro-2H-cyclopenta[b]oxepin-3-yl]butanoic acid and 4-[(3S,5aR,6R,7R,8aR)-7-hydroxy-6-{(3R)-3-hydroxy-4-[3-(trifluoromethyl)phenoxy]butyl}octahydro-2H-cyclopenta[b]oxepin-3-yl]butanoic acid, or between 4-[(3S,5aR,6R,7R,8aS)-7-hydroxy-6-{(3R)-3-hydroxy-4-[3-(trifluoromethyl)phenoxy]butyl}octahydro-2H-cyclopenta[b]oxepin-3-yl]butanoic acid and 4-[(3S,5aR,6R,7R,8aS)-7-hydroxy-6-{(3S)-3-hydroxy-4-[3-(trifluoromethyl)phenoxy]butyl}octahydro-2H-cyclopenta[b]oxepin-3-yl]butanoic acid, etc are mentioned.

In the present invention, unless otherwise is indicated, as is apparent to a person skilled in the art, a symbol:

[Chemical formula 41]

represents that a group is bound to another side of a paper plane (i.e. α configuration);

[Chemical formula 42]

represents that a group is bound to a front side of a paper plane (i.e. β configuration);

[Chemical formula 43]

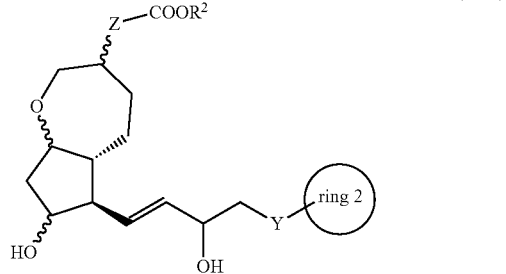

represents α configuration, β configuration or a mixture thereof; and

[Chemical formula 44]

/ represents a mixture of α configuration and β configuration.

The compound represented by the formula (I) is converted into a corresponding salt by the known method. As the salt, a water-soluble salt is preferable. Examples of a suitable salt include salts of an alkali metal (potassium, sodium etc.), salts of an alkaline earth metal (calcium, magnesium etc.), ammonium salts, salts of pharmaceutically acceptable organic amine (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine etc.) etc.

The compound represented by the formula (I) and a salt thereof can be also converted into a solvate. It is preferable that the solvate is low-toxic and water-soluble. Examples of a suitable solvate include solvates with, for example, water, or alcohol-based solvents (e.g. ethanol etc.).

In addition, a prodrug of the compound represented by the formula (I) refers to a compound which is converted into the compound represented by the formula (I) by a reaction with an enzyme or gastric acid in a living body. Examples of the prodrug of the compound represented by the formula (I), when the compound represented by the formula (I) has a hydroxyl group, include compounds in which a hydroxyl group is acylated, alkylated, phosphorylated, or boronized (e.g. compounds in which a hydroxyl group of the compound of the present invention is acetylated, palmitoylated, propanoylated, pivaloylated, succinylated, fumarylated, alanylated, or dimethylaminomethylcarbonized etc.); compounds in which a carboxyl group of the compound represented by the formula (I) is esterified, or amidated (e.g. compounds in which a carboxyl group of the compound represented by the formula (I) is ethyl-esterified, isopropyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified, or methylamidated) etc. These compounds can be produced by the known method. In addition, the prodrug of the compound represented by the formula (I) may be any of a hydrate and a non-hydrate. In addition, the prodrug of the compound represented by the formula (I) may be a prodrug which is changed to the compound represented by the formula (I) under the physiological condition, as described in "Development of Medicaments" published in 1990 by Hirokawa-Shoten Ltd., Vol. 7, "Molecular Design", p. 163-198. Further, the compound represented by the formula (I) may be labeled with an isotope element (e.g. $^{2}H$, $^{3}H$, $^{11}C$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$, $^{125}I$ etc.) etc.

Particularly, examples of a preferable prodrug of the compound represented by the formula (I), in case of ocular instillation administration of the compound represented by the formula (I), include compounds in which a carboxyl group possessed by the compound represented by the formula (I) is methyl-esterified, ethyl-esterified, propyl-esterified, isopropyl-esterified, butyl-esterified, isobutyl-esterified, sec-butyl-esterified, tert-butyl-esterified, pentyl-esterified, isopentyl-esterified, neopentyl-esterified, cyclopentyl-esterified, hexyl-esterified, cyclohexyl-esterified, trifluoroethyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified, or methylamidated etc.

[Process for Producing Compound of the Present Invention]

The compound of the present invention can be produced by the known method, for example, the method described in Comprehensive Organic Transformations: A Guide to Functional Group Preparations, 2nd Edition (Richard C. Larock, John Wiley & Sons Inc, 1999), or can be produced by appropriately improving the methods shown in Examples, and using a combination of them.

Among the compound represented by the formula (I), a compound in which

[Chemical formula 45]

----- is as described below, an ω chain represents β configuration; $R^1$ represents $COOR^2$; $R^5$ represents a hydroxyl group; and one of $R^6$ and $R^7$ represents hydrogen, and the other represents a hydroxyl group, in the compound represents by the formula (I-2), namely, a compound represented by the formula (I-2-a):

[Chemical formula 46]

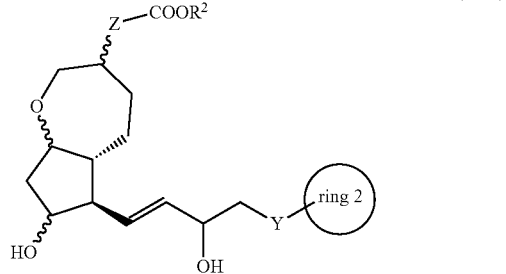

(I-2-a)

(wherein all symbols represent the same meanings as those described above) can be produced using a compound represented by the formula (II):

[Chemical formula 47]

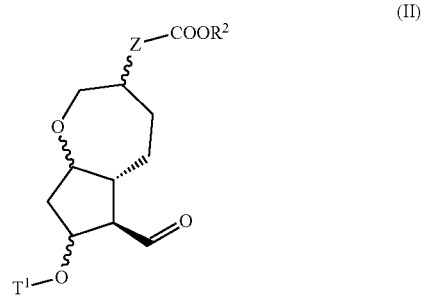

(II)

(wherein T1 represents a protective group of a hydroxyl group (e.g. 2-tetrahydropyranyl (THP) group, p-phenylbenzoyl group etc.), and other symbols represent the same meanings as those described above) as a starting substance, according to the following reaction step formula 1.

Reaction step formula 1

[Chemical formula 48]

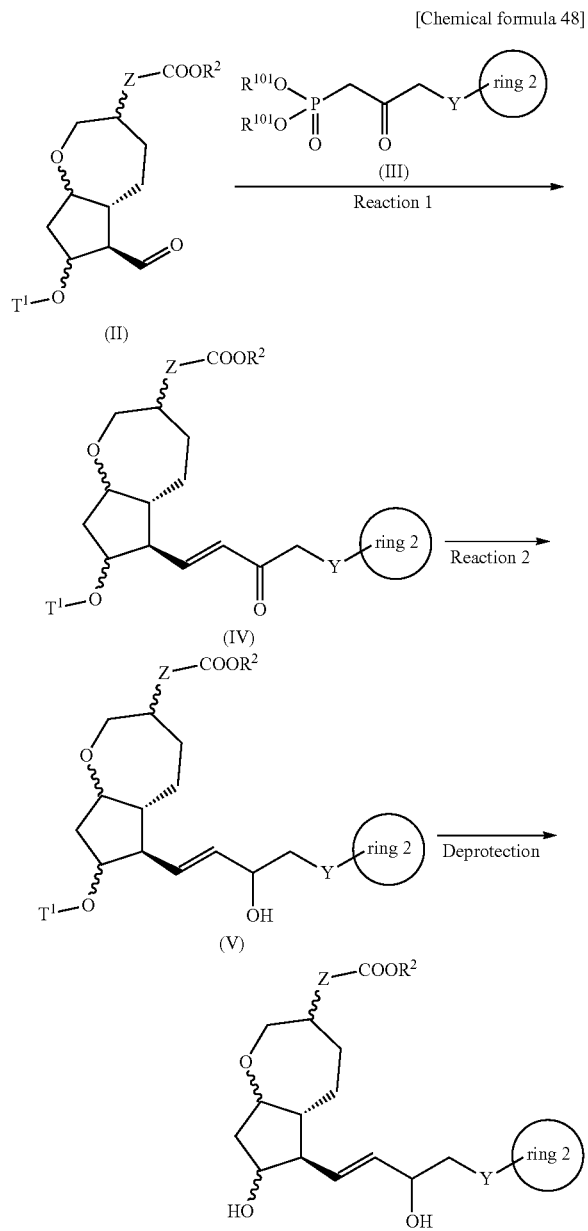

(wherein $R^{101}$ represents a C1-6 alkyl group, and other symbols represent the same meanings as those described above)

In the reaction step formula 1, the reaction 1 is known and, for example, is performed by reacting a compound represented by the formula (II) and a compound represented by the formula (III) at a temperature of −20 to 70° C. in an organic solvent (e.g. tetrahydrofuran (THF), dimethylformamide (DMF), dimethoxyethane (DME), dioxane, acetonitrile, ethanol, dichloromethane etc.) or in water, or in a mixed solution thereof, in the presence of a base (e.g. sodium hydride, sodium hydroxide, potassium hydroxide, potassium phosphate, potassium tert-butoxide, potassium carbonate, tertiary amine+lithium chloride etc.).

In the reaction step formula 1, the reaction 2 is known, and is performed by reacting a compound represented by the formula (IV) obtained in the reaction 1 at −20 to 50° C. in an organic solvent (e.g. THF, DME, toluene, dichloromethane, diethyl ether, dioxane etc.), in the presence or the absence of cerium chloride with using a reducing agent (e.g. sodium borohydride, zinc borohydride etc.). In addition, when only one of steric isomers is selectively produced, the reaction is performed at a temperature of −100 to 50° C. with using an asymmetric reducing agent (e.g. chlorodiisopinocamphenylborane etc.), or a combination of an asymmetric aid and a reducing agent ((R)-2-methyl-CBS-oxazaborolidine and boron hydride.tetrahydrofuran complex or boranedimethyl sulfide complex, (S)-(−)-binaphthol and lithium aluminum hydride etc.).

In the reaction step formula 1, a reaction of deprotecting a protective group is known, and can be performed by the following step. Examples include (1) a deprotection reaction by alkali hydrolysis, (2) a deprotection reaction under the acidic condition, (3) a deprotection reaction by hydrogenation degradation, (4) a deprotection reaction of a silyl group, (5) a deprotection reaction using a metal, (6) a deprotection reaction using a metal complex etc.

To specifically explain these methods, the (1) deprotection reaction by alkali hydrolysis is performed, for example, at 0 to 40° C. in an organic solvent (e.g. methanol, tetrahydrofuran, dioxane etc.), with using a hydroxide of an alkali metal (e.g. sodium hydroxide, potassium hydroxide, lithium hydroxide etc.), a hydroxide of an alkaline earth metal (e.g. barium hydroxide, calcium hydroxide etc.), or carbonate (e.g. sodium carbonate, potassium carbonate etc.), or an aqueous solution thereof, or a mixture thereof.

The (2) deprotection reaction under the acidic condition is performed, for example, at 0 to 100° C. in an organic solvent (e.g. dichloromethane, chloroform, dioxane, ethyl acetate, methanol, isopropyl alcohol, tetrahydrofuran, anisole etc.), in an organic acid (e.g. acetic acid, trifluoroacetic acid, methanesulfonic acid, p-tosylate etc.), or an inorganic acid (e.g. hydrochloric acid, sulfuric acid etc.) or a mixture thereof (e.g. hydrogen bromide/acetic acid etc.), in the presence or the absence of 2,2,2-trifluoroethanol.

The (3) deprotection reaction by hydrogenation degradation is performed, for example, at 0 to 200° C. in a solvent (e.g. ether-based solvent (e.g. tetrahydrofuran, dioxane, dimethoxyethane, diethyl ether etc.), alcohol-based solvent (e.g. methanol, ethanol etc.), benzene-based solvent (e.g. benzene, toluene etc.), ketone-based solvent (e.g. acetone, methyl ethyl ketone etc.), nitrile-based solvent (e.g. acetonitrile etc.), amide-based solvent (e.g. N,N-dimethylformamide etc.), water, ethyl acetate, acetic acid, or a mixed solvent of two or more of them etc.), in the presence of a catalyst (e.g. palladium-carbon, palladium black, palladium hydroxide-carbon, platinum oxide, Raney nickel etc.) under the hydrogen atmosphere at a normal pressure or under pressure, or in the presence of ammonium formate.

The (4) deprotection reaction of a silyl group is performed, for example, at 0 to 40° C. in an organic solvent which is miscible with water (e.g. tetrahydrofuran, acetonitrile etc.) with using tetrabutylammonium fluoride. Alternatively, the reaction is performed, for example, at −10 to 100° C. in an organic acid (e.g. acetic acid, trifluoroacetic acid, methanesulfonic acid, p-tosylate etc.), or an inorganic acid (e.g. hydrochloric acid, sulfuric acid etc.) or a mixture thereof (e.g. hydrogen bromide/acetic acid etc.).

The (5) deprotection reaction using a metal is performed, for example, at 0 to 40° C. in an acidic solvent (e.g. acetic acid, a buffer of pH 4.2 to 7.2, or a mixed solution of any of those solutions and an organic solvent such as tetrahydrofuran etc.) in the presence of a zinc powder, if necessary, with applying an ultrasound.

The (6) deprotection reaction using a metal complex is performed, for example, at 0 to 40° C. in an organic solvent (e.g. dichloromethane, N,N-dimethylformamide, tetrahydrofuran, ethyl acetate, acetonitrile, dioxane, ethanol etc.), water or a mixed solvent thereof, in the presence of a trap reagent (e.g. tributyltin hydride, triethylsilane, dimedone, morpholine, diethylamine, pyrrolidine etc.), an organic acid (e.g. acetic acid, formic acid, 2-ethylhexanoic acid etc.) and/or an organic acid salt (e.g. sodium 2-ethylhexanoate, potassium 2-ethylhexanoate etc.), in the presence or the absence of a phosphine-based reagent (e.g. triphenylphosphine etc.), with using a metal complex (e.g. tetrakistriphenylphosphine-palladium (0), bis(triphenylphosphine)palladium (II) dichloride, palladium (II) acetate, tris(triphenylphosphine)rhodium (I) chloride etc.).

Additionally, in addition to the above reactions, the deprotection reaction can be performed, for example, by the method described in T. W. Greene, Protective Groups in Organic Synthesis, Wiley, New York, 1999.

Examples of the protective group of a hydroxyl group include a methyl group, a trityl group, a methoxymethyl (MOM) group, a 1-ethoxyethyl (EE) group, a methoxyethoxymethyl (MEM) group, a 2-tetrahydropyranyl (THP) group, a trimethylsilyl (TMS) group, a triethylsilyl (TES) group, a t-butyldimethylsilyl (TBDMS) group, a t-butyldiphenylsilyl (TBDPS) group, an acetyl (Ac) group, a pivaloyl group, a benzoyl group, a p-phenylbenzoyl group, a benzyl (Bn) group, a p-methoxybenzyl group, an allyloxycarbonyl (Alloc) group, a 2,2,2-trichloroethoxycarbonyl (Troc) group etc.

Examples of the protective group of an amino group include a benzyloxycarbonyl group, a t-butoxycarbonyl group, an allyloxycarbonyl (Alloc) group, a 1-methyl-1-(4-biphenyl)ethoxycarbonyl (Bpoc) group, a trifluoroacetyl group, a 9-fluorenylmethoxycarbonyl group, a benzyl (Bn) group, a p-methoxybenzyl group, a benzyloxymethyl (BOM) group, a 2-(trimethylsilyl)ethoxymethyl (SEM) group etc.

The protective group of a hydroxyl group is not particularly limited, as far as it is a group which can be easily and selectively left, in addition to the aforementioned protective groups. Protective groups described in, for example, T. W. Greene, Protective Groups in Organic Synthesis, Wiley, New York, 1999 are used.

The compound represented by the formula (II) can be produced by the following reaction step formula 2.

<Reaction step formula 2>

[Chemical formula 49]

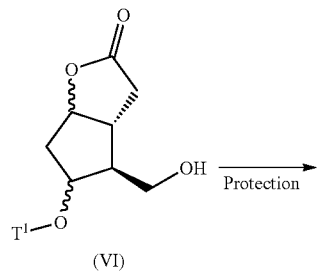

(VI)

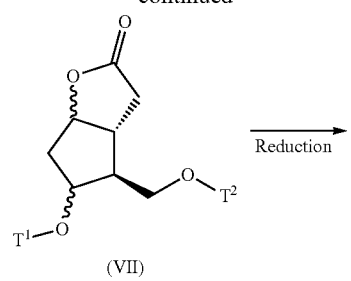

(VII)

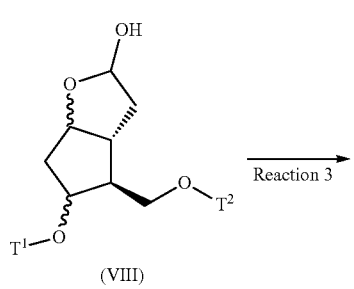

(VIII)

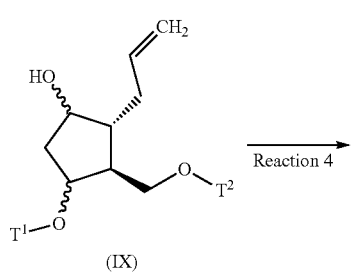

(IX)

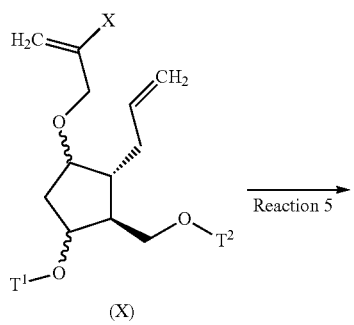

(X)

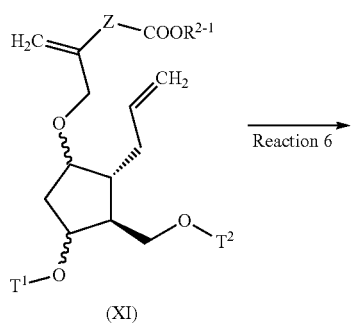

(XI)

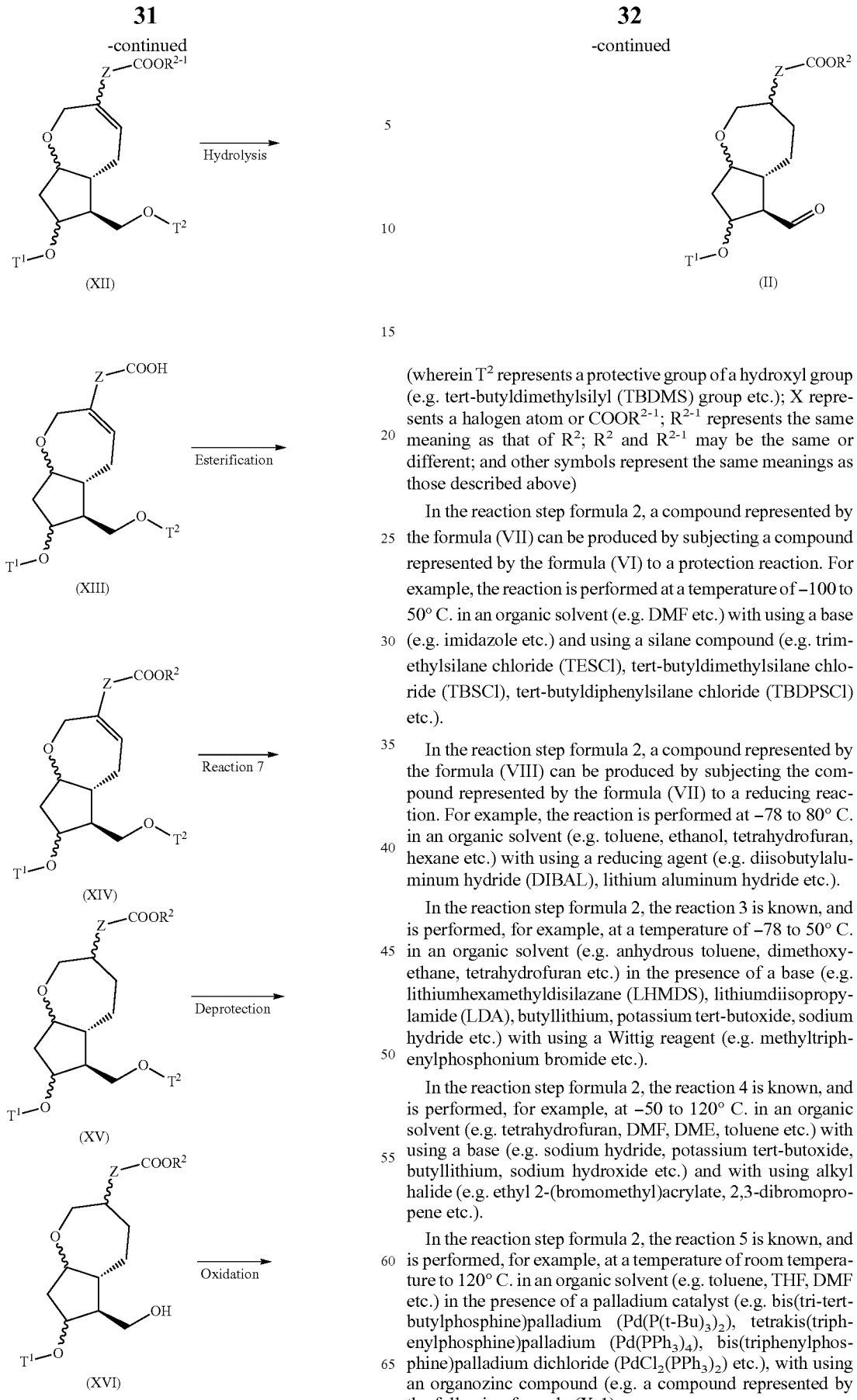

(wherein T² represents a protective group of a hydroxyl group (e.g. tert-butyldimethylsilyl (TBDMS) group etc.); X represents a halogen atom or $COOR^{2-1}$; $R^{2-1}$ represents the same meaning as that of $R^2$; $R^2$ and $R^{2-1}$ may be the same or different; and other symbols represent the same meanings as those described above)

In the reaction step formula 2, a compound represented by the formula (VII) can be produced by subjecting a compound represented by the formula (VI) to a protection reaction. For example, the reaction is performed at a temperature of −100 to 50° C. in an organic solvent (e.g. DMF etc.) with using a base (e.g. imidazole etc.) and using a silane compound (e.g. trimethylsilane chloride (TESCl), tert-butyldimethylsilane chloride (TBSCl), tert-butyldiphenylsilane chloride (TBDPSCl) etc.).

In the reaction step formula 2, a compound represented by the formula (VIII) can be produced by subjecting the compound represented by the formula (VII) to a reducing reaction. For example, the reaction is performed at −78 to 80° C. in an organic solvent (e.g. toluene, ethanol, tetrahydrofuran, hexane etc.) with using a reducing agent (e.g. diisobutylaluminum hydride (DIBAL), lithium aluminum hydride etc.).

In the reaction step formula 2, the reaction 3 is known, and is performed, for example, at a temperature of −78 to 50° C. in an organic solvent (e.g. anhydrous toluene, dimethoxyethane, tetrahydrofuran etc.) in the presence of a base (e.g. lithiumhexamethyldisilazane (LHMDS), lithiumdiisopropylamide (LDA), butyllithium, potassium tert-butoxide, sodium hydride etc.) with using a Wittig reagent (e.g. methyltriphenylphosphonium bromide etc.).

In the reaction step formula 2, the reaction 4 is known, and is performed, for example, at −50 to 120° C. in an organic solvent (e.g. tetrahydrofuran, DMF, DME, toluene etc.) with using a base (e.g. sodium hydride, potassium tert-butoxide, butyllithium, sodium hydroxide etc.) and with using alkyl halide (e.g. ethyl 2-(bromomethyl)acrylate, 2,3-dibromopropene etc.).

In the reaction step formula 2, the reaction 5 is known, and is performed, for example, at a temperature of room temperature to 120° C. in an organic solvent (e.g. toluene, THF, DMF etc.) in the presence of a palladium catalyst (e.g. bis(tri-tert-butylphosphine)palladium $(Pd(P(t-Bu)_3)_2)$, tetrakis(triphenylphosphine)palladium $(Pd(PPh_3)_4)$, bis(triphenylphosphine)palladium dichloride $(PdCl_2(PPh_3)_2)$ etc.), with using an organozinc compound (e.g. a compound represented by the following formula (X-1):

[Chemical formula 50]

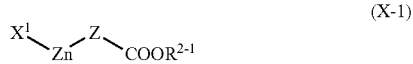

(wherein $X^1$ represents a halogen atom, and other symbols represent the same meanings as those described above), etc.), when X represents a halogen atom in the compound of the formula (X).

Herein, when X represents $COOR^{2-1}$ in the compound of the formula (X), the objective compound can be produced by subjecting the compound of the formula (X) as it is to the reaction 6, without via the reaction 5.

In the reaction step formula 2, the reaction 6 is known, and is performed, for example, at a temperature of 20 to 80° C. in an organic solvent (e.g. toluene, dichloromethane, dichloroethane etc.) with using a metathesis catalyst (e.g. 2,6-diisopropylphenylimidoneophylidenemorbidenium (VI) bis(tert-butoxide), 2,6-diisopropylphenylimidoneophylidenemorbidenium (VI) bis(hexafluorotert-butoxide) etc.).

In the reaction step formula 2, the compound represented by the formula (XIII) can be produced by subjecting the compound represented by the formula (XII) to a hydrolysis reaction. For example, the reaction is performed at 0 to 80° C. in the presence of a hydroxide of an alkali metal (e.g. sodium hydroxide, potassium hydroxide, lithium hydroxide etc.) in a hydrous solvent (e.g. a mixed solvent of an alcohol-based solvent (e.g. methanol, ethanol, propanol, isopropyl alcohol etc.) and water).

In the reaction step formula 2, a compound represented by the formula (XIV) can be produced by subjecting the compound represented by the formula (XIII) to an esterification reaction. Examples of the esterification reaction include:
(1) a method using halogenated alkyl,
(2) a method using acid halide,
(3) a method using a mixed acid anhydride,
(4) a method using a condensing agent, etc.

To specifically explain a method using halogenated alkyl as one example, for example, the method is performed by reacting carboxylic acid with halogenated alkyl at 0 to 150° C. in an organic solvent (e.g. acetonitrile, acetone, N,N-dimethylformamide, dimethyl sulfoxide, chloroform, dichloromethane, diethyl ether, tetrahydrofuran etc.) in the presence of carbonate (e.g. cesium carbonate, sodium carbonate, potassium carbonate etc.), an organic base (e.g. dimethylformamide, triethylamine, diisopropylethylamine etc,) or hydroxide of an alkyl metal (sodium hydroxide etc.).

In the reaction step formula 2, the reaction 7 is known, and is performed (1) by a reaction at 0° C. to 80° C. under the atmospheric pressure or a high pressure with using a metal catalyst (e.g. palladium carbon, platinum oxide, rhodium-alumina, Raney nickel, Wilkinson complex, ruthenium catalyst, iridium catalyst etc.) in an organic solvent (e.g. methanol, ethanol, ethyl acetate, dichloromethane, dichloroethane, etc.) with using, for example, a hydrogen gas, or (2) by a reaction at −40 to 80° C. with using a reducing agent (e.g. sodium borohydride etc.) in an organic solvent (e.g. methanol, ethanol, etc.) in the presence or the absence of cerium chloride etc. as an additive.

Among products obtained by the reaction 7, after fractionation of a desired optical isomer by optical resolution by a conventional method (e.g. method using optical resolution column), if necessary, the aforementioned protection reaction is performed, thereby, a compound represented by the formula (XV) can be produced.

Among the reaction step formula 2, a compound represented by the formula (XVI) can be produced by subjecting the compound represented by the formula (XV) to the aforementioned deprotection reaction.

In the reaction step formula 2, the compound represented by the formula (II) can be produced by subjecting the compound represented by the formula (XVI) to an oxidation reaction. Examples of the oxidation reaction include:
(1) a method using DMSO oxidation (e.g. Swern oxidation),
(2) a method using a Dess-Martin reagent,
(3) a method using a TEMPO (2,2,6,6-tetramethylpiperidine 1-oxyl) reagent, etc.

To specifically explain the method using DMSO oxidation as one example, for example, the method is performed by reacting an alcohol compound in an organic solvent (e.g. chloroform, dichloromethane, ethyl acetate etc.) in the presence of an activating agent (e.g. oxalyl chloride, acetic acid anhydride, pyridine-sulfur trioxide complex etc.), and an oxidizing agent (e.g. dimethyl sulfoxide etc.) and, further, reacting tertiary amine (e.g. triethylamine, N,N-diisopropylethylamine, N-methylmorpholine, N-ethylpiperidine, diazabicyclo[5.4.0]undec-7-ene etc.) at −78 to 40° C.

In the reaction step formula 2, as the compound having a symbol:

 [Chemical formula 51]

a compound obtained by performing optical resolution by a conventional method (e.g. method using optical resolution column) in advance, and fractionating a desired optical isomer may be used.

In each reaction in the present specification, the compound used as a starting raw material, and the compound represented by the formula (III) or the formula (VI) are known, or can be easily produced by the known method.

Among the compound represented by the formula (I), a compound in which

 [Chemical formula 52]

is as described below, an ω chain represents β configuration; $R^1$ represents $COOR^2$; $R^5$ represents a hydroxyl group; and $R^6$ and $R^7$ each represent a fluoro group, in the compound represented by formula (I-2), namely, a compound represented by the formula (I-2-b):

[Chemical formula 53]

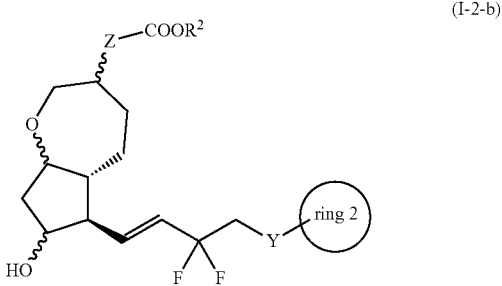

(I-2-b)

(wherein all symbols represent the same meanings as those described above) can be produced using the compound represented by the formula (IV) in the reaction step formula 1 as a starting substance, according to the following reaction step formula 3.

<Reaction step formula 3>

[Chemical formula 54]

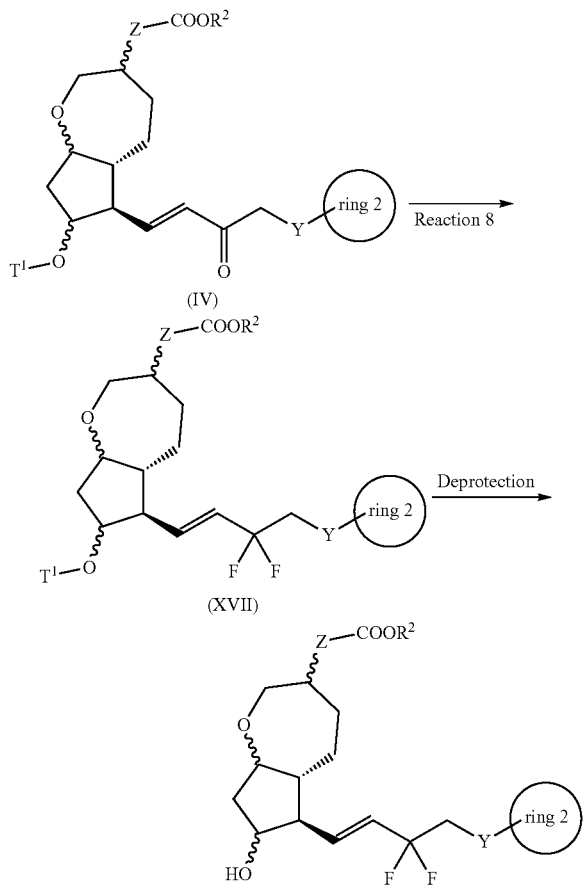

(wherein all symbols represent the same meanings as those described above)

In the reaction step formula 3, the reaction 8 is known, and is performed by, for example, reacting the compound represented by the formula (IV) in the reaction step formula 1 at a temperature of −20 to 100° C. in an organic solvent (e.g. dichloromethane, dichloroethane, chloroform etc.), in the presence or the absence of an additive (e.g. hydrogen fluoride-pyridine complex, boron trifluoride-diethyl ether complex, ethanol etc.) with using a fluorinating agent (e.g. diethylaminosulfur trifluoride, bis(2-methoxyethyl)aminosulfur trifluoride etc.).

In the reaction step formula 3, a reaction of deprotecting a protective group is known, and can be performed by the same step as that of the reaction of deprotecting a protective group as described in the reaction step formula 1.

In each reaction in the present specification, a reaction accompanying heating can be performed with using a water bath, an oil bath, a sand bath or a microwave, as is apparent to a person skilled in the art.

In each reaction in the present specification, a solid phase-supported reagent supported on a high-molecular polymer (e.g. polystyrene, polyacrylamide, polypropylene, polyethylene glycol etc.) may be appropriately used.

In each reaction in the present specification, the reaction product can be purified by a normal purification means, for example, a method such as distillation under normal pressure or under reduced pressure, high performance liquid chromatography with using silica gel or magnesium silicate, thin layer chromatography, an ion-exchange resin, a scavenger resin, or column chromatography or washing, recrystallization etc. Purification may be performed for every reaction, or may be performed after completion of some reactions.

[Toxicity]

The compound of the present invention has very low toxicity, has little, for example, eye stimulating property (hyperemia, corneal clouding etc.), aqueous humor protein rise etc., and can be safely used as a medicament.

[Application to Medicament]

Since the compound of the present invention has selective FP agonist activity, based on its intraocular pressure lowering action, it is useful as an agent for preventing and/or treating an ocular disease, for example, glaucoma (acute closed-angle glaucoma, chronic closed-angle glaucoma, secondary closed-angle glaucoma, primary open-angle glaucoma, secondary open-angle glaucoma, congenital glaucoma, normal pressure glaucoma, aqueous hyperproduction glaucoma, etc.), ocular hypertension, macular edema, macular degeneration, retina and optic nerve tensile force rise, myopia, hyperopia, astigmatism, dry eye, retinal detachment, cataract, ocular pressure rise due to trauma or inflammation, ocular pressure rise due to a drug such as a steroid or a hormone agent, intraocular pressure rise after operation etc.

In addition, since the compound of the present invention has FP agonist activity, it is also useful as a labor inducer, an ecbolic, an oxytocic, a therapeutic agent for dysmenorrhea, a therapeutic agent for osteoporosis, a sunburn revulsant, a white hair preventing agent, a hair growth promoter, an eyelash extender, a therapeutic agent for Meniere's disease, a therapeutic agent for a labyrinthian disease etc.

The compound of the present invention may be administered as a combined drug, by combining with other drug for
1) complementing and/or potentiating the preventing and/or treating effect of the compound,
2) improving pharmacokinetics and absorption of the compound, decreasing a dose, and/or
3) alleviating side effect of the compound.

The combined drug of the compound of the present invention and other drug may be administered in a form of a compounding agent in which both ingredients are incorporated into one preparation, or may take a form of administration of separate preparations. In administration by formulating into separate preparations, administration by simultaneous administration and administration with time lag is included. In addition, in administration with time lag, the compound of the present invention may be administered earlier, and other drug may be administered later, or other drug may be administered earlier, and the compound of the present invention may be administered later. Respective administration methods may be the same or different.

By the combined drug, a disease on which the preventing and/or treating effect is exerted is not particularly limited, and the disease may be a disease on which the preventing and/or treating effect of the preset invention compound is complemented and/or potentiated.

Examples of other drug for complementing and/or potentiating the preventing and/or treating effect on glaucoma of the compound of the present invention include sympathetic nerve agonists ($\alpha_2$ agonists: e.g. apraclonidine hydrochloride etc., $\beta_2$ agonist: e.g. dipivefrine hydrochloride etc.), parasympathetic nerve agonists (e.g. pilocarpine hydrochloride, carbachol, demecarium, echothiophate or distigmine bromide etc.), sympathetic nerve suppressants ($\alpha_1$ blocker: e.g. bunazosin hydrochloride etc., β blocker e.g. timolol maleate, befunolol hydrochloride, carteolol hydrochloride, or betaxolol hydrochloride etc., α₁β blocker, e.g. levobunolol hydrochloride, nipradilol etc.), prostaglandin drugs (e.g. isopropyl unoprostone, latanoprost, bimatoprost, travoprost, tafluprost, EP2 agonist, EP4 agonist or DP agonist etc.), carbonic anhydrase inhibitors (e.g. acetazolamide, diclofenamide, methazolamide, dorzolamide hydrochloride, or brinzolamide etc.), hyperosmotic agents (e.g. glycerin, preparation incorporating glycerin and fructose, isosorbide, or D-mannitol etc.), ROCK (Rho kinase) inhibitors (e.g. Y-27632 etc.), NMDA antagonists etc.

In addition, the therapeutic agent for glaucoma to be combined with the compound of the present invention includes not only therapeutic agents which have been found out until now, but also therapeutic agents which will be found out from now on.

The compound of the present invention is usually administered systemically or locally in an oral or parenteral form. Examples of the oral agent include liquid drugs for internal application (e.g. elixirs, syrups, pharmaceutically acceptable water agents, suspensions, emulsions), solid preparations for internal application (e.g. tablets (including sublingual tablets, orally disintegrating tablets), pills, capsules (including hard capsules, soft capsules, gelatin capsules, microcapsules), powders, granules, torches) etc. Examples of the parenteral agents include solutions (e.g. injectables (subcutaneous injectables, intravenous injectables, intramuscular injectables, intraperitoneal injectables, infusions etc.), eye drops (e.g. aqueous eye drops (aqueous eye drops, aqueous suspensions eye drops, viscous eye drops, solubilized eye drops etc.), nonaqueous eye drops (nonaqueous eye drops, nonaqueous suspension eye drops etc.)) etc.), external preparations (e.g. ointment (ocular ointment etc.)), ear drops etc. These preparations may be release-controlled agents such as rapid-releasing preparations and sustained-release preparations. These preparations can be produced by the known method, for example, the method described in Japanese Pharmacopoeia etc.

Solutions for internal application as the oral agent are produced by dissolving, suspending or emulsifying an active ingredient in a diluent which is generally used (e.g. purified water, ethanol or a mixed solution thereof etc.). Further, this solution may contain wetting agents, suspending agents, emulsifiers, sweeteners, flavors, aromatic agents, preservatives, buffers etc.

Solid preparations for internal application as the oral agent are formulated into preparations according to a conventional method by mixing an active ingredient with excipients (e.g. lactose, mannitol, glucose, microcrystalline cellulose, starch etc.), binders (e.g. hydroxypropylcellulose, polyvinylpyrrolidone, magnesium aluminometasilicate etc.), disintegrating agents (e.g. cellulose calcium glycolate etc.), lubricants (e.g. magnesium stearate etc.), stabilizers, solubilizers (glutamic acid, aspartic acid etc.) etc. In addition, if necessary, preparations may be covered with coating agents (e.g. white sugar, gelatin, hydroxypropylcellulose, hydroxypropylmethylcellulose phthalate etc.), or may be covered with two or more layers.

The external preparation as the parenteral agent is produced by the known method, or formulation which is usually used. For example, the ointment preparations are produced by kneading an active ingredient in a base or melting an active ingredient in a base. An ointment base is selected from bases which are known, or are usually used. For example, an ointment base selected from higher fatty acids or higher fatty acid esters (e.g. adipic acid, myristic acid, palmitic acid, stearic acid, oleic acid, adipic acid ester, myristic acid ester, palmitic acid ester, stearic acid ester, oleic acid ester, etc.), waxes (e.g. beewax, whale wax, ceresin etc.), surfactants (e.g. polyoxyethylene alkyl ether phosphoric acid ester etc.), higher alcohols (e.g. cetanol, stearyl alcohol, cetostearyl alcohol etc.), silicone oils (e.g. dimethylpolysiloxane etc.), hydrocarbons (e.g. hydrophilic vaseline, white vaseline, purified lanolin, liquid paraffin etc., glycols (e.g. ethylene glycol, diethylene glycol, propylene glycol, polyethylene glycol, macrogol etc.), vegetable oils (e.g. castor oil, olive oil, sesame oil, turpentine oil etc.), animal oils (e.g. mink oil, yolk oil, squalane, squalene etc.), water, absorption promoter, and rash preventing agents, alone, is used, or a mixture of two or more kinds is used. Further, the ointment base may contain humectants, preservatives, stabilizers, antioxidants, coloring agents etc.

The injectable as the parenteral agent includes solutions, suspensions, emulsions and solid injectables which are used by dissolving or suspending a solid in a solvent at use. The injectable is used, for example, by dissolving, suspending or emulsifying an active ingredient in a solvent. As the solvent, for example, distilled water for injection, physiological saline, vegetable oil, alcohols such as propylene glycol, polyethylene glycol and ethanol etc., and a combination thereof are used. Further, this injectable may contain stabilizers, solubilizers (e.g. glutamic acid, aspartic acid, polysorbate 80 (registered trademark) etc.), suspending agents, emulsifiers, soothing agents, buffers, preservatives etc. These are produced by sterilization in a final step, or by a sterilization operation method. Alternatively, they may be used by firstly producing a sterile solid agent such as a lyophilized product, and dissolving them in sterilized or sterile distilled water for injection or another sterile solvent prior to their use.

Examples of a preferable dosage form of the compound of the present invention include eye drops, ocular ointments, tablets etc., and more preferable is eye drops or ocular ointment. These can be formulated into preparations with using the generally used technique. For example, in the case of eye drops, as additives, tonicity agents, buffers, pH adjusting agents, solubilizers, thickeners, stabilizers, preservatives etc. can be appropriately incorporated. Alternatively, stable eye drops can be also obtained by adding pH adjusting agents, thickeners, or dispersants, and suspending drugs.

Examples of the tonicity agent include glycerin, propylene glycol, sodium chloride, potassium chloride, sorbitol, mannitol, etc.

Examples of the buffer include phosphoric acid, phosphate, citric acid, acetic acid, ε-aminocaproic acid etc.

Examples of the pH adjusting agent include hydrochloric acid, citric acid, phosphoric acid, acetic acid, sodium hydroxide, potassium hydroxide, boric acid, borax, sodium carbonate, sodium bicarbonate etc.

Examples of the solubilizer include polysorbate 80, polyoxyethylene hardened castor oil 60, macrogol 4000 etc.

Examples of the thickener and dispersant include cellulose-based polymers such as hydroxypropylmethylcellulose and hydroxypropylcellulose, polyvinyl alcohol, polyvinylpyrrolidone etc., and examples of the stabilizer include edetic acid and sodium edetate etc.

Examples of the preservative (antiseptic agent) include general-use sorbic acid, potassium sorbate, benzalkonium chloride, benzethonium chloride, methyl paraoxybenzoate, propyl paraoxybenzoate, chlorobutanol etc., and these preservatives can be also used by combining them.

In eye drops containing the active ingredient of the present invention, it is desirable that a pH is set at 4.0 to 8.5, and it is desirable that an osmotic pressure ratio is set at around 1.0.

A dose of the active ingredient of the present invention can be appropriately selected depending on a symptom, an age, a dosage form etc. and, in the case of the oral agent, preferably from 1 to 1000 mg, more preferably from 5 to 300 mg may be administered once to a few times (e.g. once to three times) per day. In the case of eye drops, one to a few drops having a concentration of preferably from 0.000001 to 5% (w/v), more preferably from 0.00001 to 0.05% (w/v) as a one time amount may be administered to eyes once to a few times (e.g. once to eight times) per day. In addition, in the case of the ocular ointment, an ocular ointment having a concentration of preferably from 0.000001 to 5% (w/w), more preferably from 0.00001 to 0.05% (w/w) may be coated once to a few times (e.g. once to four times) per day.

Of course, since a dose varies depending on a variety of conditions as described above, an amount smaller than the aforementioned dose is sufficient in some cases, or an amount exceeding the range is necessary in some cases.

EXAMPLES

Although the present invention will be described in detail below by way of Examples, the present invention is not limited by them.

A solvent in a parenthesis shown in a place of separation by chromatography and TLC indicates an eluting solvent or a developing solvent used, and a ratio represents a volumetric ratio.

NMR data is data of $^1$H-NMR unless otherwise is indicated.

A solvent used in measurement is indicated in a parenthesis shown at a place of NMR.

A compound name used in the present specification was generally named by using a computer program, ACD/Name (registered trademark) of Advanced Chemistry Development, which performs naming according to a rule of IUPAC, or according to IUPAC nomenclature.

Example 1

(3aR,4S,5R,6aS)-4-({[dimethyl(2-methyl-2-propanyl)silyl]oxy}methyl)-5-(tetrahydro-2H-pyran-2-yloxy)hexahydro-2H-cyclopenta[b]furan-2-one To a dimethylformamide (hereinafter, abbreviated as DMF in some cases) (100 mL) solution of (3aR,4S,5R,6aS)-4-(hydroxymethyl)-5-(tetrahydro-2H-pyran-2-yloxy)hexahydro-2H-cyclopenta[b]furan-2-one (50 g), imidazole (29.22 g), and tert-butyldimethylchlorosilane (30.87 g) were sequentially added under ice-cooling, and the mixture was stirred at room temperature for 3.5 hours. After completion of the reaction, a small amount of ethanol was added; the reaction solution was poured into ice water; and this was extracted with ethyl acetate:hexane (2:3). The extract was washed with 1N hydrochloric acid, an aqueous saturated sodium bicarbonate solution, water and a saturated saline, dried with sodium sulfate, and concentrated under reduced pressure to obtain a titled compound (76.2 g) having the following physical property values.

TLC: Rf 0.42 (hexane:ethyl acetate=3:1).

Example 2

(3aR,4S,5R,6aS)-4-({[dimethyl(2-methyl-2-propanyl)silyl]oxy}methyl)-5-(tetrahydro-2H-pyran-2-yloxy)hexahydro-2H-cyclopenta[b]furan-2-ol Under the argon atmosphere, an anhydrous toluene (390 mL) solution of the compound (76.2 g) produced in Example 1 was cooled to −70° C., a 1 mol/L toluene solution (212.4 mL) of diisobutylaluminum hydride was added dropwise over about 1 hour, and stirring was carried out for 30 minute as it was. After completion of the reaction, dilution with tert-butyl methyl ether (hereinafter, abbreviated as MTBE in some cases) (400 mL) was carried out, and an aqueous saturated sodium sulfate solution was added. The precipitated white precipitate was filtered with Celite (trade name), and the solvent was concentrated under reduced pressured to obtain a titled compound (80.7 g) having the following physical property values.

TLC: Rf 0.30 (hexane:ethyl acetate=3:1).

Example 3

(1S,2R,3S,4R)-2-allyl-3-({[dimethyl(2-methyl-2-propanyl)silyl]oxy}methyl)-4-(tetrahydro-2H-pyran-2-yloxy)cyclopentanol Under the argon atmosphere, a 1.6M tetrahydrofuran (hereinafter, abbreviated as THF in some cases) solution (500 mL) of lithiumhexamethyldisilazane was added dropwise to an anhydrous toluene (300 mL) suspension of methyltriphenylphosphonium bromide (326.6 g) under ice-cooling, and stirring was carried out at room temperature for 1 hour. The mixture was cooled to −70° C. again, an anhydrous toluene (400 mL) solution of the compound (85.2 g) produced in Example 2 was added dropwise over about 1.5 hours, and the mixture was stirred at room temperature for 2 hours. After completion of the reaction, an aqueous ammonium chloride solution was added, followed by extraction with ethyl acetate. The organic layer was washed with water and a saturated saline, and dried with sodium sulfate, and the solvent was concentrated under reduced pressure. The resulting residue was purified with a column apparatus (Hiflash-SI, Size 5 L×4, hexane:ethyl acetate=100:0→85:15→75:25) manufactured by Yamazen Corporation to obtain a titled compound (41.87 g) having the following physical property values.

TLC: Rf 0.57 (hexane:ethyl acetate=3:1).

Example 4

{[(1S,2R,3S,5R)-2-allyl-3-[(2-bromo-2-propen-1-yl)oxy]-5-(tetrahydro-2H-pyran-2-yloxy)cyclopentyl]methoxy}(dimethyl)(2-methyl-2-propanyl)silane Under the argon atmosphere, 2,3-dibromopropene (8.4 mL, 81.0 mmol) was placed into a flask, and this was cooled to an inner temperature of 5° C. using ice water. Sodium hydride (2.16 g, 54.1 mmol) was placed therein, and the mixture was stirred for 5 minutes. The compound (10 g, 27 mmol) produced in Example 3 was added dropwise over 50 minutes, and stirring was carried out at room temperature for 2 hours. The reaction solution was carefully poured into an aqueous saturated ammonium chloride solution; was extracted with MTBE; washed with an aqueous saturated ammonium chloride solution; dried with anhydrous sodium sulfate, and concentrated. Purification with silica gel column chromatography (hexane:ethyl acetate=95:5→80:20) was carried out to obtain a titled compound (10.9 g) having the following physical property values.

TLC: Rf 0.72 hexane:ethyl acetate=9:1).

Example 5

Ethyl 5-({[(1S,2R,3S,4R)-2-allyl-3-({[dimethyl(2-methyl-2-propanyl)silyl]oxy}methyl)-4-(tetrahydro-2H-pyran-2-yloxy)cyclopentyl]oxy}methyl)-5-hexanoate Under the argon atmosphere, the compound (10.9 g, 22.2 mmol) produced in Example 4 was dissolved in toluene (100 mL), and 4-ethoxy-4-oxobutylzinc bromide (0.5 mol/L THF solution, 133 mL, 66.7 mmol) was added at room temperature. Bis(tri-tert-butylphosphine)palladium (567 mg, 1.11 mmol) was added, and stirring was carried out at 80° C. for 2 hours. This was cooled to room temperature; an aqueous saturated ammonium chloride solution was added; and this was concentrated. The resulting residue was dissolved in MTBE, followed by filteration with using Celite (trade name). The filtrate was washed with an aqueous ammonium chloride solution, an aqueous saturated sodium bicarbonate solution, and a saturated saline; dried with magnesium sulfate; and concentrated. Purification with silica gel column chromatography (hexane:ethyl acetate=90:10→50:50) was carried out to obtain a titled compound (9.73 g) having the following physical property values.

TLC: Rf 0.65 (hexane:ethyl acetate=9:1).

Example 6

Ethyl 4-[(5aR,6S,7R,8aS)-6-({[dimethyl(2-methyl-2-propanyl)silyl]oxy}methyl)-7-(tetrahydro-2H-pyran-2-yloxy)-5,5a,6,7,8,8a-hexahydro-2H-cyclopenta[b]oxepin-3-yl]butanoate Under the argon-atmosphere, the compound (400 mg, 0.762 mmol) produced in Example 5 was dissolved in toluene (76 mL). A Schrock's catalyst (2,6-diisopropylphenylimidoneophylidenemorbidenium (VI) bis(hexafluorotert-butoxide)) (785 mg, 0.925 mmol) was added to perform a reaction at 85° C. for 18 hours. After allowing to be cool, concentration was carried out, and purification was carried out by silica gel column chromatography (hexane:ethyl acetate=90:10→50:50) to obtain a titled compound (4.8 mg) having the following physical property values.

TLC: Rf 0.47 (hexane:ethyl acetate=4:1).

Example 7

4-[(5aR,6S,7R,8aS)-6-({[dimethyl(2-methyl-2-propanyl)silyl]oxy}methyl)-7-(tetrahydro-2H-pyran-2-yloxy)-5,5a,6,7,8,8a-hexahydro-2H-cyclopenta[b]oxepin-3-yl]butanoic acid The compound (7.63 g, 15.4 mmol) produced in Example 6 was dissolved in ethanol (60 mL); a 2.0 mol/L aqueous sodium hydroxide solution (20 mL) was added; and stirring was carried out at room temperature for 2 hours. After concentration, ethyl acetate and 2 mol/L hydrochloric acid were added, followed by extraction. Washing with a saturated saline; drying with anhydrous sodium sulfate, and concentration were carried out. The resulting titled compound was used in a next reaction without purification.

TLC: Rf 0.48 (chloroform:methanol=9.1)

Example 8

2-Propanyl 4-[(5aR,6S,7R,8aS)-6-({[dimethyl(2-methyl-2-propanyl)silyl]oxy}methyl)-7-(tetrahydro-2H-pyran-2-yloxy)-5,5a,6,7,8,8a-hexahydro-2H-cyclopenta[b]oxepin-3-yl]butanoate Under the argon atmosphere, the compound (15.4 mmol) produced in Example 7 was dissolved in DMF; potassium carbonate (5.31 g, 38.5 mmol) and isopropyl iodide (2.31 mL, 23.1 mmol) were added, followed by stirring at 60° C. for 3 hours. After cooling, MTBE and water were added, and extraction; washing with a saturated saline; drying with anhydrous sodium sulfate; and concentration were carried out. Purification by silica gel column chromatography (hexane:ethyl acetate=90:10→50:50) was carried out to obtain a titled compound (7.25 g) having the following physical property values.

TLC: Rf 0.90 (ethyl acetate).

Example 9

2-Propanyl 4-[(5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-yl]butanoate Under the argon atmosphere, a dichloromethane solution (62 mL) of the compound (4.85 g, 9.45 mmol) produced in Example 8 was degassed with using an ultrasound, and argon replacement was performed. A Crabtree's catalyst (tricyclohexylphosphine) (1,5-cyclooctadiene) (pyridine)iridium (I) hexafluorophosphate) (760 mg, 0.945 mmol) was added, and stirring was carried out at room temperature for 3 hours and 50 minutes under the hydrogen atmosphere. Concentration under reduced pressure, and purification with a column apparatus (Hiflash-SI, Size 2 L, hexane→ethyl acetate:hexane=3:7) manufactured by Yamazen Corporation were carried out to obtain a titled compound (3.05 g) having the following physical property values.

TLC: Rf 0.72 (hexane:ethyl acetate=1:2).

Example 10 (1)

2-Propanyl 4-[(3S,5aR,6S,7R,8aS)-6-({[dimethyl(2-methyl-2-propanyl)silyl]oxy}methyl)-7-hydroxyoctahydro-2H-cyclopenta[b]oxepin-3-yl]butanoate

Example 10 (2)

2-Propanyl 4-[(3R,5aR,6S,7R,8aS)-6-({[dimethyl(2-methyl-2-propanyl)silyl]oxy}methyl)-7-hydroxyoctahydro-2H-cyclopenta[b]oxepin-3-yl]butanoate Under the argon atmosphere, a dichloromethane solution (60 mL) of the compound (3.02 g, 5.89 mmol) produced in Example 9 was cooled to −20° C. After addition of dimethylaluminum chloride solution (1.0M hexane solution), and stirring was carried out for 3 hours and 40 minutes while a temperature was raised to room temperature. The reaction solution was poured into an ice-cooled aqueous saturated sodium bicarbonate solution; and a Rochelle salt was added, followed by stirring for 40 minutes. The aqueous layer was extracted with ethyl acetate twice; and the collected organic layers were washed with a saturated saline, and dried with anhydrous sodium sulfate. The solution was concentrated under reduced pressure, and purified with a column apparatus (Hiflash-SI, Size 5 L, toluene: acetone=10:1) manufactured by Yamazen Corporation once, and with (Hiflash-SI, Size 2 L+YAMAZEN ULTRA PACK SI-C, Size 37×300, toluene: acetone=10:1) twice to obtain a compound (1.60 g) of Example 10 (1) and a compound (810 mg) of Example 10 (2) having the following physical property values.

TLC: Rf 0.30 (toluene: acetone=9:1) (compound of Example 10 (1));

TLC: Rf 0.31 (toluene: acetone=9:1) (compound of Example 10 (2)).

Example 11

2-Propanyl 4-[(3S,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-yl]butanoate Under the argon atmosphere, 3,4-dihydro-2H-pyran (403 µL, 4.42 mmol) and tosic acid monohydrate (10 mg, 0.111 mmol) were added to a toluene solution (1.85 mL) of the compound (1.58 g, 3.69 mmol) produced in Example 10 (1), and the mixture was stirred at room temperature for 15 minutes. Tosic acid monohydrate (10 mg, 0.111 mmol) was added; stirring was carried out for 45 minutes; and triethylamine (100 µL) was added, followed by concentration under reduced pressure. Purification with a column apparatus (Hiflash-SI, Size 2 L, hexane→ethyl acetate:hexane=3:7) manufactured by Yamazen Corporation was carried out to obtain a titled compound (1.82 g) having the following physical property values.

TLC: Rf 0.46 (hexane:ethyl acetate=1:1).

Example 12

2-Propanyl 4-[(3S,5aR,6S,7R,8aS)-6-(hydroxymethyl)-7-(tetrahydro-2H-pyran-2-yloxy)octahydro-2H-cyclopenta[b]oxepin-3-yl]butanoate Under the argon atmosphere, tetrabutylammonium fluoride (7 mL, 1.0M THF solution) was added to a THF solution (3.6 mL) of the compound (1.81 g, 3.53 mmol) produced in Example 11, followed by stirring at room temperature for 70 minutes. Tetrabutylammonium fluoride (3.5 mL, 1.0 mol/L THF solution) was added, and the mixture was further stirred at 45° C. for 100 minutes. The reaction solution was diluted with ethyl acetate (100 mL); washed with an aqueous saturated ammonium chloride solution once, and with an aqueous saturated sodium chloride solution once; and dried with anhydrous sodium sulfate. The solution was concentrated under reduced pressure, and purified with column apparatus (Hiflash-SI, Size L, ethyl acetate:hexane=2:8→ethyl acetate:hexane=8:2) manufactured by Yamazen Corporation to obtain a titled compound (1.21 g) having the following physical property values.

TLC: Rf 0.40 (hexane:ethyl acetate=1:2).

Example 13

2-Propanyl 4-[(3S,5aR,6R,7R,8aS)-6-formyl-7-(tetrahydro-2H-pyran-2-yloxy)octahydro-2H-cyclopenta[b]oxepin-3-yl]butanoate Under the argon-atmosphere, dimethyl sulfoxide (hereinafter, abbreviated as DMSO in some cases) (1.8 mL) and diisopropylethylamine (1.8 mL, 10.56 mmol) were added to an ethyl acetate solution (4 mL) of the compound (623 mg, 1.76 mmol) produced in Example 12, and the mixture was cooled to 0° C. A pyridine-sulfur trioxide complex (840 mg, 5.28 mmol) was added, followed by stirring at 0° C. for 40 minutes. The reaction solution was diluted with ethyl acetate, and poured into ice-cooled hydrochloric acid (0.5 N). The aqueous layer was extracted with ethyl acetate once; and the collected organic layers were washed with an aqueous saturated sodium bicarbonate solution once, and with a saturated saline; and dried with anhydrous sodium sulfate. The solution was concentrated under reduced pressure to obtain a crude product (634 mg) of a titled compound having a following physical property values.

TLC: Rf 0.73 (hexane:ethyl acetate=2:1).

Example 14

2-Propanyl 4-[(3S,5aR,6R,7R,8aS)-6-[(1E)-3-oxo-4-phenoxy-1-buten-1-yl]-7-(tetrahydro-2H-pyran-2-yloxy)octahydro-2H-cyclopenta[b]oxepin-3-yl]butanoate Under the argon atmosphere, dimethyl-(3-phenoxy-2-oxopropyl)-phosphonate (826 mg, 3.20 mmol) and potassium phosphate (679 mg, 3.20 mmol) were added to a THF solution (16 mL) of the compound (634 mg, 1.60 mmol) produced in Example 13, followed by stirring at room temperature for one day. The reaction solution was added to an aqueous saturated ammonium chloride solution, and the aqueous layer was extracted with ethyl acetate twice. The collected organic layers were washed with a saturated saline, and dried with anhydrous sodium sulfate. The solution was concentrated under reduced pressure, and purified with a column apparatus (Hiflash-SI, Size L, hexane→ethyl acetate:hexane=4:6) manufactured by Yamazen Corporation to obtain a titled compound (426 mg) having the following physical property values.

TLC: Rf 0.55 (hexane:ethyl acetate=1:1).

Example 15

2-Propanyl 4-[(3S,5aR,6R,7R,8aS)-6-[(1E,3R)-3-hydroxy-4-phenoxy-1-buten-1-yl]-7-(tetrahydro-2H-pyran-2-yloxy)octahydro-2H-cyclopenta[b]oxepin-3-yl]butanoate (R)-2-methyl-CBS-oxazaborolidine (65 µL, 1 mol/L toluene solution, 0.065 mmol) was added to a THF solution (16 mL) of the compound (137 mg, 0.259 mmol) produced in Example 14. A borane dimethyl sulfide complex (155 µL, 1 mol/L toluene solution, 0.155 mmol) was added dropwise. After stirred at room temperature for 45 minutes, the solution was diluted with ethyl acetate, and poured into an aqueous saturated ammonium chloride solution. The aqueous layer was extracted with ethyl acetate twice, and the collected organic layers were washed with a saturated saline, and dried with anhydrous sodium sulfate. The resulting solution was concentrated under reduced pressure to obtain a crude product (151 mg) of a titled compound having the following physical property values.

TLC: Rf 0.32 (hexane:ethyl acetate=2:1).

Example 16 (1)

2-Propanyl 4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoate

[Chemical formula 55]

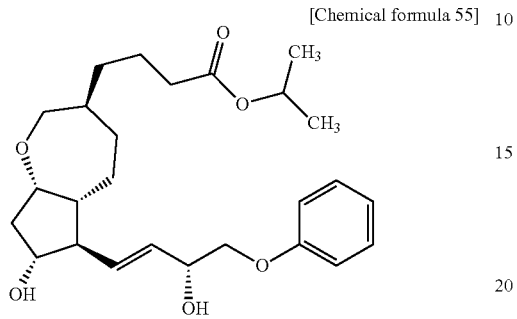

THF (400 μL) and water (400 μL) were added to an acetic acid solution (800 μL) of the compound (151 mg, 0.259 mmol) produced in Example 15, followed by stirring at 60° C. for 3 hours and 30 minutes. The reaction solution was concentrated under reduced pressure, and purified with a column apparatus (Hiflash-SI, Size S, ethyl acetate:hexane=1:1→ethyl acetate) manufactured by Yamazen Corporation to obtain a titled compound (74 mg) having the following physical property values. TLC: Rf 0.28 (dichloromethane:methanol=20:1); $^1$H-NMR (300 MHz, CDCl[3]): δ 0.90-1.19, 1.22, 1.36-1.83, 1.84-1.96, 2.03-2.18, 2.23, 2.41-2.53, 2.57, 2.84-2.97, 3.64-3.80, 3.83-3.91, 3.92-4.09, 4.44-4.59, 4.88-5.09, 5.53-5.77, 6.83-7.04, 7.14-7.35.

Example 16 (2) to Example 16 (42)

With using (3aR,4S,5R,6aS)-4-({[dimethyl(2-methyl-2-propanyl)silyl]oxy}methyl)-5-(tetrahydro-2H-pyran-2-yloxy)hexahydro-2H-cyclopenta[b]furan-2-one; using 4-ethoxy-4-oxobutylzinc bromide or a corresponding organozinc reagent in place of it; and using dimethyl-(3-phenoxy-2-oxopropyl)-sulfonate or a corresponding phosphonic acid salt in place of it, those substances were subjected to the same objective operations as those of Example 1→Example 2→Example 3→Example 4→Example 5→Example 6→Example 7→Example 8→Example 9→Example 10 (1) or Example 10 (2)→Example 11→Example 12→Example 13→Example 14→Example 15→Example 16 (1) to obtain the following Example compounds.

Example 16 (2)

2-Propanyl 4-{(3S,5aR,6R,7R,8aS)-7-hydroxy-6-[(1E,3S)-3-hydroxy-5-phenyl-1-penten-1-yl]octahydro-2H-cyclopenta[b]oxepin-3-yl}butanoate TLC: Rf 0.41 (ethyl acetate);
$^1$H-NMR (300 MHz, CDCl[3]): δ 0.87-1.19, 1.22, 1.34-1.98, 2.00-2.14, 2.23, 2.39-2.54, 2.59-2.80, 2.84-2.97, 3.59-3.78, 3.88-4.23, 4.90-5.09, 5.37-5.51, 5.53-5.65, 7.10-7.24, 7.23-7.38.

Example 16 (3)

2-Propanyl 4-{(3S,5aR,6R,7R,8aS)-6-[(1E,3R)-4-(3-chlorophenoxy)-3-hydroxy-1-buten-1-yl]-7-hydroxy-octahydro-2H-cyclopenta[b]oxepin-3-yl}butanoate

[Chemical formula 56]

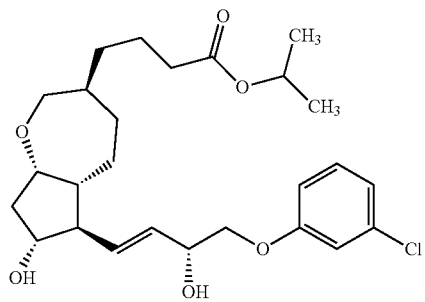

TLC: Rf 0.48 (ethyl acetate);
$^1$H-NMR (300 MHz, CDCl[3]): δ 0.88-1.19, 1.22, 1.35-1.96, 2.02-2.16, 2.23, 2.41-2.55, 2.56-2.69, 2.82-3.00, 3.63-3.79, 3.81-4.12, 4.42-4.55, 4.89-5.08, 5.54-5.72, 6.77-6.84, 6.91-6.98, 7.20.

Example 16 (4)

2-Propanyl 4-{(3S,5aR,6R,7R,8aS)-7-hydroxy-6-[(1E,3R)-3-hydroxy-4-(3-methylphenoxy)-1-buten-1-yl]octahydro-2H-cyclopenta[b]oxepin-3-yl}butanoate TLC: Rf 0.45 (ethyl acetate);
$^1$H-NMR (300 MHz, CDCl[3]): δ 0.89-1.29, 1.35-1.97, 2.01-2.17, 2.23, 2.28-2.40, 2.42-2.54, 2.66-2.83, 2.83-2.97, 3.62-3.78, 3.78-4.12, 4.40-4.56, 4.89-5.08, 5.54-5.73, 6.64-6.75, 6.78, 7.16.

Example 16 (5)

Ethyl 4-{(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}benzoate TLC: Rf 0.19 (hexane:ethyl acetate=1:2);
$^1$H-NMR (300 MHz, CDCl[3]): δ 1.32-1.43, 1.50-1.81, 1.80-2.11, 2.11-2.28, 2.41-2.60, 2.99, 3.28, 3.71-3.85, 3.84-3.94, 4.01, 4.05-4.18, 4.35, 4.48-4.62, 5.60-5.80, 6.85-7.03, 7.16-7.36, 7.90-8.02.

Example 16 (6)

Ethyl 4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}benzoate TLC: Rf 0.22 (hexane:ethyl acetate=1:2);
$^1$H-NMR (300 MHz, CDCl[3]): δ 1.33-1.43, 1.46-1.96, 1.96-2.10, 2.11-2.43, 2.43-2.58, 2.58-2.78, 2.93-3.13, 3.66-4.18, 4.25, 4.30-4.42, 4.49, 5.54-5.77, 6.83-7.02, 7.17-7.33, 7.41-7.50, 7.92-8.01.

Example 16 (7)

Ethyl 3-{(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}benzoate TLC: Rf 0.56 (ethyl acetate);
$^1$H-NMR (300 MHz, CDCl$_3$): δ 1.39, 1.53-2.32, 2.43-2.66, 2.91-3.11, 3.30, 3.69-3.84, 3.85-3.95, 3.97-4.05, 4.05-4.18, 4.37, 4.48-4.60, 5.60-5.79, 6.84-7.04, 7.19-7.43, 7.80-7.93.

Example 16 (8)

Ethyl 3-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}benzoate TLC: Rf 0.59 (ethyl acetate);
$^1$H-NMR (300 MHz, CDCl$_3$): δ 1.34-1.43, 1.47-1.95, 1.95-2.12, 2.15-2.33, 2.40-2.58, 2.66-3.19, 3.64-3.99, 4.02-4.14, 4.22, 4.30-4.42, 4.43-4.54, 5.53-5.72, 6.81-7.00, 7.19-7.30, 7.32-7.42, 7.60-7.69, 7.84-7.92, 7.94-8.01.

Example 16 (9)

2-Propanyl 4-{(3S,5aR,6R,7R,8aS)-6-[(1E,3R)-4-(4-chlorophenoxy)-3-hydroxy-1-buten-1-yl]-7-hydroxy-octahydro-2H-cyclopenta[b]oxepin-3-yl}butanoate TLC: Rf 0.44 (ethyl acetate);
$^1$H-NMR (300 MHz, CDCl$_3$): δ 0.87-1.19, 1.22, 1.32-1.97, 2.01-2.17, 2.23, 2.40-2.56, 2.70-2.99, 2.99-3.24, 3.59-3.77, 3.80-4.11, 4.38-4.56, 4.88-5.08, 5.52-5.70, 6.75-6.91, 7.18-7.25.

Example 16 (10)

2-Propanyl 4-{(3S,5aR,6R,7R,8aS)-7-hydroxy-6-[(1E,3R)-3-hydroxy-4-(4-methylphenoxy)-1-buten-1-yl]octahydro-2H-cyclopenta[b]oxepin-3-yl}butanoate TLC: Rf 0.49 (ethyl acetate);
$^1$H-NMR (300 MHz, CDCl$_3$): δ 0.90-1.18, 1.22, 1.37-1.83, 1.83-1.95, 2.01, 2.05-2.17, 2.23, 2.29, 2.40-2.56, 2.84-2.97, 3.66-3.79, 3.84, 3.90-4.09, 4.50, 4.91-5.07, 5.57-5.73, 6.76-6.85, 7.03-7.12.

Example 16 (11)

2-Propanyl 4-[(3S,5aR,6R,7R,8aS)-7-hydroxy-6-{(1E,3R)-3-hydroxy-4-[4-(trifluoromethyl)phenoxy]-1-buten-1-yl}octahydro-2H-cyclopenta[b]oxepin-3-yl]butanoate TLC: Rf 0.47 (ethyl acetate);
$^1$H-NMR (300 MHz, CDCl$_3$): δ 0.90-1.19, 1.21, 1.36-1.96, 2.06-2.29, 2.41-2.68, 2.91, 3.66-3.79, 3.88-4.10, 4.48-4.60, 4.90-5.08, 5.57-5.76, 6.97, 7.54.

Example 16 (12)

2-Propanyl 4-{(3S,5aR,6R,7R,8aS)-6-[(1E,3R)-4-(2-fluorophenoxy)-3-hydroxy-1-buten-1-yl]-7-hydroxy-octahydro-2H-cyclopenta[b]oxepin-3-yl}butanoate TLC: Rf 0.53 (ethyl acetate);
$^1$H-NMR (300 MHz, CDCl$_3$): δ 0.85-1.19, 1.22, 1.34-1.96, 2.03-2.18, 2.18-2.29, 2.39-2.57, 2.71-2.84, 2.84-2.99, 3.63-3.80, 3.85-4.13, 4.47-4.61, 4.88-5.09, 5.55-5.77, 6.84-7.15.

Example 16 (13)

2-Propanyl 4-{(3S,5aR,6R,7R,8aS)-6-[(1E,3R)-4-(3-fluorophenoxy)-3-hydroxy-1-buten-1-yl]-7-hydroxy-octahydro-2H-cyclopenta[b]oxepin-3-yl}butanoate TLC: Rf 0.55 (ethyl acetate);
$^1$H-NMR (300 MHz, CDCl$_3$): δ 0.91-1.19, 1.22, 1.34-1.97, 1.99-2.20, 2.23, 2.37-2.60, 2.91, 3.65-3.79, 3.81-4.12, 4.45-4.60, 4.91-5.10, 5.56-5.75, 6.59-6.74, 7.11-7.32.

Example 16 (14)

2-Propanyl 4-{(3S,5aR,6R,7R,8aS)-6-[(1E,3R)-4-(4-fluorophenoxy)-3-hydroxy-1-buten-1-yl]-7-hydroxy-octahydro-2H-cyclopenta[b]oxepin-3-yl}butanoate TLC: Rf 0.55 (ethyl acetate);
$^1$H-NMR (300 MHz, CDCl$_3$): δ 0.90-1.18, 1.22, 1.36-1.98, 1.99-2.18, 2.23, 2.40-2.68, 2.84-2.97, 3.64-3.79, 3.79-3.89, 3.89-4.14, 4.44-4.57, 4.89-5.11, 5.56-5.75, 6.80-6.91, 6.91-7.03.

Example 16 (15)

2-Propanyl 4-[(3S,5aR,6R,7R,8aS)-7-hydroxy-6-{(1E,3R)-3-hydroxy-4-[3-(trifluoromethyl)phenoxy]-1-buten-1-yl}octahydro-2H-cyclopenta[b]oxepin-3-yl]butanoate TLC: Rf 0.46 (ethyl acetate);
$^1$H-NMR (300 MHz, CDCl$_3$): δ 0.90-1.19, 1.19-1.25, 1.36-1.97, 2.00-2.19, 2.23, 2.41-2.56, 2.85-2.98, 3.67-3.80, 3.88-4.09, 4.48-4.60, 4.91-5.08, 5.59-5.76, 7.09, 7.12-7.17, 7.21-7.25, 7.40.

Example 16 (16)

2-Propanyl 4-{(3S,5aR,6R,7R,8aS)-7-hydroxy-6-[(1E,3R)-3-hydroxy-4-(3-methoxyphenoxy)-1-buten-1-yl]octahydro-2H-cyclopenta[b]oxepin-3-yl}butanoate TLC: Rf 0.43 (ethyl acetate);
$^1$H-NMR (300 MHz, CDCl$_3$): δ 0.89-1.18, 1.81-1.26, 1.35-1.97, 2.02-2.19, 2.23, 2.40-2.60, 2.83-2.98, 3.63-4.10, 4.45-4.58, 4.89-5.08, 5.56-5.74, 6.43-6.58, 7.17.

Example 16 (17)

2-Propanyl 4-{(3S,5aR,6R,7R,8aS)-7-hydroxy-6-[(1E,3R)-3-hydroxy-4-(4-methoxyphenoxy)-1-buten-1-yl]octahydro-2H-cyclopenta[b]oxepin-3-yl}butanoate TLC: Rf 0.44 (ethyl acetate);
$^1$H-NMR (300 MHz, CDCl$_3$): δ 0.89-1.18, 1.23, 1.35-1.96, 2.04-2.29, 2.40-2.55, 2.61, 2.84-2.97, 3.64-3.87, 3.89-4.09, 4.43-4.55, 4.91-5.06, 5.56-5.73, 6.75-6.92.

Example 16 (18)

2-Propanyl 4-{(3S,5aR,6R,7R,8aS)-7-hydroxy-6-[(1E,3R)-3-hydroxy-4-(2-methylphenoxy)-1-buten-1-yl]octahydro-2H-cyclopenta[b]oxepin-3-yl}butanoate TLC: Rf 0.50 (ethyl acetate);
$^1$H-NMR (300 MHz, CDCl$_3$): δ 0.85-1.19, 1.19-1.26, 1.33-1.97, 1.98-2.18, 2.18-2.30, 2.38-2.59, 2.82-3.00, 3.62-3.81, 3.83-4.14, 4.46-4.64, 4.88-5.09, 5.56-5.78, 6.77-6.84, 6.84-6.94, 7.05-7.21.

Example 16 (19)

2-Propanyl 4-{(3S,5aR,6R,7R,8aS)-6-[(1E,3R)-4-(2-chlorophenoxy)-3-hydroxy-1-buten-1-yl]-7-hydroxyoctahydro-2H-cyclopenta[b]oxepin-3-yl}butanoate TLC: Rf 0.48 (ethyl acetate);
$^1$H-NMR (300 MHz, CDCl$_3$): δ 0.87-1.18, 1.22, 1.35-1.95, 1.99-2.18, 2.23, 2.40-2.54, 2.62-2.74, 2.91, 3.65-3.80, 3.88-3.99, 3.99-4.11, 4.49-4.65, 4.89-5.08, 5.57-5.76, 6.86-6.98, 7.15-7.24, 7.30-7.40.

Example 16 (20)

2-Propanyl 6-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}hexanoate TLC: Rf 0.59 (ethyl acetate);
$^1$H-NMR (300 MHz, CDCl$_3$): δ 0.88-1.17, 1.18-1.37, 1.40-1.94, 1.98-2.19, 2.20-2.30, 2.36-2.56, 2.89, 3.66-4.10, 4.46-4.59, 4.91-5.07, 5.57-5.75, 6.87-7.01, 7.24-7.33.

Example 16 (21)

2-Propanyl 4-{(3S,5aR,6R,7R,8aS)-6-[(1E,3R)-4-(3,5-dichlorophenoxy)-3-hydroxy-1-buten-1-yl]-7-hydroxyoctahydro-2H-cyclopenta[b]oxepin-3-yl}butanoate TLC: Rf 0.57 (ethyl acetate);
$^1$H-NMR (300 MHz, CDCl$_3$): δ 0.87-1.19, 1.17-1.25, 1.33-1.83, 1.82-1.98, 2.00-2.19, 2.23, 2.38-2.59, 2.82-2.97, 3.63-3.79, 3.80-4.16, 4.40-4.61, 4.88-5.10, 5.52-5.75, 6.81, 6.97.

Example 16 (22)

2-Propanyl 4-[(3S,5aR,6R,7R,8aS)-6-[(1E,3R)-4-(3-chloro-5-fluorophenoxy)-3-hydroxy-1-buten-1-yl]-7-hydroxyoctahydro-2H-cyclopenta[b]oxepin-3-yl]butanoate TLC: Rf 0.56 (ethyl acetate);
$^1$H-NMR (300 MHz, CDCl$_3$): δ 0.87-1.17, 1.81-1.25, 1.34-1.83, 1.83-1.97, 2.04-2.18, 2.23, 2.40-2.55, 2.84-2.97, 3.64-3.79, 3.82-3.90, 3.91-3.99, 3.99-4.13, 4.41-4.59, 4.90-5.09, 5.53-5.74, 6.48-6.59, 6.65-6.79.

Example 16 (23)

2-Propanyl 4-{(3S,5aR,6R,7R,8aS)-6-[(1E,3R)-4-(2,3-difluorophenoxy)-3-hydroxy-1-buten-1-yl]-7-hydroxyoctahydro-2H-cyclopenta[b]oxepin-3-yl}butanoate TLC: Rf 0.51 (ethyl acetate);
$^1$H-NMR (300 MHz, CDCl$_3$): δ 0.88-1.18, 1.18-1.26, 1.34-1.81, 1.82-1.99, 2.04-2.16, 2.18-2.28, 2.37-2.56, 2.73, 2.91, 3.63-3.80, 3.87-4.15, 4.46-4.65, 4.86-5.07, 5.53-5.77, 6.67-6.85, 6.89-7.07.

Example 16 (24)

2-Propanyl 4-{(3S,5aR,6R,7R,8aS)-6-[(1E,3R)-4-(3,5-difluorophenoxy)-3-hydroxy-1-buten-1-yl]-7-hydroxyoctahydro-2H-cyclopenta[b]oxepin-3-yl}butanoate TLC: Rf 0.54 (ethyl acetate);
$^1$H-NMR (300 MHz, CDCl$_3$): δ 0.87-1.18, 1.18-1.25, 1.36-1.84, 1.82-1.97, 2.03-2.19, 2.23, 2.40-2.58, 2.83-2.99, 3.65-3.80, 3.81-3.90, 3.90-4.12, 4.41-4.59, 4.87-5.11, 5.52-5.79, 6.32-6.54.

Example 16 (25)

2-Propanyl 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate

[Chemical formula 57]

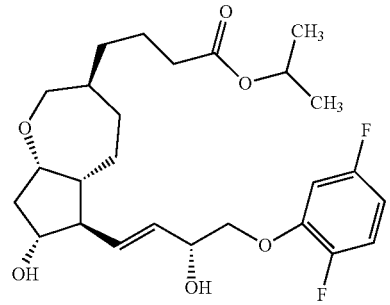

TLC: Rf 0.54 (ethyl acetate);
$^1$H-NMR (300 MHz, CDCl$_3$): δ 0.92-1.18, 1.21, 1.34-1.82, 1.82-1.96, 2.03-2.18, 2.23, 2.28, 2.41-2.54, 2.78, 2.84-2.98, 3.62-3.80, 3.86-4.11, 4.47-4.61, 4.89-5.07, 5.54-5.76, 6.54-6.66, 6.66-6.76, 6.93-7.05.

Example 16 (26)

2-Propanyl 4-{(3S,5aR,6R,7R,8aS)-6-[(1E,3R)-4-(5-chloro-2-fluorophenoxy)-3-hydroxy-1-buten-1-yl]-7-hydroxyoctahydro-2H-cyclopenta[b]oxepin-3-yl}butanoate TLC: Rf 0.69 (ethyl acetate);
$^1$H-NMR (300 MHz, CDCl$_3$): δ 0.90-1.19, 1.22, 1.37-1.96, 2.03-2.29, 2.41-2.54, 2.68, 2.91, 3.65-3.80, 3.86-4.11, 4.48-4.60, 4.91-5.08, 5.55-5.75, 6.86-6.94, 6.94-7.06.

Example 16 (27)

2-Propanyl 4-{(3S,5aR,6R,7R,8aS)-6-[(1E,3R)-4-(3-chloro-4-fluorophenoxy)-3-hydroxy-1-buten-1-yl]-7-hydroxyoctahydro-2H-cyclopenta[b]oxepin-3-yl}butanoate TLC: Rf 0.58 (ethyl acetate);
$^1$H-NMR (300 MHz, CDCl$_3$): δ 0.91-1.19, 1.21, 1.37-1.97, 2.02-2.19, 2.23, 2.41-2.54, 2.91, 3.66-3.80, 3.80-3.89, 3.89-4.10, 4.45-4.56, 4.99, 5.55-5.75, 6.73-6.81, 6.95, 7.00-7.10.

Example 16 (28)

2-Propanyl 4-{(3S,5aR,6R,7R,8aS)-6-[(1E,3R)-3-hydroxy-4-phenoxy-1-buten-1-yl]-7-methoxyoctahydro-2H-cyclopenta[b]oxepin-3-yl}butanoate TLC: Rf 0.72 (hexane:ethyl acetate=1:1);
$^1$H-NMR (300 MHz, CDCl$_3$): δ 0.88-1.19, 1.22, 1.36-1.81, 1.81-1.97, 2.15-2.29, 2.42, 2.46-2.59, 2.91, 3.25-3.47, 3.81-4.09, 4.46-4.59, 4.89-5.10, 5.56-5.67, 5.69-5.82, 6.87-7.02, 7.23-7.35.

Example 16 (29)

2-Propanyl 4-{(3S,5aR,6R,7R,8aS)-6-[(1E,3R)-4-(3-chloro-2-fluorophenoxy)-3-hydroxy-1-buten-1-yl]-7-hydroxyoctahydro-2H-cyclopenta[b]oxepin-3-yl}butanoate TLC: Rf 0.37 (ethyl acetate);
$^1$H-NMR (300 MHz, CDCl$_3$): δ 0.84-1.18, 1.19-1.27, 1.34-1.97, 2.02-2.19, 2.23, 2.39-2.54, 2.66, 2.81-2.99, 3.61-3.82, 3.86-4.12, 4.45-4.63, 4.88-5.09, 5.55-5.76, 6.82-6.91, 6.93-7.07.

Example 16 (30)

2-Propanyl {(3R,5aR,6R,7R,8aS)-6-[(1E,3R)-4-(3-chlorophenoxy)-3-hydroxy-1-buten-1-yl]-7-hydroxyoctahydro-2H-cyclopenta[b]oxepin-3-yl}acetate TLC: Rf 0.43 (ethyl acetate);
$^1$H-NMR (300 MHz, CDCl$_3$): δ 1.02-1.19, 1.22, 1.42-1.59, 1.63-1.96, 2.02-2.28, 2.41-2.55, 2.60, 2.92-3.04, 3.65-3.79, 3.82-3.92, 3.92-4.12, 4.44-4.58, 4.89-5.08, 5.55-5.75, 6.80, 6.91, 6.95, 7.19.

Example 16 (31)

2-Propanyl 4-{(3S,5aR,6R,7R,8aS)-6-[(1E,3R)-4-(2,4-difluorophenoxy)-3-hydroxy-1-buten-1-yl]-7-hydroxyoctahydro-2H-cyclopenta[b]oxepin-3-yl}butanoate TLC: Rf 0.63 (ethyl acetate);
$^1$H-NMR (300 MHz, CDCl$_3$): δ 0.89-1.18, 1.18-1.25, 1.35-1.82, 1.82-1.94, 2.03-2.16, 2.23, 2.40-2.56, 2.84-2.95, 2.97, 3.70, 3.85-4.08, 4.46-4.55, 4.92-5.06, 5.55-5.71, 6.73-6.98.

Example 16 (32)

2-Propanyl 4-{(3S,5aR,6R,7R,8aS)-6-[(1E,3R)-4-(3,4-difluorophenoxy)-3-hydroxy-1-buten-1-yl]-7-hydroxyoctahydro-2H-cyclopenta[b]oxepin-3-yl}butanoate TLC: Rf 0.62 (ethyl acetate);
$^1$H-NMR (300 MHz, CDCl$_3$): δ 0.91-1.18, 1.22, 1.36-1.83, 1.83-1.96, 2.05-2.18, 2.23, 2.48, 2.53-2.59, 2.85-2.96, 3.65-3.78, 3.79-3.87, 3.89-4.09, 4.44-4.55, 4.91-5.07, 5.56-5.73, 6.57-6.64, 6.73, 6.99-7.12.

Example 16 (33)

2-Propanyl 4-{(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoate TLC: Rf 0.28 (dichloromethane:methanol=20:1);
$^1$H-NMR (300 MHz, CDCl$_3$): δ 1.22, 1.34-1.98, 2.07-2.19, 2.21-2.33, 2.40, 2.77, 3.02, 3.40, 3.65-3.77, 3.78-4.03, 4.44-4.56, 4.92-5.08, 5.57-5.71, 6.87-7.01, 7.24-7.34.

Example 16 (34)

Ethyl 4-{(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoate TLC: Rf 0.25 (dichloromethane:methanol=20:1);
$^1$H-NMR (300 MHz, CDCl$_3$): δ 1.25, 1.35-1.88, 2.08-2.23, 2.22-2.49, 2.67, 3.41, 3.64-4.06, 4.12, 4.46-4.59, 5.58-5.78, 6.85-7.06, 7.22-7.37.

Example 16 (35)

Ethyl 4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoate

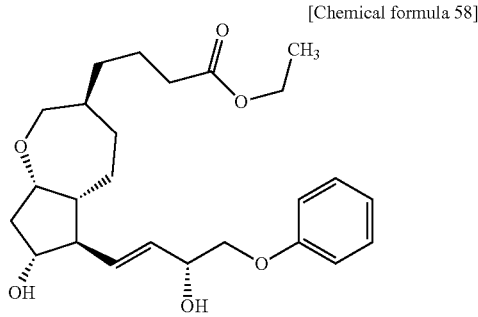 [SMILES: CCOC(=O)CCC[C@H]1CC[C@@H]2[C@@H](/C=C/[C@@H](O)COc3ccccc3)[C@H](O)C[C@@H]2OC1]

[Chemical formula 58]

TLC: Rf 0.23 (dichloromethane:methanol=20:1);
$^1$H-NMR (300 MHz, CDCl$_3$): δ 0.89-1.20, 1.25, 1.35-1.99, 2.03-2.19, 2.26, 2.41-2.54, 2.58, 2.91, 3.65-3.81, 3.83-4.08, 4.12, 4.46-4.61, 5.58-5.75, 6.84-7.05, 7.22-7.37.

Example 16 (36)

2-Propanyl 4-{(3R,5aR,6R,7R,8aS)-6-[(1E,3R)-4-(3-chlorophenoxy)-3-hydroxy-1-buten-1-yl]-7-hydroxyoctahydro-2H-cyclopenta[b]oxepin-3-yl}butanoate TLC: Rf 0.47 (ethyl acetate);
$^1$H-NMR (300 MHz, CDCl$_3$): δ 1.23, 1.34-1.89, 2.07-2.22, 2.27, 2.34-2.46, 2.47-2.67, 3.41, 3.67-4.06, 4.43-4.60, 4.91-5.10, 5.54-5.77, 6.78-6.84, 6.92, 6.93-6.99, 7.20.

Example 16 (37)

2-Propanyl 4-{(3R,5aR,6R,7R,8aS)-6-[(1E,3S)-4-(3-chlorophenoxy)-3-hydroxy-1-buten-1-yl]-7-hydroxy-octahydro-2H-cyclopenta[b]oxepin-3-yl}butanoate TLC: Rf 0.47 (ethyl acetate);
$^1$H-NMR (300 MHz, CDCl$_3$): δ 1.23, 1.33-1.87, 1.86-1.96, 2.10-2.23, 2.23-2.50, 3.42, 3.68-3.90, 3.93-4.07, 4.44-4.63, 4.91-5.10, 5.56-5.79, 6.77-6.85, 6.92, 6.93-7.00, 7.20.

Example 16 (38)

2-Propanyl 4-{(3S,5aR,6R,7R,8aS)-6-[(1E,3S)-4-(3-chlorophenoxy)-3-hydroxy-1-buten-1-yl]-7-hydroxy-octahydro-2H-cyclopenta[b]oxepin-3-yl}butanoate TLC: Rf 0.65 (ethyl acetate);
$^1$H-NMR (300 MHz, CDCl$_3$): δ 0.66-2.01, 2.04-2.18, 2.23, 2.29-2.57, 2.91, 3.73, 3.85, 3.90-4.13, 4.45-4.59, 4.90-5.07, 5.53-5.78, 6.75-6.84, 6.91, 6.92-6.98, 7.19.

Example 16 (39)

2-Propanyl 4-{(3S,5aR,6R,7R,8aS)-6-[(1E,3S)-4-(2,5-difluorophenoxy)-3-hydroxy-1-buten-1-yl]-7-hydroxyoctahydro-2H-cyclopenta[b]oxepin-3-yl}butanoate TLC: Rf 0.39 (isopropyl alcohol: hexane=1:5);
$^1$H-NMR (300 MHz, CDCl$_3$): δ 0.91-1.18, 1.18-1.26, 1.36-1.83, 1.83-1.97, 2.05-2.19, 2.23, 2.39-2.56, 2.91, 3.63-3.81, 3.82-4.11, 4.48-4.64, 4.88-5.08, 5.54-5.77, 6.53-6.65, 6.66-6.79, 6.93-7.09.

Example 16 (40)

2-Propanyl {(3R,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}acetate TLC: Rf 0.59 (ethyl acetate);
$^1$H-NMR (300 MHz, CDCl$_3$): δ 1.02-1.18, 1.19-1.26, 2.10-2.39, 2.50, 2.76-2.89, 3.00, 3.67-3.80, 3.88-4.13, 4.50-4.61, 5.00, 5.58-5.75, 6.62, 6.72, 7.03.

Example 16 (41)

2-Propanyl 4-{(3R,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate TLC: Rf 0.55 (ethyl acetate);
$^1$H-NMR (300 MHz, CDCl$_3$): δ 1.15-1.34, 1.35-1.87, 2.11-2.25, 2.29, 2.42, 2.69, 3.43, 3.70-4.09, 4.51-4.62, 4.95-5.09, 5.58-5.76, 6.62, 6.73, 7.03.

Example 16 (42)

2-Propanyl 4-{(3S,5aR,6R,7R,8aS)-6-[(1E,3R)-4-(cyclohexyloxy)-3-hydroxy-1-buten-1-yl]-7-hydroxyoctahydro-2H-cyclopenta[b]oxepin-3-yl}butanoate TLC: Rf 0.33 (ethyl acetate);
$^1$H-NMR (300 MHz, CDCl$_3$): δ 0.91-1.35, 1.42-1.76, 1.85-1.93, 2.04-2.12, 2.22-2.27, 2.42-2.51, 2.67, 2.87-2.95, 3.26-3.32, 3.50-3.55, 3.66-3.75, 3.93-4.07, 4.24-4.29, 4.96-5.05, 5.50-5.64.

Example 17 (1)

4-{(3S,5aR,6R,7R,8aS)-6-[(1E,3R)-4-(2,3-difluorophenoxy)-3-hydroxy-1-buten-1-yl]-7-hydroxyoctahydro-2H-cyclopenta[b]oxepin-3-yl}butanoic acid

[Chemical formula 59]

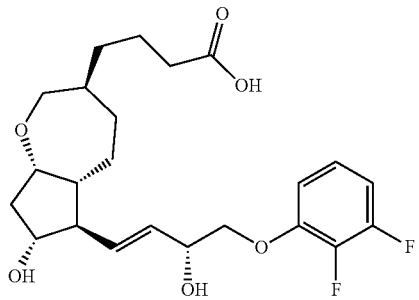

An aqueous sodium hydroxide solution (500 μL) was added to a methanol solution (1.5 mL) of the compound (49 mg, 0.102 mmol) produced in Example 16 (23), and the mixture was stirred at 40° C. for 2 hours. An ice was placed into the reaction solution, and 1N hydrochloric acid (1.2 mL) was added. Extraction with ethyl acetate twice was carried out; and the collected organic layers were washed with a saturated saline, and dried with anhydrous sodium sulfate. The solution was concentrated under reduced pressure, and purified with a silica gel column (BW-235, dichloromethane:methanol=10:1) to obtain a titled compound (45 mg) having the following physical property values.

TLC: Rf 0.56 (ethyl acetate: methanol=8:1);
$^1$H-NMR (300 MHz, CD$_3$OD): δ 0.78-1.24, 1.24-2.08, 2.25, 2.36-2.49, 2.91-3.02, 3.59-3.73, 3.86-4.07, 4.38-4.49, 5.54-5.71, 6.75-6.86, 6.86-6.94, 6.98-7.10.

Example 17 (2) to Example 17 (33)

The compounds produced in Example 16 (1) to Example 16 (22) and Example 16 (24) to Example 16 (33) were subjected to the same objective operations as those of Example 17 (1), respectively, to obtain the following Example compounds.

Example 17 (2)

4-{(3S,5aR,6R,7R,8aS)-7-hydroxy-6-[(1E,3S)-3-hydroxy-5-phenyl-1-penten-1-yl]octahydro-2H-cyclopenta[b]oxepin-3-yl}butanoic acid TLC: Rf 0.38 (dichloromethane:methanol=9:1);
$^1$H-NMR (300 MHz, CDCl$_3$): δ 0.87-1.23, 1.32-1.97, 2.00-2.13, 2.32, 2.40-2.54, 2.57-2.78, 2.91, 3.61-3.75, 3.85-4.20, 5.36-5.48, 5.52-5.66, 7.11-7.33.

Example 17 (3)

4-{(3S,5aR,6R,7R,8aS)-6-[(1E,3R)-4-(3-chlorophenoxy)-3-hydroxy-1-buten-1-yl]-7-hydroxyoctahydro-2H-cyclopenta[b]oxepin-3-yl}butanoic acid

[Chemical formula 60]

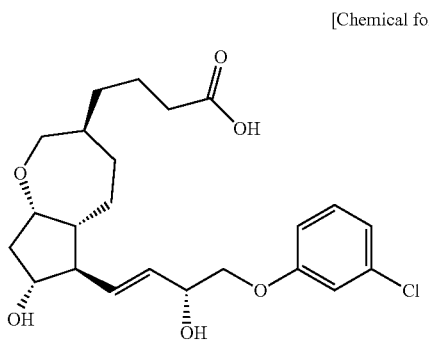

TLC: Rf 0.43 (dichloromethane:methanol=9:1);
$^1$H-NMR (300 MHz, CDCl$_3$): δ 0.83-1.27, 1.35-1.97, 2.02-2.20, 2.33, 2.41-2.55, 2.84-2.99, 3.67-3.78, 3.80-4.11, 4.45-4.58, 5.54-5.74, 6.76-6.84, 6.91-6.98, 7.20.

Example 17 (4)

4-{(3S,5aR,6R,7R,8aS)-7-hydroxy-6-[(1E,3R)-3-hydroxy-4-(3-methylphenoxy)-1-buten-1-yl]octahydro-2H-cyclopenta[b]oxepin-3-yl}butanoic acid TLC: Rf 0.46 (dichloromethane:methanol=6:1);
$^1$H-NMR (300 MHz, CDCl$_3$): δ 0.80-1.21, 1.35-1.97, 2.00-2.19, 2.24-2.38, 2.40-2.55, 2.91, 3.65-3.78, 3.82-3.90, 3.90-4.08, 4.45-4.57, 5.54-5.73, 6.65-6.75, 6.78, 7.16.

Example 17 (5)

4-{(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}benzoic acid TLC: Rf 0.36 (chloroform: methanol=9:1);
$^1$H-NMR (300 MHz, CD$_3$OD): δ 1.46-2.17, 2.40-2.56, 2.87-3.03, 3.33-3.45, 3.63-3.77, 3.83-4.23, 4.35-4.49, 5.58-5.76, 6.82-6.99, 7.16-7.37, 7.92.

Example 17 (6)

4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}benzoic acid TLC: Rf 0.34 (chloroform: methanol=9:1);
$^1$H-NMR (300 MHz, CDCl$_3$): δ 1.47-1.96, 1.95-2.12, 2.16-2.36, 2.44-2.61, 2.97-3.15, 3.67-4.18, 4.28, 4.45-4.61, 5.56-5.75, 6.85-7.02, 7.22-7.34, 7.46-7.54, 7.99-8.07.

Example 17 (7)

3-{(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}benzoic acid TLC: Rf 0.45 (chloroform:methanol:acetic acid=10:1:0.1);
$^1$H-NMR (300 MHz, CD$_3$OD): δ 1.49-2.20, 2.41-2.56, 2.86-3.03, 3.32-3.44, 3.63-3.78, 3.85-4.22, 4.37-4.49, 5.58-5.75, 6.84-6.98, 7.17-7.30, 7.33-7.48, 7.79-7.89.

Example 17 (8)

3-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}benzoic acid TLC: Rf 0.45 (chloroform:methanol:acetic acid=10:1:0.1);
$^1$H-NMR (300 MHz, CDCl$_3$): δ 1.48-1.72, 1.73-1.94, 1.95-2.13, 2.21-2.37, 2.43-2.59, 3.00-3.15, 3.66-4.00, 4.03-4.14, 4.25, 4.44-4.56, 5.56-5.74, 6.82-6.99, 7.19-7.30, 7.39, 7.65, 7.94, 8.11.

Example 17 (9)

4-{(3S,5aR,6R,7R,8aS)-6-[(1E,3R)-4-(4-chlorophenoxy)-3-hydroxy-1-buten-1-yl]-7-hydroxyoctahydro-2H-cyclopenta[b]oxepin-3-yl}butanoic acid TLC: Rf 0.40 (chloroform:methanol:acetic acid=10:1:0.1);
$^1$H-NMR (300 MHz, CD$_3$OD): δ 0.93-1.26, 1.26-1.82, 1.82-2.07, 2.25, 2.36-2.50, 2.90-3.03, 3.59-3.71, 3.83-4.05, 4.35-4.45, 5.55-5.70, 6.87-6.95, 7.19-7.28.

Example 17 (10)

4-{(3S,5aR,6R,7R,8aS)-7-hydroxy-6-[(1E,3R)-3-hydroxy-4-(4-methylphenoxy)-1-buten-1-yl]octahydro-2H-cyclopenta[b]oxepin-3-yl}butanoic acid TLC: Rf 0.40 (chloroform:methanol:acetic acid=10:1:0.1);
$^1$H-NMR (300 MHz, CD$_3$OD): δ 0.90-2.08, 2.18-2.33, 2.34-2.51, 2.97, 3.58-3.73, 3.79-4.07, 4.31-4.47, 5.54-5.71, 6.73-6.86, 7.04.

Example 17 (11)

4-[(3S,5aR,6R,7R,8aS)-7-hydroxy-6-{(1E,3R)-3-hydroxy-4-[4-(trifluoromethyl)phenoxy]-1-buten-1-yl}octahydro-2H-cyclopenta[b]oxepin-3-yl]butanoic acid TLC: Rf 0.40 (chloroform:methanol:acetic acid=10:1:0.1);
$^1$H-NMR (300 MHz, CD$_3$OD): δ 0.92-1.94, 1.94-2.08, 2.25, 2.36-2.50, 2.91-3.03, 3.59-3.73, 3.91-4.07, 4.40-4.49, 5.57-5.72, 7.01-7.13, 7.49-7.61.

Example 17 (12)

4-{(3S,5aR,6R,7R,8aS)-6-[(1E,3R)-4-(2-fluorophenoxy)-3-hydroxy-1-buten-1-yl]-7-hydroxyoctahydro-2H-cyclopenta[b]oxepin-3-yl}butanoic acid TLC: Rf 0.39 (dichloromethane:methanol=10:1);
$^1$H-NMR (300 MHz, CD$_3$OD): δ 0.78-2.10, 2.25, 2.35-2.49, 2.89-3.02, 3.58-3.74, 3.90-4.06, 4.34-4.51, 5.53-5.72, 6.83-6.96, 7.01-7.15.

Example 17 (13)

4-{(3S,5aR,6R,7R,8aS)-6-[(1E,3R)-4-(3-fluorophenoxy)-3-hydroxy-1-buten-1-yl]-7-hydroxyoctahydro-2H-cyclopenta[b]oxepin-3-yl}butanoic acid TLC: Rf 0.37 (dichloromethane:methanol=10:1);
$^1$H-NMR (300 MHz, CDCl$_3$): δ 0.80-1.22, 1.34-1.97, 2.05-2.18, 2.32, 2.40-5.56, 2.84-2.98, 3.66-3.78, 3.80-4.10, 4.46-4.57, 5.55-5.74, 6.55-6.75, 7.14-7.28.

Example 17 (14)

4-{(3S,5aR,6R,7R,8aS)-6-[(1E,3R)-4-(4-fluorophenoxy)-3-hydroxy-1-buten-1-yl]-7-hydroxyoctahydro-2H-cyclopenta[b]oxepin-3-yl}butanoic acid TLC: Rf 0.40 (dichloromethane:methanol=10:1);
$^1$H-NMR (300 MHz, CDCl$_3$): δ 0.83-1.21, 1.34-1.98, 2.05-2.18, 2.32, 2.39-2.57, 2.85-3.00, 3.66-3.79, 3.79-3.88, 3.89-4.09, 4.41-4.60, 5.54-5.76, 6.79-6.91, 6.90-7.03.

Example 17 (15)

4-[(3S,5aR,6R,7R,8aS)-7-hydroxy-6-{(1E,3R)-3-hydroxy-4-[3-(trifluoromethyl)phenoxy]-1-buten-1-yl}octahydro-2H-cyclopenta[b]oxepin-3-yl]butanoic acid TLC: Rf 0.37 (chloroform:methanol:acetic acid=10:1:0.1);
$^1$H-NMR (300 MHz, CD$_3$OD): δ 0.92-2.09, 2.25, 2.37-2.50, 2.88-3.04, 3.57-3.74, 3.89-4.07, 4.37-4.49, 5.54-5.74, 7.13-7.27, 7.38-7.51.

Example 17 (16)

4-{(3S,5aR,6R,7R,8aS)-7-hydroxy-6-[(1E,3R)-3-hydroxy-4-(3-methoxyphenoxy)-1-buten-1-yl]octahydro-2H-cyclopenta[b]oxepin-3-yl}butanoic acid TLC: Rf 0.37 (chloroform:methanol:acetic acid=10:1:0.1);
$^1$H-NMR (300 MHz, CD$_3$OD): δ 0.91-1.21, 1.27-1.83, 1.82-2.08, 2.25, 2.36-2.50, 2.90-3.03, 3.59-3.72, 3.75, 3.80-4.05, 4.34-4.45, 5.55-5.70, 6.44-6.55, 7.08-7.18.

Example 17 (17)

4-{(3S,5aR,6R,7R,8aS)-7-hydroxy-6-[(1E,3R)-3-hydroxy-4-(4-methoxyphenoxy)-1-buten-1-yl]octahydro-2H-cyclopenta[b]oxepin-3-yl}butanoic acid TLC: Rf 0.39 (chloroform:methanol:acetic acid=10:1:0.1);
$^1$H-NMR (300 MHz, CD$_3$OD): δ 0.93-1.24, 1.30-1.47, 1.47-1.82, 1.82-2.09, 2.25, 2.36-2.50, 2.90-3.03, 3.59-3.71, 3.73, 3.78-3.92, 3.93-4.05, 4.32-4.42, 5.54-5.70, 6.74-6.92.

Example 17 (18)

4-{(3S,5aR,6R,7R,8aS)-7-hydroxy-6-[(1E,3R)-3-hydroxy-4-(2-methylphenoxy)-1-buten-1-yl]octahydro-2H-cyclopenta[b]oxepin-3-yl}butanoic acid TLC: Rf 0.61 (ethyl acetate: methanol=8:1);
$^1$H-NMR (300 MHz, CD$_3$OD): δ 0.87-1.23, 1.24-1.93, 1.94-2.09, 2.15-2.32, 2.35-2.50, 2.89-3.03, 3.58-3.72, 3.85-4.07, 4.37-4.47, 5.56-5.71, 6.74-6.88, 7.03-7.15.

Example 17 (19)

4-{(3S,5aR,6R,7R,8aS)-6-[(1E,3R)-4-(2-chlorophenoxy)-3-hydroxy-1-buten-1-yl]-7-hydroxyoctahydro-2H-cyclopenta[b]oxepin-3-yl}butanoic acid TLC: Rf 0.50 (ethyl acetate: methanol=8:1);
$^1$H-NMR (300 MHz, CD$_3$OD): δ 0.84-1.21, 1.22-1.93, 1.93-2.10, 2.25, 2.35-2.49, 2.96, 3.57-3.72, 3.89-4.06, 4.39-4.49, 5.57-5.71, 6.90, 7.05, 7.19-7.27, 7.33.

Example 17 (20)

6-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}hexanoic acid TLC: Rf 0.24 (chloroform:methanol:acetic acid=10:1:0.1);
$^1$H-NMR (300 MHz, CD$_3$OD): δ 0.90-1.20, 1.22-1.47, 1.46-1.67, 1.66-1.93, 1.93-2.08, 2.21-2.32, 2.36-2.49, 2.95, 3.59-3.72, 3.83-4.07, 4.35-4.47, 5.55-5.71, 6.86-6.95, 7.19-7.30.

Example 17 (21)

4-{(3S,5aR,6R,7R,8aS)-6-[(1E,3R)-4-(3,5-dichlorophenoxy)-3-hydroxy-1-buten-1-yl]-7-hydroxyoctahydro-2H-cyclopenta[b]oxepin-3-yl}butanoic acid TLC: Rf 0.62 (ethyl acetate: methanol=8:1);
$^1$H-NMR (300 MHz, CD$_3$OD): δ 0.90-1.22, 1.25-2.09, 2.25, 2.35-2.51, 2.97, 3.58-3.72, 3.83-4.08, 4.31-4.48, 5.50-5.73, 6.93, 6.98.

Example 17 (22)

4-{(3S,5aR,6R,7R,8aS)-6-[(1E,3R)-4-(3-chloro-5-fluorophenoxy)-3-hydroxy-1-buten-1-yl]-7-hydroxyoctahydro-2H-cyclopenta[b]oxepin-3-yl}butanoic acid TLC: Rf 0.62 (ethyl acetate: methanol=8:1);
$^1$H-NMR (300 MHz, CD$_3$OD): δ 0.90-1.22, 1.27-2.10, 2.26, 2.37-2.51, 2.97, 3.58-3.73, 3.85-4.06, 4.35-4.47, 5.54-5.72, 6.69, 6.75, 6.79-6.85.

Example 17 (23)

4-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoic acid

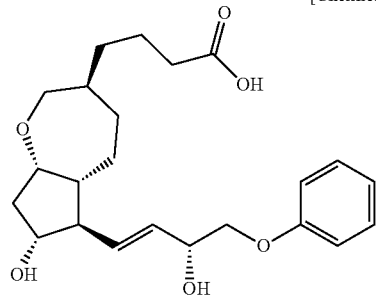

[Chemical formula 61]

TLC: Rf 0.33 (chloroform: methanol=10:1);
$^1$H-NMR (300 MHz, CDCl$_3$): δ 0.90-1.30, 1.37-1.81, 1.82-1.96, 2.04-2.19, 2.32, 2.41-2.54, 2.85-2.98, 3.65-3.79, 3.84-4.10, 4.47-4.58, 5.57-5.74, 6.86-7.03, 7.23-7.35.

Example 17 (24)

4-{(3S,5aR,6R,7R,8aS)-6-[(1E,3R)-4-(3,5-difluorophenoxy)-3-hydroxy-1-buten-1-yl]-7-hydroxyoctahydro-2H-cyclopenta[b]oxepin-3-yl}butanoic acid TLC: Rf 0.59 (ethyl acetate: methanol=8:1);
$^1$H-NMR (300 MHz, CD$_3$OD): δ 0.91-1.24, 1.24-2.11, 2.25, 2.35-2.51, 2.97, 3.57-3.75, 3.80-4.11, 4.29-4.50, 5.50-5.77, 6.38-6.68.

Example 17 (25)

4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoic acid

[Chemical formula 62]

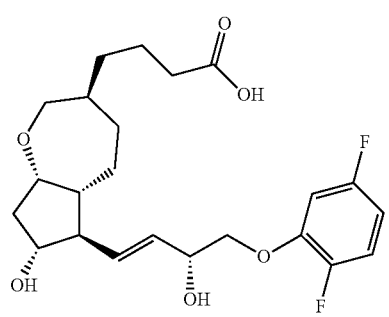

TLC: Rf 0.60 (ethyl acetate: methanol=8:1);
$^1$H-NMR (300 MHz, CD$_3$OD): δ 0.89-1.23, 1.25-1.94, 1.95-2.10, 2.25, 2.35-2.51, 2.92-3.03, 3.58-3.73, 3.87-4.09, 4.35-4.50, 5.55-5.75, 6.58-6.71, 6.84-6.97, 6.99-7.14.

Example 17 (26)

4-{(3S,5aR,6R,7R,8aS)-6-[(1E,3R)-4-(5-chloro-2-fluorophenoxy)-3-hydroxy-1-buten-1-yl]-7-hydroxyoctahydro-2H-cyclopenta[b]oxepin-3-yl}butanoic acid TLC: Rf 0.59 (chloroform:methanol:acetic acid=10:1:0.1);
$^1$H-NMR (300 MHz, CD$_3$OD): δ 0.92-1.20, 1.29-1.46, 1.46-2.08, 2.25, 2.36-2.49, 2.91-3.02, 3.59-3.71, 3.92-4.05, 4.38-4.47, 5.55-5.71, 6.88-6.94, 7.07, 7.13.

Example 17 (27)

4-{(3S,5aR,6R,7R,8aS)-6-[(1E,3R)-4-(3-chloro-4-fluorophenoxy)-3-hydroxy-1-buten-1-yl]-7-hydroxyoctahydro-2H-cyclopenta[b]oxepin-3-yl}butanoic acid TLC: Rf 0.58 (chloroform:methanol:acetic acid=10:1:0.1);
$^1$H-NMR (300 MHz, CD$_3$OD): δ 0.92-1.22, 1.30-1.47, 1.47-1.83, 1.82-2.07, 2.25, 2.36-2.49, 2.90-3.03, 3.59-3.72, 3.82-4.05, 4.35-4.44, 5.54-5.70, 6.84-6.92, 7.04, 7.13.

Example 17 (28)

4-{(3S,5aR,6R,7R,8aS)-6-[(1E,3R)-3-hydroxy-4-phenoxy-1-buten-1-yl]-7-methoxyoctahydro-2H-cyclopenta[b]oxepin-3-yl}butanoic acid TLC: Rf 0.43 (chloroform:methanol:water=10:1:0.1);
$^1$H-NMR (300 MHz, CDCl$_3$): δ 0.89-1.22, 1.35-1.81, 1.81-1.97, 2.15-2.28, 2.32, 2.46-2.59, 2.92, 3.26-3.46, 3.82-4.09, 4.48-4.58, 5.55-5.67, 5.69-5.82, 6.87-7.02, 7.24-7.34.

Example 17 (29)

4-{(3S,5aR,6R,7R,8aS)-6-[(1E,3R)-4-(3-chloro-2-fluorophenoxy)-3-hydroxy-1-buten-1-yl]-7-hydroxyoctahydro-2H-cyclopenta[b]oxepin-3-yl}butanoic acid TLC: Rf 0.26 (dichloromethane:methanol=5:1);
$^1$H-NMR (300 MHz, CD$_3$OD): δ 0.89-1.23, 1.25-2.06, 2.25, 2.31-2.51, 2.87-3.03, 3.57-3.75, 3.87-4.09, 4.35-4.50, 5.52-5.73, 6.89-7.15.

Example 17 (30)

{(3R,5aR,6R,7R,8aS)-6-[(1E,3R)-4-(3-chlorophenoxy)-3-hydroxy-1-buten-1-yl]-7-hydroxyoctahydro-2H-cyclopenta[b]oxepin-3-yl}acetic acid TLC: Rf 0.26 (chloroform:methanol:acetic acid=10:1:0.1);
$^1$H-NMR (300 MHz, CD$_3$OD): δ 1.04-1.20, 1.35-1.63, 1.65-2.19, 2.37-2.50, 2.97-3.09, 3.25-3.38, 3.59-3.72, 3.85-4.07, 4.35-4.46, 5.55-5.70, 6.86, 6.89-6.97, 7.22.

Example 17 (31)

4-{(3S,5aR,6R,7R,8aS)-6-[(1E,3R)-4-(2,4-difluorophenoxy)-3-hydroxy-1-buten-1-yl]-7-hydroxyoctahydro-2H-cyclopenta[b]oxepin-3-yl}butanoic acid TLC: Rf 0.22 (chloroform:methanol:water=10:1:0.1);
$^1$H-NMR (300 MHz, CD$_3$OD): δ 0.87-1.26, 1.26-1.82, 1.81-1.94, 1.94-2.07, 2.25, 2.43, 2.97, 3.65, 3.91-4.06, 4.36-4.47, 5.54-5.71, 6.79-6.89, 6.95, 7.09.

Example 17 (32)

4-{(3S,5aR,6R,7R,8aS)-6-[(1E,3R)-4-(3,4-difluorophenoxy)-3-hydroxy-1-buten-1-yl]-7-hydroxyoctahydro-2H-cyclopenta[b]oxepin-3-yl}butanoic acid TLC: Rf 0.22 (chloroform:methanol:water=10:1:0.1);
$^1$H-NMR (300 MHz, CD$_3$OD): δ 0.93-1.24, 1.27-1.83, 1.82-1.94, 1.94-2.07, 2.25, 2.43, 2.97, 3.65, 3.81-4.06, 4.35-4.44, 5.54-5.71, 6.67-6.76, 6.86, 7.13.

Example 17 (33)

4-{(5aR,6R,7R,8aS)-7-hydroxy-6-[(1E,3R)-3-hydroxy-4-phenoxy-1-buten-1-yl]octahydro-2H-cyclopenta[b]oxepin-3-yl}butanoic acid (low polar body)

TLC: Rf 0.40 (chloroform: methanol=10:1);
$^1$H-NMR (300 MHz, CDCl$_3$): δ 1.12-1.91, 2.07-2.91, 3.34-3.50, 3.65-4.06, 4.46-4.58, 5.56-5.73, 6.84-7.05, 7.22-7.35.

Example 17 (34)

4-{(3S,5aR,6R,7R,8aS)-7-hydroxy-6-[(1E,3S)-3-hydroxy-1-octen-1-yl]octahydro-2H-cyclopenta[b]oxepin-3-yl}butanoic acid With using (3aR,4S,5R,6aS)-4-({[dimethyl(2-methyl-2-propanyl)silyl]oxy}methyl)-5-(tetrahydro-2H-pyran-2-yloxy)hexahydro-2H-cyclopenta[b]furan-2-one; using 4-ethoxy-4-oxobutylzinc bromide; and using a corresponding phosphonic acid salt in place of dimethyl-(3-phenoxy-2-oxopropyl)-phosphonate, the substances were subjected to the same objective operations as those of Example 1→Example 2→Example 3→Example 4→Example 5→Example 6→Example 7→Example 8→Example 9→Example 10→Example 11→Example 12→Example 13→Example 14→Example 15→Example 16 (1)→Example 17 (1) to obtain a titled compound having the following physical property values.

TLC: Rf 0.53 (ethyl acetate: methanol=8:1);
$^1$H-NMR (300 MHz, CD$_3$OD): δ 0.77-1.21, 1.22-1.82, 1.82-2.05, 2.25, 2.35-2.48, 2.91-3.02, 3.56-3.69, 3.88-4.07, 5.34-5.56.

Example 17 (35) to Example 17 (41)

With using the compounds produced in Example 16 (36) to Example 16 (42), these compounds were subjected to the same objective operations as those of Example 17 (1) to obtain the following Example compounds.

Example 17 (35)

4-{(3R,5aR,6R,7R,8aS)-6-[(1E,3R)-4-(3-chlorophenoxy)-3-hydroxy-1-buten-1-yl]-7-hydroxyoctahydro-2H-cyclopenta[b]oxepin-3-yl}butanoic acid TLC: Rf 0.64 (dichloromethane:methanol=5:1);
$^1$H-NMR (300 MHz, CD$_3$OD): δ 1.36-1.86, 1.97-2.12, 2.29, 2.33-2.45, 3.45, 3.61-3.73, 3.77-3.85, 3.85-4.05, 4.34-4.47, 5.55-5.71, 6.83-6.89, 6.89-6.94, 6.94-6.97, 7.22.

Example 17 (36)

4-{(3R,5aR,6R,7R,8aS)-6-[(1E,3S)-4-(3-chlorophenoxy)-3-hydroxy-1-buten-1-yl]-7-hydroxyoctahydro-2H-cyclopenta[b]oxepin-3-yl}butanoic acid TLC: Rf 0.63 (dichloromethane:methanol=5:1);
$^1$H-NMR (300 MHz, CDCl$_3$): δ 1.37-1.88, 1.94-2.13, 2.29, 2.33-2.46, 3.45, 3.60-3.74, 3.76-3.93, 3.94-4.06, 4.36-4.47, 5.57-5.72, 6.84-6.89, 6.89-6.94, 6.96, 7.22.

Example 17 (37)

4-{(3S,5aR,6R,7R,8aS)-6-[(1E,3S)-4-(3-chlorophenoxy)-3-hydroxy-1-buten-1-yl]-7-hydroxyoctahydro-2H-cyclopenta[b]oxepin-3-yl}butanoic acid TLC: Rf 0.58 (ethyl acetate);
$^1$H-NMR (300 MHz, CDCl$_3$): δ 0.76-2.13, 2.25, 2.35-2.50, 2.90-3.03, 3.60-3.73, 3.82-3.92, 3.92-4.06, 4.35-4.49, 5.55-5.73, 6.83-6.89, 6.86-6.94, 6.96, 7.22.

Example 17 (38)

4-{(3S,5aR,6R,7R,8aS)-6-[(1E,3S)-4-(2,5-difluorophenoxy)-3-hydroxy-1-buten-1-yl]-7-hydroxyoctahydro-2H-cyclopenta[b]oxepin-3-yl}butanoic acid TLC: Rf 0.44 (dichloromethane:methanol=10:1);
$^1$H-NMR (300 MHz, CD$_3$OD): δ 0.90-1.71, 1.71-1.86, 1.84-2.11, 2.25, 2.34-2.52, 2.90-3.03, 3.56-3.75, 3.85-4.14, 4.37-4.56, 5.51-5.78, 6.49-6.73, 6.82-7.00, 7.00-7.18.

Example 17 (39)

{(3R,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}acetic acid TLC: Rf 0.50 (dichloromethane:methanol=5:1);
$^1$H-NMR (300 MHz, CD$_3$OD): δ 1.01-1.21, 1.33-1.62, 1.66-1.95, 1.95-2.18, 2.44, 2.94-3.12, 3.66, 3.94-4.08, 4.40-4.48, 5.57-5.72, 6.63, 6.92, 7.07.

Example 17 (40)

4-{(3R,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoic acid TLC: Rf 0.49 (dichloromethane:methanol=7:1);
$^1$H-NMR (300 MHz, CD$_3$OD): δ 1.38-1.86, 1.98-2.13, 2.29, 2.38, 3.46, 3.68, 3.76-3.87, 3.95-4.06, 4.40-4.49, 5.57-5.72, 6.63, 6.93, 7.08.

Example 17 (41)

4-{(3S,5aR,6R,7R,8aS)-6-[(1E,3R)-4-(cyclohexyloxy)-3-hydroxy-1-buten-1-yl]-7-hydroxyoctahydro-2H-cyclopenta[b]oxepin-3-yl}butanoic acid TLC: Rf 0.81 (dichloromethane:methanol=4:1);
$^1$H-NMR (300 MHz, CDCl$_3$): δ 0.95-1.90, 2.05-2.15, 2.32-2.37, 2.43-2.52, 2.89-2.97, 3.27-3.33, 3.51-3.55, 3.66-3.75, 3.93-4.08, 4.25-4.31, 5.50-5.64.

Example 17 (42) to Example 17 (45)

With using (3aR,4S,5R,6aS)-4-({[dimethyl(2-methyl-2-propanyl)silyl]oxy}methyl)-5-(tetrahydro-2H-pyran-2-yloxy)hexahydro-2H-cyclopenta[b]furan-2-one; using 4-ethoxy-4-oxobutylzinc bromide or a corresponding organozinc reagent in place of it; and using dimethyl-(3-phenoxy-2-oxopropyl)-phosphonate or a corresponding phosphonic acid salt in place of it, the compounds produced with using the methods described in items of Example 16 (2) to Example 16 (42) were subjected to the same objective operations as those of Example 17 (1) to obtain the following Example compounds.

Example 17 (42)

4-[(3S,5aR,6R,7R,8aS)-6-{(1E,3R)-4-[2-fluoro-5-(trifluoromethyl)phenoxy]-3-hydroxy-1-buten-1-yl}-7-hydroxyoctahydro-2H-cyclopenta[b]oxepin-3-yl]butanoic acid TLC: Rf 0.38 (ethyl acetate: methanol=9:1);
$^1$H-NMR (300 MHz, DMSO-d$_6$): δ 11.97, 7.52-7.39, 7.31, 5.55, 5.48, 5.16, 4.60, 4.30, 4.04-4.00, 3.90-3.81, 3.48, 2.83, 2.27, 2.15, 1.89-1.70, 1.66-1.18, 1.11-0.83.

Example 17 (43)

4-{(3S,5aR,6R,7R,8aS)-6-[(1E,3R)-4-(2,6-difluorophenoxy)-3-hydroxy-1-buten-1-yl]-7-hydroxyoctahydro-2H-cyclopenta[b]oxepin-3-yl}butanoic acid TLC: Rf 0.36 (ethyl acetate: methanol=9:1);
$^1$H-NMR (300 MHz, DMSO-$d_6$): δ 11.97, 7.12-7.07, 5.54, 5.47, 5.07, 4.60, 4.23, 3.97-3.82, 3.48, 2.83, 2.27, 2.15, 1.88-1.72, 1.65-1.20, 1.07-0.85.

Example 17 (44)

4-[(3S,5aR,6R,7R,8aS)-7-hydroxy-6-{(1E,3R)-3-hydroxy-4-[3-(trifluoromethoxy)phenoxy]-1-buten-1-yl}octahydro-2H-cyclopenta[b]oxepin-3-yl]butanoic acid TLC: Rf 0.36 (ethyl acetate: methanol=9:1);
$^1$H-NMR (300 MHz, DMSO-$d_6$): δ 11.96, 7.39, 6.99-6.88, 5.55, 5.48, 5.11, 4.60, 4.28, 3.90-3.83, 3.50, 2.83, 2.27, 2.15, 1.90-1.73, 1.67-1.20, 1.12-0.85.

Example 17 (45)

4-[(3S,5aR,6R,7R,8aS)-6-{(1E,3R)-4-[2-fluoro-3-(trifluoromethyl)phenoxy]-3-hydroxy-1-buten-1-yl}-7-hydroxyoctahydro-2H-cyclopenta[b]oxepin-3-yl]butanoic acid TLC: Rf 0.32 (ethyl acetate: methanol=9:1);
$^1$H-NMR (300 MHz, DMSO-$d_6$): δ 11.96, 7.53, 7.33-7.23, 5.55, 5.47, 5.18, 4.61, 4.31, 4.03-3.95, 3.89-3.81, 3.50, 2.83, 2.27, 2.15, 1.90-1.69, 1.65-1.17, 1.11-0.82.

Example 18 (1)

2-Propanyl 4-{(3S,5aR,6R,7R,8aS)-7-hydroxy-6-[(3R)-3-hydroxy-4-phenoxybutyl]octahydro-2H-cyclopenta[b]oxepin-3-yl}butanoate

[Chemical formula 63]

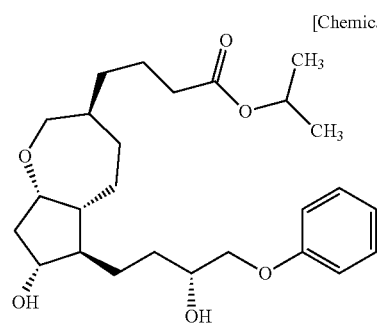

Under the hydrogen atmosphere, palladium-carbon (15 mg) was added to a 2-propanol solution (62 mL) of the compound (71 mg, 1.59 mmol) obtained in Example 16 (1), and the mixture was stirred at room temperature for 3 hours and 20 minutes. The reaction solution was filtered with Celite (trade name), concentrated under reduced pressure, and purified with a column apparatus (Hiflash-SI, Size S, ethyl acetate:hexane=1:1→ethyl acetate) manufactured by Yamazen Corporation to obtain a titled compound (63 mg) having the following physical property values.

TLC: Rf 0.55 (ethyl acetate);
$^1$H-NMR (300 MHz, CDCl$_3$): δ 0.92-1.19, 1.22, 1.35-1.99, 2.15-2.29, 2.33-2.59, 2.81-3.01, 3.58-4.18, 4.81-5.16, 6.78-7.11, 7.15-7.46.

Example 18 (2) to Example 18 (4)

With using the compounds produced in Example 16 (2), Example 16 (3) or Example 16 (25), and using dimethyl-(3-phenoxy-2-oxopropyl)-phosphonate or a corresponding phosphonic acid salt in place of it, these substances were subjected to the same objective operations as those of Example 18 (1) to obtain the following Example compounds.

Example 18 (2)

2-Propanyl 4-{(3S,5aR,6R,7R,8aS)-7-hydroxy-6-[(3R)-3-hydroxy-5-phenylpentyl]octahydro-2H-cyclopenta[b]oxepin-3-yl}butanoate TLC: Rf 0.82 (ethyl acetate: methanol=10:1);
$^1$H-NMR (300 MHz, CDCl$_3$): δ 0.94-1.18, 1.22, 1.31-1.97, 2.12-2.30, 2.59-2.73, 2.73-2.85, 2.85-2.95, 3.53-3.76, 3.86-4.08, 4.85-5.08, 7.05-7.37.

Example 18 (3)

2-Propanyl 4-{(3S,5aR,6R,7R,8aS)-6-[4-(3-chlorophenoxy)-3-hydroxybutyl]-7-hydroxyoctahydro-2H-cyclopenta[b]oxepin-3-yl}butanoate TLC: Rf 0.58 (dichloromethane:methanol=5:1);
$^1$H-NMR (300 MHz, CDCl$_3$): δ 0.70-1.99, 2.16-2.29, 2.30-2.64, 2.92, 3.66-3.78, 3.78-3.87, 3.90-4.10, 4.89-5.09, 6.80, 6.91, 6.95, 7.20.

Example 18 (4)

2-Propanyl 4-{(3S,5aR,6R,7R,8aS)-6-[4-(2,5-difluorophenoxy)-3-hydroxybutyl]-7-hydroxyoctahydro-2H-cyclopenta[b]oxepin-3-yl}butanoate TLC: Rf 0.42 (isopropyl alcohol: hexane=1:5);
$^1$H-NMR (300 MHz, CDCl$_3$): δ 0.94-1.19, 1.19-1.25, 1.33-1.97, 2.13-2.73, 2.91, 3.66-3.80, 3.81-4.16, 4.90-5.10, 6.52-6.65, 6.65-6.76, 6.93-7.09.

Example 19 (1) to Example 19 (4)

With using the compounds produced in Example 18 (1) to Example 18 (4), these compounds were subjected to the same objective operations as those of Example 17 (1) to obtain the following Example compounds.

Example 19 (1)

4-{(3S,5aR,6R,7R,8aS)-7-hydroxy-6-[(3R)-3-hydroxy-4-phenoxybutyl]octahydro-2H-cyclopenta[b]oxepin-3-yl}butanoic acid

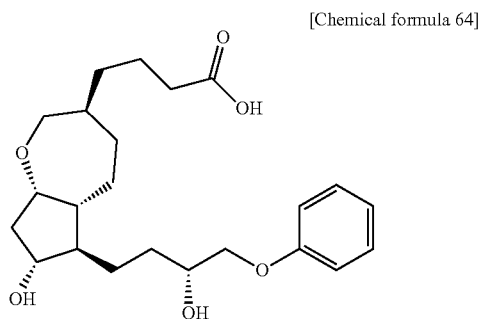 [SMILES: O=C(O)CCC[C@H]1CC[C@@H]2[C@@H](CC[C@@H](O)COc3ccccc3)[C@H](O)C[C@@H]2OC1]

[Chemical formula 64]

TLC: Rf 0.39 (dichloromethane:methanol=9:1);

$^1$H-NMR (300 MHz, CDCl$_3$): δ 0.92-1.23, 1.36-1.98, 2.15-2.29, 2.33, 2.84-2.99, 3.67-3.78, 3.79-3.87, 3.88-4.07, 6.81-7.04, 7.15-7.41.

Example 19 (2)

4-{(3S,5aR,6R,7R,8aS)-7-hydroxy-6-[(3R)-3-hydroxy-5-phenylpentyl]octahydro-2H-cyclopenta[b]oxepin-3-yl}butanoic acid TLC: Rf 0.65 (ethyl acetate: methanol=10:1);

$^1$H-NMR (300 MHz, CDCl$_3$): δ 0.94-1.18, 1.22, 1.31-1.97, 2.12-2.30, 2.59-2.73, 2.73-2.85, 2.85-2.95, 3.53-3.76, 3.86-4.08, 4.85-5.08, 7.05-7.37.

Example 19 (3)

4-{(3S,5aR,6R,7R,8aS)-6-[4-(3-chlorophenoxy)-3-hydroxybutyl]-7-hydroxyoctahydro-2H-cyclopenta[b]oxepin-3-yl}butanoic acid TLC: Rf 0.58 (dichloromethane:methanol=5:1);

$^1$H-NMR (300 MHz, CD$_3$OD): δ 0.80-1.85, 1.85-2.06, 2.17-2.43, 2.91-3.04, 3.53-3.68, 3.82-4.04, 6.83-6.89, 6.89-6.94, 6.95, 7.22.

Example 19 (4)

4-{(3S,5aR,6R,7R,8aS)-6-[4-(2,5-difluorophenoxy)-3-hydroxybutyl]-7-hydroxyoctahydro-2H-cyclopenta[b]oxepin-3-yl}butanoic acid TLC: Rf 0.41 (dichloromethane:methanol=10:1);

$^1$H-NMR (300 MHz, CD$_3$OD): δ 0.93-1.24, 1.37-1.84, 1.84-2.01, 2.16-2.38, 2.90-3.04, 3.50-3.70, 3.83-4.08, 6.53-6.71, 6.82-7.00, 6.99-7.15.

Example 20

Ethyl 2-({[(1R,2S,3R,4S)-2-allyl-3-({[dimethyl(2-methyl-2-propanyl)silyl]oxy}methyl)-4-(tetrahydro-2H-pyran-2-yloxy)cyclopentyl]oxy}methyl)acrylate Under the argon atmosphere, an anhydrous DMF (17 mL) solution of the compound (3.9 g) produced in Example 3 was added to an anhydrous DMF (20 mL) solution of sodium hydride (631 mg) under ice-cooling, and the mixture was stirred at room temperature for 1 hour. Subsequently, ethyl 2-(bromomethyl)acrylate (2.91 mL) was added, and the mixture was stirred at room temperature for 3 hours. An aqueous saturated ammonium chloride solution was added, followed by extraction with hexane:ethyl acetate (2:1). After washing the organic layer with water and a saturated saline, and drying with sodium sulfate, the solvent was concentrated under reduced pressure. The resulting residue was purified with a column apparatus (Hiflash-SI, Size 3 L, hexane:ethyl acetate=100:0→93:7→86:14) manufactured Yamazen Corporation to obtain a titled compound (4.32 g) having the following physical property values.

TLC: Rf 0.53 (hexane:ethyl acetate=5:1).

Example 21

Ethyl (5aR,6S,7R,8aS)-6-({[dimethyl(2-methyl-2-propanyl)silyl]oxy}methyl)-7-(tetrahydro-2H-pyran-2-yloxy)-5,5a,6,7,8,8a-hexahydro-2H-cyclopenta[b]oxepin-3-carboxylate Under the argon atmosphere, the compound (200 mg, 0.190 mmol) produced in Example 20 was dissolved in toluene (40 mL). A Schrock's catalyst (48 mg, 0.062 mmol) was added to react the compound at 60° C. for 18 hours. After allowing to stand, concentration was carried out, and purification by silica gel column chromatography (hexane:ethyl acetate=95:10→50:50) were carried out to obtain a titled compound (3.2 mg) having the following physical property values. TLC: Rf 0.53 (hexane:ethyl acetate=4:1).

Example 22 (1)

Ethyl (3S,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-carboxylate

Example 22 (2)

Ethyl (3R,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-carboxylate Under the argon atmosphere, a 5% rhodium-alumina powder (160 mg) and, subsequently, ethanol (40 mL) were added to the compound (1.6 g) produced in Example 21, and the mixture was stirred at room temperature for 4 hours under the hydrogen atmosphere. The reaction solution was filtered with Celite (trade name), and concentrated under reduced pressure, and the resulting residue was purified with a column apparatus (Hiflash-SI, Size 3 L, hexane:ethyl acetate=95:5→8:2) manufactured by Yamazen Corporation to obtain a compound (270 mg) of Example 22 (1) and its diastereomer (Example 22 (2) (1.2 g) having the following physical property values.

The diastereomer (1.2 g) was dissolved in absolute ethanol (13 mL), a 20% ethanol solution of sodium ethoxide (895 mg) was added at room temperature under the argon atmosphere, and the mixture was stirred at room temperature overnight. After dilution with ethyl acetate, an aqueous saturated ammonium chloride solution was added, and extraction with ethyl acetate was carried out. After washing the organic layer with water and a saturated saline, and drying with sodium sulfate, the solvent was concentrated under reduced pressure. The resulting residue was purified with a column apparatus (Hiflash-SI, Size 3 L, hexane:ethyl acetate=95:5→8:2) manufactured by Yamazen Corporation to obtain an Example compound 22 (1) (757 mg) having the following physical property values.

TLC: Rf 0.58 (hexane:ethyl acetate=4:1) (compound of Example 22 (1));
TLC: Rf 0.44 (hexane:ethyl acetate=5:1) (compound of Example 22 (2)).

Example 23

[(3R,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-yl]methanol Under the argon atmosphere, a THF (6.4 mL) solution of the compound (945 mg) produced in Example 22 (1) was added to a THF (4 mL) solution of lithium aluminum hydride (87 mg) under ice-cooling, and the mixture was stirred at room temperature for 20 minutes. After dilution with MTBE, an aqueous saturated sodium sulfate solution was added; filtered with Celite (trade name); and concentrated under reduced pressure to obtain a titled compound (884 mg) having the following physical property values.

TLC: Rf 0.16 (hexane:ethyl acetate=2:1).

Example 24

2-Methyl-2-propanyl {[(3R,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-yl]methoxy}acetate A 50% aqueous sodium hydroxide solution (0.6 mL) which had been prepared separately was added to a benzene (1.8 mL) solution of the compound (300 mg) produced in Example 23 under ice-cooling. Subsequently, a tetrabutylammonium hydrogen sulfate salt (61 mg) and tert-butyl bromoacetate (282 mg) were added, and the mixture was stirred at room temperature overnight. After dilution with MTBE, water was added, and extraction with MTBE was carried out. Washing with water and a saturated saline, and drying with sodium sulfate were carried out, and the solvent was concentrated under reduced pressure. The resulting residue was purified with a column apparatus (SMB Silica Column, 10 μm, Size 60, hexane:ethyl acetate=95:5→90:10→80:20→50:50) manufactured by Yamazen Corporation to obtain a titled compound (371 mg) having the following physical property values.

TLC: Rf 0.54 (hexane:ethyl acetate=4:1).

Example 25

{[(3R,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-yl]methoxy}acetic acid A 2N aqueous sodium hydroxide solution (1.75 mL) was added to a methanol (5.25 mL) solution of the compound (371 mg) produced in Example 24 at room temperature, and the mixture was stirred at 50° C. for 3.5 hours. After distillation of methanol by concentration under reduced pressure, the residue was diluted with MTBE; made acidic with ice-cooled 2N hydrochloric acid; and extracted with ethyl acetate. Washing with water and a saturated saline, and drying with sodium sulfate were carried out, and the solvent was concentrated under reduced pressure to obtain a titled compound (371 mg) having the following physical property values. The resulting titled compound was used in a next reaction without purification.

TLC: Rf 0.24 (ethyl acetate).

Example 26

2-Propanyl {[(3R,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-yl]methoxy}acetate Under the argon atmosphere, the compound produced in Example 25 was dissolved in DMF (2.8 mL), potassium carbonate (242 mg) and 2-iodopropane (0.105 mL) were sequentially added at room temperature, followed by stirring at 50° C. overnight. The reaction solution was diluted with ethyl acetate; water was added; and extraction with ethyl acetate was carried out. Washing with water and a saturated saline, and drying with sodium sulfate were carried out, and the solvent was concentrated under reduced pressure to obtain a titled compound (371 mg) having the following physical property values. The resulting titled compound was used in a next reaction without purification.

TLC: Rf 0.81 (hexane:ethyl acetate=1:1).

Example 27

2-Propanyl {[(3R,5aR,6S,7R,8aS)-6-(hydroxymethyl)-7-(tetrahydro-2H-pyran-2-yloxy)octahydro-2H-cyclopenta[b]oxepin-3-yl]methoxy}acetate Under the argon atmosphere, a 1M THF solution (1.4 mL) of tetrabutylammonium fluoride was added to the compound produced in Example 26 at room temperature, and the mixture was stirred for 6 hours. The reaction solution was diluted with ethyl acetate; an aqueous saturated ammonium chloride solution was added; and extraction with ethyl acetate was carried out. Washing with water and a saturated saline, and drying with sodium sulfate were carried out, and the solvent was concentrated under reduced pressure. The resulting residue was purified with a column apparatus (Hiflash-SI, Size M, hexane:ethyl acetate=90:10→50:50→20:80) manufactured by Yamazen Corporation to obtain a titled compound (240 mg) having the following physical property values.

TLC: Rf 0.21 (hexane:ethyl acetate=1:1).

Example 28

2-Propanyl({(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}methoxy)acetate

[Chemical formula 65]

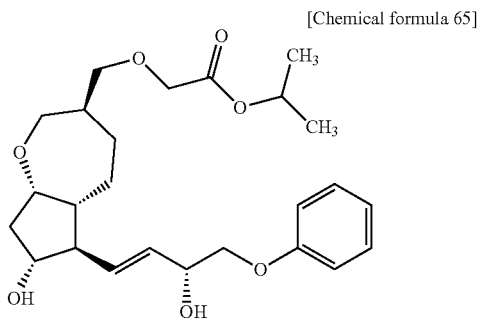 [SMILES: CC(C)OC(=O)COC[C@H]1CC[C@@H]2[C@@H](/C=C/[C@@H](O)COc3ccccc3)[C@H](O)C[C@@H]2OC1]

The compound (152 mg) produced in Example 27 was subjected to the same objective operations as those of Example 13→Example 14→Example 15→Example 16 (1) with using dimethyl-(3-phenoxy-2-oxopropyl)-phosphonate, to obtain a titled compound (72 mg) having the following physical property values.

TLC: Rf 0.33 (ethyl acetate);
$^1$H-NMR (300 MHz, CDCl$_3$): δ 1.10-1.31, 1.40-1.57, 1.58-2.19, 2.19-2.29, 2.41-2.55, 2.61-2.73, 3.24-3.41, 3.63-3.81, 3.83-4.07, 4.14-4.25, 4.42-4.60, 4.98-5.16, 5.58-5.73, 6.86-7.03, 7.23-7.34.

Example 28 (1) to Example 28 (17)

With using (3aR,4S,5R,6aS)-4-({[dimethyl(2-methyl-2-propanyl)silyl]oxy}methyl)-5-(tetrahydro-2H-pyran-2-yloxy)hexahydro-2H-cyclopenta[b]furan-2-one, using ethyl 2-(bromomethyl)acrylate, and using dimethyl-(3-phenoxy-2-oxopropyl)-phosphonate or a corresponding phosphonic acid salt in place of it, these substances were subjected to the same objective operations as those of Example 20→Example 21→Example 22 (1) or Example 22 (2)→Example 23→Example 24→Example 25→Example 26→Example 27→Example 28 to obtain the following Example compounds.

Example 28 (1)

2-Propanyl({(3R,5aR,6R,7R,8aS)-6-[(1E,3R)-4-(3-chlorophenoxy)-3-hydroxy-1-buten-1-yl]-7-hydroxy-octahydro-2H-cyclopenta[b]oxepin-3-yl}methoxy) acetate TLC: Rf 0.65 (ethyl acetate);
$^1$H-NMR (300 MHz, CDCl$_3$): δ 1.10-1.32, 1.40-1.60, 1.61-2.21, 2.40-2.56, 3.05-3.18, 3.25-3.41, 3.67-3.82, 3.82-3.92, 3.92-4.06, 4.15-4.25, 4.45-4.58, 4.99-5.17, 5.56-5.76, 6.75-6.84, 6.87-6.99, 7.15-7.24.

Example 28 (2)

2-Propanyl({(3R,5aR,6R,7R,8aS)-6-[(1E,3R)-4-(2-fluorophenoxy)-3-hydroxy-1-buten-1-yl]-7-hydroxy-octahydro-2H-cyclopenta[b]oxepin-3-yl}methoxy) acetate TLC: Rf 0.49 (ethyl acetate);
$^1$H-NMR (300 MHz, CDCl$_3$): δ 1.09-1.35, 1.39-2.24, 2.40-2.57, 2.62-2.78, 3.10, 3.24-3.41, 3.64-3.80, 3.85-4.10, 4.14-4.26, 4.48-4.60, 4.98-5.15, 5.55-5.77, 6.82-7.14.

Example 28 (3)

2-Propanyl({(3R,5aR,6R,7R,8aS)-6-[(1E,3R)-4-(3-fluorophenoxy)-3-hydroxy-1-buten-1-yl]-7-hydroxy-octahydro-2H-cyclopenta[b]oxepin-3-yl}methoxy) acetate TLC: Rf 0.45 (ethyl acetate);
$^1$H-NMR (300 MHz, CDCl$_3$): δ 1.07-1.34, 1.39-2.22, 2.37-2.58, 3.04-3.17, 3.24-3.40, 3.64-3.80, 3.83-3.91, 3.91-4.07, 4.11-4.28, 4.45-4.59, 4.95-5.17, 5.54-5.77, 6.53-6.74, 7.10-7.32.

Example 28 (4)

2-Propanyl({(3R,5aR,6R,7R,8aS)-6-[(1E,3R)-4-(4-fluorophenoxy)-3-hydroxy-1-buten-1-yl]-7-hydroxy-octahydro-2H-cyclopenta[b]oxepin-3-yl}methoxy) acetate TLC: Rf 0.42 (ethyl acetate);
$^1$H-NMR (300 MHz, CDCl$_3$): δ 1.10-1.34, 1.38-2.22, 2.39-2.57, 3.05-3.17, 3.25-3.40, 3.65-3.79, 3.80-3.88, 3.88-4.09, 4.10-4.26, 4.43-4.58, 4.97-5.15, 5.54-5.74, 6.77-6.91, 6.90-7.04.

Example 28 (5)

2-Propanyl({(3R,5aR,6R,7R,8aS)-6-[(1E,3R)-4-(4-chlorophenoxy)-3-hydroxy-1-buten-1-yl]-7-hydroxy-octahydro-2H-cyclopenta[b]oxepin-3-yl}methoxy) acetate TLC: Rf 0.57 (ethyl acetate);
$^1$H-NMR (300 MHz, CDCl$_3$): δ 1.10-1.30, 1.40-1.58, 1.61-2.22, 2.40-2.56, 3.11, 3.25-3.41, 3.65-3.80, 3.80-3.90, 3.90-4.06, 4.13-4.25, 4.44-4.59, 4.98-5.16, 5.55-5.75, 6.76-6.91, 7.16-7.30.

Example 28 (6)

2-Propanyl({(3R,5aR,6R,7R,8aS)-7-hydroxy-6-[(1E,3R)-3-hydroxy-4-(3-methylphenoxy)-1-buten-1-yl}octahydro-2H-cyclopenta[b]oxepin-3-yl]methoxy)acetate TLC: Rf 0.60 (ethyl acetate);
$^1$H-NMR (300 MHz, CDCl$_3$): δ 1.09-1.31, 1.41-1.60, 1.61-2.22, 2.33, 2.41-2.57, 3.05-3.17, 3.25-3.41, 3.66-3.81, 3.81-3.91, 3.92-4.06, 4.14-4.26, 4.45-4.58, 4.99-5.16, 5.57-5.74, 6.66-6.83, 7.16.

Example 28 (7)

2-Propanyl({(3R,5aR,6R,7R,8aS)-7-hydroxy-6-[(1E,3R)-3-hydroxy-4-(4-methylphenoxy)-1-buten-1-yl]octahydro-2H-cyclopenta[b]oxepin-3-yl}methoxy) acetate TLC: Rf 0.57 (ethyl acetate);
$^1$H-NMR (300 MHz, CDCl$_3$): δ 1.09-1.35, 1.40-1.59, 1.61-2.20, 2.29, 2.39-2.60, 3.03-3.18, 3.25-3.41, 3.65-3.79, 3.79-3.89, 3.89-4.07, 4.13-4.26, 4.44-4.56, 4.98-5.16, 5.56-5.74, 6.74-6.86, 7.07.

Example 28 (8)

2-Propanyl({(3R,5aR,6R,7R,8aS)-6-[(1E,3R)-4-(2-chlorophenoxy)-3-hydroxy-1-buten-1-yl]-7-hydroxy-octahydro-2H-cyclopenta[b]oxepin-3-yl}methoxy) acetate TLC: Rf 0.33 (ethyl acetate);
$^1$H-NMR (300 MHz, CDCl$_3$): δ 1.09-1.30, 1.40-1.57, 1.61-2.21, 2.40-2.56, 2.71, 3.04-3.18, 3.25-3.41, 3.65-3.81, 3.88-4.04, 4.08, 4.15-4.24, 4.52-4.62, 5.00-5.16, 5.95-5.76, 6.88-6.98, 7.17-7.28, 7.33-7.41.

Example 28 (9)

2-Propanyl({(3R,5aR,6R,7R,8aS)-7-hydroxy-6-[(1E,3R)-3-hydroxy-4-(2-methylphenoxy)-1-buten-1-yl]octahydro-2H-cyclopenta[b]oxepin-3-yl}methoxy)acetate TLC: Rf 0.37 (ethyl acetate);
$^1$H-NMR (300 MHz, CDCl$_3$): δ 1.10-1.29, 1.41-1.57, 1.61-2.20, 2.24, 2.41-2.55, 3.11, 3.25-3.40, 3.66-3.81, 3.86-3.94, 3.94-4.05, 4.20, 4.48-4.60, 5.00-5.17, 5.60-5.76, 6.82, 6.85-6.93, 7.10-7.20.

Example 28 (10)

2-Propanyl({(3R,5aR,6R,7R,8aS)-6-[(1E,3R)-4-(3-chloro-2-fluorophenoxy)-3-hydroxy-1-buten-1-yl]-7-hydroxyoctahydro-2H-cyclopenta[b]oxepin-3-yl}methoxy)acetate TLC: Rf 0.37 (ethyl acetate);
$^1$H-NMR (300 MHz, CDCl$_3$): δ 1.05-1.33, 1.38-2.25, 2.38-2.56, 2.65-2.74, 2.96-3.19, 3.24-3.41, 3.73, 3.87-4.10, 4.14-4.26, 4.46-4.61, 4.98-5.15, 5.56-5.75, 6.83-6.92, 6.93-7.05.

Example 28 (11)

2-Propanyl({(3R,5aR,6R,7R,8aS)-6-[(1E,3R)-4-(3,5-dichlorophenoxy)-3-hydroxy-1-buten-1-yl]-7-hydroxyoctahydro-2H-cyclopenta[b]oxepin-3-yl}methoxy)acetate TLC: Rf 0.51 (ethyl acetate);
$^1$H-NMR (300 MHz, CDCl$_3$): δ 1.10-1.32, 1.38-2.24, 2.32-2.43, 2.43-2.57, 3.05-3.19, 3.25-3.42, 3.65-3.82, 3.82-3.91, 3.92-4.06, 4.14-4.27, 4.44-4.62, 4.99-5.18, 5.25-5.77, 6.82, 6.98.

Example 28 (12)

2-Propanyl({(3R,5aR,6R,7R,8aS)-6-[(1E,3R)-4-(3-chloro-5-fluorophenoxy)-3-hydroxy-1-buten-1-yl]-7-hydroxyoctahydro-2H-cyclopenta[b]oxepin-3-yl}methoxy)acetate TLC: Rf 0.73 (ethyl acetate: methanol=9:1);
$^1$H-NMR (300 MHz, CDCl$_3$): δ 1.10-1.37, 1.37-2.24, 2.39-2.59, 3.04-3.18, 3.24-3.41, 3.65-3.80, 3.81-3.91, 3.91-4.05, 4.13-4.27, 4.43-4.58, 4.99-5.16, 5.55-5.75, 6.48-6.59, 6.64-6.78.

Example 28 (13)

2-Propanyl({(3R,5aR,6R,7R,8aS)-6-[(1E,3R)-4-(3,5-difluorophenoxy)-3-hydroxy-1-buten-1-yl]-7-hydroxyoctahydro-2H-cyclopenta[b]oxepin-3-yl}methoxy)acetate TLC: Rf 0.79 (ethyl acetate: methanol=9:1);
$^1$H-NMR (300 MHz, CDCl$_3$): δ 1.07-1.32, 1.37-2.22, 2.39-2.58, 3.04-3.18, 3.24-3.41, 3.64-3.79, 3.81-3.90, 3.90-4.06, 4.12-4.27, 4.43-4.58, 4.97-5.15, 5.55-5.74, 6.35-6.54.

Example 28 (14)

2-Propanyl({(3R,5aR,6R,7R,8aS)-6-[(1E,3R)-4-(2,3-difluorophenoxy)-3-hydroxy-1-buten-1-yl]-7-hydroxyoctahydro-2H-cyclopenta[b]oxepin-3-yl}methoxy)acetate TLC: Rf 0.77 (ethyl acetate: methanol=9:1);
$^1$H-NMR (300 MHz, CDCl$_3$): δ 1.08-1.35, 1.36-2.32, 2.38-2.57, 2.63-2.84, 3.03-3.19, 3.22-3.44, 3.62-3.82, 3.87-4.10, 4.13-4.28, 4.46-4.63, 4.98-5.20, 5.54-5.77, 6.66-6.87, 6.90-7.05.

Example 28 (15)

2-Propanyl({(3R,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}methoxy)acetate TLC: Rf 0.77 (ethyl acetate: methanol=9:1);
$^1$H-NMR (300 MHz, CDCl$_3$): δ 1.07-1.32, 1.36-2.21, 2.27, 2.40-2.56, 2.77, 3.04-3.20, 3.23-3.41, 3.64-3.80, 3.84-4.08, 4.13-4.27, 4.48-4.61, 4.98-5.16, 5.54-5.74, 6.53-6.65, 6.65-6.76, 6.94-7.08.

Example 28 (16)

2-Propanyl({(3R,5aR,6R,7R,8aS)-6-[(1E,3R)-4-(5-chloro-2-fluorophenoxy)-3-hydroxy-1-buten-1-yl]-7-hydroxyoctahydro-2H-cyclopenta[b]oxepin-3-yl}methoxy)acetate TLC: Rf 0.52 (ethyl acetate);
$^1$H-NMR (300 MHz, CDCl$_3$): δ 1.10-1.30, 1.40-1.57, 1.61-2.21, 2.42-2.55, 2.60, 3.05-3.17, 3.25-3.40, 3.66-3.82, 3.87-4.08, 4.15-4.25, 4.49-4.61, 4.99-5.16, 5.55-5.75, 6.85-6.93, 6.93-7.06.

Example 28 (17)

2-Propanyl({(3R,5aR,6R,7R,8aS)-6-[(1E,3R)-4-(3-chloro-4-fluorophenoxy)-3-hydroxy-1-buten-1-yl]-7-hydroxyoctahydro-2H-cyclopenta[b]oxepin-3-yl}methoxy)acetate TLC: Rf 0.40 (ethyl acetate);

$^1$H-NMR (300 MHz, CDCl$_3$): δ 1.11-1.30, 1.40-1.60, 1.62-2.21, 2.41-2.55, 3.05-3.17, 3.26-3.40, 3.66-3.79, 3.79-3.89, 3.89-4.06, 4.15-4.25, 4.45-4.56, 4.99-5.15, 5.56-5.73, 6.73-6.80, 6.94, 7.00-7.09.

Example 29

({(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}methoxy)acetic acid

[Chemical formula 66]

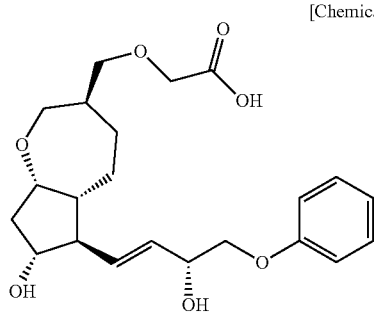

The compound (7.3 mg) produced in Example 28 was subjected to the same objective operations as those of Example 17 (1) to obtain a titled compound (7.1 mg) having the following physical property values.

TLC: Rf 0.13 (chloroform:methanol:water=10:1:0.1)

$^1$H-NMR (300 MHz, CDCl$_3$): δ 1.08-1.23, 1.39-1.57, 1.59-1.95, 1.95-2.20, 2.42-2.55, 3.03-3.16, 3.27-3.42, 3.66-3.78, 3.84-4.03, 4.05, 4.15-4.25, 4.46-4.57, 5.56-5.74, 6.86-7.02, 7.23-7.33.

Example 29 (1) to Example 29 (17)

The compounds produced in Example 28 (1) to Example 28 (17) were subjected to the same objective operations as those of Example 29, respectively, to obtain the following Example compounds.

Example 29 (1)

({(3R,5aR,6R,7R,8aS)-6-[(1E,3R)-4-(3-chlorophenoxy)-3-hydroxy-1-buten-1-yl]-7-hydroxyoctahydro-2H-cyclopenta[b]oxepin-3-yl}methoxy)acetic acid TLC: Rf 0.21 (chloroform:methanol:acetic acid=20:1:0.1);

$^1$H-NMR (300 MHz, CDCl$_3$): δ 1.09-1.31, 1.40-2.26, 2.42-2.57, 3.03-3.17, 3.29-3.46, 3.68-3.81, 3.82-3.91, 3.93-4.09, 4.14-4.23, 4.46-4.58, 5.57-5.75, 6.75-6.84, 6.87-6.99, 7.14-7.24.

Example 29 (2)

({(3R,5aR,6R,7R,8aS)-6-[(1E,3R)-4-(2-fluorophenoxy)-3-hydroxy-1-buten-1-yl]-7-hydroxyoctahydro-2H-cyclopenta[b]oxepin-3-yl}methoxy)acetic acid TLC: Rf 0.23 (chloroform: methanol=5:1);

$^1$H-NMR (300 MHz, CD$_3$OD): δ 1.07-1.24, 1.32-1.48, 1.49-1.63, 1.67-2.13, 2.35-2.51, 3.06-3.18, 3.20-3.42, 3.59-3.74, 3.90-4.08, 4.11-4.23, 4.38-4.49, 5.57-5.70, 6.83-6.95, 6.99-7.16.

Example 29 (3)

({(3R,5aR,6R,7R,8aS)-6-[(1E,3R)-4-(3-fluorophenoxy)-3-hydroxy-1-buten-1-yl]-7-hydroxyoctahydro-2H-cyclopenta[b]oxepin-3-yl}methoxy)acetic acid TLC: Rf 0.26 (chloroform: methanol=5:1);

$^1$H-NMR (300 MHz, CD$_3$OD): δ 1.09-1.24, 1.35-1.49, 1.49-1.61, 1.67-2.12, 2.37-2.50, 3.07-3.18, 3.21-3.40, 3.60-3.72, 3.83-4.05, 4.13-4.23, 4.34-4.47, 5.56-5.73, 6.56-6.83, 7.16-7.32.

Example 29 (4)

({(3R,5aR,6R,7R,8aS)-6-[(1E,3R)-4-(4-fluorophenoxy)-3-hydroxy-1-buten-1-yl]-7-hydroxyoctahydro-2H-cyclopenta[b]oxepin-3-yl}methoxy)acetic acid TLC: Rf 0.24 (chloroform: methanol=5:1);

$^1$H-NMR (300 MHz, CD$_3$OD): δ 1.09-1.24, 1.34-1.49, 1.49-1.61, 1.68-2.11, 2.35-2.51, 3.08-3.19, 3.20-3.42, 3.60-3.73, 3.80-4.07, 4.12-4.24, 4.34-4.46, 5.56-5.71, 6.83-7.06.

Example 29 (5)

({(3R,5aR,6R,7R,8aS)-6-[(1E,3R)-4-(4-chlorophenoxy)-3-hydroxy-1-buten-1-yl]-7-hydroxyoctahydro-2H-cyclopenta[b]oxepin-3-yl}methoxy)acetic acid TLC: Rf 0.42 (chloroform:methanol:acetic acid=10:1:0.1);

$^1$H-NMR (300 MHz, CD$_3$OD): δ 1.06-1.28, 1.32-1.63, 1.64-2.12, 2.35-2.51, 3.06-3.19, 3.20-3.43, 3.57-3.74, 3.81-4.10, 4.10-4.24, 4.33-4.47, 5.52-5.73, 6.84-6.97, 7.16-7.29.

Example 29 (6)

({(3R,5aR,6R,7R,8aS)-7-hydroxy-6-[(1E,3R)-3-hydroxy-4-(3-methylphenoxy)-1-buten-1-yl]octahydro-2H-cyclopenta[b]oxepin-3-yl}methoxy)acetic acid TLC: Rf 0.43 (chloroform:methanol:acetic acid=10:1:0.1);

$^1$H-NMR (300 MHz, CD$_3$OD): δ 1.07-1.26, 1.33-1.64, 1.66-2.13, 2.29, 2.37-2.51, 3.05-3.19, 3.20-3.44, 3.57-3.75, 3.82-4.08, 4.10-4.24, 4.32-4.47, 5.54-5.72, 6.62-6.80, 7.04-7.17.

Example 29 (7)

({(3R,5aR,6R,7R,8aS)-7-hydroxy-6-[(1E,3R)-3-hydroxy-4-(4-methylphenoxy)-1-buten-1-yl]octahydro-2H-cyclopenta[b]oxepin-3-yl}methoxy)acetic acid TLC: Rf 0.45 (chloroform:methanol:acetic acid=10:1:0.1);

$^1$H-NMR (300 MHz, CD$_3$OD): δ 1.06-1.27, 1.31-1.64, 1.65-2.11, 2.25, 2.35-2.52, 3.04-3.20, 3.19-3.43, 3.58-3.74, 3.77-4.10, 4.10-4.24, 4.31-4.46, 5.52-5.72, 6.79, 7.04.

Example 29 (8)

({(3R,5aR,6R,7R,8aS)-6-[(1E,3R)-4-(2-chlorophenoxy)-3-hydroxy-1-buten-1-yl]-7-hydroxyoctahydro-2H-cyclopenta[b]oxepin-3-yl}methoxy)acetic acid TLC: Rf 0.18 (chloroform:methanol:water=10:1:0.1);

$^1$H-NMR (300 MHz, CD$_3$OD): δ 1.09-1.23, 1.32-1.46, 1.48-1.62, 1.68-2.11, 2.36-2.51, 3.11, 3.22-3.40, 3.60-3.73, 3.86-4.06, 4.12-4.22, 4.40-4.50, 5.58-5.73, 6.90, 7.05, 7.23, 7.33.

Example 29 (9)

({(3R,5aR,6R,7R,8aS)-7-hydroxy-6-[(1E,3R)-3-hydroxy-4-(2-methylphenoxy)-1-buten-1-yl]octahydro-2H-cyclopenta[b]oxepin-3-yl}methoxy)acetic acid TLC: Rf 0.18 (chloroform:methanol:water=10:1:0.1)
$^{1}$H-NMR (300 MHz, CD$_{3}$OD): δ 1.08-1.22, 1.34-1.49, 1.55, 1.68-2.10, 2.20, 2.43, 3.07-3.17, 3.25-3.39, 3.66, 3.86-4.07, 4.17, 4.38-4.47, 5.57-5.73, 6.76-6.89, 7.04-7.14.

Example 29 (10)

({(3R,5aR,6R,7R,8aS)-6-[(1E,3R)-4-(3-chloro-2-fluorophenoxy)-3-hydroxy-1-buten-1-yl]-7-hydroxyoctahydro-2H-cyclopenta[b]oxepin-3-yl}methoxy)acetic acid TLC: Rf 0.29 (dichloromethane:methanol=5:1);
$^{1}$H-NMR (300 MHz, CD$_{3}$OD): δ 1.05-1.62, 1.63-2.09, 2.35-2.52, 3.06-3.19, 3.19-3.42, 3.58-3.73, 3.93-4.06, 4.12-4.22, 4.37-4.52, 5.52-5.74, 6.89-7.18.

Example 29 (11)

({(3R,5aR,6R,7R,8aS)-6-[(1E,3R)-4-(3,5-dichlorophenoxy)-3-hydroxy-1-buten-1-yl]-7-hydroxyoctahydro-2H-cyclopenta[b]oxepin-3-yl}methoxy)acetic acid TLC: Rf 0.24 (dichloromethane:methanol=5:1);
$^{1}$H-NMR (300 MHz, CD$_{3}$OD): δ 1.06-1.62, 1.65-2.13, 2.37-2.52, 3.07-3.18, 3.20-3.45, 3.60-3.74, 3.82-4.07, 4.12-4.23, 4.33-4.47, 5.53-5.73, 6.93, 6.98.

Example 29 (12)

({(3R,5aR,6R,7R,8aS)-6-[(1E,3R)-4-(3-chloro-5-fluorophenoxy)-3-hydroxy-1-buten-1-yl]-7-hydroxyoctahydro-2H-cyclopenta[b]oxepin-3-yl}methoxy)acetic acid TLC: Rf 0.46 (dichloromethane:methanol:acetic acid=3:1:0.2);
$^{1}$H-NMR (300 MHz, CD$_{3}$OD): δ 1.07-1.33, 1.32-1.63, 1.63-2.13, 2.36-2.50, 3.06-3.18, 3.20-3.41, 3.60-3.73, 3.84-4.07, 4.12-4.23, 4.35-4.46, 5.53-5.72, 6.68, 6.75, 6.79-6.85.

Example 29 (13)

({(3R,5aR,6R,7R,8aS)-6-[(1E,3R)-4-(3,5-difluorophenoxy)-3-hydroxy-1-buten-1-yl]-7-hydroxyoctahydro-2H-cyclopenta[b]oxepin-3-yl}methoxy)acetic acid TLC: Rf 0.47 (dichloromethane:methanol:acetic acid=3:1:0.2);
$^{1}$H-NMR (300 MHz, CD$_{3}$OD): δ 1.08-1.30, 1.32-1.63, 1.68-2.12, 2.36-2.51, 3.06-3.18, 3.21-3.41, 3.59-3.74, 3.82-4.06, 4.12-4.24, 4.35-4.48, 5.54-5.73, 6.39-6.64.

Example 29 (14)

({(3R,5aR,6R,7R,8aS)-6-[(1E,3R)-4-(2,3-difluorophenoxy)-3-hydroxy-1-buten-1-yl]-7-hydroxyoctahydro-2H-cyclopenta[b]oxepin-3-yl}methoxy)acetic acid TLC: Rf 0.48 (dichloromethane:methanol:acetic acid=3:1:0.2);
$^{1}$H-NMR (300 MHz, CD$_{3}$OD): δ 1.08-1.28, 1.33-1.61, 1.65-2.12, 2.36-2.52, 3.12, 3.20-3.42, 3.58-3.73, 3.90-4.07, 4.11-4.22, 4.38-4.49, 5.53-5.73, 6.75-6.86, 6.86-6.95, 6.97-7.11.

Example 29 (15)

({(3R,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}methoxy)acetic acid TLC: Rf 0.48 (dichloromethane:methanol:acetic acid=3:1:0.2);
$^{1}$H-NMR (300 MHz, CD$_{3}$OD): δ 1.06-1.24, 1.32-1.65, 1.66-2.13, 2.35-2.52, 3.05-3.18, 3.22-3.42, 3.58-3.73, 3.88-4.07, 4.11-4.24, 4.37-4.51, 5.53-5.74, 6.54-6.69, 6.84-6.96, 6.99-7.14.

Example 29 (16)

({(3R,5aR,6R,7R,8aS)-6-[(1E,3R)-4-(5-chloro-2-fluorophenoxy)-3-hydroxy-1-buten-1-yl]-7-hydroxyoctahydro-2H-cyclopenta[b]oxepin-3-yl}methoxy)acetic acid TLC: Rf 0.12 (chloroform:methanol:acetic acid=10:1:0.1);
$^{1}$H-NMR (300 MHz, CD$_{3}$OD): δ 1.07-1.24, 1.33-1.49, 1.49-1.62, 1.67-2.10, 2.36-2.51, 3.07-3.19, 3.19-3.42, 3.60-3.72, 3.93-4.07, 4.11-4.23, 4.38-4.48, 5.55-5.72, 6.90, 7.07, 7.13.

Example 29 (17)

({(3R,5aR,6R,7R,8aS)-6-[(1E,3R)-4-(3-chloro-4-fluorophenoxy)-3-hydroxy-1-buten-1-yl]-7-hydroxyoctahydro-2H-cyclopenta[b]oxepin-3-yl}methoxy)acetic acid TLC: Rf 0.11 (chloroform:methanol:acetic acid=10:1:0.1);
$^{1}$H-NMR (300 MHz, CD$_{3}$OD): δ 1.08-1.25, 1.34-1.63, 1.67-2.09, 2.37-2.51, 3.07-3.18, 3.20-3.42, 3.59-3.73, 3.82-4.07, 4.12-4.23, 4.35-4.44, 5.54-5.72, 6.87, 7.04, 7.12.

Example 30

2-Propanyl 4-[(3S,5aR,6R,7R,8aS)-6-[(1E)-3,3-difluoro-4-phenoxy-1-buten-1-yl]-7-(tetrahydro-2H-pyran-2-yloxy)octahydro-2H-cyclopenta[b]oxepin-3-yl]butanoate Under the argon atmosphere, the compound (280 mg, 0.53 mmol) produced in Example 14 was dissolved in (2-methoxyethyl)aminosulfur trifluoride (977 μL, 5.30 mmol), and stirring at room temperature for 4 days and 7 hours was carried out. The reaction solution was slowly poured into an ice-cooled aqueous saturated sodium bicarbonate solution, and the aqueous layer was extracted with ethyl acetate twice. The organic layer was washed with a saturated saline, and dried with anhydrous sodium sulfate. Purification with a column apparatus (Hiflash-SI, Size M, hexane→ethyl acetate: hexane=3:7) manufactured by Yamazen Corporation was carried out to obtain a titled compound (171 mg) having the following physical property values.

TLC: Rf 0.54 (hexane:ethyl acetate=3:7).

Example 31

2-Propanyl 4-{(3S,5aR,6R,7R,8aS)-6-[(1E)-3,3-difluoro-4-phenoxy-1-buten-1-yl]-7-hydroxyoctahydro-2H-cyclopenta[b]oxepin-3-yl}butanoate

[Chemical formula 67]

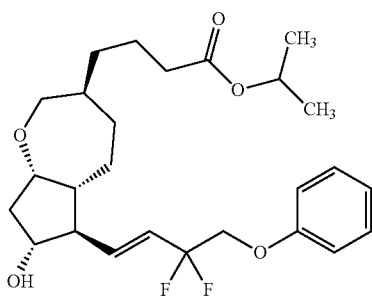

The compound produced in Example 30 was subjected to the same objective operations as those of Example 16 (1) to obtain a titled compound having the following physical property values.

TLC: Rf 0.42 (ethyl acetate:hexane=1:1):
$^1$H-NMR (300 MHz, CDCl$_3$): δ 0.87-1.19, 1.18-1.26, 1.35-1.96, 2.11-2.30, 2.35-2.56, 2.84-2.97, 3.67-3.84, 3.90-4.11, 4.19, 4.89-5.08, 5.68-5.87, 5.95-6.11, 6.85-6.95, 6.95-7.05, 7.21-7.35.

Example 32

4-{(3S,5aR,6R,7R,8aS)-6-[(1E)-3,3-difluoro-4-phenoxy-1-buten-1-yl]-7-hydroxyoctahydro-2H-cyclopenta[b]oxepin-3-yl}butanoic acid

[Chemical formula 68]

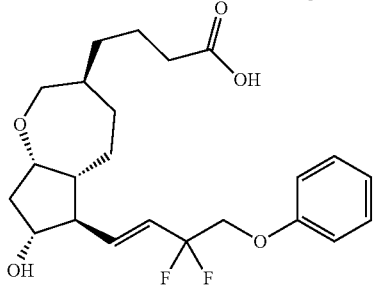

The compound produced in Example 31 was subjected to the same objective operations as those of Example 17 (1) to obtain a titled compound having the following physical property values.

TLC: Rf 0.34 (dichloromethane:methanol=9:1);
$^1$H-NMR (300 MHz, CDCl$_3$): δ 0.90-1.23, 1.36-1.96, 2.12-2.27, 2.33, 2.40-2.53, 2.84-2.98, 3.71-3.83, 3.90-4.10, 4.19, 5.69-5.88, 5.95-6.10, 6.86-6.94, 6.95-7.05, 7.21-7.35.

Example 32 (1) to Example 32 (5)

Using the compound produced in Example 13, and using a corresponding phosphonic acid salt in place of dimethyl-(3-phenoxy-2-oxopropyl)-phosphonate, these substances were subjected to the same objective operations as those of Example 14→Example 30→Example 31→Example 32 to obtain the following Example compounds.

Example 32 (1)

4-{(3S,5aR,6R,7R,8aS)-6-[(1E)-3,3-difluoro-4-(2-fluorophenoxy)-1-buten-1-yl]-7-hydroxyoctahydro-2H-cyclopenta[b]oxepin-3-yl}butanoic acid TLC: Rf 0.52 (ethyl acetate);
$^1$H-NMR (300 MHz, DMSO-d$_6$): δ 11.98, 7.28-7.19, 7.13, 6.99, 6.06, 5.75, 4.79, 4.43, 3.90-3.84, 3.57, 2.84, 2.30, 2.15, 1.97, 1.80-1.64, 1.61-1.21, 1.11-0.86.

Example 32 (2)

4-{(3S,5aR,6R,7R,8aS)-6-[(1E)-3,3-difluoro-4-(3-fluorophenoxy)-1-buten-1-yl]-7-hydroxyoctahydro-2H-cyclopenta[b]oxepin-3-yl}butanoic acid TLC: Rf 0.55 (ethyl acetate);
$^1$H-NMR (300 MHz, DMSO-d$_6$): δ 11.98, 7.33, 6.94-6.78, 6.05, 5.75, 4.81, 4.39, 3.91-3.85, 3.58, 2.85, 2.31, 2.16, 1.98, 1.81-1.67, 1.60-1.22, 1.12-0.87.

Example 32 (3)

4-{(3S,5aR,6R,7R,8aS)-6-[(1E)-4-(3-chlorophenoxy)-3,3-difluoro-1-buten-1-yl]-7-hydroxyoctahydro-2H-cyclopenta[b]oxepin-3-yl}butanoic acid TLC: Rf 0.55 (ethyl acetate);
$^1$H-NMR (300 MHz, DMSO-d$_6$): δ 11.98, 7.32, 7.11, 7.04, 6.98, 6.05, 5.74, 4.80, 4.40, 3.91-3.84, 3.58, 2.84, 2.31, 2.16, 1.97, 1.81-1.64, 1.59-1.21, 1.10-0.86.

Example 32 (4)

4-[(3S,5aR,6R,7R,8aS)-6-{(1E)-3,3-difluoro-4-[3-(trifluoromethyl)phenoxy]-1-buten-1-yl}-7-hydroxyoctahydro-2H-cyclopenta[b]oxepin-3-yl}butanoic acid TLC: Rf 0.68 (ethyl acetate);
$^1$H-NMR (300 MHz, DMSO-d$_6$): δ 11.98, 7.55, 7.35-7.32, 6.06, 5.76, 4.80, 4.48, 3.91-3.84, 3.58, 2.84, 2.31, 2.16, 1.98, 1.81-1.64, 1.59-1.21, 1.10-0.86.

Example 32 (5)

4-{(3S,5aR,6R,7R,8aS)-6-[(1E)-4-(2,5-difluorophenoxy)-3,3-difluoro-1-buten-1-yl]-7-hydroxyoctahydro-2H-cyclopenta[b]oxepin-3-yl}butanoic acid TLC: Rf 0.65 (ethyl acetate);
$^1$H-NMR (300 MHz, DMSO-d$_6$): δ 11.98, 7.33-7.23, 6.82, 6.07, 5.74, 4.80, 4.48, 3.91-3.84, 3.58, 2.85, 2.31, 2.16, 1.97, 1.81-1.64, 1.60-1.21, 1.10-0.86.

Example 33

[(3S,5aR,6S,7R,8aS)-6-(hydroxymethyl)-7-(tetrahydro-2H-pyran-2-yloxy)octahydro-2H-cyclopenta[b]oxepin-3-yl]methyl acetate Pyridine (0.335 mL), acetic acid anhydride (0.294 mL) and N-dimethylaminopyridine (small amount) were sequentially added to a dichloromethane (5 mL) solution of the compound (884 mg) produced in Example 23 at room temperature, and stirring was carried out for 3 hours. Dilution with ethyl acetate was carried out, and water was added, followed by extraction with ethyl acetate. The organic layer was sequentially washed with 1N hydrochloric acid, an aqueous saturated sodium bicarbonate solution, and a saturated saline, and dried with sodium sulfate, and the solvent was concentrated under reduced pressure. To the resulting residue, THF (0.5 mL) was added, and a 1M THF solution (5 mL) of N-tetrabutylammonium fluoride was added under the argon atmosphere and ice-cooling, followed by stirring for 5 hours. The reaction solution was poured into an ice-cooled aqueous saturated ammonium chloride solution, and extraction with ethyl acetate was carried out. The organic layer was washed with water, and a saturated saline, and dried with sodium sulfate, and the solvent was concentrated under reduced pressure. The resulting residue was purified by preparative chromatograph (Hiflash-SI, Size L, hexane:ethyl acetate=8:2→1:1→0:1) manufactured Yamazen Corporation to obtain a titled compound (616 mg) having the following physical property values.
TLC: Rf 0.19 (hexane:ethyl acetate=1:1).

Example 34

[(3S,5aR,6R,7R,8aS)-6-[(1E)-3-oxo-4-phenoxy-1-buten-1-yl]-7-(tetrahydro-2H-pyran-2-yloxy)octahydro-2H-cyclopenta[b]oxepin-3-yl]methyl acetate The compound (616 mg) produced in Example 33 was subjected to the same objective operations as those of Example 13→Example 14 to obtain a titled compound (568 mg) having the following physical property values.
TLC: Rf 0.53 (hexane:ethyl acetate=1:1).

Example 35

[(3R,5aR,6R,7R,8aS)-6-[(1E,3R)-4-phenoxy-3-(tetrahydro-2H-pyran-2-yloxy)-1-buten-1-yl]-7-(tetrahydro-2H-pyran-2-yloxy)octahydro-2H-cyclopenta[b]oxepin-3-yl]methanol The compound produced in Example 34 was subjected to the same objective operations as those of Example 15→Example 11 to obtain a titled compound (568 mg) having the following physical property values.
TLC: Rf 0.26 (hexane:ethyl acetate=1:1).

Example 36

Ethyl 2-[(3S,5aR,6R,7R,8aS)-6-[(1E,3S)-4-phenoxy-3-(tetrahydro-2H-pyran-2-yloxy)-1-buten-1-yl]-7-(tetrahydro-2H-pyran-2-yloxy)octahydro-2H-cyclopenta[b]oxepin-3-yl]-1,3-thiazole-4-carboxylate Under the argon atmosphere, diisopropylethylamine (0.3 mL) was added to a DMSO (0.5 mL)-ethyl acetate (1.0 mL) solution of the compound (150 mg) synthesized in Example 35 under ice-cooling. Subsequently, pyridine-sulfur trioxide (139 mg) were added, and the mixture was stirred for about 30 minutes. After dilution with ethyl acetate, an aqueous saturated ammonium chloride solution was added, followed by extraction with ethyl acetate. The organic layer was washed with an aqueous saturated ammonium chloride solution, an aqueous saturated sodium bicarbonate solution, water and a saturated saline; dried with sodium sulfate; and concentrated under reduced pressure. The resulting residue was dissolved in toluene (1.5 mL), triethylamine (0.061 mL) and L-cysteine ethyl ester hydrochloride (81 mg) were sequentially added under ice-cooling, followed by stirring at room temperature overnight. After dilution with ethyl acetate, water was added, and extraction with ethyl acetate was carried out. Washing with an aqueous citric acid solution, an aqueous saturated sodium bicarbonate solution, water and a saturated saline, and drying with sodium sulfate were carried out, followed by concentration under reduced pressure. The resulting residue was dissolved in toluene (5.8 mL), manganese dioxide (756 mg) was added, and the mixture was stirred at 60° C. overnight. Filteration with Celite (trade name), and washed with ethyl acetate plural times were carried out, followed by concentration under reduced pressure. The resulting residue was purified with preparative chromatograph (SMB Silica Column 10 van, Size 20, hexane:ethyl acetate=9:1→75:25→6:4→3:7) manufactured by Yamazen Corporation to obtain a title compound (65 mg) having the following physical property values.
TLC: Rf 0.42, 0.38 (hexane:ethyl acetate=3:2).

Example 37

Ethyl 2-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}-1,3-thiazole-4-carboxylate

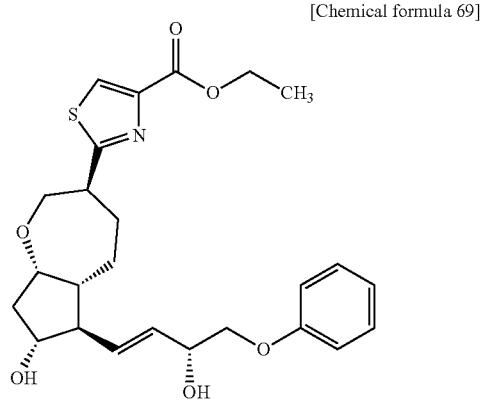 [SMILES: CCOC(=O)c1csc([C@H]2CC[C@@H]3[C@@H](/C=C/[C@@H](O)COc4ccccc4)[C@H](O)C[C@@H]3OC2)n1]

[Chemical formula 69]

To an ethanol (1.0 mL) solution of the compound (65 mg) produced in Example 36, p-toluenesulfonic acid monohydrate (2.0 mg) was added at room temperature, followed by stirring overnight. An aqueous saturated sodium bicarbonate solution was added, followed by extraction with ethyl acetate. Washing with water and a saturated saline, and drying with sodium sulfate were carried out, followed by concentration under reduced pressure. The resulting residue was purified with preparative chromatograph (SMB silica column, 10 µm, Size 20, hexane:ethyl acetate=1:1→0:1) manufactured by

Example 38

2-{(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}-1,3-thiazole-4-carboxylic acid

[Chemical formula 70]

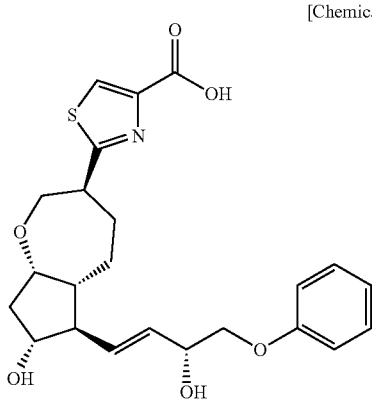

The compound produced in Example 37 was subjected to the same objective operations as those of Example 17 (1) to obtain a titled compound having the following physical property values.

TLC: Rf 0.19 (chloroform:methanol:water=10:1:0.1);
$^1$H-NMR (300 MHz, CDCl$_3$): δ 1.56-2.01, 2.10-2.39, 2.47-2.61, 3.35-3.55, 3.78, 3.85-3.94, 3.97-4.06, 4.11, 4.38, 4.51-4.60, 5.63-5.77, 6.87-7.02, 7.23-7.35, 8.15.

Example 39

Ethyl({[(3S,5aR,6R,7R,8aS)-6-[(1E,3R)-4-phenoxy-3-(tetrahydro-2H-pyran-2-yloxy)-1-buten-1-yl]-7-(tetrahydro-2H-pyran-2-yloxy)octahydro-2H-cyclopenta[b]oxepin-3-yl]methyl}thio)acetate Triethylamine (0.039 mL) and methanesulfonic acid chloride (0.020 mL) were sequentially added to an anhydrous THF (1.7 mL) solution of the compound (90 mg) produced in Example 35 under ice-cooling, followed by stirring for 1 hour. Dilution with ethyl acetate was carried out, and water was added, followed by extraction. Sequentially washing with an aqueous saturated sodium bicarbonate solution, water and a saturated saline, and drying with sodium sulfate were carried out. The solvent was concentrated under reduced pressure to obtain the residue (109 mg). The resulting residue was dissolved in an anhydrous THF (1.7 mL) solution, and ethyl thioglycolate (0.029 mL) was added. Subsequently, 60% sodium hydride (11 mg) was added at room temperature, followed by stirring at 50° C. overnight. Dilution with ethyl acetate was carried out, and water was added, followed by extraction. Sequentially washing with an aqueous saturated sodium bicarbonate solution, water and a saturated saline, and drying with sodium sulfate were carried out. The solvent was concentrated under reduced pressure, and the resulting residue was purified by preparative chromatograph (Hiflash-SI, Size S, hexane:ethyl acetate=75:25→0:100) manufactured by Yamazen Corporation to obtain a titled compound (61 mg) having the following physical property values.

TLC: Rf 0.81 (hexane:ethyl acetate=1:2).

Example 40

Ethyl [({(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}methyl)thio]acetate

[Chemical formula 71]

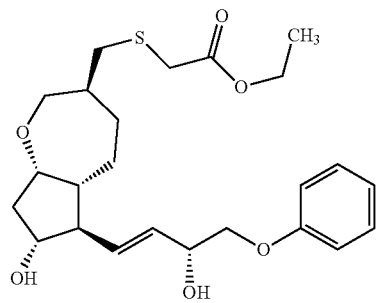

The compound produced in Example 39 was subjected to the same objective operations as those of Example 37 to obtain a titled compound having the following physical property values.

TLC: Rf 0.16 (hexane:ethyl acetate=1:2);
$^1$H-NMR (300 MHz, CDCl$_3$): δ 1.00-1.18, 1.24-1.33, 1.38-1.56, 1.56-1.85, 1.84-2.19, 2.25, 2.39-2.55, 2.68, 2.98, 3.13-3.22, 3.64-3.79, 3.83-3.92, 3.92-4.03, 4.09-4.26, 4.45-4.58, 5.57-5.72, 6.85-7.02, 7.22-7.34.

Example 41

[({(3S,5aR,6R,7R,8aS)-7-hydroxy-6-[(1E,3R)-3-hydroxy-4-phenoxy-1-buten-1-yl]octahydro-2H-cyclopenta[b]oxepin-3-yl}methyl)thio]acetic acid

[Chemical formula 72]

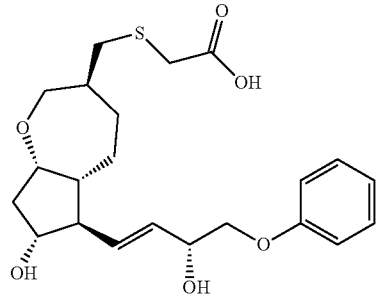

The compound produced in Example 40 was subjected to the same objective operations as those of Example 17 (1) to obtain a titled compound having the following physical property values.

TLC: Rf 0.35 (chloroform:methanol:acetic acid=10:1: 0.1);
$^1$H-NMR (300 MHz, CDCl$_3$): δ 1.01-1.17, 1.38-1.55, 1.60-1.86, 1.86-2.20, 2.41-2.55, 2.93-3.05, 3.22, 3.67-3.79, 3.84-3.93, 3.93-4.04, 4.14-4.24, 4.48-4.57, 5.59-5.74, 6.87-7.03, 7.24-7.34.

Example 42 (1) to Example 42 (2)

With using the compound produced in Example 4, and using a corresponding organozinc reagent in place of 4-ethoxy-4-oxobutylzinc bromide, these substances were subjected to the same objective operations as those of Example 5→Example 6→Example 12→Example 13→Example 14→Example 15→Example 16 (1) to obtain the following compounds.

Example 42 (1)

Ethyl 3-{(5aR,6R,7R,8aS)-7-hydroxy-6-[(1E)-3-hydroxy-4-phenoxy-1-buten-1-yl]-5,5a,6,7,8,8a-hexahydro-2H-cyclopenta[b]oxepin-3-yl}benzoate (low polar body)

[Chemical formula 73]

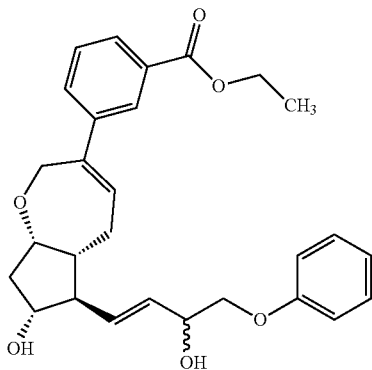

TLC: Rf 0.43 (hexane:ethyl acetate=1:2);
$^1$H-NMR (300 MHz, CDCl$_3$): δ 1.35-1.44, 1.71-1.86, 2.04, 2.11-2.32, 2.43-2.64, 2.64-2.86, 3.73-3.94, 4.02, 4.07-4.21, 4.31-4.50, 4.50-4.61, 4.81-4.95, 5.61-5.81, 5.96-6.10, 6.86-7.03, 7.21-7.46, 7.84-7.98.

Example 42 (2)

Ethyl 3-{(5aR,6R,7R,8aS)-7-hydroxy-6-[(1E)-3-hydroxy-4-phenoxy-1-buten-1-yl]-5,5a,6,7,8,8a-hexahydro-2H-cyclopenta[b]oxepin-3-yl}benzoate (high polar body)

TLC: Rf 0.33 (hexane:ethyl acetate=1:2);
$^1$H-NMR (300 MHz, CDCl$_3$): δ 1.40, 1.72-1.86, 2.08-2.32, 2.44-2.58, 2.61, 2.75, 3.74-3.86, 3.85-3.96, 3.98-4.07, 4.15, 4.33-4.51, 4.55, 4.83-4.95, 5.62-5.80, 5.97-6.08, 6.88-7.03, 7.23-7.46, 7.88-7.96.

Example 43 (1) to Example 43 (5)

With using the compound produced in Example 4; using 4-ethoxy-4-oxobutylzinc bromide or a corresponding organozinc reagent in place of it; and using dimethyl-(3-phenoxy-2-oxopropyl)-phosphonate or a corresponding phosphonic acid salt in place of it, these substances were subjected to the same objective preparations as those of Example 5→Example 6→Example 12→Example 13→Example 14→Example 15→Example 16 (1)→Example 17 (1) to obtain the following Example compounds.

Example 43 (1)

3-{(5aR,6R,7R,8aS)-7-hydroxy-6-[(1E)-3-hydroxy-4-phenoxy-1-buten-1-yl]-5,5a,6,7,8,8a-hexahydro-2H-cyclopenta[b]oxepin-3-yl}benzoic acid (low polar body)

[Chemical formula 74]

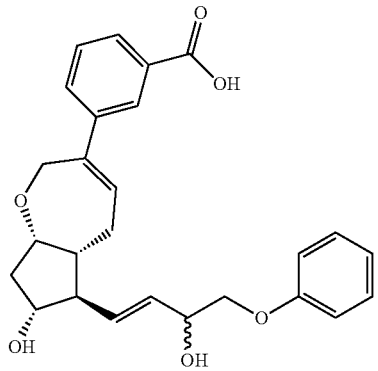

TLC: Rf 0.19 (chloroform:methanol:acetic acid=10:1: 0.1);
$^1$H-NMR (300 MHz, CD$_3$OD): δ 1.58-1.74, 2.07-2.32, 2.40-2.55, 2.60-2.78, 3.66-3.80, 3.84-3.95, 3.95-4.04, 4.10-4.22, 4.38-4.56, 4.77-4.99, 5.62-5.79, 6.04, 6.85-6.99, 7.19-7.29, 7.39, 7.45-7.54, 7.83-7.94.

Example 43 (2)

3-{(5aR,6R,7R,8aS)-7-hydroxy-6-[(1E)-3-hydroxy-4-phenoxy-1-buten-1-yl]-5,5a,6,7,8,8a-hexahydro-2H-cyclopenta[b]oxepin-3-yl}benzoic acid (high polar body)

TLC: Rf 0.20 (chloroform:methanol:acetic acid=10:1: 0.1);
$^1$H-NMR (300 MHz, CD$_3$OD): δ 1.58-1.74, 2.04-2.31, 2.40-2.55, 2.66, 3.66-3.81, 3.86-4.02, 4.15, 4.37-4.54, 4.73-5.00, 5.59-5.76, 6.01, 6.85-6.98, 7.19-7.30, 7.39, 7.45-7.53, 7.84-7.94.

Example 43 (3)

3-{(5aR,6R,7R,8aS)-7-hydroxy-6-[(1E,3R)-3-hydroxy-4-phenoxy-1-buten-1-yl]-5,5a,6,7,8,8a-hexahydro-2H-cyclopenta[b]oxepin-3-yl}propanoic acid TLC: Rf 0.56 (dichloromethane:methanol=5:1);
$^1$H-NMR (300 MHz, CDCl$_3$): δ 1.61-1.79, 1.84-2.29, 2.36-2.60, 3.67-3.83, 3.86-4.16, 4.38, 4.48-4.67, 5.41-5.57, 5.57-5.87, 6.78-7.08, 7.19-7.36.

Example 43 (4)

4-{(5aR,6R,7R,8aS)-7-hydroxy-6-[(1E,3R)-3-hydroxy-4-phenoxy-1-buten-1-yl]-5,5a,6,7,8,8a-hexahydro-2H-cyclopenta[b]oxepin-3-yl}butanoic acid TLC: Rf 0.38 (dichloromethane:methanol=9:1);
$^1$H-NMR (300 MHz, CDCl$_3$): δ 1.62-1.79, 1.81-2.26, 2.26-2.64, 3.69-3.81, 3.82-3.91, 3.92-4.07, 4.39, 4.49-4.59, 5.42-5.53, 5.55-5.79, 6.75-7.12, 7.19-7.41.

Example 43 (5)

4-{(5aR,6R,7R,8aS)-7-hydroxy-6-[(1E,3S)-3-hydroxy-1-octen-1-yl]-5,5a,6,7,8,8a-hexahydro-2H-cyclopenta[b]oxepin-3-yl}butanoic acid TLC: Rf 0.33 (dichloromethane:methanol=9:1);
$^1$H-NMR (300 MHz, CDCl$_3$): δ 0.68-1.01, 1.06-2.93, 3.58-3.87, 3.88-4.24, 4.38, 5.25-5.81.

Example 44 (1) to Example 44 (4)

With using the compound produced in Example 4, and using 4-ethoxy-4-oxobutylzinc bromide or a corresponding organozinc reagent in place of it, these substances were subjected to the same objective operations as those of Example 5→Example 6→Example 7→Example 8→Example 12→Example 13→Example 14→Example 15→Example 16 (1) to obtain the following Example compounds.

Example 44 (1)

2-Propanyl 5-{(5aR,6R,7R,8aS)-7-hydroxy-6-[(1E,3R)-3-hydroxy-4-phenoxy-1-buten-1-yl]-5,5a,6,7,8,8a-hexahydro-2H-cyclopenta[b]oxepin-3-yl}pentanoate

[Chemical formula 75]

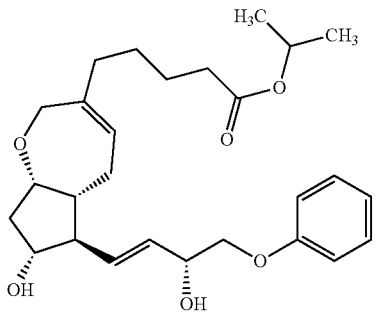

TLC: Rf 0.21 (hexane:ethyl acetate=1:2);
$^1$H-NMR (300 MHz, CDCl$_3$): δ 1.22, 1.31-1.44, 1.51-1.78, 1.77-1.98, 2.01-2.31, 2.37-2.61, 3.49, 3.68-3.82, 3.83-3.93, 3.93-4.06, 4.39, 4.47-4.59, 4.92-5.06, 5.37-5.49, 5.57-5.75, 6.86-7.02, 7.22-7.35.

Example 44 (2)

2-Propanyl 5-{(5aR,6R,7R,8aS)-6-[(1E,3R)-4-(3-chlorophenoxy)-3-hydroxy-1-buten-1-yl]-7-hydroxy-5,5a,6,7,8,8a-hexahydro-2H-cyclopenta[b]oxepin-3-yl}pentanoate TLC: Rf 0.26 (hexane:ethyl acetate=2:3);
$^1$H-NMR (300 MHz, CDCl$_3$): δ 1.22, 1.31-1.46, 1.52-1.65, 1.65-1.77, 1.77-1.97, 2.01-2.32, 2.37-2.65, 3.68-3.82, 3.82-3.92, 3.92-4.05, 4.39, 4.51, 4.91-5.08, 5.39-5.50, 5.57-5.75, 6.77-6.84, 6.89-6.99, 7.20.

Example 44 (3)

2-Propanyl 5-{(5aR,6R,7R,8aS)-7-hydroxy-6-[(1E,3R)-3-hydroxy-4-(3-methylphenoxy)-1-buten-1-yl]-5,5a,6,7,8,8a-hexahydro-2H-cyclopenta[b]oxepin-3-yl}pentanoate TLC: Rf 0.29 (hexane:ethyl acetate=1:2);
$^1$H-NMR (300 MHz, CDCl$_3$): δ 1.20-1.25, 1.31-1.45, 1.51-1.65, 1.65-1.77, 1.77-1.98, 2.00-2.21, 2.21-2.30, 2.30-2.36, 2.38-2.61, 3.68-3.80, 3.81-3.91, 3.91-4.06, 4.32-4.45, 4.51, 4.92-5.07, 5.38-5.49, 5.57-5.74, 6.66-6.83, 7.16.

Example 44 (4)

2-Propanyl 6-{(5aR,6R,7R,8aS)-7-hydroxy-6-[(1E)-3-hydroxy-4-phenoxy-1-buten-1-yl]-5,5a,6,7,8,8a-hexahydro-2H-cyclopenta[b]oxepin-3-yl}hexanoate TLC: Rf 0.15 (hexane:ethyl acetate=1:1);
$^1$H-NMR (300 MHz, CDCl$_3$): δ 1.18-1.46, 1.52-1.99, 2.00-2.30, 2.30-2.62, 2.77, 3.65-3.81, 3.81-4.08, 4.39, 4.46-4.59, 4.90-5.09, 5.42, 5.55-5.75, 6.85-7.03, 7.22-7.35.

Example 45 (1) to Example 45 (4)

The compounds produced in Example 44 (1) to Example 44 (4) were subjected to the same objective operations as those of Example 17 (1), respectively, to obtain the following Example compounds.

Example 45 (1)

5-{(5aR,6R,7R,8aS)-7-hydroxy-6-[(1E,3R)-3-hydroxy-4-phenoxy-1-buten-1-yl]-5,5a,6,7,8,8a-hexahydro-2H-cyclopenta[b]oxepin-3-yl}pentanoic acid

[Chemical formula 76]

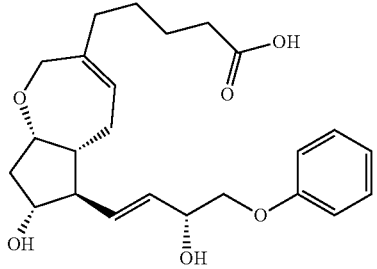

TLC: Rf 0.53 (ethyl acetate: methanol=9:1);
$^1$H-NMR (300 MHz, CDCl$_3$): δ 1.31-1.48, 1.52-1.77, 1.77-1.98, 2.00-2.25, 2.34, 2.38-2.59, 3.67-3.81, 3.84-4.06, 4.38, 4.46-4.58, 5.43, 5.57-5.73, 6.85-7.02, 7.21-7.35.

Example 45 (2)

5-{(5aR,6R,7R,8aS)-6-[(1E,3R)-4-(3-chlorophenoxy)-3-hydroxy-1-buten-1-yl]-7-hydroxy-5,5a,6,7,8,8a-hexahydro-2H-cyclopenta[b]oxepin-3-yl}pentanoic acid TLC: Rf 0.36 (chloroform:methanol:acetic acid=10:1:0.1);
$^1$H-NMR (300 MHz, CDCl$_3$): δ 1.22-1.49, 1.53-1.76, 1.78-1.98, 1.98-2.28, 2.34, 2.38-2.57, 3.67-3.80, 3.84-3.93, 3.93-4.05, 4.32-4.44, 4.45-4.55, 5.44, 5.56-5.73, 6.77-6.84, 6.89-6.98, 7.20.

Example 45 (3)

5-{(5aR,6R,7R,8aS)-7-hydroxy-6-[(1E,3R)-3-hydroxy-4-(3-methylphenoxy)-1-buten-1-yl]-5,5a,6,7,8,8a-hexahydro-2H-cyclopenta[b]oxepin-3-yl}pentanoic acid TLC: Rf 0.43 (chloroform:methanol:acetic acid=10:1:0.1):
$^1$H-NMR (300 MHz, CD$_3$OD): δ 1.32-1.47, 1.49-1.65, 1.79-1.94, 2.01-2.13, 2.21-2.34, 2.34-2.54, 3.62-3.75, 3.83-4.08, 4.32-4.45, 5.44, 5.54-5.72, 6.66-6.78, 7.06-7.17.

Example 45 (4)

6-{(5aR,6R,7R,8aS)-7-hydroxy-6-[(1E)-3-hydroxy-4-phenoxy-1-buten-1-yl]-5,5a,6,7,8,8a-hexahydro-2H-cyclopenta[b]oxepin-3-yl}hexanoic acid TLC: Rf 0.57 (chloroform:methanol:acetic acid=10:1:0.1);
$^1$H-NMR (300 MHz, CD$_3$OD): δ 1.22-1.46, 1.50-1.67, 1.77-1.94, 1.98-2.13, 2.27, 2.36-2.55, 3.60-3.76, 3.85-4.08, 4.31-4.47, 5.38-5.48, 5.56-5.72, 6.86-6.97, 7.20-7.30.

Example 46

Ethyl 4-{(5aR,6R,7R,8aS)-7-hydroxy-6-[(1E)-3-hydroxy-4-phenoxy-1-buten-1-yl]octahydro-2H-cyclopenta[b]oxepin-3-yl}butanoate (diastereomer mixture)

With using the compound produced in Example 6, the compound was subjected to the same objective preparations as those of Example 9→Example 12→Example 13→Example 14→Example 15→Example 16 (1) to obtain a titled compound having the following physical property values.
TLC: Rf 0.33 (dichloromethane:methanol=20:1);
$^1$H-NMR (300 MHz, CDCl$_3$): δ 1.21-1.34, 1.37-1.89, 2.09-2.53, 2.57-2.67, 3.41, 3.66-4.06, 4.07-4.23, 4.45-4.56, 5.57-5.73, 6.87-7.05, 7.20-7.36.

Example 47

4-{(5aR,6R,7R,8aS)-7-hydroxy-6-[(1E)-3-hydroxy-4-phenoxy-1-buten-1-yl]octahydro-2H-cyclopenta[b]oxepin-3-yl}butanoic acid (diastereomer mixture)

With using the compound produced in Example 46, the compound was subjected to the same objective operations as those of Example 17 (1) to obtain a titled compound having the following physical property values.

TLC: Rf 0.36 (dichloromethane:methanol=10:1);
$^1$H-NMR (300 MHz, CDCl$_3$): δ 1.09-1.88, 2.08-2.23, 2.26-2.59, 2.85-3.55, 3.60-4.17, 4.45-4.60, 5.52-5.84, 6.84-7.03, 7.13-7.43.

Example 48 (1) to Example 48 (2)

With using the compound produced in Example 3, and using a corresponding alkyl halide in place of 2,3-dibromopropene, these substances were subjected to the same objective preparations as those of Example 4→Example 5→Example 6→Example 7→Example 8→Example 9→Example 12→Example 13→Example 14→Example 15→Example 16 (1) to obtain the following Example compounds.

Example 48 (1)

2-Propanyl 3-{(5aR,6R,7R,8aS)-7-hydroxy-6-[(1E,3R)-3-hydroxy-4-phenoxy-1-buten-1-yl]octahydro-2H-cyclopenta[b]oxepin-3-yl}propanoate (diastereomer mixture)

TLC: Rf 0.47 (ethyl acetate);
$^1$H-NMR (300 MHz, CDCl$_3$): δ 1.23, 1.33-1.94, 2.01-2.60, 2.86-3.46, 3.66-4.09, 4.47-4.59, 4.92-5.07, 5.58-5.75, 6.86-7.02, 7.24-7.35.

Example 48 (2)

2-Propanyl 5-{(5aR,6R,7R,8aS)-7-hydroxy-6-[(1E,3R)-3-hydroxy-4-phenoxy-1-buten-1-yl]octahydro-2H-cyclopenta[b]oxepin-3-yl}pentanoate (diastereomer mixture)

TLC: Rf 0.19 (hexane:ethyl acetate=1:2);
$^1$H-NMR (300 MHz, CDCl$_3$): δ 0.87-2.03, 2.03-2.33, 2.33-2.57, 2.89, 3.65-4.10, 4.46-4.59, 4.91-5.07, 5.57-5.74, 6.86-7.02, 7.19-7.34.

Example 49 (1) to Example 49 (2)

The compounds produced in Example 48 (1) to Example 48 (2) were subjected to the same objective operations as those of Example 17 (1), respectively, to obtain the following Example compounds.

Example 49 (1)

3-{(5aR,6R,7R,8aS)-7-hydroxy-6-[(1E,3R)-3-hydroxy-4-phenoxy-1-buten-1-yl]octahydro-2H-cyclopenta[b]oxepin-3-yl}propanoic acid (diastereomer mixture)

TLC: Rf 0.51 (chloroform:methanol:water=10:1:0.1);
$^1$H-NMR (300 MHz, CDCl$_3$): δ 1.30-1.96, 2.06-2.55, 2.85-3.47, 3.57-4.10, 4.41-4.61, 5.55-5.74, 6.86-7.02, 7.22-7.37.

Example 49 (2)

5-{(5aR,6R,7R,8aS)-7-hydroxy-6-[(1E,3R)-3-hydroxy-4-phenoxy-1-buten-1-yl]octahydro-2H-cyclopenta[b]oxepin-3-yl}pentanoic acid (diastereomer mixture)

TLC: Rf 0.53 (ethyl acetate: methanol=9:1);
$^1$H-NMR (300 MHz, CDCl$_3$): δ 0.88-1.19, 1.20-1.52, 1.52-1.93, 2.05-2.19, 2.27-2.39, 2.40-2.54, 2.89, 3.64-3.77, 3.77-4.08, 4.44-4.57, 5.55-5.72, 6.85-7.03, 7.21-7.36.

Example 50

(1S,2R,3S,4R)-3-({[dimethyl(2-methyl-2-propanyl)silyl]oxy}methyl)-2-(1-propen-1-yl)-4-(tetrahydro-2H-pyran-2-yloxy)cyclopentanol Under the argon atmosphere, carbonylchlorohydridotris(triphenylphosphine)ruthenium (9.5 mg) was added to a toluene solution (1 mL) of the compound (74.1 mg) produced in Example 3, and the reaction mixture was stirred at 80° C. for 3 hours and 30 minutes. Thereafter, a small amount of the reaction mixture was taken, and concentrated to obtain a titled compound having the following physical property values.

TLC: Rf 0.45 (hexane:ethyl acetate=75:25).

Example 51

2-Methyl-2-propanyl {[(1S,2R,3S,4R)-3-({[dimethyl(2-methyl-2-propanyl)silyl]oxy}methyl)-2-(1-propen-1-yl)-4-(tetrahydro-2H-pyran-2-yloxy)cyclopentyl]oxy}acetate Under the argon atmosphere, the compound (3.70 g) produced in Example 50 was dissolved in DMF (20 mL). After addition of t-butyl bromoacetate (7.4 mL), sodium hydride (400 mg, 60% in oil) was added four times for every 30 minutes to 60 minutes (total 1600 mg). After stirring at room temperature overnight, water was added to the reaction mixture. The extract obtained by extraction with ethyl acetate was washed with water and a saturated saline, dried with anhydrous magnesium sulfate, and concentrated under reduced pressure. The residue was purified by silica gel column chromatography (hexane:ethyl acetate=95:5→75:25) to obtain a titled compound (3.5 g) having the following physical property values.

TLC: Rf 0.50 (hexane:ethyl acetate=80:20).

Example 52

Allyl {[(1S,2R,3S,4R)-3-({[dimethyl(2-methyl-2-propanyl)silyl]oxy}methyl)-2-(1-propen-1-yl)-4-(tetrahydro-2H-pyran-2-yloxy)cyclopentyl]oxy}acetate The compound (3.37 g) produced in Example 51 was dissolved in THF (10 mL) and a 5N aqueous sodium hydroxide solution (5 mL) and methanol (20 mL) were added, followed by stirring at room temperature for 2 hours. To the reaction mixture, 2N hydrochloric acid was added. The extract obtained by extraction with ethyl acetate was washed with water and a saturated saline; dried with anhydrous magnesium sulfate; and concentrated under reduced pressure to obtain carboxylic acid (3.02 g). The carboxylic acid (3.02 g) was dissolved in DMF (15 mL); potassium carbonate (1.60 g) and allyl bromide (1.0 mL) were added; and the mixture was stirred at room temperature overnight. Water was added to the reaction mixture. The extract obtained by extraction with hexane/ethyl acetate (1/1) was washed with water and a saturated saline; dried with anhydrous magnesium sulfate; and concentrated under reduced pressure. The residue was purified by silica gel column chromatography (hexane:ethyl acetate=97:3→80:20) to obtain a titled compound (2.93 g) having the following physical property values.

TLC: Rf 0.50 (hexane:ethyl acetate=80:20).

Example 53 (1)

Methyl (2R)-2-{[(1S,2R,3S,4R)-3-({[dimethyl(2-methyl-2-propanyl)silyl]oxy}methyl)-2-(1-propen-1-yl)-4-(tetrahydro-2H-pyran-2-yloxy)cyclopentyl]oxy}-4-pentenoate

Example 53 (2)

Methyl (2S)-2-{[(1S,2R,3S,4R)-3-({[dimethyl(2-methyl-2-propanyl)silyl]oxy}methyl)-2-(1-propen-1-yl)-4-(tetrahydro-2H-pyran-2-yloxy)cyclopentyl]oxy}-4-pentenoate Under the argon atmosphere, diisopropylamine (2.0 mL) was dissolved in THF (16 mL), and the solution was cooled to 0° C. After addition of a 1.66M n-butyllithiumhexane solution (8.0 mL) dropwise, the mixture was stirred at the same temperature for 30 minutes. After cooling to −78° C., and addition of trimethylchlorosilane (2.0 mL) dropwise, a THF (7 mL) solution of the compound (3.28 g) produced in Example 52 was added dropwise. After stirring at −78° C. for 30 minutes, a temperature was raised to room temperature, and stirring for 1 hour was carried out. After addition of water to the reaction mixture and stirring for 1 hour, 1N hydrochloric acid was added, and the extract obtained by extraction with ethyl acetate was washed with water and a saturated saline; dried with anhydrous magnesium sulfate; and concentrated under reduced pressure. The residue was dissolved in ethyl acetate (40 mL), methanol (4 mL), and a 2.0M trimethylsilyldiazomethanehexane solution (7 mL) were added, followed by stirring at room temperature for 1 hour. After concentration of the reaction mixture under reduced pressure, the residue was purified by silica gel column chromatography (hexane:ethyl acetate=97:3→80:20) to obtain an Example compound 53 (1) (1.26 g) and an Example compound 53 (2) (1.16 g) having the following physical property values.

TLC: Rf 0.42 (hexane:ethyl acetate=86:14) (compound of Example 53 (1));
TLC: Rf 0.36 (hexane:ethyl acetate=86:14) (compound of Example 53 (2)).

Example 54

Methyl (2R,5aR,6S,7R,8aS)-6-({[dimethyl(2-methyl-2-propanyl)silyl]oxy}methyl)-7-(tetrahydro-2H-pyran-2-yloxy)-3,5a,6,7,8,8a-hexahydro-2H-cyclopenta[b]oxepin-2-carboxylate The compound (1.26 g) produced in Example 53 (1) was dissolved in dichloromethane (30 mL) and a Schrock's catalyst (0.44 g) was added, followed by stirring at room temperature overnight. After concentration of the reaction mixture under reduced pressure, the residue was purified by silica gel column chromatography (hexane:ethyl acetate=95:5→75:25) to obtain a titled compound (0.95 g) having the following physical property values.

TLC: Rf 0.48 (hexane:ethyl acetate=75:25).

Example 55

[(2R,5aR,6S,7R,8aS)-6-({[dimethyl(2-methyl-2-propanyl)silyl]oxy}methyl)-7-(tetrahydro-2H-pyran-2-yloxy)-3,5a,6,7,8,8a-hexahydro-2H-cyclopenta[b]oxepin-2-yl]methanol Lithium aluminum hydride (84 mg) was suspended in THF (2 mL), followed by cooling to 0° C. A THF (3 mL) solution of the compound (0.95 g) produced in Example 54 was added dropwise, followed by stirring at 0° C. for 15 minutes. After addition of water to the reaction mixture, the extract obtained by addition of 1N hydrochloric acid was washed with water, an aqueous saturated sodium bicarbonate solution and a saturated saline, and dried with anhydrous magnesium sulfate, followed by concentration under reduced pressure. The residue was purified by silica gel column chromatography (hexane:ethyl acetate=60:40→40:60) to obtain a titled compound (793 mg) having the following physical property values.
TLC: Rf 0.43 (hexane:ethyl acetate=50:50).

Example 56

2-Propanyl (2E)-3-[(2R,5aR,6S,7R,8aS)-6-({[dimethyl(2-methyl-2-propanyl)silyl]oxy}methyl)-7-(tetrahydro-2H-pyran-2-yloxy)-3,5a,6,7,8,8a-hexahydro-2H-cyclopenta[b]oxepin-2-yl]acrylate The compound (165 mg) produced in Example 55 was dissolved in DMSO (2 mL), a Wittig reagent (carboisopropoxymethylenetriphenylphosphorane, 218 mg) and 1-hydroxy-1,2-benziodoxol-3(1H)-one 1-oxide (IBX, 169 mg) were added, followed by stirring at 50° C. for 5 hours. Ethyl acetate and water were added to the reaction mixture, and insolubles were filtered. Extraction with ethyl acetate, and washing with an aqueous saturated sodium bicarbonate solution and a saline, and drying with anhydrous magnesium sulfate were carried out, followed by concentration under reduced pressure. The residue was purified by silica gel column chromatography (hexane:ethyl acetate=97:3→80:20) to obtain a titled compound (174 mg) having the following physical property values.
TLC: Rf 0.50 (hexane:ethyl acetate=80:20).

Example 57

2-Propanyl 3-[(2R,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-2-yl]propanoate The compound (174 mg) produced in Example 56 was dissolved in 2-propanol (2 mL), sodium bicarbonate (20 mg) and 10% palladium carbon (20 mg) were added, followed by stirring at room temperature for 1 hour under the hydrogen atmosphere. The filtrate obtained by filtering the reaction mixture with Celite (trade name) was concentrated under reduced pressure, and the residue was purified by silica gel column chromatography (hexane:ethyl acetate=97:3→80:20) to obtain a titled compound (150 mg) having the following physical property values.
TLC: Rf 0.50 (hexane:ethyl acetate=80:20).

Example 58

2-Propanyl 3-[(2R,5aR,6S,7R,8aS)-6-(hydroxymethyl)-7-(tetrahydro-2H-pyran-2-yloxy)octahydro-2H-cyclopenta[b]oxepin-2-yl]propanoate To the compound (143 mg) produced in Example 57, 1 mL of 1 mol/L tetrabutylammonium fluoride (THF solution) was added, followed by stirring at room temperature overnight. After concentration of the reaction mixture under reduced pressure, the residue was purified by silica gel column chromatography (hexane:ethyl acetate=60:40→20:80) to obtain a titled compound (98 mg) having the following physical property values.
TLC: Rf 0.32 (hexane:ethyl acetate=50:50).

Example 59

2-Propanyl 3-{(2R,5aR,6R,7R,8aS)-7-hydroxy-6-[(1E,3R)-3-hydroxy-4-phenoxy-1-buten-1-yl]octahydro-2H-cyclopenta[b]oxepin-2-yl}propanoate

[Chemical formula 77]

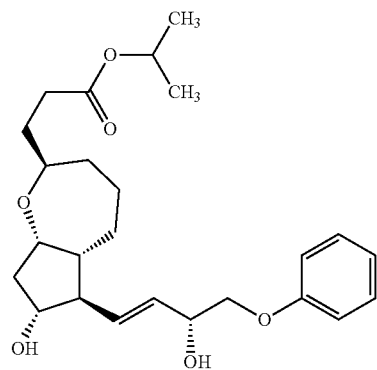

The compound produced in Example 58 was subjected to the same objective operations as those of Example 13→Example 14→Example 15→Example 16 (1) to obtain a titled compound having the following physical property values.
TLC: Rf 0.32 (hexane:ethyl acetate=1:3);
$^1$H-NMR (300 MHz, CDCl$_3$): δ 7.27-7.31, 6.89-6.99, 5.59-5.72, 4.93-5.05, 4.49-4.55, 4.21, 3.99, 3.88, 3.69-3.83, 2.55, 2.19-2.44, 1.45-1.88, 1.23.

Example 60

[(2S,5aR,6S,7R,8aS)-6-({[dimethyl(2-methyl-2-propanyl)silyl]oxy}methyl)-7-(tetrahydro-2H-pyran-2-yloxy)-3,5a,6,7,8,8a-hexahydro-2H-cyclopenta[b]oxepin-2-yl]methanol With Using the compound produced in Example 53 (2), the compound was subjected to the same objective operations as those of Example 54→Example 55 to obtain a titled compound having the following physical property values.
TLC: Rf 0.58 (hexane:ethyl acetate=50:50).

Example 61

2-Propanyl 3-{(2S,5aR,6R,7R,8aS)-7-hydroxy-6-[(1E,3R)-3-hydroxy-4-phenoxy-1-buten-1-yl]octahydro-2H-cyclopenta[b]oxepin-2-yl}propanoate

[Chemical formula 78]

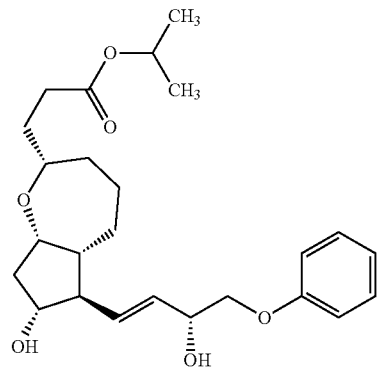

With using the compound produced in Example 60, this compound was subjected to the same objective operations as those of Example 56→Example 57→Example 58→Example 59 to obtain a titled compound having the following physical property values.

TLC: Rf 0.34 (hexane:ethyl acetate=1:3);

$^1$H-NMR (300 MHz, CDCl$_3$): δ 7.27-7.32, 6.90-7.00, 5.59-5.72, 4.94-5.06, 4.49-4.55, 3.93-4.01, 3.88, 3.69-3.79, 3.17-3.25, 2.52, 2.27-2.46, 2.06-2.19, 1.65-1.84, 1.26-1.49, 1.23.

Example 62

[(2R,5aR,6S,7R,8aS)-6-({[dimethyl(2-methyl-2-propanyl)silyl]oxy}methyl)-7-(tetrahydro-2H-pyran-2-yloxy)-3,5a,6,7,8,8a-hexahydro-2H-cyclopenta[b]oxepin-2-yl]methylmethanesulfonate Under the argon atmosphere, the compound (207 mg) produced in Example 55 was dissolved in dichloromethane (2 mL), followed by cooling to 0° C. Triethylamine (0.14 mL) and methanesulfonyl chloride (0.040 mL) were added, followed by stirring at 0° C. for 15 minutes. Water was added to the reaction mixture, and the extract obtained by extraction with ethyl acetate was washed with water and a saturated saline; dried with anhydrous magnesium sulfate; and concentrated under reduced pressure to obtain a titled compound (273 mg) having the following physical property values.

TLC: Rf 0.40 (hexane:ethyl acetate=67:33).

Example 63

[(2R,5aR,6S,7R,8aS)-6-({[dimethyl(2-methyl-2-propanyl)silyl]oxy}methyl)-7-(tetrahydro-2H-pyran-2-yloxy)-3,5a,6,7,8,8a-hexahydro-2H-cyclopenta[b]oxepin-2-yl]acetonitrile The compound (273 mg) produced in Example 62 was dissolved in DMSO (1 mL) and sodium cyanide (55 mg) was added, followed by stirring at 80° C. overnight. Water was added to the reaction mixture, and the extract obtained by extraction with ethyl acetate was washed with water and a saturated saline; dried with anhydrous magnesium sulfate; and concentrated under reduced pressure. The residue was purified by silica gel column chromatography (hexane: ethyl acetate=90:10→70:30) to obtain a titled compound (205 mg) having the following physical property values.

TLC: Rf 0.55 (hexane:ethyl acetate=75:25).

Example 64

2-Propanyl (2E)-3-[(2R,5aR,6S,7R,8aS)-6-({[dimethyl(2-methyl-2-propanyl)silyl]oxy}methyl)-7-(tetrahydro-2H-pyran-2-yloxy)-3,5a,6,7,8,8a-hexahydro-2H-cyclopenta[b]oxepin-2-yl]acrylate The compound (195 mg) produced in Example 63 was dissolved in toluene (4 mL), followed by cooling to −15° C. A 1M toluene solution (0.8 mL) of diisobutylaluminum hydride was added, followed by stirring at the same temperature for 1 hour and 30 minutes. An aqueous saturated ammonium chloride solution was added to the reaction mixture was added. The extract obtained by extraction with ethyl acetate was washed with 1N hydrochloric acid, an aqueous saturated sodium bicarbonate solution, water and a saturated saline, dried with anhydrous magnesium sulfate, and concentrated under reduced pressure. The residue was dissolved in dichloromethane (2 mL), phosphorane (250 mg) was added, followed by stirring at room temperature overnight. After concentration of the reaction mixture under reduced pressure, the residue was purified by silica gel column chromatography (hexane:ethyl acetate=95:5→75:25) to obtain a titled compound (39 mg) having the following physical property values.

TLC: Rf 0.46 (hexane:ethyl acetate=80:20).

Example 65

2-Propanyl 4-{(2R,5aR,6R,7R,8aS)-7-hydroxy-6-[(1E,3R)-3-hydroxy-4-phenoxy-1-buten-1-yl]octahydro-2H-cyclopenta[b]oxepin-2-yl}butanoate

[Chemical formula 79]

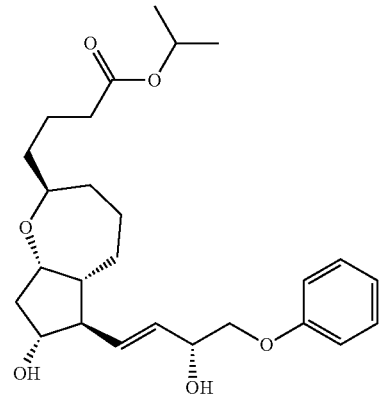

With using the compound produced in Example 64, the compound was subjected to the same objective operations as those of Example 56→Example 57→Example 58→Example 59 to obtain a titled compound having the following physical property values.

TLC: Rf 0.36 (hexane:ethyl acetate=1:3);

$^1$H-NMR (300 MHz, CDCl$_3$): δ 7.26-7.31, 6.89-6.99, 5.60-5.72, 4.93-5.06, 4.50-4.55, 4.17-4.24, 3.99, 3.88, 3.70-3.82, 2.56-2.61, 2.21-2.34, 1.51-1.78, 1.26-1.37, 1.23.

Example 66

2-Propanyl 4-{(2S,5aR,6R,7R,8aS)-7-hydroxy-6-[(1E,3R)-3-hydroxy-4-phenoxy-1-buten-1-yl]octahydro-2H-cyclopenta[b]oxepin-2-yl}butanoate

[Chemical formula 80]

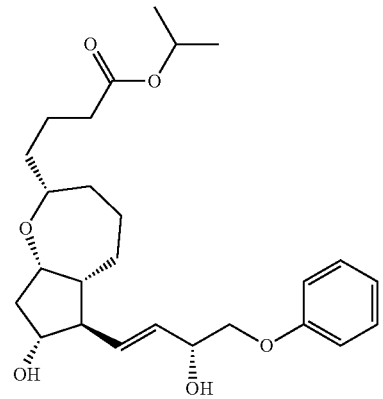

With using the compound produced in Example 60, the compound was subjected to the same objective operations as those of Example 62→Example 63→Example 64→Example 56→Example 57→Example 58→Example 59 to obtain a titled compound having the following physical property values.

TLC: Rf 0.42 (hexane:ethyl acetate=1:3);
$^1$H-NMR (300 MHz, CDCl$_3$): δ 7.26-7.31, 6.89-6.99, 5.58-5.72, 4.93-5.05, 4.48-4.55, 3.97-4.03, 3.87, 3.69-3.77, 3.13-3.22, 2.52-2.59, 2.38-2.47, 2.23-2.29, 2.11-2.19, 1.28-1.84, 1.22.

Example 67 (1) to Example 67 (4)

With using the compounds produced in Example 59, Example 61, Example 65 and Example 66, the compounds were subjected to the same objective operations as those of Example 17 (1) to obtain the following Example compounds.

Example 67 (1)

3-{(2R,5aR,6R,7R,8aS)-7-hydroxy-6[(1E,3R)-3-hydroxy-4-phenoxy-1-buten-1-yl]octahydro-2H-cyclopenta[b]oxepin-2-yl}propanoic acid

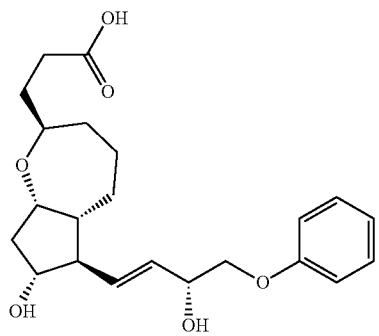

[Chemical formula 81]

TLC: Rf 0.36 (chloroform: methanol=5:1):
$^1$H-NMR (300 MHz, CDCl$_3$): δ 7.24-7.30, 6.89-6.98, 5.54-5.70, 4.48, 4.19, 3.95, 3.69-3.85, 2.19-2.54, 1.47-1.93.

Example 67 (2)

3-{(2S,5aR,6R,7R,8aS)-7-hydroxy-6-[(1E,3R)-3-hydroxy-4-phenoxy-1-buten-1-yl]octahydro-2H-cyclopenta[b]oxepin-2-yl}propanoic acid TLC: Rf 0.39 (chloroform:methanol=5:1);
$^1$H-NMR (300 MHz, CDCl$_3$): δ 7.24-7.30, 6.88-6.98, 5.56-5.67, 4.45-4.52, 3.86-4.02, 3.67-3.76, 3.20-3.29, 2.33-2.52, 2.09-2.18, 1.63-1.86, 1.22-1.48.

Example 67 (3)

4-{(2R,5aR,6R,7R,8aS)-7-hydroxy-6-[(1E,3R)-3-hydroxy-4-phenoxy-1-buten-1-yl]octahydro-2H-cyclopenta[b]oxepin-2-yl}butanoic acid TLC: Rf 0.37 (chloroform:methanol=5:1);
$^1$H-NMR (300 MHz, CD$_3$OD): δ 7.21-7.26, 6.87-6.93, 5.56-5.69, 4.38-4.44, 4.21-4.29, 3.84-4.00, 3.65-3.77, 2.27-2.36, 2.07-2.17, 1.50-1.84, 1.28-1.40.

Example 67 (4)

4-{(2S,5aR,6R,7R,8aS)-7-hydroxy-6-[(1E,3R)-3-hydroxy-4-phenoxy-1-buten-1-yl]octahydro-2H-cyclopenta[b]oxepin-2-yl}butanoic acid TLC: Rf 0.42 (chloroform:methanol=5:1);
$^1$H-NMR (300 MHz, CDCl$_3$): δ 7.25-7.30, 6.88-6.98, 5.56-5.69, 4.46-4.53, 3.86-4.02, 3.67-3.75, 3.14-3.23, 2.40-2.49, 2.35, 2.09-2.18, 1.24-1.84.

Example 68

4-{(3S,5aR,6R,7R,8aS)-6-[(1E)-4-(3-chlorophenoxy)-3-oxo-1-buten-1-yl]-7-hydroxyoctahydro-2H-cyclopenta[b]oxepin-3-yl}butanoic acid

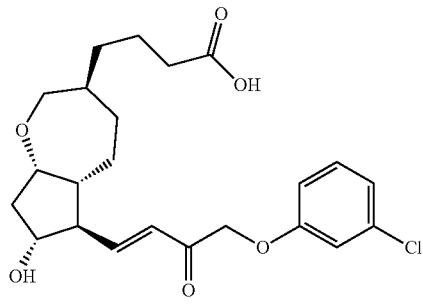

[Chemical formula 82]

The compound (102 mg) produced in Example 17 (3) was dissolved in methylene chloride (2 mL) and acetone (1.5 mL) and manganese dioxide (613 mg) was added, followed by stirring at 50° C. for 4 hours. Manganese dioxide was removed with Celite (trade name), followed by washing with chloroform-acetone. After concentration of the solvent under reduced pressure, the resulting residue was purified with a PLC glass plate (20×20 cm, silica gel 60 F$_{254}$, 0.5 mm, chloroform:methanol=19:1) to obtain a titled compound (7.8 mg) having the following physical property values.

TLC: Rf 0.24 (chloroform: methanol=19:1);
$^1$H-NMR (300 MHz, CD$_3$OD): δ 0.96-1.22, 1.36-1.51, 1.51-1.72, 1.84-2.00, 2.15-2.31, 2.43-2.55, 2.99, 3.81, 3.96-4.10, 4.93, 6.37, 6.81-7.00, 7.19-7.29.

Example 68 (1)

4-{(3S,5aR,6R,7R,8aS)-6-[(1E)-4-(2,5-difluorophenoxy)-3-oxo-1-buten-1-yl]-7-hydroxyoctahydro-2H-cyclopenta[b]oxepin-3-yl}butanoic acid With using the compound produced in Example 17 (25), the compound was subjected to the same objective operations as those of Example 68 to obtain the following Example compound.

TLC: Rf 0.42 (dichloromethane:methanol=10:1);
$^1$H-NMR (CD$_3$OD): δ 0.96-1.25, 1.36-1.75, 1.84-2.03, 2.15-2.33, 2.50, 2.99, 3.81, 3.96-4.11, 5.00, 6.37, 6.67, 6.79, 6.91, 7.11.

Example 69

(5aR,6S,7R,8aS)-6-({[dimethyl(2-methyl-2-propanyl)silyl]oxy}methyl)-3-[4-oxo-4-(2-propanyloxy)butyl]octahydro-2H-cyclopenta[b]oxepin-7-yl 4-biphenylcarboxylate To a methylene chloride (2.3 mL) solution of the compound (500 mg) produced in Example 10, triethylamine (0.246 mL), 4-phenylbenzoyl chloride (303 mg) and dimethylaminopyridine (2 mg) were added under ice-cooling and the argon atmosphere, followed by stirring at room temperature for 6 hours. Further, triethylamine (0.123 mL) and 4-phenylbenzoyl chloride (151 mg) were added, followed by stirring at room temperature overnight. After completion of the reaction, dilution with ethyl acetate was carried out and water was added, followed by extraction with ethyl acetate. The organic layer was washed with an aqueous saturated sodium bicarbonate solution, water and a saturated saline. After drying with anhydrous sodium sulfate, the solvent was distilled off under reduced pressure. The precipitated crystal was removed with MTBE, and the filtrate was concentrated under reduced pressure. The resulting residue was purified by preparative chromatograph (Hiflash-SI, size L, hexane:ethyl acetate=100:0→9:1→4:1→3:2) manufactured by Yamazen Corporation to obtain a titled compound (641 mg) having the following physical property values.

TLC: Rf 0.64 (hexane:ethyl acetate=3:1).

Example 70

(3S,5aR,6S,7R,8aS)-6-(hydroxymethyl)-3-[4-oxo-4-(2-propanyloxy)butyl]octahydro-2H-cyclopenta[b]oxepin-7-yl 4-biphenylcarboxylate To a THF (0.5 mL) solution of the compound (640 mg) produced in Example 69, a 1M THF solution (2.1 mL) of tetrabutylammonium fluoride was added at room temperature, followed by stirring for 2 hours. After completion of the reaction, the reaction mixture was diluted with ethyl acetate, and the reaction was stopped with an ice-cooled aqueous saturated ammonium chloride solution. After extraction with ethyl acetate, the organic layer was washed with water and a saturated saline, and dried with anhydrous sodium sulfate. Additionally, the solvent was concentrated under reduced pressure. The resulting residue was purified by preparative chromatograph (Hiflash-SI, Size L, hexane:ethyl acetate=85:15→7:3→1:1→3:7) manufactured by Yamazen Corporation to obtain a titled compound (214 mg) having the following physical property values.

TLC: Rf 0.30 (hexane:ethyl acetate=2:1).

Example 71

(3S,5aR,6R,7R,8aS)-6-[(1E,3R)-4-(2,5-difluorophenoxy)-3-(tetrahydro-2H-pyran-2-yloxy)-1-buten-1-yl]-3-[4-oxo-4-(2-propanyloxy)butyl]octahydro-2H-cyclopenta[b]oxepin-7-yl 4-biphenylcarboxylate With using the compound produced in Example 70, the compound was subjected to the same objective operations as those of Example 13→Example 14→Example 15→Example 11 to obtain a titled compound having the following physical property values.

TLC: Rf 0.58 (hexane:ethyl acetate=2:1).

Example 72

2-Propanyl 4-{(3S,5aR,6R,7R,8aS)-6-[(1E,3R)-4-(2,5-difluorophenoxy)-3-(tetrahydro-2H-pyran-2-yloxy)-1-buten-1-yl]-7-hydroxyoctahydro-2H-cyclopenta[b]oxepin-3-yl}butanoate Lithium isopropoxide (2.0M THF solution, 2.3 mL) was added to a 2-propanol (5 mL) solution of the compound (950 mg) produced in Example 71 was added, and the reaction mixture was stirred at 50° C. for 5 hours. The reaction mixture was cooled to 0° C., and poured into a water-ethyl acetate mixed solution which had been similarly cooled to 0° C. The organic layer was washed with water and a saturated saline; dried with magnesium sulfate; and concentrated under reduced pressure. The resulting residue was purified by silica gel column chromatography (hexane:ethyl acetate=1:1→only ethyl acetate) to obtain a titled compound (530 mg) having the following physical property values.

TLC: Rf 0.26 (hexane:ethyl acetate=1:1).

Example 73

2-Propanyl 4-[(3S,5aR,6R,7S,8aS)-6-[(1E,3R)-4-(2,5-difluorophenoxy)-3-(tetrahydro-2H-pyran-2-yloxy)-1-buten-1-yl]-7-(formyloxy)octahydro-2H-cyclopenta[b]oxepin-3-yl]butanoate To a THF (0.3 mL) solution of the compound (29 mg) produced in Example 72, triphenylphosphine (27 mg), formic acid (4 μL) and a toluene solution of diethyl azodicarboxylate (47 μL, 2.2 mol/L) were added at −15° C., and the reaction mixture was stirred at 0° C. for 1.5 hours. Further, triphenylphosphine (27 mg), formic acid (4 μL) and a toluene solution of diethyl azodicarboxylate (47 μL, 2.2 mol/L) were added at 0° C., and the reaction mixture was stirred at room temperature for 2 hours. To the reaction mixture, an aqueous saturated sodium bicarbonate solution was added, followed by extraction with ethyl acetate. The organic layer was washed with water and an aqueous saturated sodium chloride solution; dried with anhydrous sodium sulfate; and concentrated under reduced pressure. The residue was purified by silica gel column chromatography (hexane:ethyl acetate=8:2→5:5) to obtain a titled compound (10 mg) having the following physical property values.

TLC: Rf 0.32 (hexane:ethyl acetate=2:3).

Example 74

2-Propanyl 4-[(3S,5aR,6R,7S,8aS)-6-[(1E,3R)-4-(2,5-difluorophenoxy)-3-(tetrahydro-2H-pyran-2-yloxy)-1-buten-1-yl]-7-hydroxyoctahydro-2H-cyclopenta[b]oxepin-3-yl]butanoate To a 2-propanol (0.35 mL) solution of the compound (10 mg) produced in Example 73, potassium carbonate (3 mg) was added at 0° C., and the reaction mixture was stirred at 40° C. for 1 hour. To the reaction mixture, an aqueous saturated ammonium chloride solution was added, followed by extraction with ethyl acetate. The organic layer was washed with a saturated saline; dried with anhydrous magnesium sulfate; and concentrated under reduced pressure to obtain a titled compound (8 mg) having the following physical property values.

TLC: Rf 0.39 (hexane:ethyl acetate=1:1).

Example 75

2-Propanyl 4-{(3S,5aR,6R,7S,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate Using the compound produced in Example 74, the compound was subjected to the same objective operations as those of Example 16 (1) to obtain a titled compound having the following physical property values.

TLC: Rf 0.47 (hexane:ethyl acetate=1:4);
$^1$H-NMR (300 MHz, CDCl$_3$): δ 7.00, 6.71, 6.60, 5.90, 5.63, 4.99, 4.56, 4.28, 4.18, 4.08-3.88, 2.97, 2.78, 2.15-2.00, 1.95-0.95.

Example 76

4-{(3S,5aR,6R,7S,8aS)-6-[(1E,3R)-4-(2,5-difluorophenoxy)-3-hydroxy-buten-1-yl]-7-hydroxyoctahydro-2H-cyclopenta[b]oxepin-3-yl}butanoic acid With using the compound produced in Example 75, the compound was subjected to the same objective operations as those of Example 17 (1) to obtain a titled compound having the following physical property values.

TLC: Rf 0.28 (dichloromethane:methanol=9:1);
$^1$H-NMR (300 MHz, CDCl$_3$): δ 7.08-6.90, 6.78-6.52, 5.90, 5.63, 4.57, 4.29, 4.22-3.85, 2.97, 2.40-2.20, 2.13, 1.98-1.80, 1.80-1.50, 1.45-0.95.

Example 77

(1R,2R,3S,4R)-2-allyl-3-({[dimethyl(2-methyl-2-propanyl)silyl]oxy}methyl)-4-(tetrahydro-2H-pyran-2-yloxy)cyclopentanol With using the compound produced in Example 3, the compound was subjected to the same objective operations as those of Example 73 to obtain a titled compound having the following physical property values.

TLC: Rf 0.59 (hexane:ethyl acetate=2:1).

Example 78

2-Propanyl 4-[(5aR,6S,7R,8aR)-6-({[dimethyl(2-methyl-2-propanyl)silyl]oxy}methyl)-7-(tetrahydro-2H-pyran-2-yloxy)-5,5a,6,7,8,8a-hexahydro-2H-cyclopenta[b]oxepin-3-yl]butanoate With using the compound produced in Example 77, the compound was subjected to the same objective operations as those of Example 4→Example 5→Example 6→Example 7→Example 8 to obtain a titled compound having the following physical property values.

TLC: Rf 0.39 (hexane:ethyl acetate=4:1).

Example 79

2-Propanyl 4-{(5aR,6R,7R,8aR)-7-hydroxy-6-[(1E,3R)-3-hydroxy-4-phenoxy-1-buten-1-yl]-5,5a,6,7,8,8a-hexahydro-2H-cyclopenta[b]oxepin-3-yl}butanoate With using the compound produced in Example 78, the compound was subjected to the same objective operations as those of Example 12→Example 13→Example 14→Example 15→Example 16 (1) to obtain a titled compound having the following physical property values.

TLC: Rf 0.52 (ethyl acetate);
$^1$H-NMR (300 MHz, CDCl$_3$): δ 1.19-1.33, 1.43-1.58, 1.65-1.79, 1.86-2.16, 2.16-2.34, 2.59, 3.77, 3.92, 3.97-4.19, 4.51-4.62, 5.01, 5.58-5.82, 6.89-7.04, 7.25-7.36.

Example 80

4-{(5aR,6R,7R,8aR)-7-hydroxy-6-[(1E,3R)-3-hydroxy-4-phenoxy-1-buten-1-yl]-5,5a,6,7,8,8a-hexahydro-2H-cyclopenta[b]oxepin-3-yl}butanoic acid With using the compound produced in Example 79, the compound was subjected to the same objective operations as those of Example 17 (1) to obtain a titled compound having the following physical property values.

TLC: Rf 0.64 (dichloromethane:methanol=7:1);
$^1$H-NMR (300 MHz, CD$_3$OD): δ 1.25-1.49, 1.57-1.76, 1.87-2.12, 2.18-2.34, 3.77, 3.89-4.19, 4.44, 5.57-5.77, 6.84-7.01, 7.21-7.33.

Example 81

2-Propanyl 4-{(5aR,6R,7R,8aR)-7-hydroxy-6-[(1E,3R)-3-hydroxy-4-phenoxy-1-buten-1-yl]octahydro-2H-cyclopenta[b]oxepin-3-yl}butanoate With using the compound produced in Example 78, the compound was subjected to the same objective operations as those of Example 9→Example 10→Example 11→Example 12→Example 13→Example 14→Example 15→Example 16 (1) to obtain a titled compound having the following physical property values.

TLC: Rf 0.46 (ethyl acetate);
$^1$H-NMR (300 MHz, CDCl$_3$): δ 0.97-2.14, 2.18-2.34, 2.53-2.63, 3.23, 3.44, 3.71-4.18, 4.49-4.61, 4.93-5.09, 5.58-5.82, 6.88-7.04, 7.24-7.36.

Example 81 (1)

2-Propanyl 4-{(5aR,6R,7R,8aR)-6-[(1E,3R)-4-(2,5-difluorophenoxy)-3-hydroxy-1-buten-1-yl]-7-hydroxyoctahydro-2H-cyclopenta[b]oxepin-3-yl}butanoate With using the compound produced in Example 78, and using dimethyl-(3-phenoxy-2-oxopropyl)-phosphonate or a corresponding phosphonic acid salt in place of it, these substances were subjected to the same objective operations as those of Example 81 to obtain a titled compound having the following physical property values.

TLC: Rf 0.52 (ethyl acetate);
$^1$H-NMR (300 MHz, CDCl$_3$): δ 1.00-1.91, 1.91-2.13, 2.22-2.33, 2.59-2.68, 3.23, 3.44, 3.73-4.19, 4.52-4.63, 4.95-5.07, 5.56-5.83, 6.57-6.68, 6.68-6.78, 6.97-7.10.

Example 82 to Example 82 (1)

With using the compounds produced in Example 81 or Example 81 (1), these compounds were subjected to the same objective operations as those of Example 17 (1) to obtain the following Example compounds.

Example 82

4-{(5aR,6R,7R,8aR)-7-hydroxy-6-[(1E,3R)-3-hydroxy-4-phenoxy-1-buten-1-yl]octahydro-2H-cyclopenta[b]oxepin-3-yl}butanoic acid TLC: Rf 0.53 (dichloromethane:methanol=7:1);
$^1$H-NMR (300 MHz, CD$_3$OD): δ 0.99-2.04, 2.21-2.33, 3.20-3.46, 3.73-4.03, 4.43, 5.56-5.77, 6.86-5.77, 6.86-6.95, 7.20-7.30.

Example 82 (1)

4-{(5aR,6R,7R,8aR)-6-[(1E,3R)-4-(2,5-difluorophenoxy)-3-hydroxy-1-buten-1-yl]-7-hydroxyoctahydro-2H-cyclopenta[b]oxepin-3-yl}butanoic acid TLC: Rf 0.47 (dichloromethane:methanol=7:1);
$^1$H-NMR (300 MHz, CD$_3$OD): δ 1.00-2.06, 2.22-2.33, 3.20-3.47, 3.74-3.86, 3.88-4.02, 4.45, 5.54-5.79, 6.57-6.68, 6.68-6.96, 7.01-7.13.

Example 83

4-[(3S,5aR,6R,7R,8aS)-6-(3,3-difluoro-4-phenoxybutyl)-7-hydroxyoctahydro-2H-cyclopenta[b]oxepin-3-yl]butanoic acid With using the compound produced in Example 30, the compound was subjected to the same objective operations as those of Example 18→Example 19 to obtain a titled compound having the following physical property values.
TLC: Rf 0.51 (ethyl acetate);
$^1$H-NMR (300 MHz, CDCl$_3$): δ 7.35-7.29, 7.02, 6.95-6.91, 4.13, 4.04, 3.97, 3.74, 2.93, 2.34, 2.28-2.03, 1.95-1.51, 1.22-1.00.

Example 84

[(3S,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-yl]methyl methanesulfonate To a methylene chloride (300 mL) solution of the compound (40.7 g) produced in Example 23, triethylamine (27.36 mL) and mesyl chloride (7.98 mL) were sequentially added under ice-cooling, followed by stirring for 1 hour. The reaction solution was poured into ice-water (300 mL), followed by extraction with ethyl acetate. Washing with water (100 mL) and a saturated saline (100 mL), and drying with anhydrous sodium sulfate were carried out. Concentration of the solvent under reduced pressure was carried out to obtain a titled compound (50.2 g) having the following physical property values.
TLC: Rf 0.71, 0.63 (methylene chloride:ethyl acetate=2:1).

Example 85

[(3R,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-yl] acetonitrile To a DMSO (250 mL) solution of the compound (50.2 g) produced in Example 84, sodium cyanide (8.18 g) was added at room temperature, followed by stirring at 70° C. overnight. The reaction solution was poured into ice water (750 mL), followed by extraction with ethyl acetate. The organic layer was washed with water (200 mL) and a saturated saline (200 mL), and dried with anhydrous sodium sulfate. The solvent was concentrated under reduced pressure, and the resulting residue was purified by preparative chromatograph (Hiflash-SI, Size 5 L×2, hexane:ethyl acetate=90:10→2:1→4:1) manufactured by Yamazen Corporation to obtain a titled compound (36.4 g) having the following physical property values.
TLC: Rf 0.42 (hexane:ethyl acetate=2:1).

Example 86

[(3R,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-yl] acetaldehyde Under the argon atmosphere, a toluene (350 mL) solution of the compound (29.4 g) produced in Example 85 was cooled to −18° C., and a 1M toluene solution (103 mL) of DIBAL was added dropwise over 40 minutes. The reaction solution was diluted with MTBE (300 mL) and an aqueous saturated sodium tartrate solution (50 mL) was added under ice-cooling, followed by stirring for a while. Thereafter, ice-cooled hydrochloric acid (1N, 300 mL) was added, followed by extraction with ethyl acetate. The organic layer was washed with an aqueous saturated ammonium chloride solution, water and a saturated saline, and dried with anhydrous sodium sulfate. Concentration of the solvent under reduced pressure was carried out to obtain a titled compound (31.3 g) having the following physical property values.
TLC: Rf 0.45 (hexane:ethyl acetate=3:1).

Example 87

2-Propanyl (2E)-4-[(3R,5aR,6S,7R,8aS)-6-({[dimethyl(2-methyl-2-propanyl)silyl]oxy}methyl)-7-(tetrahydro-2H-pyran-2-yloxy)octahydro-2H-cyclopenta[b]oxepin-3-yl]-2-butenoate To a methylene chloride (422 mL) solution of the compound (38.0 g) produced in Example 86, isopropyl(triphenylphosphoranylidene) acetate (45.93 g) was added at room temperature, followed by stirring at room temperature overnight. After completion of the reaction, the solution was concentrated under reduced pressure, and diethyl ether-hexane (1:1, 200 mL) were added. After removal of the analysis product with a glass filter, the filtrate was concentrated under reduced pressure. The resulting residue was purified by preparative chromatograph (Hiflash-SI, Size 5 L×2, hexane:ethyl acetate=100:0→4:1→7:3) manufactured by Yamazen Corporation to obtain a titled compound (36.0 g) having the following physical property values.
TLC: Rf 0.56, 0.49 (hexane:ethyl acetate=4:1).

Example 88

Ethyl (2E)-4-{(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}-2-butenoate With using the compound produced in Example 87, the compound was subjected to the same objective operations as those of Example 12→Example 13→Example 14→Example 15→Example 16 (1) to obtain a titled compound having the following physical property values.

TLC; Rf 0.46 (ethyl acetate);
$^1$H-NMR (300 MHz, CDCl$_3$): δ 0.98-1.12, 1.25-1.33, 1.41-1.54, 1.63-2.18, 2.45-2.54, 2.69, 2.92-2.30, 3.69-3.78, 3.87-4.23, 4.52-4.55, 5.61-5.74, 5.77-5.83, 6.84-7.01, 7.24-7.33.

Example 89

(2E)-4-{(3R,5aR,6R,7R,8aS)-7-hydroxy-6-[(1E,3R)-3-hydroxy-4-phenoxy-1-buten-1-yl]octahydro-2H-cyclopenta[b]oxepin-3-yl}-2-butenoic acid With using the compound produced in Example 88, the compound was subjected to the same objective operations as those of Example 17 (1) to obtain a titled compound having the following physical property values.

TLC: Rf 0.31 (dichloromethane:methanol=9:1);
$^1$H-NMR (300 MHz, CDCl$_3$): δ 1.00-1.51, 1.68-2.14, 2.45-2.54, 2.93-3.00, 3.69-3.77, 3.87-4.07, 4.52-4.54, 5.65-5.67, 5.79-5.84, 6.91-7.04, 7.27-7.32.

Example 90

4-{(3S,5aR,6R,7S,8aS)-6-[(1E,3R)-4-(2,5-difluorophenoxy)-3-hydroxy-1-buten-1-yl]-7-fluorooctahydro-2H-cyclopenta[b]oxepin-3-yl}butanoic acid With using the compound (100 mg) produced in Example 72, the compound was subjected to the same objective operations as those of Example 30→Example 31→Example 32 to obtain a titled compound (4 mg) having the following physical property values.

[Chemical formula 83]

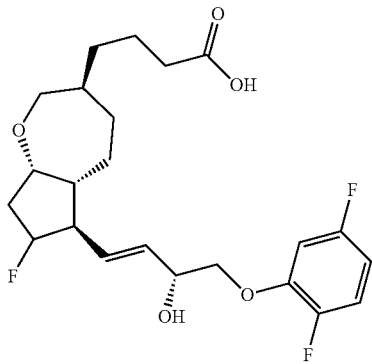

TLC: Rf 0.52 (dichloromethane:methanol=9:1);
$^1$H-NMR (300 MHz, CDCl$_3$): δ 0.85-2.62, 2.96-3.04, 3.92-4.09, 4.24-4.31, 4.55-4.61, 4.84-4.86, 5.02-5.04, 5.60-5.67, 5.85-5.93, 6.58-6.66, 6.70-6.76, 6.99-7.08.

Example 91

Ethyl 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate To a DMF (0.3 mL) solution of the compound (50 mg) produced in Example 17 (25), ethyl iodide (21 mg) and potassium carbonate (19 mg) were added, and the reaction mixture was stirred at 50° C. for 30 minutes. The reaction mixture was poured into water, followed by extraction with MTBE. Herein, the aqueous layer was made acidic (pH=4) with 1N hydrochloric acid, and extracted with ethyl acetate, and the organic layer was washed with water and a saturated saline; dried with magnesium sulfate; and concentrated under reduced pressure to recover an unreacted raw material (15 mg). The reaction was tried on the recovered raw material with the aforementioned reagents (ethyl iodide 12 mg, potassium carbonate 6 mg), followed by stirring at 50° C. for 1 hour. The reaction mixture was poured into water, followed by extraction with MTBE. The organic layer was washed with water and an aqueous saturated sodium chloride solution; dried with sodium sulfate; and concentrated under reduced pressure, and the resulting residue was purified by silica gel column chromatography (hexane:ethyl acetate=1:1→0:100) to obtain a titled compound (21 mg) having the following physical property values.

TLC: Rf 0.53 (dichloromethane:methanol=9:1);
$^1$H-NMR (300 MHz, CDCl$_3$): δ 0.94-1.30, 1.40-1.95, 2.09-2.31, 2.45-2.54, 2.71-2.73, 2.89-2.97, 3.70-3.79, 3.90-4.17, 4.53-4.60, 5.59-5.74, 6.58-6.66, 6.69-6.76, 6.99-7.08.

Example 91 (1)

3-Hydroxypropyl 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate With using the compound produced in Example 17 (25), and using 3-bromo-1-propanol in place of ethyl iodide, these substances were subjected to the same objective operations as those of Example 91 to obtain a titled compound having the following physical property values.

TLC: Rf 0.38 (dichloromethane: acetone=1:1);
$^1$H-NMR (300 MHz, CDCl$_3$): δ 0.90-1.20, 1.40-1.94, 2.08-2.17, 2.28-2.33, 2.45-2.54, 2.89-2.96, 3.67-3.80, 3.91-4.07, 4.22-4.26, 4.52-4.58, 5.59-5.74, 6.58-6.66, 6.69-6.75, 6.99-7.07.

Example 92

(3S,5aR,6R,7R,8aS)-6-[(1E,3R)-4-(2,5-difluorophenoxy)-3-hydroxy-1-buten-1-yl]-3-(4-hydroxybutyl)octahydro-2H-cyclopenta[b]oxepine-7-ol To a THF (1.4 mL) solution of the compound (25 mg) produced in Example 91, lithium aluminum hydride (6 mg) was added at 0° C., and the reaction mixture was stirred as it was for 1 hour. To the reaction mixture, an aqueous saturated sodium sulfate solution was added, and the mixture was filtered with Celite (trade name), and concentrated under reduced pressure. The resulting residue was purified by silica gel column chromatography (ethyl acetate→dichloromethane methanol=9:1) to obtain a titled compound (22 mg) having the following physical property values:

TLC: Rf 0.24 (ethyl acetate);
$^1$H-NMR (300 MHz, CDCl$_3$): δ 0.95-1.95, 2.01-2.18, 2.45-2.54, 2.62-2.64, 2.89-2.97, 3.62-3.80, 3.90-4.09, 4.54-4.61, 5.60-5.75, 6.58-6.66, 6.69-6.76, 6.99-7.08.

Example 93

4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}-N-ethylbutaneamide To a THF (0.2 mL) solution of the compound (10 mg) produced in Example 17 (25), 4-(4,6-dimethoxy-1,3,5-triazin-2-yl)-4-methylmorpholinium chloride (7 mg) and an aqueous ethylamine solution (12M, 19 μL) were added, and the reaction mixture was stirred at room temperature for 6 hours. The reaction mixture was poured into water, followed by extraction with ethyl acetate. The organic layer was washed with 1N hydrochloric acid, an aqueous saturated sodium bicarbonate solution, and a saturated saline; dried with magnesium sulfate; and concentrated under reduced pressure to obtain the residue. The resulting residue was purified by silica gel column chromatography (dichloromethane:methanol=9:1) to obtain a titled compound (10 mg) having the following physical property values.

TLC: Rf 0.44 (dichloromethane:methanol=9:1);
$^1$H-NMR (300 MHz, CD$_3$OD): δ 0.85-1.20, 1.30-1.92, 1.97-2.06, 2.11-2.16, 2.39-2.48, 2.92-3.01, 3.14-3.23, 3.62-3.71, 3.96-4.03, 4.41-4.47, 5.58-5.71, 6.59-6.67, 6.88-6.95, 7.03-7.12, 7.94.

Example 94

3-(3-Pyridinyl)propanal

To an ethyl acetate (30 mL) solution of 3-(3-pyridyl)propanol (1.5 g), dimethyl sulfoxide (15 mL) and triethylamine (9 mL) were added. Additionally, a pyridine sulfur trioxide complex (5.2 g) was added with stirring at 0° C. for 2 hours as it was. The reaction mixture was concentrated under reduced pressure, and purified by silica gel column chromatography (hexane:ethyl acetate=30:70→0:100) to obtain a titled compound (1:1 g) having the following physical property values.

TLC: Rf 0.23 (hexane:ethyl acetate=1:2).

Example 95

(3S,5aR,6S,7R,8aS)-6-[(E)-2-iodovinyl]-3-[4-oxo-4-(2-propanyloxy)butyl]octahydro-2H-cyclopenta[b]oxepin-7-yl 4-biphenylcarboxylate To a THF (10 mL) solution of the compound (0.85 g) produced in Example 70, chromium chloride (1.7 g) was added and a THF (7 mL) solution of iodoform (1.4 g) was added with stirring at 0° C. for 4 hours as it was. The reaction mixture was poured into water, followed by extraction with ethyl acetate. The organic layer was washed with water and a saturated saline; dried with magnesium sulfate; and concentrated under reduced pressure. The resulting residue was purified by silica gel column chromatography (hexane:ethyl acetate=95:5→75:25) to obtain a titled compound (600 mg) having the following physical property values.

TLC: Rf 0.47 (hexane:ethyl acetate=3:1).

Example 96

(3S,5aR,6R,7R,8aS)-6-[(1E)-3-hydroxy-5-(3-pyridinyl)-1-penten-1-yl]-3-[4-oxo-4-(2-propanyloxy)butyl]octahydro-2H-cyclopenta[b]oxepin-7-yl 4-biphenylcarboxylate To a THF (10 mL) solution of the compound (590 mg) produced in Example 95 and the compound (258 mg) produced in Example 94, chromium chloride (470 mg) and nickel chloride (2.5 mg) were added, followed by stirring stirred at room temperature overnight. The reaction mixture was poured into water, and extracted with ethyl acetate. An aqueous saturated sodium bicarbonate solution was added to both of the aqueous layer and the organic layer, respectively, followed by stirring. After combination of both layers, filtration with Celite (trade name) was carried out, and separation was carried out again. The resulting organic layer was dried with magnesium sulfate, and concentrated under reduced pressure. The resulting residue was purified by silica gel column chromatography (hexane:ethyl acetate=30:70→0:100) to obtain a titled compound (210 mg) having the following physical property values.

TLC: Rf 0.38 (ethyl acetate).

Example 97

2-Propanyl 4-{(3S,5aR,6R,7R,8aS)-7-hydroxy-6-[(1E)-3-hydroxy-5-(3-pyridinyl)-1-penten-1-yl]octahydro-2H-cyclopenta[b]oxepin-3-yl}butanoate To a 2-propanol (0.4 mL) solution of the compound (210 mg) produced in Example 96, lithium isopropoxide (2.0M THF solution, 0.33 mL) was added, and the reaction mixture was stirred at 50° C. for 4 hours. The reaction mixture was cooled to 0° C., and poured into a water-ethyl acetate mixed solution which had been similarly cooled to 0° C. The organic layer was washed with water and a saturated saline; dried with magnesium sulfate; and concentrated under reduced pressure. The resulting residue was purified by silica gel column chromatography (dichloromethane:methanol=100:0→90:10) to obtain a titled compound (108 mg) having the following physical property values.

TLC: Rf 0.53 (dichloromethane:methanol=9:1);
$^1$H-NMR (300 MHz, CDCl$_3$): δ 0.93-1.29, 1.39-1.93, 2.04-2.14, 2.22-2.27, 2.42-2.52, 2.63-2.82, 2.88-2.96, 3.65-3.75, 3.92-4.14, 4.94-5.06, 5.42-5.67, 7.20-7.24, 7.52-7.54, 8.44-8.46.

Example 98

4-{(3S,5aR,6R,7R,8aS)-7-hydroxy-6-[(1E)-3-hydroxy-5-(3-pyridinyl)-1-penten-1-yl]octahydro-2H-cyclopenta[b]oxepin-3-yl}butanoic acid With using the compound produced in Example 97, the compound was subjected to the same objective operations as those of Example 17 (1) to obtain a titled compound having the following physical property values.

TLC: Rf 0.64 (dichloromethane:methanol=4:1);
$^1$H-NMR (300 MHz, CD$_3$OD): δ 0.97-2.04, 2.24-2.29, 2.37-2.47, 2.70-2.77, 2.94-3.02, 3.58-3.68, 3.96-4.05, 5.54-5.60, 7.33-7.38, 7.71-7.74, 8.33-8.40.

Example 99

5-[(3-Phenoxypropyl)thio]-1-phenyl-1H-tetrazole 3-phenoxypropyl bromide (1.53 g) was dissolved in acetone (9 mL), 1-phenyl-5-mercapto-1H-tetrazole (1.27 g) and potassium carbonate (985 mg) were added, and the mixture was stirred at room temperature for 3 hours. To the reaction solution, water was added, and the extract obtained by extraction with ethyl acetate was washed with water and a saturated saline; dried with anhydrous magnesium sulfate; and concentrated under reduced pressure to obtain a titled compound (2.23 g) having the following physical property values.

TLC: Rf 0.62 (hexane:ethyl acetate=67:33).

Example 100

5-[(3-Phenoxypropyl)sulfonyl]-1-phenyl-1H-tetrazole

The compound (2.23 g) produced in Example 99 was dissolved in dichloromethane (10 mL) and m-chloroperbenzoic acid (4.5 g) was added, followed by stirring at room temperature overnight. To the reaction solution, a 5% aqueous sodium sulfide solution was added, and the extract obtained by extraction with ethyl acetate was washed with an aqueous saturated sodium bicarbonate solution, water and a saturated saline. The organic layer was dried with anhydrous magnesium sulfate, and concentrated under reduced pressure. The residue was purified by silica gel column chromatography (hexane:ethyl acetate=85:15→65:35) to obtain a titled compound (1.78 g) having the following physical property values.
TLC: Rf 0.59 (hexane:ethyl acetate=67:33).

Example 101

2-Propanyl 4-[(3S,5aR,6R,7R,8aS)-6-[(1E)-4-phenoxy-1-buten-1-yl)-7-(tetrahydro-2H-pyran-2-yloxy)octahydro-2H-cyclopenta[b]oxepin-3-yl]butanoate Under the argon atmosphere, the compound (165 mg) produced in Example 100 was dissolved in DME (2 mL), the solution was cooled to −78° C., followed by addition of a 0.5M potassium hexamethyldisilazane/toluene solution (0.90 mL). After stirring the mixture at −78° C. for 20 minutes, a DME (1.5 mL) solution of the compound produced in Example 13 was added dropwise, and stirring at the same temperature was carried out for 10 minutes. After raising a temperature of the reaction solution to 0° C., water was added, and the extract obtained by extraction with ethyl acetate was washed with water and a saturated saline; dried with anhydrous magnesium sulfate; and concentrated under reduced pressure. The residue was purified by silica gel column chromatography (hexane:ethyl acetate=90:10→65:35) to obtain a titled compound (177 mg) having the following physical property values.
TLC: Rf 0.58 (hexane:ethyl acetate=67:33).

Example 102

2-Propanyl 4-{(3S,5aR,6R,7R,8aS)-7-hydroxy-6-[(1E)-4-phenoxy-1-buten-1-yl]octahydro-2H-cyclopenta[b]oxepin-3-yl}butanoate With using the compound produced in Example 101, the compound was subjected to the same objective operations as those of Example 16 (1) to obtain a titled compound having the following physical property values.
TLC: Rf 0.52 (hexane:ethyl acetate=33:67);
$^1$H-NMR (300 MHz, CDCl$_3$): δ 7.32-7.25, 6.97-6.88, 5.62, 5.37, 5.01, 4.08-3.93, 3.68, 2.92, 2.57-2.43, 2.25, 2.06, 1.91, 1.82-1.40, 1.24, 1.18-0.93.

Example 103

4-{(3S,5aR,6R,7R,8aS)-7-hydroxy-6-[(1E)-4-phenoxy-1-buten-1-yl]octahydro-2H-cyclopenta[b]oxepin-3-yl}butanoic acid With using the compound produced in Example 102, the compound was subjected to the same objective operations as those of Example 17 (1) to obtain a titled compound having the following physical property values.
TLC: Rf 0.69 (ethyl acetate: methanol=9:1);
$^1$H-NMR (300 MHz, DMSO-d$_6$): δ 11.98, 7.27, 6.93-6.88, 5.51-5.32, 4.61, 3.99-3.93, 3.90-3.81, 3.47, 2.84, 2.42, 2.26, 2.15, 1.87-1.74, 1.65-1.20, 1.10-0.86.

Example 104

4-(Nitrooxy)butylamine nitrate

Fuming nitric acid (1.5 mL) was added dropwise to acetic acid (25 mL) which had been cooled to an inner temperature of −8° C. with keeping an inner temperature of 0° C. or lower. After stirring the mixed solution for 10 minutes, 4-amino-1-butanol (3.1 mL) was added dropwise with keeping an inner temperature of 0° C. or lower. After stirring the mixture for 10 minutes, a temperature was raised to room temperature with a water bath. After stirring the mixture for 10 minutes, diethyl ether (100 mL) was added, followed by concentration under reduced pressure. To the resulting concentrated material, diethyl ether (100 mL) was added, followed by stirring and removing the supernatant. The resulting residue was concentrated under reduced pressure to obtain a titled compound (6.31 g) having the following physical property values.
$^1$H-NMR (300 MHz, DMSO-d$_6$): δ 1.44-1.82, 2.68-2.93, 4.53, 7.20-8.15.

Example 105

4-[(4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoyl)amino]butyl nitrate To a DMF solution (1 mL) of the compound (68 mg) produced in Example 104, the compound (50 mg) produced in Example 17(25), 1-ethyl-3-(3-dimethylaminopropyl)carbodiimide hydrochloride (87 mg) and triethylamine (95 μL) were added sequentially at room temperature. After stirring overnight, the solution was diluted with ethyl acetate, and washed with 1N hydrochloric acid twice, with water once, and with a saturated saline once. Drying with anhydrous sodium sulfate, and concentration under reduced pressure were carried out. The resulting crude purified product was purified with a column apparatus (Hi-Flash M, ethyl acetate→ethyl acetate: methanol=7:3). Further purification with preparative TLC (toluene: acetone=1:1) and preparative TLC (ethyl acetate: methanol=5:1) was carried out to obtain a titled compound (7.5 mg) having the following physical property values.
TLC: Rf 0.72 (ethyl acetate: methanol=7:1);
$^1$H-NMR (300 MHz, CDCl$_3$): δ 0.83-1.54, 1.54-1.97, 1.97-2.43, 2.49, 2.71-3.01, 3.30, 3.74, 3.89-4.10, 4.48, 4.52-4.60, 5.42-5.55, 5.58-5.75, 6.62, 6.72, 7.03.

Example 106 (1) to Example 106 (17)

With using the compound produced in Example 7; using isopropyl iodide or methyl iodide in place thereof; using dimethyl-(3-phenoxy-2-oxopropyl)-phosphonate or a corresponding phosphonate in place thereof, and using (S)-2-methyl-CBS-oxazaborolidine or (R)-2-methyl-CBS-oxazaborolidine in place thereof, these substances were subjected to the same objective operations as those of Example 8→Example 9→Example 10 (1)→Example 11→Example 12→Example 13→Example 14→Example 15→Example 16 (1) to obtain the following Example compounds.

Example 106 (1)

2-Propanyl 4-{(3S,5aR,6R,7R,8aS)-7-hydroxy-6-[(1E,3S)-3-hydroxy-4-phenoxy-1-buten-1-yl]octahydro-2H-cyclopenta[b]oxepin-3-yl}butanoate TLC: Rf 0.21 (ethyl acetate:hexane=2:1);
$^1$H-NMR (300 MHz, CDCl$_3$): δ 0.95-1.20, 1.22, 1.40-1.95, 2.12, 2.23, 2.45, 2.60, 2.91, 3.72, 3.86, 3.90-4.10, 4.55, 4.99, 5.58-5.75, 6.90, 6.96, 7.28.

Example 106 (2)

Methyl 4-{(3S,5aR,6R,7R,8aS)-7-hydroxy-6-[(1E,3R)-3-hydroxy-5-phenyl-1-penten-1-yl]octahydro-2H-cyclopenta[b]oxepin-3-yl}butanoate TLC: Rf 0.53 (ethyl acetate);
$^1$H-NMR (300 MHz, CDCl$_3$): δ 0.89-1.21, 1.40-1.93, 2.09, 2.29, 2.47, 2.64-2.81, 2.92, 3.67, 3.70, 3.96, 4.05, 4.14, 5.48, 5.63, 7.17-7.22, 7.28-7.32.

Example 106 (3)

Methyl 4-{(3S,5aR,6R,7R,8aS)-6-[(1E,3R)-5-(3-fluorophenyl)-3-hydroxy-1-penten-1-yl]-7-hydroxy-octahydro-2H-cyclopenta[b]oxepin-3-yl}butanoate TLC: Rf 0.46 (ethyl acetate:hexane=9:1);
$^1$H-NMR (300 MHz, CDCl$_3$): δ 0.95-1.20, 1.37-1.95, 2.05, 2.28, 2.45, 2.61-2.80, 2.90, 3.66, 3.69, 3.90-4.18, 5.46, 5.61, 6.81-7.00, 7.22.

Example 106 (4)

Methyl 4-{(3S,5aR,6R,7R,8aS)-6-[(1E,3S)-5-(3-fluorophenyl)-3-hydroxy-1-penten-1-yl]-7-hydroxy-octahydro-2H-cyclopenta[b]oxepin-3-yl}butanoate TLC: Rf 0.31 (ethyl acetate:hexane=9:1);
$^1$H-NMR (300 MHz, CDCl$_3$): δ 0.95-1.20, 1.39-1.95, 2.07, 2.28, 2.46, 2.60-2.80, 2.90, 3.66, 3.69, 3.90-4.15, 5.44, 5.58, 6.81-7.00, 7.22.

Example 106 (5)

Methyl 4-{(3S,5aR,6R,7R,8aS)-6-[(1E,3R)-5-(4-fluorophenyl)-3-hydroxy-1-penten-1-yl]-7-hydroxy-octahydro-2H-cyclopenta[b]oxepin-3-yl}butanoate TLC: Rf 0.46 (ethyl acetate:hexane=9:1);
$^1$H-NMR (300 MHz, CDCl$_3$): δ 0.91-1.20, 1.39-1.95, 2.07, 2.28, 2.46, 2.60-2.80, 2.90, 3.66, 3.69, 3.90-4.15, 5.46, 5.61, 6.91-7.00, 7.10-7.18.

Example 106 (6)

Methyl 4-{(3S,5aR,6R,7R,8aS)-6-[(1E,3S)-5-(4-fluorophenyl)-3-hydroxy-1-penten-1-yl]-7-hydroxy-octahydro-2H-cyclopenta[b]oxepin-3-yl}butanoate TLC: Rf 0.30 (ethyl acetate:hexane=9:1);
$^1$H-NMR (300 MHz, CDCl$_3$): δ 0.91-1.20, 1.39-1.95, 2.07, 2.28, 2.46, 2.58-2.78, 2.90, 3.66, 3.69, 3.90-4.15, 5.44, 5.60, 6.91-7.00, 7.10-7.18.

Example 106 (7)

Methyl 4-{(3S,5aR,6R,7R,8aS)-6-[(1E,3R)-5-(2-fluorophenyl)-3-hydroxy-1-penten-1-yl]-7-hydroxy-octahydro-2H-cyclopenta[b]oxepin-3-yl}butanoate TLC: Rf 0.57 (ethyl acetate);
$^1$H-NMR (300 MHz, CDCl$_3$): δ 0.92-1.17, 1.39-1.92, 2.03-2.12, 2.26-2.30, 2.41-2.50, 2.65-2.81, 2.87-2.95, 3.66-3.71, 3.92-4.15, 5.44-5.52, 5.59-5.66, 6.97-7.07, 7.14-7.24.

Example 106 (8)

Methyl 4-{(3S,5aR,6R,7R,8aS)-6-[(1E,3S)-5-(2-fluorophenyl)-3-hydroxy-1-penten-1-yl]-7-hydroxy-octahydro-2H-cyclopenta[b]oxepin-3-yl}butanoate TLC: Rf 0.42 (ethyl acetate);
$^1$H-NMR (300 MHz, CDCl$_3$): δ 0.92-1.19, 1.38-1.92, 2.04-2.12, 2.25-2.30, 2.42-2.51, 2.64-2.80, 2.87-2.95, 3.66-3.74, 3.92-4.14, 5.43-5.51, 5.58-5.65, 6.97-7.08, 7.14-7.24.

Example 106 (9)

Methyl 4-{(3S,5aR,6R,7R,8aS)-6-[(1E,3R)-5-(3-chlorophenyl)-3-hydroxy-1-penten-1-yl]-7-hydroxy-octahydro-2H-cyclopenta[b]oxepin-3-yl}butanoate TLC: Rf 0.46 (ethyl acetate:hexane=9:1);
$^1$H-NMR (300 MHz, CDCl$_3$): δ 0.91-1.20, 1.39-1.95, 2.07, 2.28, 2.46, 2.60-2.80, 2.90, 3.66, 3.69, 3.90-4.15, 5.46, 5.61, 7.05, 7.11-7.22.

Example 106 (10)

Methyl 4-{(3S,5aR,6R,7R,8aS)-6-[(1E,3S)-5-(3-chlorophenyl)-3-hydroxy-1-penten-1-yl]-7-hydroxy-octahydro-2H-cyclopenta[b]oxepin-3-yl}butanoate TLC: Rf 0.32 (ethyl acetate:hexane=9:1);
$^1$H-NMR (300 MHz, CDCl$_3$): δ 0.91-1.20, 1.39-1.95, 2.07, 2.28, 2.46, 2.58-2.78, 2.90, 3.66, 3.69, 3.90-4.15, 5.44, 5.60, 7.05, 7.11-7.22.

Example 106 (11)

Methyl 4-[(3S,5aR,6R,7R,8aS)-7-hydroxy-6-{(1E,3R)-3-hydroxy-5-[3-(trifluoromethyl)phenyl]-1-penten-1-yl}octahydro-2H-cyclopenta[b]oxepin-3-yl]butanoate TLC: Rf 0.54 (ethyl acetate);
$^1$H-NMR (300 MHz, CDCl$_3$): δ 0.92-1.18, 1.39-1.89, 2.05-2.13, 2.26-2.31, 2.42-2.51, 2.69-2.95, 3.66-3.72, 3.90-4.12, 5.44-5.52, 5.59-5.66, 7.37-7.45.

Example 106 (12)

Methyl 4-[(3S,5aR,6R,7R,8aS)-7-hydroxy-6-{(1E,3S)-3-hydroxy-5-[3-(trifluoromethyl)phenyl]-1-penten-1-yl}octahydro-2H-cyclopenta[b]oxepin-3-yl]butanoate TLC: Rf 0.41 (ethyl acetate);
$^1$H-NMR (300 MHz, CDCl$_3$): δ 0.93-1.20, 1.43-1.96, 2.05-2.13, 2.25-2.30, 2.43-2.51, 2.68-2.95, 3.66-3.74, 3.90-4.10, 5.42-5.50, 5.58-5.65, 7.38-7.45.

Example 106 (13)

2-Propanyl 4-[(3S,5aR,6R,7R,8aS)-7-hydroxy-6-{(1E,3S)-3-hydroxy-4-[3-(trifluoromethyl)phenoxy]-1-buten-1-yl}octahydro-2H-cyclopenta[b]oxepin-3-yl]butanoate TLC: Rf 0.25 (ethyl acetate:hexane=2:1);
$^1$H-NMR (300 MHz, CDCl$_3$): δ 0.95-1.20, 1.22, 1.40-1.95, 2.16, 2.24, 2.36, 2.49, 2.91, 3.72, 3.80-4.10, 4.55, 4.99, 5.60-5.78, 7.08, 7.14, 7.22, 7.39.

Example 106 (14)

2-Propanyl 4-{(3S,5aR,6R,7R,8aS)-6-[(1E,3S)-4-(2-fluorophenoxy)-3-hydroxy-1-buten-1-yl]-7-hydroxyoctahydro-2H-cyclopenta[b]oxepin-3-yl}butanoate TLC: Rf 0.25 (ethyl acetate:hexane=2:1);
$^1$H-NMR (300 MHz, CDCl$_3$): δ 0.95-1.20, 1.22, 1.40-1.95, 2.16, 2.24, 2.40-2.53, 2.91, 3.72, 3.80-4.10, 4.55, 4.99, 5.58-5.75, 6.88-7.12.

Example 106 (15)

2-Propanyl 4-{(3S,5aR,6R,7R,8aS)-6-[(1E,3S)-4-(3-fluorophenoxy)-3-hydroxy-1-buten-1-yl]-7-hydroxyoctahydro-2H-cyclopenta[b]oxepin-3-yl}butanoate TLC: Rf 0.25 (ethyl acetate:hexane=2:1);
$^1$H-NMR (300 MHz, CDCl$_3$): δ 0.95-1.20, 1.22, 1.40-1.95, 2.16, 2.24, 2.45, 2.91, 3.72, 3.85, 3.90-4.10, 4.55, 4.99, 5.58-5.75, 6.60-6.72, 7.21.

Example 106 (16)

2-Propanyl 4-{(3S,5aR,6R,7R,8aS)-6-[(1E,3S)-4-(4-fluorophenoxy)-3-hydroxy-1-buten-1-yl]-7-hydroxyoctahydro-2H-cyclopenta[b]oxepin-3-yl}butanoate TLC: Rf 0.25 (ethyl acetate:hexane=2:1);
$^1$H-NMR (300 MHz, CDCl$_3$): δ 0.95-1.20, 1.22, 1.40-1.95, 2.16, 2.24, 2.45, 2.49, 2.91, 3.72, 3.82, 3.90-4.10, 4.55, 4.99, 5.58-5.75, 6.80-6.88, 6.97.

Example 106 (17)

Methyl 4-{(3S,5aR,6R,7R,8aS)-6-[(1E,3S)-5-cyclohexyl-3-hydroxy-1-penten-1-yl]-7-hydroxyoctahydro-2H-cyclopenta[b]oxepin-3-yl}butanoate TLC: Rf 0.37 (ethyl acetate);
$^1$H-NMR (300 MHz, CDCl$_3$): δ 0.85-1.30, 1.38-1.78, 1.86-1.93, 2.02-2.14, 2.26-2.31, 2.42-2.51, 2.87-2.95, 3.66-3.73, 3.90-4.07, 5.38-5.46, 5.53-5.60.

Example 107 (1) to Example 107 (17)

The compounds produced in Example 106 (1) to Example 106 (17) were subjected to the same objective operations as those of Example 17 (1), respectively, to obtain the following Example compounds.

Example 107 (1)

4-{(3S,5aR,6R,7R,8aS)-7-hydroxy-6-[(1E,3S)-3-hydroxy-4-phenoxy-1-buten-1-yl]octahydro-2H-cyclopenta[b]oxepin-3-yl}butanoic acid TLC: Rf 0.17 (ethyl acetate; hexane=6:1);
$^1$H-NMR (300 MHz, CDCl$_3$): δ 0.95-1.20, 1.40-1.98, 2.16, 2.33, 2.46, 2.92, 3.74, 3.86, 3.90-4.08, 4.55, 5.58-5.75, 6.90, 6.93, 7.28.

Example 107 (2)

4-{(3S,5aR,6R,7R,8aS)-7-hydroxy-6-[(1E,3R)-3-hydroxy-5-phenyl-1-penten-1-yl]octahydro-2H-cyclopenta[b]oxepin-3-yl}butanoic acid TLC: Rf 0.44 (ethyl acetate: acetic acid=100:1);
$^1$H-NMR (300 MHz, CDCl$_3$); δ 0.89-1.22, 1.39-1.93, 2.08, 2.32, 2.47, 2.63-2.81, 2.92, 3.70, 3.96, 4.05, 4.14, 5.48, 5.63, 7.17-7.22, 7.28-7.32.

Example 107 (3)

4-{(3S,5aR,6R,7R,8aS)-6-[(1E,3R)-5-(3-fluorophenyl)-3-hydroxy-1-penten-1-yl]-7-hydroxyoctahydro-2H-cyclopenta[b]oxepin-3-yl}butanoic acid TLC: Rf 0.42 (dichloromethane:methanol=6:1);
$^1$H-NMR (300 MHz, CDCl$_3$): δ 0.95-1.20, 1.40-1.95, 2.16, 2.32, 2.48, 2.61-2.80, 2.91, 3.71, 3.95, 4.00-4.17, 5.47, 5.62, 6.83-7.00, 7.21.

Example 107 (4)

4-{(3S,5aR,6R,7R,8aS)-6-[(1E,3S)-5-(3-fluorophenyl)-3-hydroxy-1-penten-1-yl]-7-hydroxyoctahydro-2H-cyclopenta[b]oxepin-3-yl}butanoic acid TLC: Rf 0.42 (dichloromethane:methanol=6:1);
$^1$H-NMR (300 MHz, CDCl$_3$): δ 0.95-1.20, 1.38-1.95, 2.16, 2.32, 2.48, 2.60-2.80, 2.91, 3.71, 3.95, 4.00-4.17, 5.43, 5.58, 6.83-7.00, 7.21.

Example 107 (5)

4-{(3S,5aR,6R,7R,8aS)-6-[(1E,3R)-5-(4-fluorophenyl)-3-hydroxy-1-penten-1-yl]-7-hydroxyoctahydro-2H-cyclopenta[b]oxepin-3-yl}butanoic acid TLC: Rf 0.42 (dichloromethane:methanol=6:1);
$^1$H-NMR (300 MHz, CDCl$_3$): δ 0.95-1.20, 1.40-1.95, 2.16, 2.32, 2.48, 2.60-2.80, 2.91, 3.71, 3.95, 4.00-4.17, 5.46, 5.62, 6.90-7.00, 7.10-7.20.

Example 107 (6)

4-{(3S,5aR,6R,7R,8aS)-6-[(1E,3S)-5-(4-fluorophenyl)-3-hydroxy-1-penten-1-yl]-7-hydroxyoctahydro-2H-cyclopenta[b]oxepin-3-yl}butanoic acid TLC: Rf 0.42 (dichloromethane:methanol=6:1);
$^1$H-NMR (300 MHz, CDCl$_3$): δ 0.95-1.20, 1.38-1.95, 2.16, 2.32, 2.48, 2.60-2.80, 2.91, 3.71, 3.95, 4.00-4.17, 5.42, 5.58, 6.90-7.00, 7.10-7.20.

Example 107 (7)

4-{(3S,5aR,6R,7R,8aS)-6-[(1E,3R)-5-(2-fluorophenyl)-3-hydroxy-1-penten-1-yl]-7-hydroxyoctahydro-2H-cyclopenta[b]oxepin-3}butanoic acid TLC: Rf 0.23 (dichloromethane:methanol=9:1);
$^1$H-NMR (300 MHz, CDCl$_3$): δ 0.92-1.20, 1.39-1.92, 2.04-2.13, 2.30-2.35, 2.41-2.50, 2.64-2.82, 2.87-2.95, 3.65-3.73, 3.92-4.08, 5.43-5.52, 5.59-5.66, 6.97-7.07, 7.13-7.23.

Example 107 (8)

4-{(3S,5aR,6R,7R,8aS)-6-[(1E,3S)-5-(2-fluorophenyl)-3-hydroxy-1-penten-1-yl]-7-hydroxyoctahydro-2H-cyclopenta[b]oxepin-3-yl}butanoic acid TLC: Rf 0.25 (dichloromethane:methanol=9:1);
$^1$H-NMR (300 MHz, CDCl$_3$): δ 0.92-1.20, 1.40-1.92, 2.04-2.12, 2.25-2.30, 2.42-2.51, 2.63-2.80, 2.87-2.95, 3.66-3.74, 3.92-4.14, 5.42-5.50, 5.57-5.64, 6.97-7.07, 7.13-7.24.

Example 107 (9)

4-{(3S,5aR,6R,7R,8aS)-6-[(1E,3R)-5-(3-chlorophenyl)-3-hydroxy-1-penten-1-yl]-7-hydroxyoctahydro-2H-cyclopenta[b]oxepin-3-yl}butanoic acid TLC: Rf 0.42 (dichloromethane:methanol=6:1);
$^1$H-NMR (300 MHz, CDCl$_3$): δ 0.90-1.20, 1.38-1.95, 2.08, 2.33, 2.46, 2.60-2.80, 2.91, 3.69, 3.92-4.18, 5.47, 5.62, 7.07, 7.11-7.22.

Example 107 (10)

4-{(3S,5aR,6R,7R,8aS)-6-[(1E,3S)-5-(3-chlorophenyl)-3-hydroxy-1-penten-1-yl]-7-hydroxyoctahydro-2H-cyclopenta[b]oxepin-3-yl}butanoic acid TLC: Rf 0.42 (dichloromethane:methanol=6:1);
$^1$H-NMR (300 MHz, CDCl$_3$): δ 0.94-1.20, 1.38-1.98, 2.06, 2.32, 2.47, 2.58-2.78, 2.91, 3.68, 3.92-4.18, 5.43, 5.58, 7.07, 7.11-7.22.

Example 107 (11)

4-[(3S,5aR,6R,7R,8aS)-7-hydroxy-6-{(1E,3R)-3-hydroxy-5-[3-(trifluoromethyl)phenyl]-1-penten-1-yl}octahydro-2H-cyclopenta[b]oxepin-3-yl]butanoic acid TLC: Rf 0.39 (dichloromethane:methanol=9:1);
$^1$H-NMR (300 MHz, CDCl$_3$): δ 0.92-1.21, 1.39-1.92, 2.04-2.14, 2.30-2.35, 2.42-2.51, 2.69-2.95, 3.66-3.74, 3.92-4.12, 5.44-5.52, 5.59-5.66, 7.37-7.44.

Example 107 (12)

4-[(3S,5aR,6R,7R,8aS)-7-hydroxy-6-{(1E,3S)-3-hydroxy-5-[3-(trifluoromethyl)phenyl]-1-penten-1-yl]octahydro-2H-cyclopenta[b]oxepin-3-yl}butanoic acid TLC: Rf 0.21 (dichloromethane:methanol=9:1);
$^1$H-NMR (300 MHz, CDCl$_3$): δ 0.94-1.20, 1.39-1.91, 2.04-2.13, 2.30-2.35, 2.43-2.51, 2.67-2.85, 2.87-2.95, 3.66-3.74, 3.92-4.12, 5.41-5.49, 5.57-5.64, 7.37-7.44.

Example 107 (13)

4-[(3S,5aR,6R,7R,8aS)-7-hydroxy-6-{(1E,3S)-3-hydroxy-4-[3-(trifluoromethyl)phenoxy]-1-buten-1-yl}octahydro-2H-cyclopenta[b]oxepin-3-yl]butanoic acid TLC: Rf 0.48 (dichloromethane:methanol:water=60:10:1);
$^1$H-NMR (300 MHz, CDCl$_3$): δ 0.95-1.20, 1.40-1.98, 2.16, 2.33, 2.46, 2.92, 3.75, 3.88-4.10, 4.55, 5.60-5.78, 7.08, 7.14, 7.22, 7.39.

Example 107 (14)

4-{(3S,5aR,6R,7R,8aS)-6-[(1E,3S)-4-(2-fluorophenoxy)-3-hydroxy-1-buten-1-yl]-7-hydroxyoctahydro-2H-cyclopenta[b]oxepin-3-yl}butanoic acid TLC: Rf 0.48 (dichloromethane:methanol:water=60:10:1);
$^1$H-NMR (300 MHz, CDCl$_3$): δ 0.95-1.20, 1.40-1.98, 2.16, 2.32, 2.46, 2.91, 3.72, 3.88-4.10, 4.54, 5.60-5.78, 6.88-7.10.

Example 107 (15)

4-{(3S,5aR,6R,7R,8aS)-6-[(1E,3S)-4-(3-fluorophenoxy)-3-hydroxy-1-buten-1-yl]-7-hydroxyoctahydro-2H-cyclopenta[b]oxepin-3-yl}butanoic acid TLC: Rf 0.48 (dichloromethane:methanol:water=60:10:1);
$^1$H-NMR (300 MHz, CDCl$_3$): δ 0.95-1.20, 1.40-1.98, 2.11, 2.33, 2.46, 2.92, 3.72, 3.85, 3.90-4.10, 4.52, 5.58-5.78, 6.58-6.70, 7.20.

Example 107 (16)

4-{(3S,5aR,6R,7R,8aS)-6-[(1E,3S)-4-(4-fluorophenoxy)-3-hydroxy-1-buten-1-yl]-7-hydroxyoctahydro-2H-cyclopenta[b]oxepin-3-yl}butanoic acid TLC: Rf 0.48 (dichloromethane:methanol:water=60:10:1);
$^1$H-NMR (300 MHz, CDCl$_3$); δ 0.95-1.20, 1.40-1.98, 2.12, 2.33, 2.46, 2.92, 3.72, 3.82, 3.90-4.10, 4.52, 5.58-5.78, 6.80-6.88, 6.97.

Example 107 (17)

4-{(3S,5aR,6R,7R,8aS)-6-[(1E,3S)-5-cyclohexyl-3-hydroxy-1-penten-1-yl]-7-hydroxyoctahydro-2H-cyclopenta[b]oxepin-3-yl}butanoic acid TLC: Rf 0.34 (dichloromethane:methanol=9:1);
$^1$H-NMR (300 MHz, CDCl$_3$): δ 0.85-1.30, 1.38-1.77, 1.86-1.93, 2.02-2.11, 2.30-2.35, 2.42-2.51, 2.87-2.95, 3.65-3.73, 3.91-4.06, 5.38-5.46, 5.52-5.59.

Example 108 (1) to Example 108 (13)

The compounds produced in Example 107 (1) to Example 107 (12) or Example 17 (15) were subjected to the same objective operations as those of Example 18 (1), respectively, to obtain the following Example compounds.

Example 108 (1)

4-{(3S,5aR,6R,7R,8aS)-7-hydroxy-6-[(3S)-3-hydroxy-4-phenoxybutyl]octahydro-2H-cyclopenta[b]oxepin-3-yl}butanoic acid TLC: Rf 0.44 (ethyl acetate; acetic acid=100:1);
$^1$H-NMR (300 MHz, CDCl$_3$): δ 1.00-1.22, 1.45-1.94, 2.22-2.37, 2.94, 3.75, 3.85, 3.94-4.07, 6.90-7.00, 7.30-7.32.

Example 108 (2)

4-{(3S,5aR,6R,7R,8aS)-7-hydroxy-6-[(3S)-3-hydroxy-5-phenylpentyl]octahydro-2H-cyclopenta[b]oxepin-3-yl}butanoic acid TLC: Rf 0.40 (ethyl acetate: acetic acid=100:1);
$^1$H-NMR (300 MHz, CDCl$_3$): δ 0.98-1.22, 1.30-1.94, 2.24, 2.34, 2.63-2.85, 2.93, 3.64, 3.72, 3.95, 4.03, 7.17-7.22, 7.28-7.32.

Example 108 (3)

4-{(3S,5aR,6R,7R,8aS)-6-[(3S)-5-(3-fluorophenyl)-3-hydroxypentyl]-7-hydroxyoctahydro-2H-cyclopenta[b]oxepin-3-yl}butanoic acid TLC: Rf 0.42 (dichloromethane:methanol=6:1);
$^1$H-NMR (300 MHz, CDCl$_3$): δ 0.98-1.20, 1.35-1.95, 2.21, 2.31, 2.68, 2.77, 2.90, 3.62, 3.70, 3.92, 4.00, 6.82-7.00, 7.24.

Example 108 (4)

4-{(3S,5aR,6R,7R,8aS)-6-[(3R)-5-(3-fluorophenyl)-3-hydroxypentyl]-7-hydroxyoctahydro-2H-cyclopenta[b]oxepin-3-yl}butanoic acid TLC: Rf 0.42 (dichloromethane:methanol=6:1);
$^1$H-NMR (300 MHz, CDCl$_3$): δ 0.98-1.20, 1.35-1.95, 2.21, 2.31, 2.68, 2.77, 2.91, 3.62, 3.70, 3.92, 4.00, 6.82-7.00, 7.24.

Example 108 (5)

4-{(3S,5aR,6R,7R,8aS)-6-[(3S)-5-(4-fluorophenyl)-3-hydroxypentyl]-7-hydroxyoctahydro-2H-cyclopenta[b]oxepin-3-yl}butanoic acid TLC: Rf 0.42 (dichloromethane:methanol=6:1);
$^1$H-NMR (300 MHz, CDCl$_3$): δ 0.98-1.20, 1.30-1.95, 2.21, 2.32, 2.68, 2.77, 2.91, 3.62, 3.70, 3.92, 4.00, 6.90-7.00, 7.10-7.18.

Example 108 (6)

4-{(3S,5aR,6R,7R,8aS)-6-[(3R)-5-(4-fluorophenyl)-3-hydroxypentyl]-7-hydroxyoctahydro-2H-cyclopenta[b]oxepin-3-yl}butanoic acid TLC: Rf 0.42 (dichloromethane:methanol=6:1);
$^1$H-NMR (300 MHz, CDCl$_3$): δ 0.98-1.20, 1.30-1.95, 2.21, 2.32, 2.68, 2.77, 2.91, 3.61, 3.70, 3.93, 4.00, 6.90-7.00, 7.10-7.18.

Example 108 (7)

4-{(3S,5aR,6R,7R,8aS)-6-[(3S)-5-(2-fluorophenyl)-3-hydroxypentyl]-7-hydroxyoctahydro-2H-cyclopenta[b]oxepin-3-yl}butanoic acid TLC: Rf 0.45 (dichloromethane methanol=9:1);
$^1$H-NMR (300 MHz, CDCl$_3$): δ 0.96-1.20, 1.37-1.92, 2.18-2.26, 2.30-2.35, 2.66-2.85, 2.87-2.95, 3.57-3.62, 3.67-3.73, 3.90-4.04, 6.97-7.07, 7.13-7.21.

Example 108 (8)

4-{(3S,5aR,6R,7R,8aS)-6-[(3R)-5-(2-fluorophenyl)-3-hydroxypentyl]-7-hydroxyoctahydro-2H-cyclopenta[b]oxepin-3-yl}butanoic acid TLC: Rf 0.32 (dichloromethane:methanol=9:1);
$^1$H-NMR (300 MHz, CDCl$_3$): δ 0.97-1.20, 1.25-1.92, 2.16-2.25, 2.30-2.35, 2.66-2.86, 2.87-2.95, 3.57-3.65, 3.68-3.73, 3.90-4.04, 6.97-7.07, 7.13-7.21.

Example 108 (9)

4-{(3S,5aR,6R,7R,8aS)-6-[(3S)-5-(3-chlorophenyl)-3-hydroxypentyl]-7-hydroxyoctahydro-2H-cyclopenta[b]oxepin-3-yl}butanoic acid TLC: Rf 0.42 (dichloromethane:methanol=6:1);
$^1$H-NMR (300 MHz, CDCl$_3$): δ 0.98-1.20, 1.32-1.95, 2.22, 2.33, 2.67, 2.78, 2.91, 3.61, 3.69, 3.93, 4.00, 7.07, 7.11-7.22.

Example 108 (10)

4-{(3S,5aR,6R,7R,8aS)-6-[(3R)-5-(3-chlorophenyl)-3-hydroxypentyl]-7-hydroxyoctahydro-2H-cyclopenta[b]oxepin-3-yl}butanoic acid TLC: Rf 0.42 (dichloromethane:methanol=6:1);
$^1$H-NMR (300 MHz, CDCl$_3$): δ 0.98-1.20, 1.32-1.95, 2.22, 2.33, 2.67, 2.78, 2.91, 3.61, 3.70, 3.93, 4.00, 7.07, 7.11-7.22.

Example 108 (11)

4-[(3S,5aR,6R,7R,8aS)-7-hydroxy-6-{(3S)-3-hydroxy-5-[3-(trifluoromethyl)phenyl]pentyl}octahydro-2H-cyclopenta[b]oxepin-3-yl]butanoic acid TLC: Rf 0.43 (dichloromethane:methanol=9:1);
$^1$H-NMR (300 MHz, CDCl$_3$): δ 0.95-1.16, 1.37-1.92, 2.20-2.33, 2.66-2.76, 2.81-2.94, 3.58-3.73, 3.89-4.03, 7.35-7.44.

Example 108 (12)

4-[(3S,5aR,6R,7R,8aS)-7-hydroxy-6-{(3R)-3-hydroxy-5-[3-(trifluoromethyl)phenyl]pentyl}octahydro-2H-cyclopenta[b]oxepin-3-yl]butanoic acid TLC: Rf 0.41 (dichloromethane:methanol=9:1);
$^1$H-NMR (300 MHz, CDCl$_3$): δ 0.97-1.20, 1.32-1.92, 2.17-2.25, 2.30-2.35, 2.67-2.77, 2.81-2.95, 3.58-3.73, 3.90-4.03, 7.36-7.44.

Example 108 (13)

4-[(3S,5aR,6R,7R,8aS)-7-hydroxy-6-{(3R)-3-hydroxy-4-[3-(trifluoromethyl)phenoxy]butyl}octahydro-2H-cyclopenta[b]oxepin-3-yl]butanoic

[Chemical formula 84]

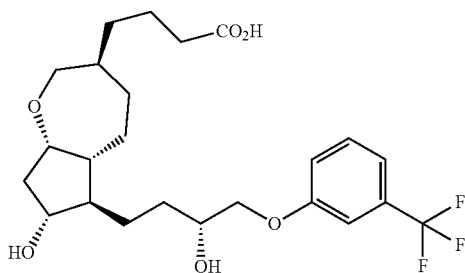

TLC: Rf 0.47 (ethyl acetate: acetic acid=100:1);
$^1$H-NMR (300 MHz, CDCl$_3$): δ 1.00-1.20, 1.45-1.95, 2.25, 2.34, 2.93, 3.76, 3.86-4.08, 7.09, 7.15, 7.24, 7.41.

Example 109

2-Propanyl 4-[(3S,5aR,6S,7R,8aS)-7-hydroxy-6-({[(2E)-3-phenyl-2-propen-1-yl]oxy}methyl)octahydro-2H-cyclopenta[b]oxepin-3-yl]butanoate To a DMF (1.5 mL) solution of the compound (150 mg) produced in Example 12 and cinnamyl bromide (220 mg), sodium hydride (17 mg) was added at 0° C., followed by stirring at room temperature overnight. The reaction mixture was diluted with MTBE, washed with an aqueous saturated ammonium chloride solution, water and saturated saline; then dried with magnesium sulfate; filtered; and concentrated under reduced pressure. The residue was purified by silica gel column chromatography (hexane:ethyl acetate=97:3→34:66) to obtain a titled compound (39 mg) having the following physical property values.

TLC: Rf 0.42 (hexane:ethyl acetate=1:1);
$^1$H-NMR (300 MHz, CDCl$_3$): δ 0.91-1.16, 1.21-1.29, 1.51-1.76, 1.82-1.91, 2.20-2.25, 2.32-2.41, 2.86-2.94, 3.36-3.42, 3.61-3.66, 3.82-3.90, 3.92-4.02, 4.13-4.16, 4.94-5.03, 6.20-6.30, 6.55-6.60, 7.21-7.39.

Example 110

4-[(3S,5aR,6S,7R,8aS)-7-hydroxy-6-({[(2E)-3-phenyl-2-propen-1-yl]oxy}methyl)octahydro-2H-cyclopenta[b]oxepin-3-yl]butanoic acid

[Chemical formula 85]

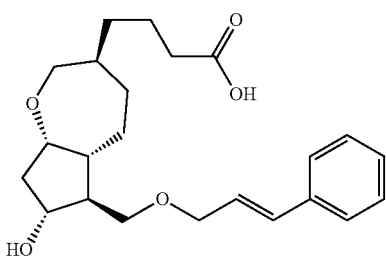

With using the compound produced in Example 109, the compound was subjected to the same objective operations as those of Example 17 (1) to obtain a titled compound having the following physical property values.

TLC: Rf 0.53 (dichloromethane:methanol=9:1);
$^1$H-NMR (300 MHz, CDCl$_3$): δ 0.92-1.17, 1.51-1.76, 1.82-1.92, 2.26-2.42, 2.87-2.94, 3.36-3.42, 3.61-3.65, 3.82-4.04, 4.09-4.18, 6.20-6.30, 6.55-6.60, 7.21-7.39.

Example 111

2-Propanyl 4-[(3S,5aR,6R,7R,8aS)-7-(tetrahydro-2H-pyran-2-yloxy)-6-vinyloctahydro-2H-cyclopenta[b]oxepin-3-yl]butanoate Methyltriphenylphosphonium bromide (2.60 g) was suspended in THF (10 mL), and followed by cooling to 0° C. Sodium hexamethyldisilazane (7.0 mL, 1 mol/L THF solution) was added, followed by stirring at the same temperature for 30 minutes. A THF (1 mL) solution of the compound (1.0 g) produced in Example 13 was added dropwise, followed by stirring at the same temperature for 1 hour. An extract obtained by pouring the reaction solution to 1 N hydrochloric acid cooled to 0° C. and extracting with ethyl acetate was washed with water, an aqueous saturated sodium bicarbonate solution and a saturated saline; dried with anhydrous magnesium sulfate; and then concentrated under reduced pressure. The residue was purified by silica gel column chromatography to obtain a titled compound (967 mg) having the following physical property values.

TLC: Rf 0.67 (hexane:ethyl acetate=2:1).

Example 112

2-Propanyl 4-[(3S,5aR,6R,7R,8aS)-6-(2-hydroxyethyl)-7-(tetrahydro-2H-pyran-2-yloxy)octahydro-2H-cyclopenta[b]oxepin-3-yl]butanoate To a borane tetrahydrofuran complex (0.44 mL) cooled to −30° C. or lower, 2-Methyl-2-butene (110 µL) was added, followed by stirring at 0° C. for 2 and a half hours. A THF solution (1 mL) of the compound (170 mg) produced in Example 111 was added, followed by stirring at room temperature overnight. The mixture was cooled again to 0° C.; a 5N aqueous sodium hydroxide solution (260 µL); and 30% hydrogen peroxide water (2604) were added, and the mixture was stirred for 1 hour. The reaction mixture was diluted with MTBE; washed with an aqueous saturated ammonium chloride solution, an aqueous sodium sulfite solution, water and a saturated saline; then dried with magnesium sulfate, filtered; and concentrated under reduced pressure. The residue was purified by silica gel column chromatography (hexane:ethyl acetate=97:3-÷ 35:65) to obtain a titled compound (58 mg) having the following physical property values.

TLC: Rf 0.61 (hexane:ethyl acetate=1:3).

Example 113

2-Propanyl 4-{(3S,5aR,6R,7R,8aS)-7-hydroxy-6-[2-(2-oxo-2-phenylethoxy)ethyl]octahydro-2H-cyclopenta[b]oxepin-3-yl}butanoate To a toluene (0.5 mL) solution of the compound (29 mg) produced in Example 112 and 2-diazoacetophenone (14 mg), indium triflate (4 ml) was added at room temperature, followed by stirring for 5 hours. An aqueous saturated sodium bicarbonate solution was added to stop the reaction, and the reaction solution was extracted with MTBE. The organic layer was washed with water and a saturated saline; then dried with magnesium sulfate; filtered; and concentrated under reduced pressure. The residue was dissolved in methanol (1 mL) and tosylate hydrate was added, followed by stirring at room temperature. The reaction mixture was concentrated, and the residue was purified by silica gel column chromatography (hexane:ethyl acetate=95:5→35:65) to obtain a titled compound (3 mg) having the following physical property values.

TLC: Rf 0.27 (hexane:ethyl acetate=1:1).

Example 114

2-Propanyl 4-{(3S,5aR,6R,7R,8aS)-7-hydroxy-6-[2-(2-phenylethoxy)ethyl]octahydro-2H-cyclopenta[b]oxepin-3-yl}butanoate To an ethyl acetate (0.25 mL) solution of the compound (2.5 mg) produced in Example 113, 5% palladium carbon (1.0 mg) was added, and the mixture was stirred at room temperature for 3 days under a hydrogen atmosphere. The reaction mixture was filtered with Celite (trade name), and then concentrated under reduced pressure, and the residue was purified by silica gel column chromatography (hexane:ethyl acetate=70:30) to obtain a titled compound (1 mg) having the following physical property values.

TLC: Rf 0.48 (hexane:ethyl acetate=1:1);
$^1$H-NMR (300 MHz, CDCl$_3$): δ 0.86-1.28, 1.40-1.72, 1.87-1.91, 2.20-2.26, 2.36-2.44, 2.87-2.94, 3.48-3.70, 3.90-4.03, 4.37, 4.95-5.03, 7.18-7.32.

Example 115

4-{(3S,5aR,6R,7R,8aS)-7-hydroxy-6-[2-(2-phenylethoxy)ethyl]octahydro-2H-cyclopenta[b]oxepin-3-yl}butanoic acid

[Chemical formula 86]

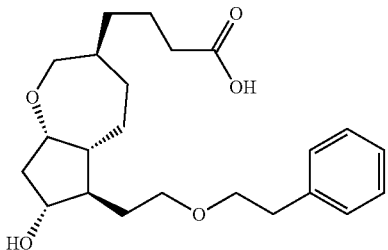

With using the compound produced in Example 114, the compound was subjected to the same objective operations as those of Example 17 (1) to obtain a titled compound having the following physical property values.

TLC: Rf 0.44 (dichloromethane:methanol=9:1);
$^1$H-NMR (300 MHz, CDCl$_3$): δ 0.83-1.72, 1.88-1.95, 2.30-2.45, 2.87-2.94, 3.48-3.70, 3.90-4.03, 4.40, 7.18-7.28.

Example 116

Methyl 4-[(3S,5aR,6S,7R,8aS)-6-ethynyl-7-(tetrahydro-2H-pyran-2-yloxy)octahydro-2H-cyclopenta[b]oxepin-3-yl]butanoate To a methanol solution (2.3 mL) of the compound (180 mg) produced in Example 13, potassium carbonate (94 mg) and a Bestmann reagent (dimethyl-1-diazo-2-oxopropyl phosphonate) (105 mg) were added, followed by stirring at room temperature for 6 hours. Further, potassium carbonate (47 mg) and the Bestmann reagent (53 mg) were added, followed by stirring at room temperature overnight. The reaction mixture was cooled to 0° C.; diluted with ethyl acetate; and then separated by adding water. The organic layer was washed with water and a saturated saline; dried with magnesium sulfate; then filtered; and concentrated under reduced pressure, and the residue was purified by silica gel column chromatography (hexane:ethyl acetate=97:3→65:35) to obtain a titled compound (47 mg) having the following physical property values.

TLC: Rf 0.50 (hexane:ethyl acetate=2:1).

Example 117

Methyl 4-[(3S,5aR,6S,7R,8aS)-6-(3-hydroxy-5-phenyl-1-pentyn-1-yl)-7-(tetrahydro-2H-pyran-2-yloxy)octahydro-2H-cyclopenta[b]oxepin-3-yl]butanoate A THF solution (0.5 mL) of the compound (52 mg) produced in Example 116 was cooled to −78° C. and a n-butyllithium hexane solution (1.67 M, 0.7 mL) was added, followed by stirring for 30 minutes. 3-Phenylpropionaldehyde (28 mg) was added, and stirring was carried out as it was overnight to allow a temperature to naturally raise to room temperature. The reaction mixture was diluted with MTBE; separated by adding an aqueous saturated ammonium chloride solution; washed with a saturated saline; then dried with magnesium sulfate; filtered; and concentrated under reduced pressure. The residue was purified by silica gel column chromatography (hexane:ethyl acetate=95:5→50:50) to obtain a titled compound (5 mg) having the following physical property values.

TLC: Rf 0.68 (hexane:ethyl acetate=1:2).

Example 118

Methyl 4-[(3S,5aR,6S,7R,8aS)-7-hydroxy-6-(3-hydroxy-5-phenyl-1-pentyn-1-yl)octahydro-2H-cyclopenta[b]oxepin-3-yl]butanoate With using the compound produced in Example 117, the compound was subjected to the same objective operations as those of Example 16 (1) to obtain a titled compound having the following physical property values.

TLC: Rf 0.20 (hexane:ethyl acetate=1:2);

$^1$H-NMR (300 MHz, CDCl$_3$): δ 0.83-1.37, 1.51-1.76, 1.88-2.09, 2.25-2.31, 2.37-2.46, 2.75-2.80, 2.86-2.94, 3.66, 3.90-4.06, 4.37, 7.17-7.31.

Example 119

4-[(3S,5aR,6S,7R,8aS)-7-hydroxy-6-(3-hydroxy-5-phenyl-1-pentyn-1-yl)octahydro-2H-cyclopenta[b]oxepin-3-yl]butanoic acid (mixture of 4-[(3S,5aR,6S,7R,8aS)-7-hydroxy-6-((3R)-3-hydroxy-5-phenyl-1-pentyn-1-yl)octahydro-2H-cyclopenta[b]oxepin-3-yl]butanoic acid and 4-[(3S,5aR, 6S,7R,8aS)-7-hydroxy-6-((3S)-3-hydroxy-5-phenyl-1-pentyn-1-yl)octahydro-2H-cyclopenta[b]oxepin-3-yl]butanoic acid)

[Chemical formula 87]

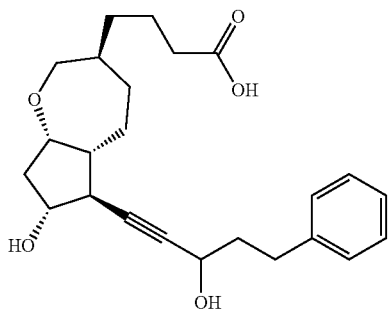

With using the compound produced in Example 118, the compound was subjected to the same objective operations as those of Example 17 (1) to obtain a titled compound having the following physical property values.

TLC: Rf 0.28 (dichloromethane:methanol=9:1);

$^1$H-NMR (300 MHz, CDCl$_3$): δ 0.83-0.90, 0.98-1.28, 1.42-1.75, 1.90-2.06, 2.31-2.46, 2.75-2.80, 2.87-2.94, 3.89-4.08, 4.35-4.40, 7.16-7.31.

Example 120

2-Propanyl 4-[(3S,5aR,6R,7R,8aS)-6-[(1E)-3-hydroxy-4-phenoxy-1-buten-1-yl]-7-(tetrahydro-2H-pyran-2-yloxy)octahydro-2H-cyclopenta[b]oxepin-3-yl]butanoate To a methanol solution (2.5 mL) of the compound (260 mg) produced in Example 14, cerium chloride heptahydrate (220 mg) and sodium borohydride (22 mg) were added sequentially under ice-cooling and stirring, followed by stirring for 20 minutes. Water was added, and the mixture was extracted with ethyl acetate. The organic layer was washed with a saturated saline; dried with anhydrous magnesium sulfate; and concentrated. The resulting residue was purified by silica gel column chromatography (ethyl acetate:hexane=30:70→50:50) to obtain a titled compound (280 mg) having the following physical property values.

TLC: Rf 0.33 (ethyl acetate:hexane=1:2).

Example 121 (1)

2-Propanyl 4-{(3S,5aR,6R,7R,8aS)-6-[(1E)-3-fluoro-4-phenoxy-1-buten-1-yl]-7-hydroxyoctahydro-2H-cyclopenta[b]oxepin-3-yl}butanoate Example 121 (2)

2-Propanyl 4-{(3S,5aR,6R,7R,8aS)-6-[(2E)-1-fluoro-4-phenoxy-2-buten-1-yl]-7-hydroxyoctahydro-2H-cyclopenta[b]oxepin-3-yl}butanoate To a dichloromethane solution (2.5 mL) of the compound (280 mg) produced in Example 120, diethylsulfur trifluoride (98 μL) was added at −78° C. under stirring. A temperature of the mixture was slowly raised to 0° C. over 4 hours. An aqueous saturated sodium bicarbonate solution was added, and extraction with ethyl acetate was carried out. The organic layer was washed with a saturated saline; dried with anhydrous magnesium sulfate; and concentrated. The resulting residue was purified by silica gel column chromatography (ethyl acetate:hexane=15:85→30:70) to obtain a regioisomer mixture (241 mg).

TLC: Rf 0.50 (ethyl acetate:hexane=1:2).

To a methanol solution (3 mL) of the regioisomer mixture (241 mg), pyridinium paratoluenesulfonate (13 mg) was added at room temperature under stirring, and stirring was carried out at room temperature for 18 hours. An aqueous saturated sodium bicarbonate solution was added, followed by extraction with ethyl acetate. The organic layer was washed with a saturated saline; dried with anhydrous magnesium sulfate; and concentrated. The resulting residue was purified by silica gel column chromatography (ethyl acetate:hexane=30:70→50:50) to obtain a compound (151 mg) of Example 121 (1) having the following physical property values and a compound (27 mg) of Example 121 (2) having the following physical property values.

Compound of Example 121 (1)

TLC: Rf 0.20 (ethyl acetate:hexane=1:2);

$^1$H-NMR (300 MHz, CDCl$_3$): δ 0.90-1.20, 1.22, 1.40-2.00, 2.23, 2.53, 2.92, 3.45, 3.60-4.20, 4.60, 4.99, 5.02-5.32, 5.60-5.90, 6.89, 6.94, 7.27.

Compound of Example 121 (2)

TLC: Rf 0.22 (ethyl acetate:hexane=1:2);

$^1$H-NMR (300 MHz, CDCl$_3$): δ 0.95-1.20, 1.22, 1.45-2.20, 2.32, 2.92, 3.92-4.10, 4.55-4.61, 4.75-5.15, 5.80-6.08, 6.89, 6.94, 7.27.

Example 122

4-{(3S,5aR,6R,7R,8aS)-6-[(1E)-3-fluoro-4-phenoxy-1-buten-1-yl]-7-hydroxyoctahydro-2H-cyclopenta[b]oxepin-3-yl}butanoic acid (mixture of 4-{(3S,5aR, 6R,7R,8aS)-6-[(1E,3R)-3-fluoro-4-phenoxy-1-buten-1-yl]-7-hydroxyoctahydro-2H-cyclopenta[b]oxepin-3-yl}butanoic acid and 4-{(3S,5aR, 6R,7R,8aS)-6-[(1E,3S)-3-fluoro-4-phenoxy-1-buten-1-yl]-7-hydroxyoctahydro-2H-cyclopenta[b]oxepin-3-yl}butanoic acid)

[Chemical formula 88]

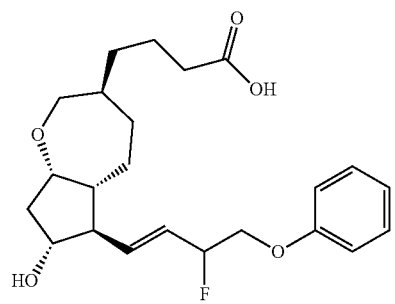

With using the compound produced in Example 121 (1), the compound was subjected to the same objective operations as those of Example 17 (1) to obtain a titled compound having the following physical property values.
TLC: Rf 0.21 (ethyl acetate:hexane=3:1);
$^1$H-NMR (300 MHz, CDCl$_3$): δ 0.95-1.28, 1.40-1.98, 2.16, 2.33, 2.46, 2.92, 3.75, 3.92-4.20, 5.12-5.35, 5.63-5.82, 6.90, 6.93, 7.28.

Example 123

4-{(3S,5aR,6R,7R,8aS)-6-[(2E)-1-fluoro-4-phenoxy-2-buten-1-yl]-7-hydroxyoctahydro-2H-cyclopenta[b]oxepin-3-yl}butanoic acid (mixture of 4-{(3S,5aR,6R,7R,8aS)-6-[(1R,2E)-1-fluoro-4-phenoxy-2-buten-1-yl]-7-hydroxyoctahydro-2H-cyclopenta[b]oxepin-3-yl}butanoic acid and 4-{(3S,5aR, 6R,7R,8aS)-6-[(1S,2E)-1-fluoro-4-phenoxy-2-buten-1-yl]-7-hydroxyoctahydro-2H-cyclopenta[b]oxepin-3-yl}butanoic acid)

[Chemical formula 89]

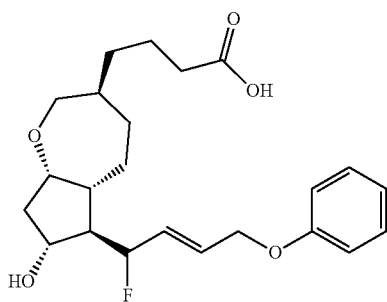

With using the compound produced in Example 121 (2), the compound was subjected to the same objective operations as those of Example 17 (1) to obtain a titled compound having the following physical property values.
TLC: Rf 0.21 (ethyl acetate:hexane=3:1);
$^1$H-NMR (300 MHz, CDCl$_3$): δ 0.95-1.28, 1.45-2.20, 2.32, 2.92, 3.60-3.82, 3.92-4.20, 4.50-4.62, 4.75-5.15, 5.80-6.08, 6.89, 6.94, 7.27).

Example 124 (1) to Example 124 (5)

With using the compound produced in Example 13, and using a corresponding sulfone in place of the compound produced in Example 100, these compounds were subjected to the same objective operations as those of Example 101→Example 16 (1) to obtain the following Example compounds.

Example 124 (1)

2-Propanyl 4-{(3S,5aR,6R,7R,8aS)-6-[(1E)-4-(3-chlorophenoxy)-1-buten-1-yl]-7-hydroxyoctahydro-2H-cyclopenta[b]oxepin-3-yl}butanoate TLC: Rf 0.44 (hexane:ethyl acetate=50:50):
$^1$H-NMR (300 MHz, CDCl$_3$): δ 0.95-1.16, 1.24, 1.40-1.80, 1.91, 2.06, 2.25, 2.44-2.56, 2.92, 3.69, 3.93-4.08, 5.01, 5.37, 5.60, 6.78, 6.89-6.94, 7.20.

Example 124 (2)

2-Propanyl 4-{(3S,5aR,6R,7R,8aS)-6-[(1E)-4-(2-fluorophenoxy)-1-buten-1-yl]-7-hydroxyoctahydro-2H-cyclopenta[b]oxepin-3-yl}butanoate TLC: Rf 0.40 (hexane:ethyl acetate=50:50);
$^1$H-NMR (300 MHz, CDCl$_3$): δ 0.94-1.16, 1.24, 1.42-1.83, 1.90, 2.06, 2.25, 2.48, 2.57, 2.92, 3.69, 3.93-4.10, 5.01, 5.38, 5.61, 6.86-7.11.

Example 124 (3)

2-Propanyl 4-{(3S,5aR,6R,7R,8aS)-6-[(1E)-4-(3-fluorophenoxy)-1-buten-1-yl]-7-hydroxyoctahydro-2H-cyclopenta[b]oxepin-3-yl}butanoate TLC: Rf 0.42 (hexane:ethyl acetate=50:50);
$^1$H-NMR (300 MHz, CDCl$_3$): δ 0.94-1.16, 1.24, 1.42-1.80, 1.90, 2.06, 2.25, 2.43-2.56, 2.92, 3.69, 3.93-4.08, 5.01, 5.37, 5.60, 6.58-6.69, 7.22.

Example 124 (4)

2-Propanyl 4-{(3S,5aR,6R,7R,8aS)-6-[(1E)-4-(2,5-difluorophenoxy)-1-buten-1-yl]-7-hydroxyoctahydro-2H-cyclopenta[b]oxepin-3-yl}butanoate TLC: Rf 0.44 (hexane:ethyl acetate=50:50);
$^1$H-NMR (300 MHz, CDCl$_3$): δ 0.93-1.16, 1.24, 1.38-1.82, 1.90, 2.06, 2.25, 2.43-2.60, 2.92, 3.69, 3.92-4.08, 5.01, 5.38, 5.60, 6.58, 6.69, 7.01.

Example 124 (5)

Methyl 4-{(3S,5aR,6R,7R,8aS)-7-hydroxy-6-[(1E)-4-hydroxy-6-phenyl-1-hexen-1-yl]octahydro-2H-cyclopenta[b]oxepin-3-yl}butanoate With using the compound produced in Example 7, using methyl iodide in place of isopropyl iodide, and using a corresponding sulfone in place of the compound produced in Example 100, these substances were subjected to the same objective operations as those of Example 8→Example 9 Example 10→Example 11→Example 12→Example 13→Example 101→Example 16 (1) to obtain a titled compound having the following physical property values.
TLC: Rf 0.24 (hexane:ethyl acetate=1:3);
$^1$H-NMR (CDCl$_3$): δ 0.91-1.19, 1.36-1.50, 1.52-1.91, 2.00-2.19, 2.25-2.33, 2.41-2.50, 2.62-2.94, 3.58-3.70, 3.89-4.04, 5.25-5.35, 5.44-5.59, 7.15-7.30.

Example 125 (1) to Example 125 (5)

With using the compounds produced in Examples 124 (1) to 124 (5), these compounds were subjected to the same objective operations as those of Example 17 (1), respectively, to obtain the following Example compounds.

Example 125 (1)

4-{(3S,5aR,6R,7R,8aS)-6-[(1E)-4-(3-chlorophenoxy)-1-buten-1-yl]-7-hydroxyoctahydro-2H-cyclopenta[b]oxepin-3-yl}butanoic acid TLC: Rf 0.49 (ethyl acetate);
$^1$H-NMR (300 MHz, CDCl$_3$): δ 0.94-1.21, 1.37-1.79, 1.90, 2.06, 2.33, 2.43-2.60, 2.92, 3.68, 3.93-4.08, 5.37, 5.60, 6.78, 6.88-6.94, 7.19.

Example 125 (2) 4-{(3S,5aR,6R,7R,8aS)-6-[(1E)-4-(2-fluorophenoxy)-1-buten-1-yl]-7-hydroxyoctahydro-2H-cyclopenta[b]oxepin-3-yl}butanoic acid TLC: Rf 0.51 (ethyl acetate);
$^1$H-NMR (300 MHz, CDCl$_3$): δ 0.94-1.23, 1.38-1.79, 1.90, 2.06, 2.33, 2.43-2.60, 2.92, 3.68, 3.93-4.09, 5.38, 5.60, 6.86-7.11.

Example 125 (3)

4-{(3S,5aR,6R,7R,8aS)-6-[(1E)-4-(3-fluorophenoxy)-1-buten-1-yl]-7-hydroxyoctahydro-2H-cyclopenta[b]oxepin-3-yl}butanoic acid TLC: Rf 0.49 (ethyl acetate);
$^1$H-NMR (300 MHz, CDCl$_3$): δ 0.94-1.24, 1.39-1.79, 1.90, 2.06, 2.34, 2.43-2.56, 2.92, 3.68, 3.93-4.08, 5.37, 5.60, 6.58-6.69, 7.22.

Example 125 (4)

4-{(3S,5aR,6R,7R,8aS)-6-[(1E)-4-(2,5-difluorophenoxy)-1-buten-1-yl]-7-hydroxyoctahydro-2H-cyclopenta[b]oxepin-3-yl}butanoic acid TLC: Rf 0.46 (ethyl acetate);
$^1$H-NMR (300 MHz, CDCl$_3$): δ 0.94-1.23, 1.38-1.79, 1.90, 2.06, 2.34, 2.43-2.60, 2.92, 3.69, 3.93-4.08, 5.38, 5.60, 6.58, 6.69, 7.01.

Example 125 (5)

4-{(3S,5aR,6R,7R,8aS)-7-hydroxy-6-[(1E)-4-hydroxy-6-phenyl-1-hexen-1-yl]octahydro-2H-cyclopenta[b]oxepin-3-yl}butanoic acid (mixture of 4-{(3S,5aR,6R,7R,8aS)-7-hydroxy-6-[(1E,4R)-4-hydroxy-6-phenyl-1-hexen-1-yl]octahydro-2H-cyclopenta[b]oxepin-3-yl}butanoic acid and 4-{(3S, 5aR, 6R,7R,8aS)-7-hydroxy-6-[(1E,4S)-4-hydroxy-6-phenyl-1-hexen-1-yl]octahydro-2H-cyclopenta[b]oxepin-3-yl}butanoic acid)

TLC: Rf 0.36 (dichloromethane:methanol=9:1);
$^1$H-NMR (300 MHz, CDCl$_3$): δ 0.92-1.20, 1.37-1.50, 1.54-1.90, 2.00-2.19, 2.24-2.35, 2.42-2.50, 2.62-2.95, 3.60-3.70, 3.90-4.05, 5.27-5.36, 5.45-5.58, 7.15-7.31.

Example 126

4-[(3S,5aR,6R,7R,8aS)-7-hydroxy-6-(4-phenoxybutyl)octahydro-2H-cyclopenta[b]oxepin-3-yl]butanoic acid With using the compound produced in Example 103, the compound was subjected to the same objective operations as those of Example 18 (1) to obtain a titled compound having the following physical property values.
TLC: Rf 0.57 (ethyl acetate: acetic acid=100:1);
$^1$H-NMR (300 MHz, CDCl$_3$): δ 1.00-1.24, 1.30-1.93, 2.20, 2.34, 2.93, 3.74, 3.97, 4.04, 6.88-6.97, 7.25-7.31.

Example 127

(3S,5aR,6S,7R,8aS)-6-formyl-3-[4-oxo-4-(2-propanyloxy)butyl]octahydro-2H-cyclopenta[b]oxepin-7-yl 4-biphenylcarboxylate With using the compound produced in Example 70, the compound was subjected to the same objective operations as those of Example 13 to obtain a titled compound having the following physical property values.
TLC: Rf 0.47 (hexane:ethyl acetate=2:1).

Example 128

(3S,5aR,6S,7R,8aS)-6-[(E)-2-iodovinyl]-3-[4-oxo-4-(2-propanyloxy)butyl]octahydro-2H-cyclopenta[b]oxepin-7-yl 4-biphenylcarboxylate To a THF (10 mL) solution of the compound (0.85 g) produced in Example 127, chromium chloride (1.7 g) was added and a THF (7 mL) solution of iodoform (1.4 g) was added with stirring at 0° C., followed by stirring as it was for 4 hours. The reaction mixture was poured into water, and was extracted with ethyl acetate. The organic layer was washed with water and a saturated saline; dried with magnesium sulfate; and then concentrated under reduced pressure. The residue was purified by silica gel column chromatography (hexane:ethyl acetate=95:5→75:25) to obtain a titled compound (600 mg) having the following physical property values.
TLC: Rf 0.47 (hexane:ethyl acetate=3:1).

Example 129

Methyl 4-{(3S,5aR,6R,7R,8aS)-7-hydroxy-6-[(E)-2-iodovinyl]octahydro-2H-cyclopenta[b]oxepin-3-yl}butanoate To a THF (30 mL) solution of the compound (9.0 g) produced in Example 128, methanol (70 mL) and potassium carbonate (2.2 g) were added, followed by stirring at room temperature overnight. The reaction mixture was filtered with Celite (trade name), and concentrated. MTBE and water were added to separate the concentrate, and the organic layer was washed with a saturated saline; dried with magnesium sulfate; and then concentrated under reduced pressure. The residue was purified by silica gel column chromatography (hexane:ethyl acetate=80:20→45:55) to obtain a titled compound (5.0 g) having the following physical property values.
TLC: Rf 0.53 (hexane:ethyl acetate=1:1).

Example 130

Methyl 4-{(3S,5aR,6R,7R,8aS)-7-acetoxy-6-[(E)-2-iodovinyl]octahydro-2H-cyclopenta[b]oxepin-3-yl}butanoate To a pyridine (25 mL) solution of the compound (5.0 g) produced in Example 129, acetic anhydride (2.3 mL) was added, and the reaction mixture was stirred at room temperature overnight. Water was added to stop the reaction, and the reaction mixture was poured into ice-cooled 1N hydrochloric acid. Extraction with ethyl acetate was carried out, and the organic layer was washed with 1N hydrochloric acid, an aqueous saturated sodium bicarbonate solution, water and a saturated saline; dried with magnesium sulfate; then filtered; and concentrated under reduced pressure. The residue was purified by silica gel column chromatography (hexane:ethyl acetate=95:5→70:30) to obtain a titled compound (5.2 g) having the following physical property values.

TLC: Rf 0.53 (hexane:ethyl acetate=3:1).

Example 131

Methyl 4-{(3S,5aR,6R,7R,8aS)-7-acetoxy-6-[(1E)-3-hydroxy-8-methyl-1,7-nonadien-1-yl]octahydro-2H-cyclopenta[b]oxepin-3-yl}butanoate To a dimethyl sulfoxide (4 mL) solution of the compound (400 mg) produced in Example 130 and 6-methylhepto-5-enal (220 mg), chromium chloride (440 mg) and nickel chloride (2.0 mg) were added, followed by stirring at room temperature for 3 and a half hours. The reaction mixture was poured into water and extraction with ethyl acetate was carried out. The organic layer was washed with water and a saturated saline; dried with magnesium sulfate; then filtered; and concentrated under reduced pressure. The residue was purified by silica gel column chromatography (hexane:ethyl acetate=97:3→55:45) to obtain a titled compound (380 mg) having the following physical property values.

TLC: Rf 0.50 (hexane:ethyl acetate=1:1).

Example 132 (1)

4-{(3S,5aR,6R,7R,8aS)-7-hydroxy-6-[(1E)-3-hydroxy-8-methyl-1,7-nonadien-1-yl]octahydro-2H-cyclopenta[b]oxepin-3-yl}butanoic acid (mixture of 4-{(3S,5aR,6R,7R,8aS)-7-hydroxy-6-[(1E,3R)-3-hydroxy-8-methyl-1,7-nonadien-1-yl]octahydro-2H-cyclopenta[b]oxepin-3-yl}butanoic acid and 4-{(3S,5aR,6R,7R,8aS)-7-hydroxy-6-[(1E,3S)-3-hydroxy-8-methyl-1,7-nonadien-1-yl]octahydro-2H-cyclopenta[b]oxepin-3-yl}butanoic acid)

To a methanol solution (3 mL) of the compound (110 mg) produced in Example 131, a 2N aqueous sodium hydroxide solution (1 mL) was added, and the reaction mixture was stirred at room temperature for 5 hours. Water was added; the mixture was neutralized with 2N hydrochloric acid; and then extracted with ethyl acetate. The organic layer was washed with water and a saturated saline; dried with magnesium sulfate; then filtered; and concentrated under reduced pressure to obtain a titled compound (95 mg) having the following physical property values.

TLC: Rf 0.36 (dichloromethane:methanol=9:1);

$^1$H-NMR (300 MHz, CDCl$_3$): δ 0.93-1.20, 1.31-1.80, 1.85-2.11, 2.29-2.34, 2.41-2.51, 2.87-2.95, 3.61-3.72, 3.90-4.10, 5.07-5.12, 5.35-5.62.

Example 132 (2) to Example 132 (10)

With using the compounds produced in Example 130, and using a corresponding aldehyde in place of 6-methylhepto-5-enal, these compounds were subjected to the same objective operations as those of Example 131→Example 132 (1) to obtain the following Example compounds.

Example 132 (2)

4-{(3S,5aR,6R,7R,8aS)-7-hydroxy-6-[(1E)-3-hydroxy-1-decen-1-yl]octahydro-2H-cyclopenta[b]oxepin-3-yl}butanoic acid (mixture of 4-{(3S,5aR,6R,7R,8aS)-7-hydroxy-6-[(1E,3R)-3-hydroxy-1-decen-1-yl]octahydro-2H-cyclopenta[b]oxepin-3-yl}butanoic acid and 4-{(3S,5aR,6R,7R,8aS)-7-hydroxy-6-[(1E,3S)-3-hydroxy-1-decen-1-yl]octahydro-2H-cyclopenta[b]oxepin-3-yl}butanoic acid)

Low Polar Body
TLC: Rf 0.59 (ethyl acetate: acetic acid=100:1).
High Polar Body
TLC: Rf 0.46 (ethyl acetate: acetic acid=100:1).
$^1$H-NMR (500 MHz, DMSO-d$_6$): δ 0.85, 0.88-1.09, 1.20-1.53, 1.57-1.66, 1.77-1.84, 2.15, 2.26, 2.84, 3.46, 3.82-3.88, 4.47, 4.54, 5.28-5.39.

Example 132 (3)

4-{(3S,5aR,6R,7R,8aS)-6-[(1E)-4-(benzyloxy)-3-hydroxy-1-buten-1-yl]-7-hydroxyoctahydro-2H-cyclopenta[b]oxepin-3-yl}butanoic acid (mixture of 4-{(3S,5aR,6R,7R,8aS)-6-[(1E,3R)-4-(benzyloxy)-3-hydroxy-1-buten-1-yl]-7-hydroxyoctahydro-2H-cyclopenta[b]oxepin-3-yl}butanoic acid and 4-{(3S,5aR,6R,7R,8aS)-6-[(1E,3S)-4-(benzyloxy)-3-hydroxy-1-buten-1-yl]-7-hydroxyoctahydro-2H-cyclopenta[b]oxepin-3-yl}butanoic acid)

[Chemical formula 90]

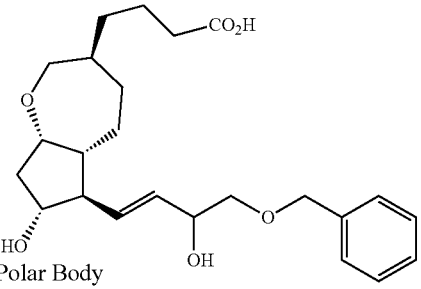

Low Polar Body
TLC: Rf 0.46 (ethyl acetate: acetic acid=100:1).
High Polar Body
TLC: Rf 0.40 (ethyl acetate: acetic acid=100:1).
$^1$H-NMR (500 MHz, DMSO-d$_6$): δ 0.85-1.10, 1.25-1.32, 1.35-1.52, 1.55-1.65, 1.75-1.85, 2.15, 2.26, 2.84, 3.47, 3.83-3.89, 4.11, 4.48-4.50, 4.58, 4.81, 5.39-5.51, 7.13-7.35.

Example 132 (4)

4-{(3S,5aR,6R,7R,8aS)-7-hydroxy-6-[(1E)-3-hydroxy-1,7-octadien-1-yl]octahydro-2H-cyclopenta[b]oxepin-3-yl}butanoic acid (mixture of 4-{(3S,5aR,6R,7R,8aS)-7-hydroxy-6-[(1E,3R)-3-hydroxy-1,7-octadien-1-yl]octahydro-2H-cyclopenta[b]oxepin-3-yl}butanoic acid and 4-{(3S,5aR,6R,7R,8aS)-7-hydroxy-6-[(1E,3S)-3-hydroxy-1,7-octadien-1-yl]octahydro-2H-cyclopenta[b]oxepin-3-yl}butanoic acid)

Low Polar Body
TLC: Rf 0.52 (ethyl acetate: acetic acid=100:1).
High Polar Body
TLC: Rf 0.44 (ethyl acetate: acetic acid=100:1).
$^1$H-NMR (500 MHz, DMSO-d$_6$): δ 0.88-1.09, 1.24-1.52, 1.57-1.66, 1.77-1.83, 1.98-2.02, 2.15, 2.26, 2.84, 3.46, 3.83-3.89, 4.51, 4.56, 4.92-5.01, 5.30-5.39, 5.78.

Example 132 (5)

4-{(3S,5aR,6R,7R,8aS)-7-hydroxy-6-[(1E)-3-hydroxy-5-(5-methyl-2-furyl)-1-penten-1-yl]octahydro-2H-cyclopenta[b]oxepin-3-yl}butanoic acid (mixture of 4-{(3S,5aR,6R,7R,8aS)-7-hydroxy-6-[(1E,3R)-3-hydroxy-5-(5-methyl-2-furyl)-1-penten-1-yl]octahydro-2H-cyclopenta[b]oxepin-3-yl}butanoic acid and 4-{(3S,5aR,6R,7R,8aS)-7-hydroxy-6-[(1E,3S)-3-hydroxy-5-(5-methyl-2-furyl)-1-penten-1-yl]octahydro-2H-cyclopenta[b]oxepin-3-yl}butanoic acid)

Low Polar Body
TLC: Rf 0.56 (ethyl acetate: acetic acid=100:1).
High Polar Body
TLC: Rf 0.49 (ethyl acetate: acetic acid=100:1).
$^1$H-NMR (500 MHz, DMSO-$d_6$): δ 0.89-1.09, 1.25-1.53, 1.58-1.66, 1.77-1.85, 2.15, 2.19, 2.27, 2.50-2.60, 2.84, 3.47, 3.84-3.91, 4.57, 4.67, 5.34-5.42, 5.88-5.91.

Example 132 (6)

4-{(3S,5aR,6R,7R,8aS)-7-hydroxy-6-[(1E,6Z)-3-hydroxy-1,6-nonadien-1-yl]octahydro-2H-cyclopenta[b]oxepin-3-yl}butanoic acid (mixture of 4-{(3S,5aR,6R,7R,8aS)-7-hydroxy-6-[(1E,3R,6Z)-3-hydroxy-1,6-nonadien-1-yl]octahydro-2H-cyclopenta[b]oxepin-3-yl}butanoic acid and 4-{(3S, 5aR, 6R,7R,8aS)-7-hydroxy-6-[(1E,3S,6Z)-3-hydroxy-1,6-nonadien-1-yl]octahydro-2H-cyclopenta[b]oxepin-3-yl}butanoic acid)

Low Polar Body
TLC: Rf 0.48 (ethyl acetate: acetic acid=100:1).
High Polar Body
TLC: Rf 0.38 (ethyl acetate: acetic acid=100:1).
$^1$H-NMR (500 MHz, DMSO-$d_6$): δ 0.89-1.09, 1.23-1.54, 1.56-1.66, 1.76-1.85, 1.96-2.04, 2.15, 2.26, 2.84, 3.46, 3.83-3.89, 4.55, 5.28-5.41.

Example 132 (7)

4-{(3S,5aR,6R,7R,8aS)-6-[(1E)-5-cyclopentyl-3-hydroxy-1-penten-1-yl]-7-hydroxyoctahydro-2H-cyclopenta[b]oxepin-3-yl}butanoic acid (mixture of 4-{(3S,5aR,6R,7R,8aS)-6-[(1E,3R)-5-cyclopentyl-3-hydroxy-1-penten-1-yl]-7-hydroxyoctahydro-2H-cyclopenta[b]oxepin-3-yl}butanoic acid and 4-{(3S, 5aR,6R,7R,8aS)-6-[(1E,3S)-5-cyclopentyl-3-hydroxy-1-penten-1-yl]-7-hydroxyoctahydro-2H-cyclopenta[b]oxepin-3-yl}butanoic acid)

[Chemical formula 91]

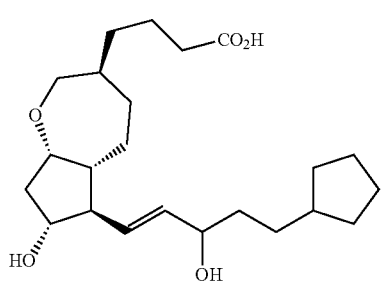

Low Polar Body
TLC: Rf 0.48 (ethyl acetate: acetic acid=100:1).
High Polar Body
TLC: Rf 0.38 (ethyl acetate: acetic acid=100:1).
$^1$H-NMR (500 MHz, DMSO-$d_6$): δ 0.89-1.09, 1.20-1.72, 1.77-1.84, 2.15, 2.26, 2.84, 3.46, 3.81-3.88, 4.47, 4.54, 5.29-5.40.

Example 132 (8)

4-{(3S,5aR,6R,7R,8aS)-7-hydroxy-6-[(1E)-3-hydroxy-4,8-dimethyl-1,7-nonadien-1-yl]octahydro-2H-cyclopenta[b]oxepin-3-yl}butanoic acid (mixture of 4-{(3S,5aR,6R,7R,8aS)-7-hydroxy-6-[(1E,3R,4R)-3-hydroxy-4,8-dimethyl-1,7-nonadien-1-yl]octahydro-2H-cyclopenta[b]oxepin-3-yl}butanoic acid, 4-{(3S,5aR,6R,7R,8aS)-7-hydroxy-6-[(1E,3R,4S)-3-hydroxy-4,8-dimethyl-1,7-nonadien-1-yl]octahydro-2H-cyclopenta[b]oxepin-3-yl}butanoic acid, 4-{(3S, 5aR, 6R,7R,8aS)-7-hydroxy-6-[(1E,3S,4R)-3-hydroxy-4,8-dimethyl-1,7-nonadien-1-yl]octahydro-2H-cyclopenta[b]oxepin-3-yl}butanoic acid and 4-{(3S,5aR,6R,7R,8aS)-7-hydroxy-6-[(1E,3S,4S)-3-hydroxy-4,8-dimethyl-1,7-nonadien-1-yl]octahydro-2H-cyclopenta[b]oxepin-3-yl}butanoic acid)

Low Polar Body
TLC: Rf 0.54 (ethyl acetate: acetic acid=100:1).
High Polar Body
TLC: Rf 0.41 (ethyl acetate: acetic acid=100:1).
$^1$H-NMR (500 MHz, DMSO-$d_6$): δ 0.78-0.81, 0.89-1.09, 1.25-1.53, 1.56, 1.57-1.62, 1.64, 1.77-2.00, 2.15, 2.26, 2.84, 3.46, 3.71-3.79, 3.83-3.89, 4.42-4.53, 5.07, 5.32-5.36.

Example 132 (9)

4-{(3S,5aR,6R,7R,8aS)-6-[(1E)-3-(1-benzofuran-2-yl)-3-hydroxy-1-propen-1-yl]-7-hydroxyoctahydro-2H-cyclopenta[b]oxepin-3-yl}butanoic acid (mixture of 4-{(3S,5aR,6R,7R,8aS)-6-[(1E,3R)-3-(1-benzofuran-2-yl)-3-hydroxy-1-propen-1-yl]-7-hydroxyoctahydro-2H-cyclopenta[b]oxepin-3-yl}butanoic acid and 4-{(3S,5aR,6R,7R,8aS)-6-[(1E,3S)-3-(1-benzofuran-2-yl)-3-hydroxy-1-propen-1-yl]-7-hydroxyoctahydro-2H-cyclopenta[b]oxepin-3-yl}butanoic acid)

Low Polar Body
TLC: Rf 0.48 (ethyl acetate: acetic acid=100:1).
High Polar Body
TLC: Rf 0.39 (ethyl acetate: acetic acid=100:1).
$^1$H-NMR (500 MHz, DMSO-$d_6$): δ 0.89-1.08, 1.26-1.53, 1.59-1.70, 1.75-1.83, 1.92, 2.15, 2.27, 2.85, 3.52, 3.85-3.90, 4.65, 5.17, 5.62-5.74, 6.67, 7.20, 7.25, 7.52, 7.59

Example 132 (10)

4-{(3S,5aR,6R,7R,8aS)-7-hydroxy-6-[(1E)-3-hydroxy-5-(3-hydroxyphenyl)-1-penten-1-yl]octahydro-2H-cyclopenta[b]oxepin-3-yl}butanoic acid (mixture of 4-{(3S,5aR,6R,7R,8aS)-7-hydroxy-6-[(1E,3R)-3-hydroxy-5-(3-hydroxyphenyl)-1-penten-1-yl]octahydro-2H-cyclopenta[b]oxepin-3-yl}butanoic acid and 4-{(3S,5aR,6R,7R,8aS)-7-hydroxy-6-[(1E,3S)-3-hydroxy-5-(3-hydroxyphenyl)-1-penten-1-yl]octahydro-2H-cyclopenta[b]oxepin-3-yl}butanoic acid)

TLC: Rf 0.65 (dichloromethane:methanol=4:1);
$^1$H-NMR (300 MHz, CDCl$_3$): δ 0.88-2.02, 2.23-2.27, 2.37-2.46, 2.57-2.62, 2.93-3.01, 3.58-3.67, 3.98-4.02, 5.41-5.58, 6.55-6.66, 7.01-7.07.

Example 133

(3S,5aR,6S,7R,8aS)-3-[4-oxo-4-(2-propanyloxy)butyl]-6-[(tetrahydro-2H-pyran-2-yloxy)methyl]octahydro-2H-cyclopenta[b]oxepin-7-yl 4-biphenylcarboxylate To a dichloromethane solution (30 mL) of the compound (2.9 g) produced in Example 70, 3,4-dihydro-2H-pyran (803 μL) and pyridinium paratoluenesulfonate (150 mg) were added at room temperature under stirring, followed by stirring at room temperature for 5 hours. An aqueous saturated sodium bicarbonate solution was added, followed by extraction with ethyl acetate. The organic layer was washed with a saturated saline; dried with anhydrous magnesium sulfate; and concentrated. The resulting residue was purified by silica gel column chromatography (ethyl acetate:hexane=5:95→25:75) to obtain a titled compound (3.84 g) having the following physical property values.
TLC: Rf 0.44 (ethyl acetate:hexane=1:4).

Example 134

2-Propanyl 4-{(3S,5aR,6S,7R,8aS)-7-hydroxy-6-[(tetrahydro-2H-pyran-2-yloxy)methyl]octahydro-2H-cyclopenta[b]oxepin-3-yl}butanoate To an isopropanol solution (30 mL) of the compound (3.84 g) produced in Example 133, lithium isopropoxide (2.0 M tetrahydrofuran solution, 5.9 mL) was added, followed by stirring at 45° C. for 1.5 hours. The mixture was ice-cooled and 1N hydrochloric acid (12 mL) and water were added, followed by extraction with ethyl acetate. The organic layer was washed with a saturated saline; dried with anhydrous magnesium sulfate; and concentrated. The resulting residue was purified by silica gel column chromatography (ethyl acetate:hexane=35:65→70:30) to obtain a titled compound (2.23 g) having the following physical property values.
TLC: Rf 0.34 (ethyl acetate:hexane=1:2).

Example 135

2-Propanyl 4-{(3S,5aR,6S,8aS)-7-oxo-6-[(tetrahydro-2H-pyran-2-yloxy)methyl]octahydro-2H-cyclopenta[b]oxepin-3-yl}butanoate To a dichloromethane solution (18 mL) of the compound (2.23 g) produced in Example 134, dimethyl sulfoxide (9 mL) and diisopropylethylamine (5.8 mL) were added under ice-cooling and stirring, and a sulfur trioxide/pyridine complex (2.67 g) was added little by little. The mixture was stirred at 0° C. for 1 hour. Water was added, followed by extraction with ethyl acetate. The organic layer was sequentially washed with water and a saturated saline; dried with anhydrous magnesium sulfate; and concentrated. The resulting residue was purified by silica gel column chromatography (ethyl acetate:hexane=15:85→35:65) to obtain a titled compound (2.21 g) having the following physical property values.
TLC: Rf 0.71 (ethyl acetate:hexane=1:1).

Example 136

2-Propanyl 4-[(3S,5aR,6S,8aS)-7,7-difluoro-6-(hydroxymethyl)octahydro-2H-cyclopenta[b]oxepin-3-yl]butanoate To a dichloroethane solution (8 mL) of the compound (1.3 g) produced in Example 135, morpholylsulfur trifluoride (1.2 mL) was added, followed by stirring at 45° C. for 50 hours. Water was added, and the mixture was extracted with ethyl acetate. The organic layer was washed with a saturated saline; dried with anhydrous magnesium sulfate; and concentrated. To a methanol solution (6 mL) of the residue, pyridinium paratoluenesulfonate (30 mg) was added, and the mixture was stirred at room temperature for 8 hours. An aqueous saturated sodium bicarbonate solution was added, followed by extraction with ethyl acetate. The organic layer was washed with a saturated saline; dried with anhydrous magnesium sulfate; and concentrated. The resulting residue was purified by silica gel column chromatography (ethyl acetate:hexane=30:70→45:55) to obtain a titled compound (329 mg) having the following physical property values.
TLC: Rf 0.30 (ethyl acetate:hexane=1:2).

Example 137

2-Propanyl 4-{(3S,5aR,6S,8aS)-7,7-difluoro-6-[(E)-2-iodovinyl]octahydro-2H-cyclopenta[b]oxepin-3-yl}butanoate To a dichloromethane solution (3.5 mL) of the compound (245 mg) produced in Example 136, Dess-Martin Periodinane (372 mg) was added under ice-cooling and stirring, followed by stirring for 1 hour. An aqueous saturated sodium thiosulfate solution and an aqueous saturated sodium bicarbonate solution were added, followed by extraction with ethyl acetate. The organic layer was washed with a saturated saline; dried with anhydrous magnesium sulfate; and concentrated. To a tetrahydrofuran solution (7 mL) of the residue, anhydrous chromium chloride (720 mg) and iodoform (577 mg) were sequentially added under ice-cooling and stirring, followed by stirring at room temperature for 1.5 hours. Water was added, followed by extraction with ethyl acetate. The organic layer was sequentially washed with water twice and with a saturated saline once; dried with anhydrous magnesium sulfate; and concentrated. The resulting residue was purified by silica gel column chromatography (ethyl acetate:hexane=5:95) to obtain a titled compound (206 mg) having the following physical property values.
TLC: Rf 0.50 (ethyl acetate:hexane=1:4).

Example 138 (1) and Example 138 (2)

With using the compound produced in Example 137, and using a corresponding aldehyde in place of 6-methylhepto-5-enal, these compounds were subjected to the same objective operations as those of Example 131 to obtain the Example compounds shown below.

Example 138 (1)

2-Propanyl 4-{(3S,5aR,6R,8aS)-7,7-difluoro-6-[(1E)-3-hydroxy-1-octen-1-yl]octahydro-2H-cyclopenta[b]oxepin-3-yl}butanoate TLC: Rf 0.28 (ethyl acetate:hexane=1:4);
$^1$H-NMR (300 MHz, CDCl$_3$): δ 0.80-0.96, 0.98-2.22, 2.23, 2.42-2.70, 2.93, 4.00-4.18, 4.99, 5.52, 5.64.

Example 138 (2)

2-Propanyl 4-{(3S,5aR,6R,8aS)-7,7-difluoro-6-[(1E)-3-hydroxy-5-phenyl-1-penten-1-yl]octahydro-2H-cyclopenta[b]oxepin-3-yl}butanoate TLC: Rf 0.28 (ethyl acetate:hexane=1:4);
$^1$H-NMR (300 MHz, CDCl$_3$): δ 0.98-1.20, 1.22, 1.40-2.20, 2.24, 2.45-2.80, 2.94, 4.02-4.20, 4.99, 5.42-5.62, 5.67, 7.15-7.32.

Example 139 (1) and Example 139 (2)

With using the compound produced in Example 138 (1) or Example 138 (2), the compound was subjected to the same objective operations as those of Example 17 (1) to obtain the Example compounds shown below.

Example 139 (1)

4-{(3S,5aR,6R,8aS)-7,7-difluoro-6-[(1E)-3-hydroxy-1-octen-1-yl]octahydro-2H-cyclopenta[b]oxepin-3-yl}butanoic acid (mixture of 4-{(3S,5aR,6R,8aS)-7,7-difluoro-6-[(1E,3R)-3-hydroxy-1-octen-1-yl]octahydro-2H-cyclopenta[b]oxepin-3-yl}butanoic acid and 4-{(3S,5aR,6R,8aS)-7,7-difluoro-6-[(1E,3S)-3-hydroxy-1-octen-1-yl]octahydro-2H-cyclopenta[b]oxepin-3-yl}butanoic acid)

TLC: Rf 0.27 (ethyl acetate:hexane=1:1);
$^1$H-NMR (300 MHz, CDCl$_3$): δ 0.80-0.96, 0.98-2.22, 2.33, 2.42-2.70, 2.95, 4.02-4.18, 5.53, 5.64.

Example 139 (2)

4-{(3S,5aR,6R,8aS)-7,7-difluoro-6-[(1E)-3-hydroxy-5-phenyl-1-penten-1-yl]octahydro-2H-cyclopenta[b]oxepin-3-yl}butanoic acid (mixture of 4-{(3S,5aR,6R,8aS)-7,7-difluoro-6-[(1E,3R)-3-hydroxy-5-phenyl-1-penten-1-yl]octahydro-2H-cyclopenta[b]oxepin-3-yl}butanoic acid and 4-{(3S,5aR,6R,8aS)-7,7-difluoro-6-[(1E,3S)-3-hydroxy-5-phenyl-1-penten-1-yl]octahydro-2H-cyclopenta[b]oxepin-3-yl}butanoic acid)

[Chemical formula 92]

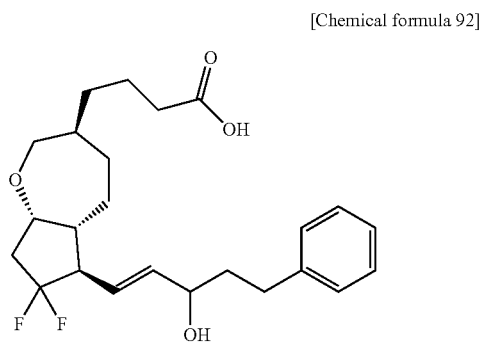 [SMILES: O=C(O)CCC[C@H]1CC[C@H]2[C@H](CC(F)(F)[C@@H]2/C=C/C(O)CCc2ccccc2)OC1]

TLC: Rf 0.23 (ethyl acetate:hexane=1:1);
$^1$H-NMR (300 MHz, CDCl$_3$): δ 0.98-1.20, 1.41, 1.55-2.24, 2.33, 2.44-2.80, 2.94, 4.02-4.18, 5.53, 5.67, 7.18-7.32.

Example 140 (1) to Example 140 (4)

With using the compound produced in Example 127, and using a corresponding phosphonic acid salt in place of dimethyl-(3-phenoxy-2-oxopropyl)-phosphonate, these substances were subjected to the same objective operations as those of Example 14→Example 30→Example 129 to obtain the following Example compounds.

Example 140 (1)

Methyl 4-{(3S,5aR,6R,7R,8aS)-6-[(1E)-3,3-difluoro-5-phenyl-1-penten-1-yl]-7-hydroxyoctahydro-2H-cyclopenta[b]oxepin-3-yl}butanoate TLC: Rf 0.39 (hexane:ethyl acetate=1:1);
$^1$H-NMR (300 MHz, CDCl$_3$): δ 0.93-1.20, 1.40-1.92, 2.10-2.30, 2.41-2.50, 2.76-2.81, 2.87-2.95, 3.66, 3.70-3.79, 3.92-4.05, 5.60-5.72, 5.85-5.93, 7.16-7.22, 7.25-7.31.

Example 140 (2)

Methyl 4-{(3S,5aR,6R,7R,8aS)-6-[(1E)-5-cyclopentyl-3,3-difluoro-1-penten-1-yl]-7-hydroxyoctahydro-2H-cyclopenta[b]oxepin-3-yl}butanoate TLC: Rf 0.44 (hexane:ethyl acetate=1:1);
$^1$H-NMR (CDCl$_3$); 80.94-1.18, 1.41-1.98, 2.11-2.31, 2.42-2.51, 2.88-2.95, 3.66, 3.72-3.81, 3.94-4.06, 5.57-5.69, 5.81-5.89.

Example 140 (3)

Methyl 4-{(3S,5aR,6R,7R,8aS)-6-{(1E)-5-cyclohexyl-3,3-difluoro-1-penten-1-yl}-7-hydroxyoctahydro-2H-cyclopenta[b]oxepin-3-yl}butanoate TLC: Rf 0.45 (hexane:ethyl acetate=1:1);
$^1$H-NMR (CDCl$_3$): δ 0.82-1.36, 1.41-1.97, 2.11-2.20, 2.26-2.31, 2.42-2.51, 2.88-2.95, 3.66, 3.71-3.81, 3.94-4.06, 5.56-5.69, 5.81-5.89.

Example 140 (4)

Methyl 4-{(3S,5aR,6R,7R,8aS)-6-[(1E)-3,3-difluoro-1-octen-1-yl]-7-hydroxyoctahydro-2H-cyclopenta[b]oxepin-3-yl}butanoate TLC: Rf 0.46 (hexane:ethyl acetate=1:1);
$^1$H-NMR (CDCl$_3$): 0.87-0.92, 0.94-1.16, 1.25-1.96, 2.11-2.20, 2.26-2.31, 2.42-2.51, 2.88-2.95, 3.66, 3.72-3.81, 3.94-4.07, 5.57-5.69, 5.81-5.89.

Example 141 (1) to Example 141 (4)

The compounds produced in Example 140 (1) to Example 140 (4) were subjected to the same objective operations as those of Example 17 (1), respectively, to obtain the following Example compounds.

Example 141 (1)

4-{(3S,5aR,6R,7R,8aS)-6-[(1E)-3,3-difluoro-5-phenyl-1-penten-1-yl]-7-hydroxyoctahydro-2H-cyclopenta[b]oxepin-3-yl}butanoic acid

[Chemical formula 93]

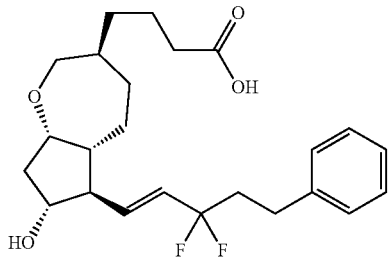

TLC: Rf 0.29 (ethyl acetate);
$^1$H-NMR (300 MHz, CDCl$_3$): δ 0.94-1.28, 1.40-1.93, 2.11-2.35, 2.42-2.51, 2.76-2.82, 2.88-2.96, 3.72-3.80, 3.93-4.08, 5.60-5.73, 5.86-5.94, 7.17-7.23, 7.26-7.32.

Example 141 (2)

4-{(3S,5aR,6R,7R,8aS)-6-[(1E)-5-cyclopentyl-3,3-difluoro-1-penten-1-yl]-7-hydroxyoctahydro-2H-cyclopenta[b]oxepin-3-yl}butanoic acid TLC: Rf 0.50 (dichloromethane:methanol=9:1);
$^1$H-NMR (CDCl$_3$): 0.95-1.20, 1.40-1.97, 2.11-2.20, 2.30-2.35, 2.42-2.51, 2.88-2.96, 3.72-3.80, 3.94-4.07, 5.56-5.68, 5.80-5.88.

Example 141 (3)

4-{(3S,5aR,6R,7R,8aS)-6-[(1E)-5-cyclohexyl-3,3-difluoro-1-penten-1-yl]-7-hydroxyoctahydro-2H-cyclopenta[b]oxepin-3-yl}butanoic acid TLC: Rf 0.45 (dichloromethane:methanol=9:1);
$^1$H-NMR (CDCl$_3$): 0.82-1.36, 1.40-1.96, 2.11-2.20, 2.30-2.35, 2.42-2.51, 2.88-2.96, 3.72-3.80, 3.93-4.07, 5.56-5.68, 5.80-5.88.

Example 141 (4)

4-{(3S,5aR,6R,7R,8aS)-6-[(1E)-3,3-difluoro-1-octen-1-yl]-7-hydroxyoctahydro-2H-cyclopenta[b]oxepin-3-yl}butanoic acid TLC: Rf 0.45 (dichloromethane:methanol=9:1);
$^1$H-NMR (CDCl$_3$): 0.87-0.92, 0.95-1.19, 1.25-1.95, 2.11-2.20, 2.30-2.35, 2.42-2.51, 2.88-2.96, 3.72-3.80, 3.94-4.07, 5.56-5.69, 5.80-5.88.

Example 141 (5)

4-{(3S,5aR,6R,7R,8aS)-6-[(1E)-3,3-difluoro-8-methyl-1,7-nonadien-1-yl]-7-hydroxyoctahydro-2H-cyclopenta[b]oxepin-3-yl}butanoic acid

[Chemical formula 94]

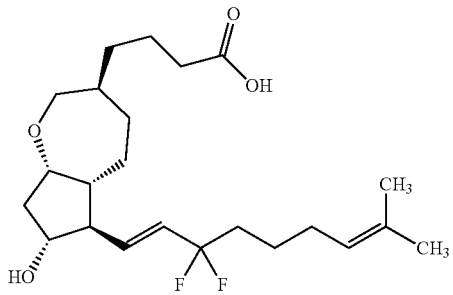

With using the compound produced in Example 127, and using a corresponding phosphonic acid salt in place of dimethyl-(3-phenoxy-2-oxopropyl)-phosphonate, these substances were subjected to the same objective operations as those of Example 14→Example 30→Example 17 (1) to obtain a titled compound having the following physical property values.

TLC: Rf 0.34 (dichloromethane:methanol=9:1);
$^1$H-NMR (CDCl$_3$): 0.95-1.38, 1.40-2.04, 2.11-2.20, 2.30-2.35, 2.42-2.51, 2.88-2.96, 3.72-3.80, 3.93-4.07, 5.05-5.09, 5.56-5.68, 5.80-5.88.

Example 142

4-[(3S,5aR,6R,7R,8aS)-6-(3,3-difluoro-5-phenylpentyl)-7-hydroxyoctahydro-2H-cyclopenta[b]oxepin-3-yl]butanoic acid With using the compound produced in Example 141 (1), the compound was subjected to the same objective operations as those of Example 18 (1) to obtain a titled compound having the following physical property values.

TLC: Rf 0.25 (ethyl acetate);
$^1$H-NMR (300 MHz, CDCl$_3$): δ 0.91-0.96, 0.98-1.28, 1.49-2.25, 2.30-2.35, 2.77-2.83, 2.87-2.95, 3.66-3.71, 3.91-4.05, 7.17-7.31.

[Pharmacological Experimental Example]

(1) In Vitro Test (1-1) Measurement of Agonist Activity on Various Mouse Prostanoid Receptors With using CHO cells (FP-CHO, EP1-CHO and IP-CHO, respectively) in which various mouse prostanoid receptors were forcibly expressed, respectively, agonist activity of test compounds on various prostanoid receptors was studied employing an intracellular calcium concentration regarding FP and EP1, and an intracellular cyclic AMP (hereinafter, abbreviated as cAMP) production amount regarding IP, as an index.

<Compound Treatment>

The test compound was dissolved with dimethyl sulfoxide (DMSO) to prepare a 10 mmol/L solution. Regarding the prepared 10 mmol/L solution, upon use, the 10 mmol/L solution was thawed; step wisely-diluted using DMSO; and diluted with a buffer solution for measurement or a buffer solution for measurement 2, which was subjected to an experiment.

<Cell Culturing>

Cells forcibly expressing various mouse prostanoid receptors were standing-cultured at 37° C. in the presence of 5% $CO_2$ with using an α-MEM medium (Sigma) (for culturing FP-CHO and EP1-CHO) containing inactivated (56° C., 30 minutes) 9.8 vol % dialysed-FBS (Invitrogen) and penicillin-streptomycin-glutamine (GIBCO-BRL), or nucleic acid-containing α-MEM (Sigma) (for culturing IP-CHO) containing inactivated (56° C., 30 minutes) 9.8 vol % dialysed-FBS (Invitrogen) and penicillin-streptomycin glutamine (Invitrogen). Subculturing was performed by the following method.

The medium was removed, and washed with a phosphate-buffered physiological saline which does not contain $Ca^{2+}$ and $Mg^{2+}$ twice A suitable amount of trypsin-EDTA (Invitrogen) was added, followed by incubation at 37° C. for about 3 minutes; cells were peeled; and a medium having a volume which is 10-fold a volume of trypsin-EDTA was added to stop an enzymatic reaction. After collecting cells into a centrifuging tube, cells were centrifuged at 120 g for 3 minutes at room temperature and the supernatant was removed. Cells were suspended in a suitable amount of a medium, and seeded in a culturing flask.

(1-2) Measurement of FP and EP1 Agonist Activity (Measurement of Intracellular Calcium Concentration)

Regarding FP-CHO and EP1-CHO, by the same method as that of subculturing, cells were peeled and suspended. Before two days from measurement, cells were seeded at a density of $1.0 \times 10^4$ cells/well into a 96-well UV plate, and standing-cultured at 37° C. in the presence of 5% $CO_2$. On the measurement day, after removing the medium from each well of the 96-well UV plate, cells were washed with a phosphate-buffered physiological saline which does not contain $Ca^{2+}$ and $Mg^{2+}$ once. To each well, 100 μL of a medium containing 5 μmol/L fura 2-AM (DOJINDO), 2.5 mmol/L Probenecid (Sigma), 20 μmol/L indometacin (Sigma) and 10 mmol/L HEPES (Invitrogen) was added, and cells were incubated for about 60 minutes in a $CO_2$ incubator. After completion of the incubation, the medium was removed, and cells were washed with a buffer solution for measurement (Hank's balanced salt solution (Nissui Pharmaceutical Co., Ltd., 9.8 g of the present product was dissolved in 1 L distilled water) containing 0.1 or 1 w/v % bovine serum albumin, 2 μmol/L indometacin, 2.5 mmol/L Probenecid and 10 mmol/L HEPES-NaOH (pH 7.4)) twice. To each well, 120 μL of a buffer solution for measurement was added; and cells were incubated in a $CO_2$ incubator for 30 minutes; and then cells were subjected to an experiment.

The 96-well UV plate was set in a fluorescent spectral photometer (FDSS-3000, Hamamatsu Photonics K.K.), and an intracellular calcium concentration was measured. To perform a reaction, 30 μL of a buffered solution for measurement containing an agonist at a variety of concentrations was added. Measurement of an intracellular calcium concentration was performed by irradiating cells with excited light of 340 nm and 380 nm alternately, with measuring a fluorescent intensity at 500 nm, and obtaining a fluorescent intensity ratio of 2-wavelength excitation.

(1-3) Measurement of IP Agonist Activity (Measurement of cAMP Concentration)

On the measurement day, a medium was removed, and IP-CHO was washed with a phosphate-buffered physiological saline which contains 2 mmol/L EDTA and does not contain $Ca^{2+}$ and $Mg^{2+}$ once. A suitable amount of a phosphate-buffered physiological saline which contains 2 mmol/L EDTA and does not contain $Ca^{2+}$ and $Mg^{2+}$ was added, and cells were incubated at 37° C. for about 10 minutes; cells were peeled; cells were collected into a centrifuging tube; and centrifuged at room temperature for 3 minutes at 500 g, followed by removal of the supernatant. Cells were suspended in a suitable amount of a buffer solution for measurement 1 (MEM medium (Invitrogen) containing 0.1 w/v % bovine serum albumin (Sigma) and 2 μmol/L diclofenac (Sigma)), and centrifuged at room temperature for 3 minutes at 500 g, and the supernatant was removed. Cells were suspended in a buffer solution for measurement 2 (MEM medium (Invitrogen) containing 0.1 w/v % bovine serum albumin (Sigma), 2 μmol/L diclofenac (Sigma) and 1 mmol/L 3-isobutyl-1-methylxanthine), and each 25 μL of the suspension was dispensed at a density of $5.0 \times 10^4$ cells/well into a 96-well ½ area plate. A buffer solution for measurement 2 (25 μL) containing an agonist at a variety of concentrations was added to perform a reaction at room temperature for 30 minutes. Measurement of a cAMP concentration was performed with using the cAMP HTRF HiRange kit (CIS bio International). According to the two step protocol of the kit manual, each 25 μL of cAMP-D2 and cryptase diluted with a lysis buffer were added, followed by incubation at room temperature for 1 hour. After incubation for 1 hour, time resolved fluorescence at 620 nm and 660 nm in case of beging excited at 340 nm was measured using Analyst GT (Molecular Device), and a ratio (TRF ratio) was obtained, by which a cAMP concentration was calculated from a calibration line.

<Result>

With using measured values obtained from the above method, an $EC_{50}$ value as an index of agonist activity of the compound of the present invention on mouse FP, mouse EP1 and mouse IP receptors was calculated.

For example, results for the compound described in Example 108 (13), the compound described in Example 110, the compound described in Example 115, the compound described in Example 119, the compound described in Example 122, the compound described in Example 123, the compound described in Example 132 (3), the compound described in Example 132 (7), the compound described in Example 139 (2), the compound described in Example 141 (1), the compound described in Example 141 (5), and the compound of Example 12 described in Patent Literature 2, which is represented by the following structural formula, as a comparative compound (hereinafter, abbreviated as Comparative Compound A in some cases) are shown in Table 1.

[Chemical formula 95]

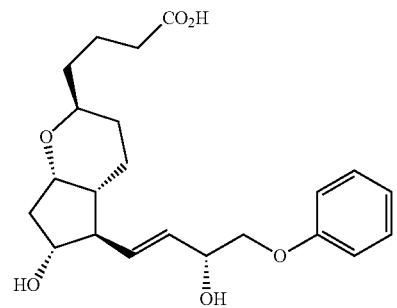

TABLE 1

| | Agonist activity on various prostanoid receptors: $EC_{50}$ value (nmol/L) | | |
|---|---|---|---|
| | FP | EP1 | IP |
| Example 108 (13) | 9.7 | >10000 | >10000 |
| Example 110 | 707.1 | >10000 | >10000 |
| Example 115 | 508.8 | >10000 | >10000 |
| Example 119 | 50.8 | >10000 | >10000 |
| Example 122 | 9.8 | 9273 | >10000 |
| Example 123 | 99.2 | >10000 | >10000 |
| Example 132 (3) | 113.6 | >10000 | >10000 |
| Example 132 (7) | 21.1 | >10000 | >10000 |
| Example 139 (2) | 39.0 | >10000 | >10000 |
| Example 141 (1) | 4.6 | >10000 | >10000 |
| Example 141 (5) | 39.1 | >10000 | >10000 |
| Comparative Compound A | 1.1 | 3 | 710 |

From the above results, it was seen that the Comparative Compound A has agonist activity not only on an FP receptor, but also on an EP1 receptor and an IP receptor, while all of the compound of the present inventions have low agonist activity on an EP1 receptor and an IP receptor, and have selective agonist activity on an FP receptor.

(2) In Vivo Test

As can be easily understood by a person skilled in the art, in an in vivo test, since regarding all test compounds, carboxylic acid which is an active body has bad corneal permeability, pharmacological action of the active body was assessed by ocular instillation administration of a compound which had been converted into an ester such as a methyl ester, an ethyl ester, an isopropyl ester etc. In addition, in a group of the compound of the present inventions, by ocular instillation administration of the ester body in an experimental animal (rabbit, dog etc.) by which pharmacological action is confirmed below and, thereafter, measurement of a drug concentration of carboxylic acid in an aqueous humor, it was confirmed that the ester is rapidly converted into corresponding carboxylic acid.

(2-1) Intraocular Pressure Lowering Action

To one eye of a male dog (TOYO Beagle) which had been sufficiently acclimated in advance, 30 µL of each test compound (the compound of Example 16 (35), the compound of Example 16 (3) and the compound of Example 16 (25)) which had been adjusted with a base (containing citrate buffer pH 6.5, 0.5% polysorbate 80, 1% propylene glycol, 0.01% benzalkonium chloride) to 0.01% (w/v) or 0.001% (w/v), was ocular-instilled respectively. The other eye was not treated. As a positive control compound, latanoprost which is the known compound was used.

Thereafter, an ocular surface anesthetic (Benoxil eye drops 0.4%, Santen Pharmaceutical Co., Ltd.) was subjected to ocular instillation to locally anesthetize eyes, and an intraocular pressure of each test compound before ocular instillation and after 2, 4, 6, 8, and 24 hours from ocular instillation was measured. An intraocular pressure was measured using a pneumatic applanation flat tonometer (Model 30 Classic, REICHERT). An intraocular pressure lowering rate (%) was calculated by the following equation.

Among measured values at each point, the result showing the maximum action is shown in Table 2. An intraocular pressure of dogs to which each of the compound of Example 16 (35), the compound of Example 16 (3) and the compound of Example 16 (25) was ocular instillation-administered exhibited the stronger intraocular pressure lowering action as compared with latanoprost which is a positive control compound.

TABLE 2

| Compound | Administration dose (µg/mL) | Number of examples | Maximum of intraocular pressure lowering rate (%) |
|---|---|---|---|
| Example 16 (35) | 10 | 5 | 31 |
| Example 16 (3) | 10 | 5 | 35.7 |
| Example 16 (25) | 10 | 5 | 40.6 |
| Latanoprost | 50 | 10 | 25.4 |

(2-2) Assessment of Ocular Stimulating Property and Aqueous Humor Protein Concentration To one eye of a male rabbit (NewZealandWhite, 2.0 to 3.0 kg), 30 µL of the compound of Example 16 (35), the compound of Example 16 (3) and the compound of Example 16 (25) which had been adjusted to 0.1% (w/v) with a base (containing citrate buffer pH 6.5, 0.5% polysorbate 80, 1% propylene glycol, 0.01% benzalkonium chloride), was ocular-instilled respectively. Thereafter, an aqueous humor in anterior chamber after 0, 1, 2, 4, 6 and 8 hours from ocular instillation was collected, and a protein concentration in the humor was measured. As a comparative compound, the aforementioned methyl ester of the compound of Example 12 described in Patent Literature 2 (i.e. compound of Example 10 described in Patent Literature 2) (hereinafter, abbreviated as Comparative Compound B in some cases) was used.

Observation of the ocular general state was performed after 0, 1, 2, 4, 6 and 8 hours from ocular instillation, and visual remark of cornea, iris, and conjunctiva was observed according to determination criteria of the Draize method. A total of points of the resulting assessment points of each item ($=A_1 \times B_1 \times 5 + A_2 \times 5 + (A_3 + B_3 + C_3) \times 2$) was assessed as a Draize score. Classification criteria of the Draize score was produced by referring to "Regarding Reference Material concerning Basic Idea of Biological Safety Test, Administrative Notice Medical Device Examination No. 36 dated Mar. 19, 2003, Pharmaceutical and Medical Devices Agency". Classification criteria was as follows: A Draize score of 0 or more and 5 or less was a non-stimulating substance; 5 or more and 15 or less was a slightly stimulating substance; 15 or more and 30 or less was a stimulating substance; 30 or more and 60 or less was an intermediate stimulating substance; 60 or more and 80 or less was an intermediate to strongly stimulating substance; and 80 or more and 110 or less was a strongly stimulating substance.

Regarding any test compound, a dose until a dissolution limit (150 to 1000 µg/mL) was administered and action of each active body was assessed.

Figure 2:
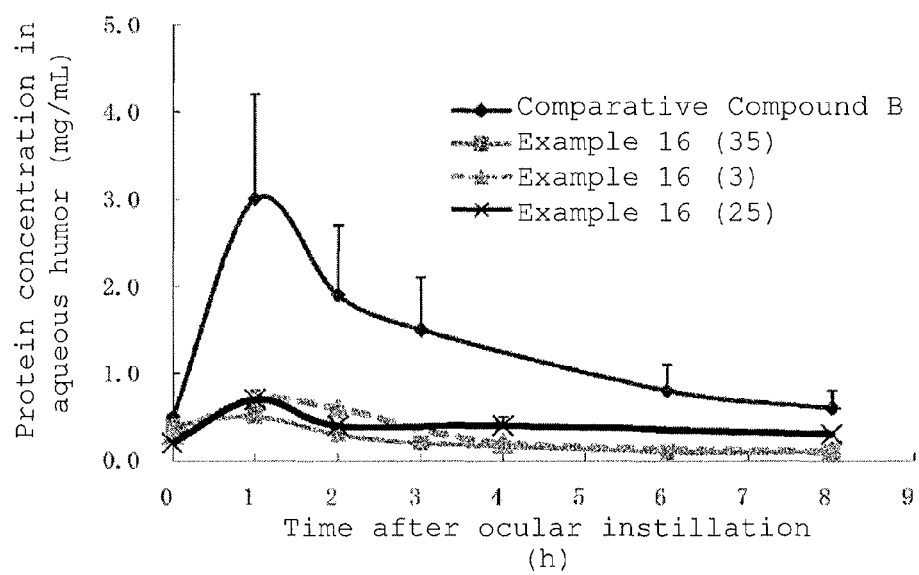
FIG. 2 A graph showing transition of a concentration of a protein in an aqueous humor after ocular instillation of the compound of the present invention and a comparative compound.

Results are shown in the following FIG. 1 and FIG. 2. The Comparative Compound B was classified as a slightly stimulating substance from a maximum of the Draize score, based

[Mathematic 1]

$$\text{Intraocular pressure lowering rate (\%)} = \frac{(\text{intraocular pressure value before ocular instillation} - \text{intraocular pressure value at each point})}{(\text{intraocular pressure value before ocular instillation})} \times 100$$

on its agonist activity on an IP receptor and, further, since it also raises a protein concentration in an aqueous humor, induction of the side effect on eyes was shown. To the contrary, it was seen that all of the compounds of Example 16 (35), Example 16 (3) and Example 16 (25) which are the compound of the present inventions were a non-stimulating substance by the Draize score, and had no action of raising a protein concentration in an aqueous humor.

From the foregoing, since the compound of the present invention has low agonist activity on an EP1 receptor and an IP receptor, and has selective agonist activity on an FP receptor, it was suggested that not only it has strong intraocular pressure lowering action, but also side effects on eyes such as ocular itching action based on EP1 receptor agonist activity, and ocular stimulating property such as hyperemia etc. and aqueous humor protein rise etc. based on IP receptor agonist activity can be avoided.

(2-3) Intraocular Pressure Lowering Action in Monkey Under Consciousness

To a left eye of a male monkey (crab-eating monkey) under consciousness, 30 μL of a solution obtained by adjusting a test substance with using the same base as that described above was ocular instillation-administered and, to a right eye, 30 μL of a solution of only a base as a control was ocular instillation-administered, respectively. An intraocular pressure after administration was measured with time from administration initiation until 24 hours. In case of measurement of an intraocular pressure, a crab-eating monkey was fixed on a monkey chair, and the monkey was anesthetized by ocular instillation-administering an ocular surface anesthetic (Benoxil eye drops 0.4% Santen Pharmaceutical Co., Ltd.). After mounting of a blepharostat (Handaya Co., Ltd.), an intraocular pressure of both eyes was measured (5 to 8 examples per group) with using a pneumatic applanation flat tonometer (Model 30 Classic, REICHERT). A difference in an intraocular pressure value between control eyes and eyes to which a test substance had been administered, was calculated as an intraocular pressure lowering rate with using the following equation, and sustainability of intraocular eye lowering action was assessed using a maximum intraocular pressure lowering rate during measurement and an intraocular pressure lowering rate after 24 hours. As the test substance, the Comparative Compound B, and the compounds of Example 16 (3), Example 16 (25) and Example 16 (35) were used, and an administration dose was 10 μg/mL in all cases.

The results are shown in the following Table 3. It was seen that, in the Comparative Compound B, a maximum intraocular pressure lowering rate was insufficient and, additionally, the lowering rate was reduced to less than 10% after 24 hours, and intraocular pressure lowering action cannot be sufficiently maintained. To the contrary, it was seen that all of the compound of the present inventions are compounds which have a high maximum intraocular pressure lowering rate, and can maintain an intraocular pressure lowering rate of about 15% or more even after 24 hours, and have strong and sustaining intraocular pressure lowering action.

TABLE 3

| Compound | Number of examples | Maximum intraocular pressure lowering rate (%) | Intraocular pressure lowering rate (%) after 24 hours |
| --- | --- | --- | --- |
| Comparative Compound B | 5 | 13.2 ± 3.2 | 7.0 ± 0.9 |
| Example 16 (35) | 5 | 19.2 ± 2.6 | 14.9 ± 4.7 |
| Example 16 (3) | 8 | 28.8 ± 2.2 | 15.1 ± 2.0 |
| Example 16 (25) | 8 | 26.5 ± 1.7 | 17.5 ± 2.1 |

Preparation Examples

Representative preparation examples used in the present invention will be shown below.

Preparation Example 1

Eye Drops

Eye drops according to the following formulation was prepared with using the general-use method.

After adding glycerin (2.5 g) and polysorbate 80 (500 mg) to sterile purified water, the compound (1 mg) of Example 16 (35) was added to dissolve and sterile purified water was added to a total amount of 100 mL, followed by sterile-filteration with a membrane filter, and filling into a predetermined container to obtain eye drops.

According to the same manner as that described above, eye drops etc. containing 0.1 mg and 0.5 mg of the compound of Example 140 (1) in 100 mL can be prepared. Alternatively, other compound of the present invention can be used in place of the compound of Example 140 (1).

Preparation Example 2

Ocular Ointment

An ocular ointment of the following formulation was prepared using the general-use method.

[Mathematic 2]

$$\text{Intraocular pressure lowering rate (\%)} = \frac{(\text{intraocular pressure value of control eye} - \text{intraocular pressure value of test substance-adiministered eye})}{\text{intraocular pressure value of control eye}} \times 100$$

A liquid paraffin and white vaseline were heat-sterilized in advance. After kneading the compound (1 mg) of Example 140 (1) with a liquid paraffin (10 g) sufficiently, white vaseline was added to a total amount of 100 g, followed by sufficiently kneading to obtain an ocular ointment.

INDUSTRIAL APPLICABILITY

Since the compound of the present invention has strong sustaining intraocular pressure lowering action and, further, has no side effects of eyes such as ocular stimulating property (hyperemia, corneal clouding etc.), aqueous humor protein rise etc., it is useful as an excellent agent for preventing and/or treating glaucoma etc.

The invention claimed is:

1. A compound represented by the formula (I):

[Chemical formula 1]

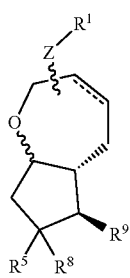
(I)

wherein Z represents (1)-$(CH_2)_m$—, (2)-$(CH_2)_n$—CH=CH—, (3)-$(CH_2)_p$-A-$CH_2$— or (4) ring 1;

A represents an oxygen atom or a sulfur atom;

$R^1$ represents (1) COOH, (2) $COOR^2$, (3) $CH_2OH$ or (4) $CONR^3R^4$;

$R^2$ represents a C1-6 alkyl group which may be substituted with a hydroxyl group, $ONO_2$ or a C1-4 alkoxy group, $R^3$ and $R^4$ each independently represent a hydrogen atom, or a C1-4 alkyl group which may be substituted with $ONO_2$;

$R^5$ represents a halogen atom, a hydroxyl group or a C1-4 alkoxy group;

$R^8$ represents a hydrogen atom or a halogen atom;

$R^9$ represents

[Chemical formula 2]

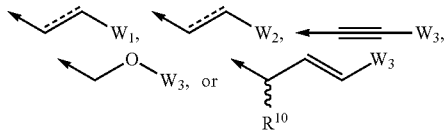

wherein the arrow represents a bonding site, $W_1$ represents a C1-6 alkyl group which may be substituted with 1 to 5 substituents selected from the group consisting of (1) a hydroxyl group, (2) an oxo group, (3) a halogen atom, (4) a C1-4 alkyl group, (5) a C1-4 alkoxy group, (6) ring 2, (7) —O-ring 2 and (8) —S-ring 2;

$W_2$ represents a C2-6 alkenyl group, a C1-3 alkoxy group or an alkyl ether group having 1 to 3 carbon atoms, wherein said carbon atoms may be substituted with 1 to 5 substituents selected from the group consisting of (1) a hydroxyl group, (2) an oxo group, (3) a halogen atom, (4) a C1-4 alkyl group, (5) a C1-4 alkoxy group, (6) ring 2, (7) —O-ring 2 and (8) —S-ring 2;

$W_3$ represents a C1-6 alkyl group, a C1-3 alkoxy group or an alkyl ether group having 1 to 3 carbon atoms, wherein said carbon atoms may be substituted with 1 to 5 substituents selected from the group consisting of (1) a hydroxyl group, (2) an oxo group, (3) a halogen atom, (4) a C1-4 alkyl group, (5) a C1-4 alkoxy group, (6) ring 2, (7) —O-ring 2 and (8) —S-ring 2; $R^{10}$ represents a hydrogen atom or a halogen atom;

ring 1 and ring 2 each independently represent a C3-10 carbocyclic ring or a 3- to 10-membered heterocyclic ring which may be substituted with 1 to 5 substituents selected from the group consisting of (1) a halogen atom, (2) $CF_3$, (3) $OCF_3$, (4) a C1-4 alkoxy group, (5) a C1-4 alkyl group, (6) a hydroxyl group and (7) a nitrile group;

m represents an integer of 1 to 6;

n represents an integer of 1 to 4;

p represents an integer of 1 to 4:

[Chemical formula 3]

represents a single bond or a double bond,

[Chemical formula 4]

represents α configuration,

[Chemical formula 5]

represents β configuration, and

[Chemical formula 6]

represents α configuration, β configuration or an arbitrary mixture thereof, a salt thereof, a solvate thereof, or a prodrug thereof.

2. The compound according to claim 1, wherein $R^8$ is a halogen atom, and $R^9$ is

[Chemical formula 7]

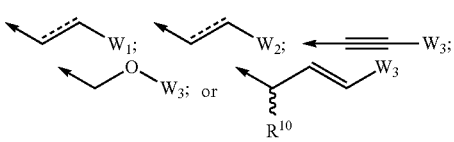

wherein all symbols represent the same meanings as those described in claim 1; or $R^8$ is a hydrogen atom, and $R^9$ is

[Chemical formula 8]

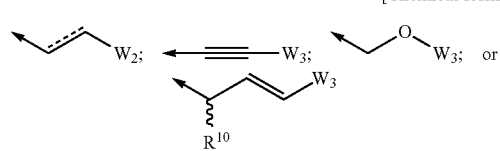

wherein all symbols represent the same meanings as those described in claim 1, or a salt thereof, a solvate thereof, or a prodrug thereof.

3. The compound according to claim 2, which is represented by the formula (I-1):

[Chemical formula 9]

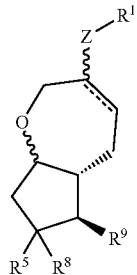

(I-1)

wherein all symbols represent the same meanings as those described in claim 2, or a salt thereof, a solvate thereof, or a prodrug thereof.

4. The compound according to claim 1, which is a compound selected from the group consisting of (1) 4-{(3S,5aR,6R,7R,8aS)-7-hydroxy-6-[(1E,3S)-3-hydroxy-4-phenoxy-1-buten-1-yl]octahydro-2H-cyclopenta[b]oxepin-3-yl}butanoic acid, (2) 4-{(3S,5aR,6R,7R,8aS)-7-hydroxy-6-[(1E,3R)-3-hydroxy-5-phenyl-1-penten-1-yl]octahydro-2H-cyclopenta[b]oxepin-3-yl}butanoic acid, (3) 4-{(3S,5aR,6R,7R,8aS)-6-[(1E,3R)-5-(3-fluorophenyl)-3-hydroxy-1-penten-1-yl]-7-hydroxyoctahydro-2H-cyclopenta[b]oxepin-3-yl}butanoic acid, (4) 4-{(3S,5aR,6R,7R,8aS)-6-[(1E,3S)-5-(3-fluorophenyl)-3-hydroxy-1-penten-1-yl]-7-hydroxyoctahydro-2H-cyclopenta[b]oxepin-3-yl}butanoic acid, (5) 4-{(3S,5aR,6R,7R,8aS)-6-[(1E,3R)-5-(4-fluorophenyl)-3-hydroxy-1-penten-1-yl]-7-hydroxyoctahydro-2H-cyclopenta[b]oxepin-3-yl}butanoic acid, (6) 4-{(3S,5aR,6R,7R,8aS)-6-[(1E,3S)-5-(4-fluorophenyl)-3-hydroxy-1-penten-1-yl]-7-hydroxyoctahydro-2H-cyclopenta[b]oxepin-3-yl}butanoic acid, (7) 4-{(3S,5aR,6R,7R,8aS)-6-[(1E,3R)-5-(2-fluorophenyl)-3-hydroxy-1-penten-1-yl]-7-hydroxyoctahydro-2H-cyclopenta[b]oxepin-3-yl}butanoic acid, (8) 4-{(3S,5aR,6R,7R,8aS)-6-[(1E,3S)-5-(2-fluorophenyl)-3-hydroxy-1-penten-1-yl]-7-hydroxyoctahydro-2H-cyclopenta[b]oxepin-3-yl}butanoic acid, (9) 4-{(3S,5aR,6R,7R,8aS)-6-[(1E,3R)-5-(3-chlorophenyl)-3-hydroxy-1-penten-1-yl]-7-hydroxyoctahydro-2H-cyclopenta[b]oxepin-3-yl}butanoic acid,

(10) 4-{(3S,5aR,6R,7R,8aS)-6-[(1E,3S)-5-(3-chlorophenyl)-3-hydroxy-1-penten-1-yl]-7-hydroxyoctahydro-2H-cyclopenta[b]oxepin-3-yl}butanoic acid,

(11) 4-[(3S,5aR,6R,7R,8aS)-7-hydroxy-6-{(1E,3R)-3-hydroxy-5-[3-(trifluoromethyl)phenyl]-1-penten-1-yl}octahydro-2H-cyclopenta[b]oxepin-3-yl]butanoic acid,

(12) 4-[(3S,5aR,6R,7R,8aS)-7-hydroxy-6-{(1E,3S)-3-hydroxy-5-[3-(trifluoromethyl)phenyl]-1-penten-1-yl}octahydro-2H-cyclopenta[b]oxepin-3-yl]butanoic acid,

(13) 4-[(3S,5aR,6R,7R,8aS)-7-hydroxy-6-{(1E,3S)-3-hydroxy-4-[3-(trifluoromethyl)phenoxy]-1-buten-1-yl}octahydro-2H-cyclopenta[b]oxepin-3-yl]butanoic acid,

(14) 4-{(3S,5aR,6R,7R,8aS)-6-[(1E,3S)-4-(2-fluorophenoxy)-3-hydroxy-1-buten-1-yl]-7-hydroxyoctahydro-2H-cyclopenta[b]oxepin-3-yl}butanoic acid,

(15) 4-{(3S,5aR,6R,7R,8aS)-6-[(1E,3S)-4-(3-fluorophenoxy)-3-hydroxy-1-buten-1-yl]-7-hydroxyoctahydro-2H-cyclopenta[b]oxepin-3-yl}butanoic acid,

(16) 4-{(3S,5aR,6R,7R,8aS)-6-[(1E,3S)-4-(4-fluorophenoxy)-3-hydroxy-1-buten-1-yl]-7-hydroxyoctahydro-2H-cyclopenta[b]oxepin-3-yl}butanoic acid,

(17) 4-{(3S,5aR,6R,7R,8aS)-6-[(1E,3S)-5-cyclohexyl-3-hydroxy-1-penten-1-yl]-7-hydroxyoctahydro-2H-cyclopenta[b]oxepin-3-yl}butanoic acid,

(18) 4-{(3S,5aR,6R,7R,8aS)-7-hydroxy-6-[(3S)-3-hydroxy-4-phenoxybutyl]octahydro-2H-cyclopenta[b]oxepin-3-yl}butanoic acid,

(19) 4-{(3S,5aR,6R,7R,8aS)-7-hydroxy-6-[(3S)-3-hydroxy-5-phenylpentyl]octahydro-2H-cyclopenta[b]oxepin-3-yl}butanoic acid,

(20) 4-{(3S,5aR,6R,7R,8aS)-6-[(3S)-5-(3-fluorophenyl)-3-hydroxypentyl]-7-hydroxyoctahydro-2H-cyclopenta[b]oxepin-3-yl}butanoic acid,

(21) 4-{(3S,5aR,6R,7R,8aS)-6-[(3R)-5-(3-fluorophenyl)-3-hydroxypentyl]-7-hydroxyoctahydro-2H-cyclopenta[b]oxepin-3-yl}butanoic acid,

(22) 4-{(3S,5aR,6R,7R,8aS)-6-[(3S)-5-(4-fluorophenyl)-3-hydroxypentyl]-7-hydroxyoctahydro-2H-cyclopenta[b]oxepin-3-yl}butanoic acid,

(23) 4-{(3S,5aR,6R,7R,8aS)-6-[(3R)-5-(4-fluorophenyl)-3-hydroxypentyl]-7-hydroxyoctahydro-2H-cyclopenta[b]oxepin-3-yl}butanoic acid,

(24) 4-{(3S,5aR,6R,7R,8aS)-6-[(3S)-5-(2-fluorophenyl)-3-hydroxypentyl]-7-hydroxyoctahydro-2H-cyclopenta[b]oxepin-3-yl}butanoic acid,

(25) 4-{(3S,5aR,6R,7R,8aS)-6-[(3R)-5-(2-fluorophenyl)-3-hydroxypentyl]-7-hydroxyoctahydro-2H-cyclopenta[b]oxepin-3-yl}butanoic acid,

(26) 4-{(3S,5aR,6R,7R,8aS)-6-[(3S)-5-(3-chlorophenyl)-3-hydroxypentyl]-7-hydroxyoctahydro-2H-cyclopenta[b]oxepin-3-yl}butanoic acid,

(27) 4-{(3S,5aR,6R,7R,8aS)-6-[(3R)-5-(3-chlorophenyl)-3-hydroxypentyl]-7-hydroxyoctahydro-2H-cyclopenta[b]oxepin-3-yl}butanoic acid,

(28) 4-[(3S,5aR,6R,7R,8aS)-7-hydroxy-6-{(3S)-3-hydroxy-5-[3-(trifluoromethyl)phenyl]pentyl}octahydro-2H-cyclopenta[b]oxepin-3-yl]butanoic acid,

(29) 4-[(3S,5aR,6R,7R,8aS)-7-hydroxy-6-{(3R)-3-hydroxy-5-[3-(trifluoromethyl)phenyl]pentyl}octahydro-2H-cyclopenta[b]oxepin-3-yl]butanoic acid,

(30) 4-[(3S,5aR,6R,7R,8aS)-7-hydroxy-6-{(3R)-3-hydroxy-4-[3-(trifluoromethyl)phenoxy]butyl}octahydro-2H-cyclopenta[b]oxepin-3-yl]butanoic acid,

(31) 4-{(3S,5aR,6R,7R,8aS)-6-[(1E)-3-fluoro-4-phenoxy-1-buten-1-yl]-7-hydroxyoctahydro-2H-cyclopenta[b]oxepin-3-yl}butanoic acid,

(32) 4-{(3S,5aR,6R,7R,8aS)-6-[(1E)-4-(3-chlorophenoxy)-1-buten-1-yl]-7-hydroxyoctahydro-2H-cyclopenta[b]oxepin-3-yl}butanoic acid,

(33) 4-{(3S,5aR,6R,7R,8aS)-6-[(1E)-4-(2-fluorophenoxy)-1-buten-1-yl]-7-hydroxyoctahydro-2H-cyclopenta[b]oxepin-3-yl}butanoic acid,

(34) 4-{(3S,5aR,6R,7R,8aS)-6-[(1E)-4-(3-fluorophenoxy)-1-buten-1-yl]-7-hydroxyoctahydro-2H-cyclopenta[b]oxepin-3-yl}butanoic acid,

(35) 4-{(3S,5aR,6R,7R,8aS)-6-[(1E)-4-(2,5-difluorophenoxy)-1-buten-1-yl]-7-hydroxyoctahydro-2H-cyclopenta[b]oxepin-3-yl}butanoic acid,

(36) 4-{(3S,5aR,6R,7R,8aS)-7-hydroxy-6-[(1E)-4-hydroxy-6-phenyl-1-hexen-1-yl]octahydro-2H-cyclopenta[b]oxepin-3-yl}butanoic acid,

(37) 4-[(3S,5aR,6R,7R,8aS)-7-hydroxy-6-(4-phenoxybutyl)octahydro-2H-cyclopenta[b]oxepin-3-yl]butanoic acid,

(38) 4-{(3S,5aR,6R,7R,8aS)-7-hydroxy-6-[(1E)-3-hydroxy-1-decen-1-yl]octahydro-2H-cyclopenta[b]oxepin-3-yl}butanoic acid,

(39) 4-{(3S,5aR,6R,7R,8aS)-7-hydroxy-6-[(1E)-3-hydroxy-5-(5-methyl-2-furyl)-1-penten-1-yl]octahydro-2H-cyclopenta[b]oxepin-3-yl}butanoic acid,

(40) 4-{(3S,5aR,6R,7R,8aS)-6-[(1E)-5-cyclopentyl-3-hydroxy-1-penten-1-yl]-7-hydroxyoctahydro-2H-cyclopenta[b]oxepin-3-yl}butanoic acid,

(41) 4-{(3S,5aR,6R,7R,8aS)-6-[(1E)-3-(1-benzofuran-2-yl)-3-hydroxy-1-propen-1-yl]-7-hydroxyoctahydro-2H-cyclopenta[b]oxepin-3-yl}butanoic acid,

(42) 4-{(3S,5aR,6R,7R,8aS)-7-hydroxy-6-[(1E)-3-hydroxy-5-(3-hydroxyphenyl)-1-penten-1-yl]octahydro-2H-cyclopenta[b]oxepin-3-yl}butanoic acid,

(43) 4-{(3S,5aR,6R,7R,8aS)-6-[(1E)-3,3-difluoro-5-phenyl-1-penten-1-yl]-7-hydroxyoctahydro-2H-cyclopenta[b]oxepin-3-yl}butanoic acid,

(44) 4-[(3S,5aR,6R,7R,8aS)-6-(3,3-difluoro-5-phenylpentyl)-7-hydroxyoctahydro-2H-cyclopenta[b]oxepin-3-yl]butanoic acid,

(45) 4-{(3S,5aR,6R,7R,8aS)-6-[(1E)-5-cyclopentyl-3,3-difluoro-1-penten-1-yl]-7-hydroxyoctahydro-2H-cyclopenta[b]oxepin-3-yl}butanoic acid,

(46) 4-{(3S,5aR,6R,7R,8aS)-6-[(1E)-5-cyclohexyl-3,3-difluoro-1-penten-1-yl]-7-hydroxyoctahydro-2H-cyclopenta[b]oxepin-3-yl}butanoic acid,

(47) 4-{(3S,5aR,6R,7R,8aS)-6-[(1E)-3,3-difluoro-1-octen-1-yl]-7-hydroxyoctahydro-2H-cyclopenta[b]oxepin-3-yl}butanoic acid, and isomers thereof, or a salt thereof, a solvate thereof, or a prodrug thereof.

5. The compound according to claim 2, which is a compound selected from the group consisting of (1) 4-[(3S,5aR,6S,7R,8aS)-7-hydroxy-6-({[(2E)-3-phenyl-2-propen-1-yl]oxy}methyl)octahydro-2H-cyclopenta[b]oxepin-3-yl]butanoic acid, (2) 4-{(3S,5aR,6R,7R,8aS)-7-hydroxy-6-[2-(2-phenylethoxy)ethyl]octahydro-2H-cyclopenta[b]oxepin-3-yl}butanoic acid, (3) 4-[(3S,5aR,6S,7R,8aS)-7-hydroxy-6-(3-hydroxy-5-phenyl-1-pentyn-1-yl)octahydro-2H-cyclopenta[b]oxepin-3-yl]butanoic acid, (4) 4-{(3S,5aR,6R,7R,8aS)-6-[(2E)-1-fluoro-4-phenoxy-2-buten-1-yl]-7-hydroxyoctahydro-2H-cyclopenta[b]oxepin-3-yl}butanoic acid, (5) 4-{(3S,5aR,6R,7R,8aS)-7-hydroxy-6-[(1E)-3-hydroxy-8-methyl-1,7-nonadien-1-yl]octahydro-2H-cyclopenta[b]oxepin-3-yl}butanoic acid, (6) 4-{(3S,5aR,6R,7R,8aS)-6-[(1E)-4-(benzyloxy)-3-hydroxy-1-buten-1-yl]-7-hydroxyoctahydro-2H-cyclopenta[b]oxepin-3-yl}butanoic acid, (7) 4-{(3S,5aR,6R,7R,8aS)-7-hydroxy-6-[(1E)-3-hydroxy-1,7-octadien-1-yl]octahydro-2H-cyclopenta[b]oxepin-3-yl}butanoic acid, (8) 4-{(3S,5aR,6R,7R,8aS)-7-hydroxy-6-[(1E,6Z)-3-hydroxy-1,6-nonadien-1-yl]octahydro-2H-cyclopenta[b]oxepin-3-yl}butanoic acid, (9) 4-{(3S,5aR,6R,7R,8aS)-7-hydroxy-6-[(1E)-3-hydroxy-4,8-dimethyl-1,7-nonadien-1-yl]octahydro-2H-cyclopenta[b]oxepin-3-yl}butanoic acid,

(10) 4-{(3S,5aR,6R,8aS)-7,7-difluoro-6-[(1E)-3-hydroxy-1-octen-1-yl]octahydro-2H-cyclopenta[b]oxepin-3-yl}butanoic acid,

(11) 4-{(3S,5aR,6R,8aS)-7,7-difluoro-6-[(1E)-3-hydroxy-5-phenyl-1-penten-1-yl]octahydro-2H-cyclopenta[b]oxepin-3-yl}butanoic acid,

(12) 4-{(3S,5aR,6R,7R,8aS)-6-[(1E)-3,3-difluoro-8-methyl-1,7-nonadien-1-yl]-7-hydroxyoctahydro-2H-cyclopenta[b]oxepin-3-yl}butanoic acid, and isomers thereof, or a salt thereof, a solvate thereof, or a prodrug thereof.

6. A pharmaceutical composition comprising the compound, or a salt thereof, a solvate thereof, or a prodrug thereof described in claim 2 and a pharmaceutically acceptable diluent or excipient.

7. A method of treating an ocular disease, comprising administering an effective amount of the compound, or a salt thereof, a solvate thereof, or a prodrug thereof described in claim 2 to a mammal.

8. A pharmaceutical composition comprising the compound, or a salt thereof, a solvate thereof, or a prodrug thereof described in claim 1 and a pharmaceutically acceptable diluent or excipient.

* * * * *